(12) United States Patent
Varasi et al.

(10) Patent No.: US 8,592,444 B2
(45) Date of Patent: Nov. 26, 2013

(54) SPIROCYCLIC DERIVATIVES AS HISTONE DEACETYLASE INHIBITORS

(75) Inventors: Mario Varasi, Milan (IT); Florian Thaler, Gerenzano (IT); Agnese Abate, Vimodrone (IT); Giacomo Carenzi, Busto Arsizio (IT); Ciro Mercurio, Legnano (IT); Saverio Minucci, Noverasco di Opera (IT)

(73) Assignee: DAC S.R.L., Milan (IT)

( * ) Notice: Subject to any disclaimer, the term of this patent is extended or adjusted under 35 U.S.C. 154(b) by 258 days.

(21) Appl. No.: 12/988,197

(22) PCT Filed: Apr. 14, 2009

(86) PCT No.: PCT/EP2009/054376
§ 371 (c)(1),
(2), (4) Date: Oct. 15, 2010

(87) PCT Pub. No.: WO2009/127609
PCT Pub. Date: Oct. 22, 2009

(65) Prior Publication Data
US 2011/0039840 A1 Feb. 17, 2011

(30) Foreign Application Priority Data
Apr. 15, 2008 (EP) .................................... 08154528

(51) Int. Cl.
*C07D 401/04* (2006.01)
*A61K 31/438* (2006.01)

(52) U.S. Cl.
USPC ............................... 514/278; 546/17; 546/19

(58) Field of Classification Search
USPC ...................... 546/17, 19; 514/278
See application file for complete search history.

(56) References Cited

FOREIGN PATENT DOCUMENTS

WO 2004/113336 A1 12/2004
WO 2007/061880 A1 5/2007

OTHER PUBLICATIONS

Dorwald F. A. Side Reactions in Organic Synthesis, 2005, Wiley: VCH, Weinheim p. IX of Preface.*
James R Davie, "Covalent modifications of histones: expression from chromatin templates," Current Opinion in Genetics & Development, 1998, 173-178, vol. 8, Current Biology Ltd ISSN 0959-437X.
Jiansheng Wu et al., "25 years after the nucleosome model: chromatin modifications," TIBS 25, Dec. 2000, 619-623, Elsevier Science Ltd.
S. Timmermann et al., "Histone acetylation and disease," CMLS, Cell. Mol. Life Sci., 2001, 728-736, vol. 58, Birkhauser Verlag, Basel.
Lili Huang, "Targeting Histone Deacetylases for the Treatment of Cancer and Inflammatory Diseases," Journal of Cellular Physiology, 2006, 611-616, vol. 209, Wiley-Liss, Inc.

Saverio Minucci et al., "Histone deacetylase inhibitors and the promise of epigenetic (and more) treatments for cancer," Nature Reviews—Cancer, Jan. 2006, 38-51, vol. 6, Nature Publishing Group.
Mehdi Ouaissi et al., "Histone Deacetylase Enzymes as Potential Drug Targets in Cancer and Parasitic Diseases" Journal of Biomedicine and Biotechnology, 2006, 1-10, vol. 2006, Article ID 13474, Hindawi Publishing Corporation.
Rajiv P. Sharma et al., "Valproic acid and chromatin remodeling in schizophrenia and bipolar disorder: Preliminary results from a clinical population," Schizophrenia Research, 2006, 227-231, vol. 88, Elsevier B. V.
Ma Glozak et al., "Histone deacetylases and cancer," Oncogene, 2007, 5420-5432, vol. 26, Nature Publishing Group.
Greetje Elaut et al., "The Pharmaceutical Potential of Histone Deacetylase Inhibitors," Current Pharmaceutical Design, 2007, 2584-2620, vol. 13, Bentham Science Publishers Ltd.
Konstantin V. Balakin et al., "Histone Deacetylase Inhibitors in Cancer Therapy: Latest Developments, Trends and Medicinal Chemistry Perspective," Anti-Cancer Agents in Medicinal Chemistry, 2007, 000-000, vol. 7, Bentham Science Publishers Ltd.
HB Lee et al., "Histone deacetylase inhibitors: a novel class of therapeutic agents in diabetic nephropathy," Kidney International, 2007, S61-S66, vol. 72, International Society of Nephrology.
B. E. Morrison et al., "Histone deacetylases: Focus on the nervous system," Cell. Mol. Life. Sci., 2007, 2258-2269, vol. 64, Birkhauser Verlag, Basel.

(Continued)

*Primary Examiner* — Rita Desai
(74) *Attorney, Agent, or Firm* — McCormick, Paulding & Huber LLP

(57) ABSTRACT

This invention is related to new histone deacetylase inhibitors according to the general formula (I) wherein: the dotted line is an optional additional bond; n is zero or an integer from 1 to 4; $R^1$ is hydrogen; $C_1$-$C_6$ alkyl, optionally substituted by cycloalkyl, aryl or by heteroaryl; $(CO)R^3$; $(SO_2)R^4$; cycloalkyl; aryl; or heteroaryl; $R^2$ is $C_1$-$C_6$ alkyl, optionally substituted by aryl or by heteroaryl; aryl; heteroaryl; or (CO)$R^5$; X is $CH_2$, oxygen or $NR^6$; Y is a bond, $CHR^7$ or $NR^8$; Z is oxygen, $CR^9R^{10}$ or C=$R^{11}$; and $R^3$, $R^4$, $R^5$, $R^6$, $R^7$, $R^8$, $R^9$, $R^{10}$ and $R^{11}$ are as further defined in the specification; and pharmaceutical acceptable salts thereof.

(I)

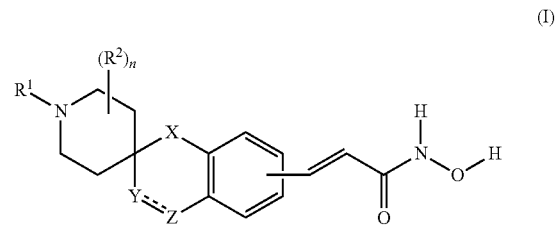

9 Claims, No Drawings

(56) References Cited

OTHER PUBLICATIONS

Aleksey G. Kazantsev et al., "Therapeutic application of histone deacetylase inhibitors for central nervous system disorders," Nature Reviews/Drug Discovery, Oct. 2008, 854-868, vol. 7, Macmillan Publishers Limited.

David M Vigushin et al., "Histone deacetylase inhibitors in cancer treatment," Anti-Cancer Drugs, 2002, 1-13, vol. 13, Lippincott Williams & Wilkins.

International Search Report from PCT/EP2009/054376 dated Jun. 25, 2009 (2 pages).

* cited by examiner

SPIROCYCLIC DERIVATIVES AS HISTONE DEACETYLASE INHIBITORS

CROSS REFERENCE TO RELATED APPLICATIONS

This application is entitled to the benefit of and incorporates by reference essential subject matter disclosed in European Patent Application No. 08154528.7 filed on Apr. 15, 2008 and International Patent Application No. PCT/EP2009/054376 filed on Apr. 14, 2009.

FIELD OF THE INVENTION

The present invention relates to inhibitors of histone deacetylases (HDACs), to a process for their preparation, pharmaceutical compositions comprising them, and to their use as therapeutic agents, in particular for the treatment of cancer.

BACKGROUND OF THE INVENTION

The reversible acetylation of the ε-amino groups of several lysine residues in the N-terminal histone tails mediates important conformational modifications in nucleosomes. These modifications influence the access of transcription factor to DNA and regulate gene expression (Davie, J. R. *Curr. Opin. Genet. Dev.* 1998, 8, 173-178). Two enzyme classes are involved in the process of acetylation and deacetylation of histones: histone acetyltransferases (HAT), which catalyse histone acetylation by acting as transcriptional co-activators, and histone deacetylases (HDAC).

After their recruitment to the promoter regions induced by transcription repressors and co-repressors such as Sin3, SMRT and N-CoR, histone deacetylases induce the formation of hypoacetylated histones and ultimately lead to transcriptional silencing (Wu, J. et al. *Trends Biochem. Sci.* 2000, 25, 619-623). The aberrant recruitment of histone deacetylases by oncogene proteins, or the disruption of the equilibrium between the activities of histone acetyltransferases and histone deacetylases are implicated in a series of pathologies, such as cancer, diseases of the central and peripheral nervous system, infections, immune diseases, cardiovascular diseases, muscular disorders, fibrosis or psoriasis.

The following (non exhausitive) selection of references demonstrate the involvement of HDACs in different diseases and the potential therapeutic benefit, which can be achieved by inhibiting them: Timmermann S. et al. *Cell Mol Life Sci.* 2001 58, 728-736; Huang, L. *J. Cell. Physiol.* 2006, 209, 611-616; Minucci, S. et al. *Nature Reviews Cancer,* 2006, 6, 38-51; Ouaissi, M. et al. *J Biomed Biotechnol.* 2006, 1-10; Sharma, P. et al. *Schizophr. Res.* 2006, 88, 227-231. Glozak M. A. et al. *Oncogene.* 2007, 26, 5420-5432; Elaut G. et al. *Curr Pharm Des.* 2007, 13, 2584-2620; Balakin K. V. et al. *Anticancer Agents Med. Chem.* 2007 7, 576-92; Lee H. B. et al. *Kidney Int. Suppl.* 2007, 106, S61-66; Morrison B. E. et al. *Cell Mol Life Sci.* 2007, 64, 2258-2269 Kazantsev A. G et al. *Nat Rev Drug Discov.* 2008, 7, 854-868.

In recent years there has been a considerable effort to develop inhibitors of histone deacetylases and several classes of compounds have been found to have potent and specific activities in preclinical studies. Their clinical benefits, however, are limited by toxicity problems, poor pharmacokinetic properties, poor potency and lack of selectivity (Elaut G. et al. *Curr Pharm Des.* 2007, 13, 2584-2620; Vigushin, D. et al. *Anti-Cancer Drugs* 2002, 13, 1-13).

PCT application WO 2004/113336 (Chroma Therapeutics) discloses carboline and betacarboline derivatives as HDAC inhibitors with the following general formula:

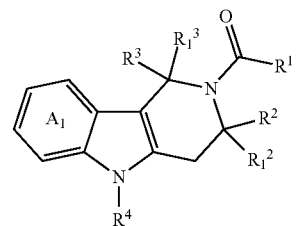

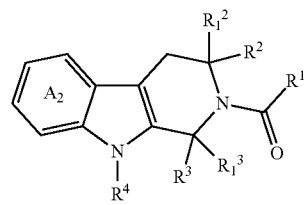

wherein fused rings $A_1$ and $A_2$ are optional substituted, $R^1$ represents a radical of formula -(Alk$^1$)$_n$-(X)$_m$-(Alk$^2$)$_p$-Z, Z represents a radical of formula —C(=O)NH(OH) or N(OH)C(=O)Y.

PCT application WO 2007/061880 (Merck) discloses spirocyclic compounds as HDAC inhibitors with the following general formula:

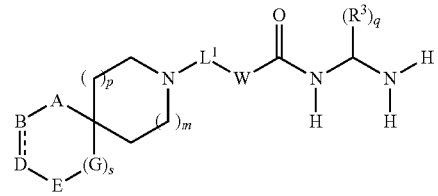

wherein A, B and D are independently selected from CR$^1_2$, NR$^{1a}$, C(O) and O; E is selected from a bond, CR$^1_2$, NR$^{1a}$, C(O) and O; wherein at least one of A, B, D or E is CR$^1_2$; G is CR$^1_2$; R is selected from NH$_2$ and OH; W and Z are aryl or heteroaryl.

The present inventors have now found that certain substituted spirocyclic derivatives are highly potent inhibitors of the HDAC enzymes.

SUMMARY OF THE INVENTION

According to the present invention there are provided compounds, endowed with a potent HDAC inhibitory activity, of general formula (I)

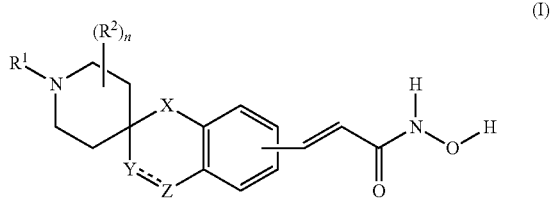

wherein:
the dotted line is an optional additional bond;
n is zero or an integer from 1 to 4;
$R^1$ is hydrogen; $C_1$-$C_6$ alkyl, optionally substituted by cycloalkyl, aryl or heteroaryl; (CO)$R^3$; (SO$_2$)$R^4$; cycloalkyl; aryl; or heteroaryl;
$R^2$ is $C_1$-$C_6$ alkyl, optionally substituted by aryl or by heteroaryl; aryl; heteroaryl; or (CO)$R^5$;
X is CH$_2$; oxygen or NR$^6$;
Y is a bond; CHR$^7$ or NR$^8$;
Z is oxygen; CR$^9$R$^{10}$ or C=R$^{11}$;
$R^3$ is $C_1$-$C_6$ alkyl, optionally substituted by aryl or by heteroaryl; aryl; heteroaryl; O—$C_1$-$C_6$ alkyl, optionally substituted by aryl; O-aryl; or NR$^{12}$R$^{13}$;
$R^4$ is $C_1$-$C_6$ alkyl, optionally substituted by aryl or by heteroaryl; aryl; or heteroaryl;
$R^5$ is OH; $C_1$-$C_6$ alkyl; O—$C_1$-$C_6$ alkyl or NR$^{14}$R$^{15}$;
$R^6$ is hydrogen; $C_1$-$C_6$ alkyl, optionally substituted by aryl or by heteroaryl;
$R^7$ is hydrogen; or is absent, when said additional bond is present;
$R^8$ is hydrogen; $C_1$-$C_6$ alkyl, optionally substituted by aryl or by heteroaryl;
$R^9$ is hydrogen; or is absent, when said additional bond is present;
$R^{10}$ is hydrogen; hydroxyl; $C_1$-$C_6$-alkoxy; $C_1$-$C_6$ acylamino;
$R^{11}$ is oxygen; sulphur or NOR$^{16}$;
$R^{12}$ is hydrogen; $C_1$-$C_6$ alkyl, optionally substituted by aryl or by heteroaryl; aryl; or heteroaryl;
$R^{13}$ is hydrogen; $C_1$-$C_6$ alkyl, optionally substituted by aryl, heteroaryl; or
$R^{12}$ and $R^{13}$ together with the nitrogen to which they are bound form a $C_4$-$C_9$-heterocyclic ring, optionally containing one or more further heteroatoms in the ring selected from NR$^{17}$, O or S;
$R^{14}$, $R^{15}$ are, independently, hydrogen; $C_1$-$C_6$ alkyl, optionally substituted by aryl or by heteroaryl; aryl or heteroaryl; or $R^{14}$ and $R^{15}$ together with the nitrogen to which they are bound form a $C_4$-$C_9$-heterocyclic ring, optionally containing one or more further heteroatoms in the ring selected from NR$^{18}$, O or S;
$R^{16}$ is hydrogen; $C_1$-$C_6$ alkyl, optionally substituted by aryl;
$R^{17}$, $R^{18}$ are, independently, hydrogen; $C_1$-$C_6$ alkyl, optionally substituted by aryl or by heteroaryl; aryl; heteroaryl; (CO)—$C_1$-$C_6$ alkyl, optionally substituted by aryl or by heteroaryl; (CO)—O—$C_1$-$C_6$ alkyl, optionally substituted by aryl; (CO)—O-aryl; (CO)—NR$^{19}$NR$^{20}$; (SO$_2$)—$C_1$-$C_6$ alkyl, optionally substituted by aryl or by heteroaryl; (SO$_2$)-aryl; or (SO$_2$)-heteroaryl;
$R^{19}$ is hydrogen; $C_1$-$C_6$ alkyl, optionally substituted by aryl or by heteroaryl; aryl; or heteroaryl;
$R^{20}$ is hydrogen; $C_1$-$C_6$ alkyl, optionally substituted by aryl or heteroaryl;
and the pharmaceutically acceptable salts thereof; provided that when said additional bond is present, then Y and Z are CH.

DETAILED DESCRIPTION OF THE INVENTION

According to the description and claims, "aryl" represents a mono or bicyclic aromatic ring system of, respectively, 6, 9 or 10 atoms, such as benzene, indene and naphthalene and includes also indan and tetrahydronaphthalene.

According to the description and claims, "heteroaryl" represents a mono or bicyclic heteroaromatic ring system of, respectively, 5 to 10 members, which contains one, two or three heteroatoms selected from nitrogen, oxygen or sulphur.

Examples of said heteroaryls include, but are not limited to: pyrrolyl, imidazolyl, pyridyl, pyrimidinyl, pyridazinyl, furyl, thienyl, thiazolyl, indolyl, isoindolyl, benzimidazolyl, purinyl, quinolyl, isoquinolyl, quinazolinyl, quinoxalinyl, benzofuranyl, and benzopyranyl.

The aryl and heteroaryl may be optionally substituted with one or more substituents selected from halogen, CN, $C_1$-$C_6$ alkyl, $C_1$-$C_6$ haloalkyl, $C_1$-$C_6$ alkoxy, $C_1$-$C_6$ haloalkoxy, amino, $C_1$-$C_6$ alkylamino, or phenyl.

According to the description and claims, the term "cycloalkyl" refers to a saturated monocyclic, hydrocarbon ring system having three to eight carbon atoms and zero heteroatoms. Representative examples of cycloalkyl groups include, but are not limited to, cyclopropyl, cyclopentyl, and cyclohexyl.

According to the description and claims, the term "$C_1$-$C_6$ alkyl" refers to a straight or branched hydrocarbon chain radical, consisting solely of carbon and hydrogen atoms, having from one to six carbon atoms. The "$C_1$-$C_6$ alkyl" group is preferably a linear or branched $C_1$-$C_4$ alkyl group, more preferably a $C_1$-$C_2$ alkyl group.

According to the description and claims, the term "$C_1$-$C_6$ alkoxy" refers to a straight or branched O—$C_1$-$C_6$ alkyl, where alkyl is as defined herein. The "$C_1$-$C_6$ alkoxy" group is preferably a linear or branched $C_1$-$C_4$ alkoxy group, more preferably a $C_1$-$C_2$ alkoxy group.

According to the description and claims, the term "$C_1$-$C_6$ haloalkyl" refers to a straight or branched hydrocarbon chain radical, which is substituted by one or more halogen atoms and having from one to six carbon atoms. The "$C_1$-$C_6$ haloalkyl" group is preferably a linear or branched $C_1$-$C_4$ haloalkyl group, more preferably a $C_1$-$C_2$ haloalkyl group, being in particular CF$_3$.

According to the description and claims, the term "$C_1$-$C_6$ haloalkoxy" refers to a straight or branched O—$C_1$-$C_6$ haloalkyl, where haloalkyl is as defined herein. The "$C_1$-$C_6$ haloalkoxy" group is preferably a linear or branched $C_1$-$C_4$ haloalkoxy group, more preferably a $C_1$-$C_2$ haloalkoxy group, being in particular OCF$_3$, OCHF$_2$ or OCH$_2$F.

According to the description and claims, the term "$C_1$-$C_6$ acylamino" refers to a straight or branched —NH—C(O)—$C_1$-$C_6$ alkyl, where $C_1$-$C_6$ alkyl is as defined herein.

According to the description and claims, the term "$C_1$-$C_6$ alkylamino" refers to a straight or branched —NH—$C_1$-$C_6$ alkyl, where $C_1$-$C_6$ alkyl is as defined herein.

"Halogens" are preferably fluorine, chlorine or bromine, being in particular fluorine or chlorine.

When in formula (I) n is 2, 3 or 4, it is provided that the $R^2$ groups attached to the piperidine ring may be equal or different from each other.

"Pharmaceutically acceptable salts" comprise conventional non-toxic salts obtained by salification with inorganic acids (e.g. hydrochloric, hydrobromide, sulphuric or phosphoric acids), or with organic acids (e.g. acetic, propionic, succinic, benzoic, cinnamic, mandelic, salicylic, glycolic, lactic, oxalic, malic, maleic, malonic, fumaric, tartaric, citric, p-toluenesulfonic or methanesulfonic acids).

In addition, the compounds of the present invention can exist in unsolvated as well as in solvated forms with pharmaceutically acceptable solvents such as water, ethanol and the like.

The compounds of the invention and their pharmaceutical acceptable salts can exist as single stereoisomers, racemates, and as mixtures of diastereoisomers. The compounds can exist also as geometric isomers. All such geometric isomers, single stereoisomers, racemates and mixtures thereof, are intended to be within the scope of the invention.

The present invention comprises metabolic precursors of formula (I) compounds. The term "metabolic precursors" means compounds having a different structure from that of the relevant formula (I), which after administration to the patient are directly or indirectly transformed into a compound of said formula (I). Methods for selecting metabolic precursors and their relative preparation are described for example in the book by Bundgaard (Bundgaard, H. ed., "Design of Prodrugs", Elsevier, 1985).

As defined above, the additional bond defined by the dotted line in formula (I) is optional, i.e. it may be present or absent; however, its presence is subordinate respecting the valencies of the atoms involved in the additional bond: thus for example, to respect the valence of the spiro-carbon, when Y is a bond, the additional bond cannot be present. In this case the formula (I) is represented as follows, where $R^1$, $R^2$, n, X and Z are as defined above.

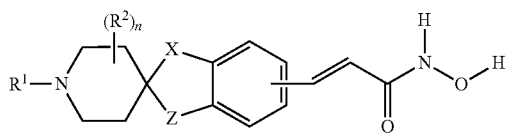

For similar reasons, when the additional bond is present, Y cannot be a bond, neither Z can be oxygen.

A preferred sub-group of compounds is that defined by the structure of formula (I) as drawn above in the summary, wherein:
the dotted line is an optional additional bond;
n is zero or 1;
$R^1$ is hydrogen; $C_1$-$C_4$ alkyl, optionally substituted by phenyl or by a 5 to 10 membered heteroaryl; cycloalkyl; (CO)$R^3$; (SO$_2$)$R^4$; phenyl; or a 5 to 10 membered heteroaryl, wherein said heteroaryls contain 1 or 2 heteroatoms selected from nitrogen, oxygen or sulphur;
$R^2$ is phenyl or (CO)$NR^{14}R^{15}$;
X is oxygen or $NR^6$;
Y is a bond; $CHR^7$ or $NR^8$;
Z is oxygen; $CR^9R^{10}$ or C=$R^{11}$;
$R^3$ is $C_1$-$C_4$ alkyl, optionally substituted by phenyl; phenyl; O—$C_1$-$C_4$ alkyl; or $NR^{12}R^{13}$;
$R^4$ is $C_1$-$C_4$ alkyl or phenyl;
$R^6$ is hydrogen or $C_1$-$C_4$ alkyl;
$R^7$ when present, is hydrogen;
$R^8$ is hydrogen, $C_1$-$C_4$ alkyl or benzyl;
$R^9$ when present, is hydrogen;
$R^{10}$ is hydrogen, or hydroxyl or $C_1$-$C_4$ acylamino;
$R^{11}$ is oxygen or $NOR^{16}$;
$R^{12}$ is hydrogen; $C_1$-$C_4$ alkyl, optionally substituted by phenyl; or phenyl;
$R^{13}$ is hydrogen; $C_1$-$C_4$ alkyl, optionally substituted by phenyl;
$R^{14}$, $R^{15}$ are, independently, hydrogen or phenyl;
$R^{16}$ is hydrogen; $C_1$-$C_4$ alkyl, optionally substituted by phenyl;
and the pharmaceutically acceptable salts thereof. Also for this sub-group of compounds, when the additional bond is present, then Y and Z are CH.

Examples of specific compounds belonging to formula (I) are the following:
(E)-3-{4-Oxo-spiro[chromane-2,4'-piperidine]-6-yl}-N-hydroxy-acrylamide;
(E)-3-{1'-Benzyl-4-oxo-spiro[chromane-2,4'-piperidine]-6-yl}-N-hydroxy-acrylamide;
(E)-3-{1'-Acetyl-4-oxo-spiro[chromane-2,4'-piperidine]-6-yl}-N-hydroxy-acrylamide;
(E)-3-{1'-Benzoyl-4-oxo-spiro[chromane-2,4'-piperidine]-6-yl}-N-hydroxy-acrylamide;
(E)-3-{1'-Methyl-4-oxo-spiro[chromane-2,4'-piperidine]-6-yl}-N-hydroxy-acrylamide;
(E)-3-{1'-Ethyloxycarbonyl-4-oxo-spiro[chromane-2,4'-piperidine]-6-yl}-N-hydroxy-acrylamide;
(E)-3-{1'-Phenyl-4-oxo-spiro[chromane-2,4'-piperidine]-6-yl}-N-hydroxy-acrylamide;
(E)-3-{4-Oxo-spiro[chromane-2,4'-piperidine]-7-yl}-N-hydroxy-acrylamide;
(E)-3-{1'-Benzyl-4-oxo-spiro[chromane-2,4'-piperidine]-7-yl}-N-hydroxy-acrylamide;
(E)-3-{1'-Acetyl-4-oxo-spiro[chromane-2,4'-piperidine]-7-yl}-N-hydroxy-acrylamide;
(E)-3-{1'-Benzoyl-4-oxo-spiro[chromane-2,4'-piperidine]-7-yl}-N-hydroxy-acrylamide;
(E)-3-{1'-Ethyloxycarbonyl-4-oxo-spiro[chromane-2,4'-piperidine]-7-yl}-N-hydroxy-acrylamide;
(E)-3-{1'-Benzyl-spiro[chromane-2,4'-piperidine]-6-yl}-N-hydroxy-acrylamide;
(E)-3-{1'-Benzyl-4-hydroxy-spiro[chromane-2,4'-piperidine]-6-yl}-N-hydroxy-acrylamide;
(E)-3-{1'-Benzyl-spiro[chromene-2,4'-piperidine]-6-yl}-N-hydroxy-acrylamide;
(E)-3-{1'-Benzyl-4-acetylamino-spiro[chromane-2,4'-piperidine]-6-yl}-N-hydroxy-acrylamide;
(E)-3-{1'-Benzyl-4-benzoyloxyimino-spiro[chromane-2,4'-piperidine]-6-yl}-N-hydroxy-acrylamide;
(E)-3-{1'-Benzyl-4-methyloxyimino-spiro[chromane-2,4'-piperidine]-6-yl}-N-hydroxy-acrylamide;
(E)-3-{1'-Benzyl-4-hydroxyimino-spiro[chromane-2,4'-piperidine]-6-yl}-N-hydroxy-acrylamide;
(E)-3-{3-oxo-spiro[benzofuran-2(3H),4'-piperidin]-5-yl}-N-hydroxy-acrylamide;
(E)-3-{1'-Benzyl-3-oxo-spiro[benzofuran-2(3H),4'-piperidin]-5-yl}-N-hydroxy-acrylamide;
(E)-3-{1'-Acetyl-3-oxo-spiro[benzofuran-2(3H),4'-piperidin]-5-yl}-N-hydroxy-acrylamide;
(E)-3-{1'-Benzoyl-3-oxo-spiro[benzofuran-2(3H),4'-piperidin]-5-yl}-N-hydroxy-acrylamide;
(E)-3-{1'-Ethyloxycarbonyl-3-oxo-spiro[benzofuran-2(3H),4'-piperidin]-5-yl}-N-hydroxy-acrylamide;
(E)-3-{1'-Benzyl-3,4-dihydro-4-oxo-spiro[2H-(1,3)-benzoxazine-2,4'-piperidin]-6-yl}-N-hydroxy-acrylamide;
(E)-3-{1-Benzyl-3',4'-dihydro-4'-oxo-spiro[piperidine-4,2'(1'H)-quinazoline]-6'-yl}-N-hydroxy-acrylamide;
(E)-3-{1'-Pyrimidin-2-yl-4-oxo-spiro[chromane-2,4'-piperidine]-6-yl}-N-hydroxy-acrylamide;
(E)-3-{1'-(2-Methyl-benzyl)-4-oxo-spiro[chromane-2,4'-piperidine]-6-yl}-N-hydroxy-acrylamide;
(E)-3-{1'-(3-Methyl-benzyl)-4-oxo-spiro[chromane-2,4'-piperidine]-6-yl}-N-hydroxy-acrylamide;
(E)-3-{1'-(4-Methyl-benzyl)-4-oxo-spiro[chromane-2,4'-piperidine]-6-yl}-N-hydroxy-acrylamide;
(E)-3-{1'-(2-Methoxy-benzyl)-4-oxo-spiro[chromane-2,4'-piperidine]-6-yl}-N-hydroxy-acrylamide;
(E)-3-{1'-(3-Methoxy-benzyl)-4-oxo-spiro[chromane-2,4'-piperidine]-6-yl}-N-hydroxy-acrylamide;
(E)-3-{1'-(4-Methoxy-benzyl)-4-oxo-spiro[chromane-2,4'-piperidine]-6-yl}-N-hydroxy-acrylamide;
(E)-3-{1'-(2-Fluoro-benzyl)-4-oxo-spiro[chromane-2,4'-piperidine]-6-yl}-N-hydroxy-acrylamide;
(E)-3-{1'-(3-Fluoro-benzyl)-4-oxo-spiro[chromane-2,4'-piperidine]-6-yl}-N-hydroxy-acrylamide;

(E)-3-{1'-(4-Fluoro-benzyl)-4-oxo-spiro[chromane-2,4'-piperidine]-6-yl}-N-hydroxy-acrylamide;
(E)-3-{1'-(2-Chloro-benzyl)-4-oxo-spiro[chromane-2,4'-piperidine]-6-yl}-N-hydroxy-acrylamide;
(E)-3-{1'-(3-Chloro-benzyl)-4-oxo-spiro[chromane-2,4'-piperidine]-6-yl}-N-hydroxy-acrylamide;
(E)-3-{1'-(4-Chloro-benzyl)-4-oxo-spiro[chromane-2,4'-piperidine]-6-yl}-N-hydroxy-acrylamide;
(E)-3-{1'-(Pyridin-2-ylmethyl)-4-oxo-spiro[chromane-2,4'-piperidine]-6-yl}-N-hydroxy-acrylamide;
(E)-3-{1'-(Pyridin-3-ylmethyl)-4-oxo-spiro[chromane-2,4'-piperidine]-6-yl}-N-hydroxy-acrylamide;
(E)-3-{1'-(Pyridin-4-ylmethyl)-4-oxo-spiro[chromane-2,4'-piperidine]-6-yl}-N-hydroxy-acrylamide;
(E)-3-{1'-Methanesulfonyl-4-oxo-spiro[chromane-2,4'-piperidine]-6-yl}-N-hydroxy-acrylamide;
(E)-3-{1'-Phenylsulfonyl-4-oxo-spiro[chromane-2,4'-piperidine]-6-yl}-N-hydroxy-acrylamide;
(E)-3-{1'-(3-Phenyl-propyl)-4-oxo-spiro[chromane-2,4'-piperidine]-6-yl}-N-hydroxy-acrylamide;
(E)-3-{1'-Ethylcarbamoyl-4-oxo-spiro[chromane-2,4'-piperidine]-6-yl}-N-hydroxy-acrylamide;
(E)-3-{1'-Benzylcarbamoyl-4-oxo-spiro[chromane-2,4'-piperidine]-6-yl}-N-hydroxy-acrylamide;
(E)-3-{1'-Phenylcarbamoyl-4-oxo-spiro[chromane-2,4'-piperidine]-6-yl}-N-hydroxy-acrylamide;
(E)-3-{1'-[2-(1H-Indol-3-yl)ethyl]-4-oxo-spiro[chromane-2,4'-piperidine]-6-yl}-N-hydroxy-acrylamide;
(E)-3-{1'-(1H-Indol-3-ylmethyl)-4-oxo-spiro[chromane-2,4'-piperidine]-6-yl}-N-hydroxy-acrylamide;
(E)-3-{1'-(2-Methyl-1H-indol-3-ylmethyl)-4-oxo-spiro[chromane-2,4'-piperidine]-6-yl}-N-hydroxy-acrylamide;
(E)-3-{1'-(Biphenyl-4-ylmethyl)-4-oxo-spiro[chromane-2,4'-piperidine]-6-yl}-N-hydroxy-acrylamide;
(E)-3-{1'-(6-Fluoro-1H-indol-3-ylmethyl)-4-oxo-spiro[chromane-2,4'-piperidine]-6-yl}-N-hydroxy-acrylamide;
(E)-3-{1'-(5-Fluoro-1H-indol-3-ylmethyl)-4-oxo-spiro[chromane-2,4'-piperidine]-6-yl}-N-hydroxy-acrylamide;
(E)-3-{1'-(2-Phenyl-ethyl)-4-oxo-spiro[chromane-2,4'-piperidine]-6-yl}-N-hydroxy-acrylamide;
(E)-3-{1'-[2-(4-Fluoro-phenyl)-ethyl]-4-oxo-spiro[chromane-2,4'-piperidine]-6-yl}-N-hydroxy-acrylamide;
(E)-3-{1'-[2-(4-Chloro-phenyl)-ethyl]-4-oxo-spiro[chromane-2,4'-piperidine]-6-yl}-N-hydroxy-acrylamide;
(E)-3-{1'-[2-(4-Methoxy-phenyl)-ethyl]-4-oxo-spiro[chromane-2,4'-piperidine]-6-yl}-N-hydroxy-acrylamide;
(E)-3-{1'-[2-(2-Fluoro-phenyl)-ethyl]-4-oxo-spiro[chromane-2,4'-piperidine]-6-yl}-N-hydroxy-acrylamide;
(E)-3-{1'-[2-(3-Methoxy-phenyl)-ethyl]-4-oxo-spiro[chromane-2,4'-piperidine]-6-yl}-N-hydroxy-acrylamide;
(E)-3-{1'-[2-(4-Methyl-phenyl)-ethyl]-4-oxo-spiro[chromane-2,4'-piperidine]-6-yl}-N-hydroxy-acrylamide;
(E)-3-{1'-[2-(4-Amino-phenyl)-ethyl]-4-oxo-spiro[chromane-2,4'-piperidine]-6-yl}-N-hydroxy-acrylamide;
(E)-3-{1'-[2-(4-Methylamino-phenyl)-ethyl]-4-oxo-spiro[chromane-2,4'-piperidine]-6-yl}-N-hydroxy-acrylamide;
(E)-3-{1'-(1-Methyl-1H-indol-2-ylmethyl)-4-oxo-spiro[chromane-2,4'-piperidine]-6-yl}-N-hydroxy-acrylamide;
(E)-3-{1'-(Quinolin-2-ylmethyl)-4-oxo-spiro[chromane-2,4'-piperidine]-6-yl}-N-hydroxy-acrylamide;
(E)-3-{1'-(Quinolin-3-ylmethyl)-4-oxo-spiro[chromane-2,4'-piperidine]-6-yl}-N-hydroxy-acrylamide;
(E)-3-{1'-(Biphenyl-2-yl-methyl)-4-oxo-spiro[chromane-2,4'-piperidine]-6-yl}-N-hydroxy-acrylamide;
(E)-3-{1'-Ethyl-4-oxo-spiro[chromane-2,4'-piperidine]-6-yl}-N-hydroxy-acrylamide;
(E)-3-{1'-Isopropyl-4-oxo-spiro[chromane-2,4'-piperidine]-6-yl}-N-hydroxy-acrylamide;
(E)-3-{1'-Cyclopentyl-4-oxo-spiro[chromane-2,4'-piperidine]-6-yl}-N-hydroxy-acrylamide;
(E)-3-{1'-(2-Phenyl-ethyl)-3,4-dihydro-4-oxo-spiro[2H-(1,3)-benzoxazine-2,4'-piperidin]-6-yl}-N-hydroxy-acrylamide;
(E)-3-{3,4-Dihydro-4-oxo-spiro[2H-(1,3)-benzoxazine-2,4'-piperidin]-6-yl}-N-hydroxy-acrylamide;
(E)-3-{1'-Methyl-3,4-dihydro-4-oxo-spiro[2H-(1,3)-benzoxazine-2,4'-piperidin]-6-yl}-N-hydroxy-acrylamide;
(E)-3-{1'-(4-Fluoro-benzyl)-3,4-dihydro-4-oxo-spiro[2H-(1,3)-benzoxazine-2,4'-piperidin]-6-yl}-N-hydroxy-acrylamide;
(E)-3-{1'-(4-Fluoro-benzyl)-3,4-dihydro-3-methyl-4-oxo-spiro[2H-(1,3)-benzoxazine-2,4'-piperidin]-6-yl}-N-hydroxy-acrylamide;
(E)-3-{1'-Benzyl-3,4-dihydro-3-methyl-4-oxo-spiro[2H-(1,3)-benzoxazine-2,4'-piperidin]-6-yl}-N-hydroxy-acrylamide;
(E)-3-{1'-(2-Phenyl-ethyl)-3,4-dihydro-3-methyl-4-oxo-spiro[2H-(1,3)-benzoxazine-2,4'-piperidin]-6-yl}-N-hydroxy-acrylamide;
(E)-3-{1'-Methyl-3,4-dihydro-3-methyl-4-oxo-spiro[2H-(1,3)-benzoxazine-2,4'-piperidin]-6-yl}-N-hydroxy-acrylamide;
(E)-3-{3,4-Dihydro-3-methyl-4-oxo-spiro[2H-(1,3)-benzoxazine-2,4'-piperidin]-6-yl}N-hydroxy-acrylamide;
(E)-3-{1'-Benzyl-3,4-dihydro-3-benzyl-4-oxo-spiro[2H-(1,3)-benzoxazine-2,4'-piperidin]-6-yl}-N-hydroxy-acrylamide;
(E)-3-{1'-Methyl-3,4-dihydro-3-benzyl-4-oxo-spiro[2H-(1,3)-benzoxazine-2,4'-piperidin]-6-yl}-N-hydroxy-acrylamide;
(E)-3-{3,4-Dihydro-3-benzyl-4-oxo-spiro[2H-(1,3)-benzoxazine-2,4'-piperidin]-6-yl}-N-hydroxy-acrylamide;
(E)-3-{1'-(4-Fluoro-benzyl)-3,4-dihydro-3-benzyl-4-oxo-spiro[2H-(1,3)-benzoxazine-2,4'-piperidin]-6-yl}-N-hydroxy-acrylamide;
(E)-3-{1'-(2-Phenyl-ethyl)-3,4-dihydro-3-benzyl-4-oxo-spiro[2H-(1,3)-benzoxazine-2,4'-piperidin]-6-yl}-N-hydroxy-acrylamide;
(E)-3-{1'-(1-Phenyl-ethyl)-4-oxo-spiro[chromane-2,4'-piperidine]-6-yl}-N-hydroxy-acrylamide;
(E)-3-{1'-(2-Phenyl-thiazolyl-4-yl-methyl)-4-oxo-spiro[chromane-2,4'-piperidine]-6-yl}-N-hydroxy-acrylamide;
(E)-3-{1'-Ethyl-3,4-dihydro-3-butyl-4-oxo-spiro[2H-(1,3)-benzoxazine-2,4'-piperidin]-6-yl}-N-hydroxy-acrylamide;
(E)-3-{1'-[2-(4-Fluoro-phenyl)-ethyl]-3,4-dihydro-4-oxo-spiro[2H-(1,3)-benzoxazine-2,4'-piperidin]-6-yl}-N-hydroxy-acrylamide;
(E)-3-{2'-Phenyl-4-oxo-spiro[chromane-2,4'-piperidine]-6-yl}-N-hydroxy-acrylamide;
(E)-3-{1'-Methyl-2'-phenyl-4-oxo-spiro[chromane-2,4'-piperidine]-6-yl}-N-hydroxy-acrylamide;
(E)-3-{1'-Acetyl-2'-phenyl-4-oxo-spiro[chromane-2,4'-piperidine]-6-yl}-N-hydroxy-acrylamide;
(E)-3-{1'-Benzyl-2'-phenyl-4-oxo-spiro[chromane-2,4'-piperidine]-6-yl}-N-hydroxy-acrylamide;
(E)-3-{1'-Benzoyl-2'-phenyl-4-oxo-spiro[chromane-2,4'-piperidine]-6-yl}-N-hydroxy-acrylamide;
(E)-3-{1'-(2-Phenyl-ethyl)-2'-phenyl-4-oxo-spiro[chromane-2,4'-piperidine]-6-yl}-N-hydroxy-acrylamide;
(E)-3-{2'-Phenylcarbamoyl-4-oxo-spiro[chromane-2,4'-piperidine]-6-yl}-N-hydroxy-acrylamide;

(E)-3-{1'-Methyl-2'-phenylcarbamoyl-4-oxo-spiro[chromane-2,4'-piperidine]-6-yl}-N-hydroxy-acrylamide;
(E)-3-{1'-Acetyl-2'-phenylcarbamoyl-4-oxo-spiro[chromane-2,4'-piperidine]-6-yl}-N-hydroxy-acrylamide;
(E)-3-{1'-Benzyl-2'-phenylcarbamoyl-4-oxo-spiro[chromane-2,4'-piperidine]-6-yl}-N-hydroxy-acrylamide;
(E)-3-{1'-Benzoyl-2'-phenylcarbamoyl-4-oxo-spiro[chromane-2,4'-piperidine]-6-yl}-N-hydroxy-acrylamide;
(E)-3-{1'-(2-Phenyl-ethyl)-2'-phenylcarbamoyl-4-oxo-spiro[chromane-2,4'-piperidine]-6-yl}-N-hydroxy-acrylamide.

The compounds according to the present invention can be prepared, for example, as shown in the reaction schemes below and according to the reaction steps specified as follows, or, particularly, in a manner as described by way of example in the following examples, or analogously or similarly thereto using preparation procedures and synthesis strategies known to the person skilled in the art.

Compounds of general formula (I), wherein Z is C=NOR$^{16}$, with R$^{16}$ as defined above, can be prepared by treating compounds of formula (I), wherein Z is C=O with HNOR$^{16}$, in the presence of a suitable base (e.g. pyridine) in a suitable solvent (e.g. ethanol or DMF). The reaction can be carried out at a temperature between room temperature and the boiling point of the solvent.

Compounds of general formula (I), wherein Z is other than C=NOR$^{16}$, with R$^{16}$ as defined above, can be prepared according to Scheme A:

roacetic acid) in a suitable solvent such as dichloromethane at a temperature ranging from 0° C. to room temperature or by treatment of a methylester with LiOH or NaOH in a suitable solvent, for example methanol or a methanol/water mixture at a temperature ranging from 0° C. to the boiling point of the solvent.

The reaction of a compound of formula A2 with the protected hydroxylamine NH$_2$OPG$^1$ can be carried out with condensating agents such as EDC (1-(3-dimethylaminopropyl)-3-ethylcarbodiimide), optionally in the presence of a suitable base (e.g. triethylamine or di-isopropylethylamine) in a suitable solvent (e.g. tetrahydrofuran, dichloromethane or DMF). Generally an activator of the condensation reaction, such as HOBT (1-hydroxybenzotriazole) or HOAT (1-hydroxy-7-aza-benzotriazole), can be added to the reaction mixture. The reaction can be carried out at room temperature for a period lasting between about 2 and 12 h. Deprotection of the hydroxylamine, in the case of tetrahydropyranyl, can be achieved by known methods, for example using HCl in aprotic solvents (such as THF, diethylether or dioxane).

The compounds of formula A1 can be prepared by synthetic methods and chemical reactions per se well-known in the art. For example, the compounds of formula A1 wherein X is oxygen or NR$^6$, Y is CHR$^7$ or NR$^8$, R$^6$, R$^7$ and R$^8$ are as defined above, and Z is C=O or C=S, can be prepared according to Scheme B:

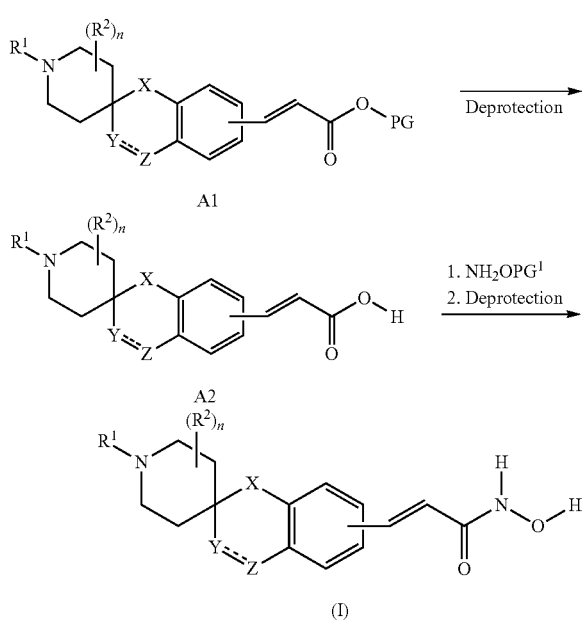

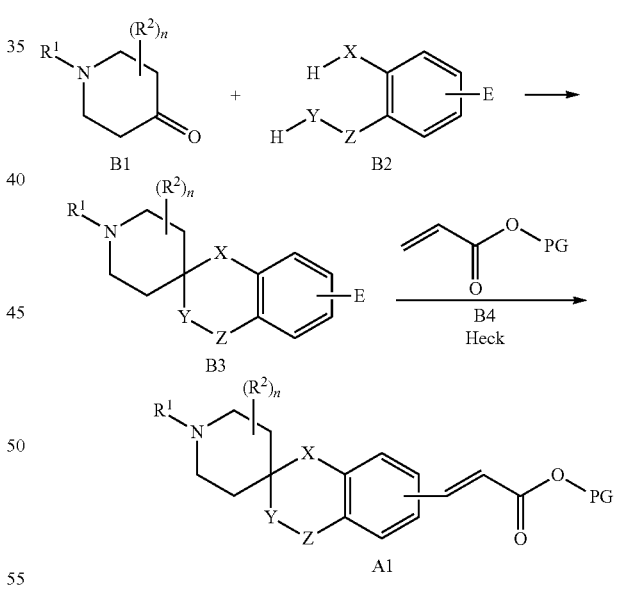

wherein n, R$^1$, R$^2$, X, and Y, are as defined above in formula (I), Z is as defined above with the exclusion of C=NOR$^{16}$, PG and PG$^1$ are protecting groups chosen among those known in the art, for example methyl, tert-butyl, etc. for PG and O-(tetrahydro-2H-pyran-2-yl), etc. for PG$^1$.

A compound of formula A1 can be deprotected into a compound of formula A2 according to known methods, e.g. by treatment of a tert-butyl ester derivative with TFA (trifluowherein n, R$^1$, R$^2$, and PG are as defined above and X is oxygen or amino group, Y is CHR$^7$ or NR$^8$, wherein R$^7$ and R$^8$ are as defined above, Z is C=O or C=S, H is hydrogen, and E is bromine or iodine.

Compounds of formula B1 and B2 are known compounds or can be prepared by known methods. Reaction between a compound of formula B1 and B2 can be carried out in presence of a base (e.g. pyrrolidine) in an appropriate solvent (e.g. methanol) at a temperature ranging from 0° C. to the boiling point of the solvent.

Reaction of a compound of formula B3 with the protected acroylester B4 can be carried out according to the Heck reaction. The reaction conditions are described for example in the book by Larhed and Hallberg (Larhed, M.; Hallberg, A. "Handbook of Organopalladium Chemistry for Organic Synthesis", Negishi, E., Ed.; Wiley-Interscience, 2002). The reaction can be carried out in a suitable organic solvent (e.g. DMF) in the presence of palladium salts (e.g. palladium acetate), organic or inorganic bases (e.g. triethylamine, 1,4-diazabicyclo[2,2,2]-octane, sodium or potassium carbonate) and phosphine ligand derivatives, such as triphenylphosphine, at a temperature between room temperature and the boiling point of the solvent.

Alternatively, compounds of formula A1, wherein X is oxygen or $NR^6$, Y is $CHR^7$ or $NR^8$, $R^6$, $R^7$ and $R^8$ are as defined above, and Z is C=O or C=S, can be prepared according to Scheme C:

a compound of formula B1 and a compound of formula B2 as outlined in Scheme B. The Heck reaction between a compound of formula C3 with a protected acroylester C4 can be carried out at the same conditions like the reaction between a compound of formula B3 with the protected acroylester B4 as outlined in Scheme B. A compound of formula C5 can be deprotected into a compound of formula C6 according to known methods, e.g. by treatment of a t-BOC derivative with TFA (trifluoroacetic acid) in a suitable solvent such as dichloromethane or dioxane, at a temperature ranging from 0° C. to room temperature. The compound of formula A1 can be prepared starting from compound of formula C6 and a compound of formula $R^1$—W, $R^3$—(CO)W or $R^4$—($SO_2$)W, wherein $R^1$ is as defined above, W is a halogen atom, e.g. chloride, $R^3$ and $R^4$ are $C_1$-$C_6$ alkyl, optionally substituted by aryl or by heteroaryl, aryl, or heteroaryl. The reaction between the compound of formula C6 and a compound of formula $R^1$—W, a compound of formula $R^3$—(CO)W or a

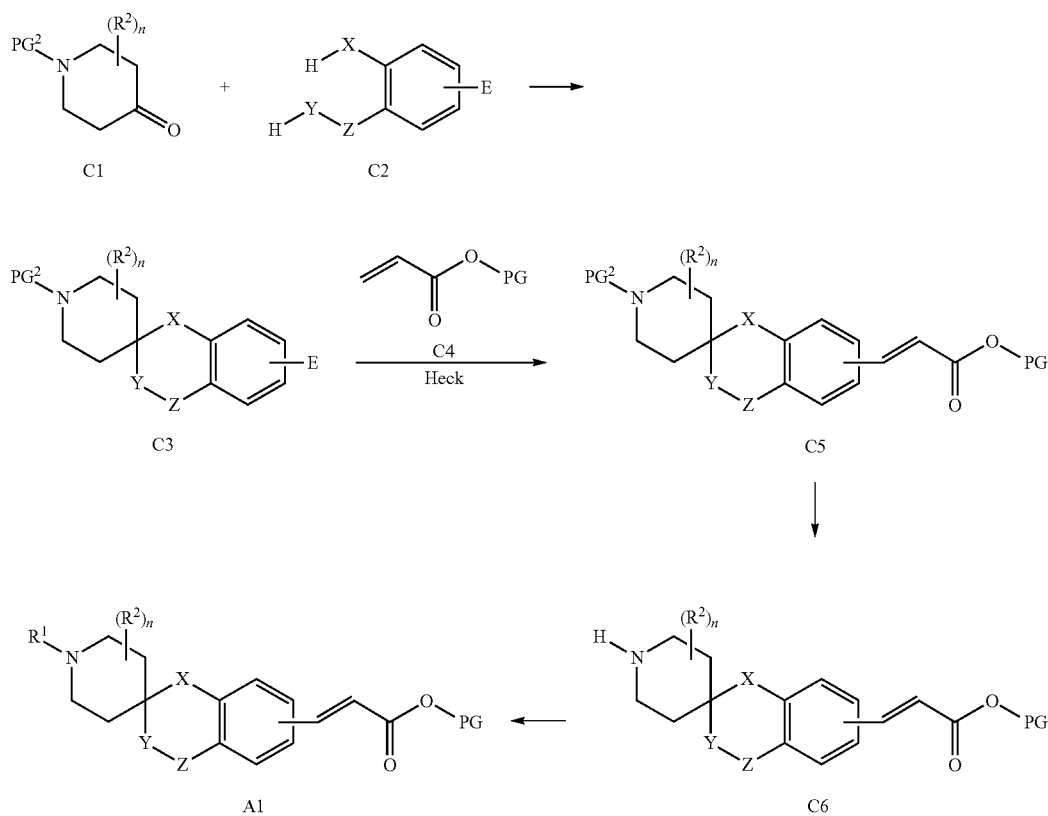

Scheme C wherein n, $R^1$, $R^2$, E and PG are as defined above, X is oxygen or amino group, Y is $CHR^7$ or $NR^8$, wherein $R^7$ and $R^8$ are as defined above, Z is C=O or C=S, H is hydrogen, and $PG^2$ is a protecting group chosen among those known in the art, for example carboxybenzyl, tert-butyloxycarbonyl, 9-fluorenylmethyloxycarbonyl etc.

Compounds of formula C1 and C2 are known compounds or can be prepared by known methods. Reaction between a compound of formula C1 and a compound of formula C2 can be carried out at the same conditions like the reaction between compound of formula $R^4$—($SO_2$)W can be carried out in a suitable organic solvent, e.g. dichloromethane, in presence of a base (e.g. triethylamine) at a temperature ranging from about 0° C. to about 50° C.

Compounds of formula A1, wherein X is oxygen, Y is $CHR^7$, Z is $CR^9R^{10}$, and $R^9$ and $R^{10}$ are as defined above, can be prepared from a compound of formula D1, via an intermediate compound being indifferently chosen from one of formula D2, D3, D4 or D5, according to Scheme D:

Scheme D

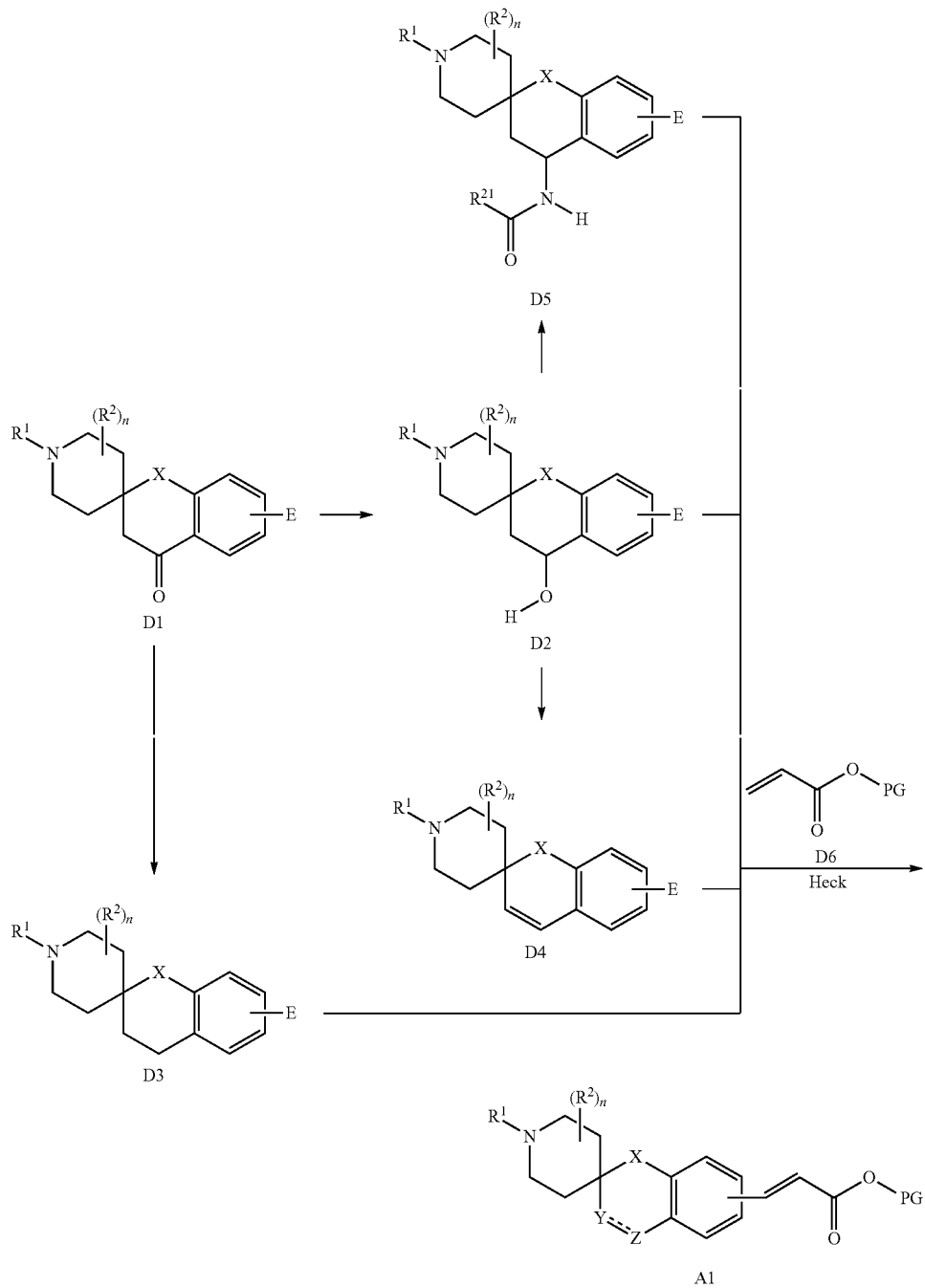

wherein n, $R^1$, $R^2$, and PG are as defined above and X is oxygen, Y is $CHR^7$, and Z is $CR^9R^{10}$, with $R^9$ and $R^{10}$ as defined above, and $R^{21}$ is $C_1$-$C_6$ alkyl.

A compound of formula D1 is a known compound or can be prepared by known procedures, for example in the same manner as the synthesis of compound of formula B3 starting from a compound of formula B1 and a compound of formula B2. A compound of formula D1 can be converted into a compound of formula D2 by treatment with a reducing agent, for example $NaBH_4$, in an appropriate solvent, e.g. methanol, at room temperature. A compound of formula D3 can be obtained by treating a compound of formula D1 with a reducing agent, e.g. Zn/HCl in an appropriate solvent, e.g. ethanol. A compound of formula D4 can be obtained by treating a compound of formula D2 with p-toluenesulfonic acid in an appropriate solvent, e.g. THF, at a temperature ranging from room temperature to the boiling point of the solvent. A compound of formula D2 can be converted into a compound of formula D5 according to the Ritter reaction, e.g. treating a compound of formula D2 with a $C_1$-$C_6$ alkyl-nitrile in acidic media, e.g. sulfuric acid, at a temperature ranging from −10° C. to room temperature. The Heck reaction between a compound of formula D2, D3, D4, or D5 with a protected acroylester D6 can be carried out at the same conditions like the reaction between a compound of formula B3 with the protected acroylester B4 as outlined in Scheme B. Alternatively, a compound of formula D1 can be first treated according to the Heck reaction and then converted into a compound of A1 at the same conditions like the conversion of a compound of formula D1 into a compound of formula D2, or the conversion of a compound of D2 into a compound of D4 or into a compound of D5.

Compounds of formula A1 wherein X is oxygen, Y is a bond, and Z is C=O, can be prepared according to Scheme E:

B3 with the protected acroylester B4 as outlined in Scheme B. Deprotection of E6 and introduction of the $R^1$ group can achieved at the same conditions like described for the conversion of a compound of formula C5 into a compound of formula A1 as outlined in Scheme C.

In the case it is necessary to protect a chemical group of a compound of the present invention and/or an intermediate thereof, before carrying out one of the aforedescribed reactions, said chemical group can be protected and deprotected according to known methods. A thorough discussion for protection/deprotection steps is provided for example in Greene and Wuts (Greene, T. W.; Wuts, P. G. M. "Protective Groups

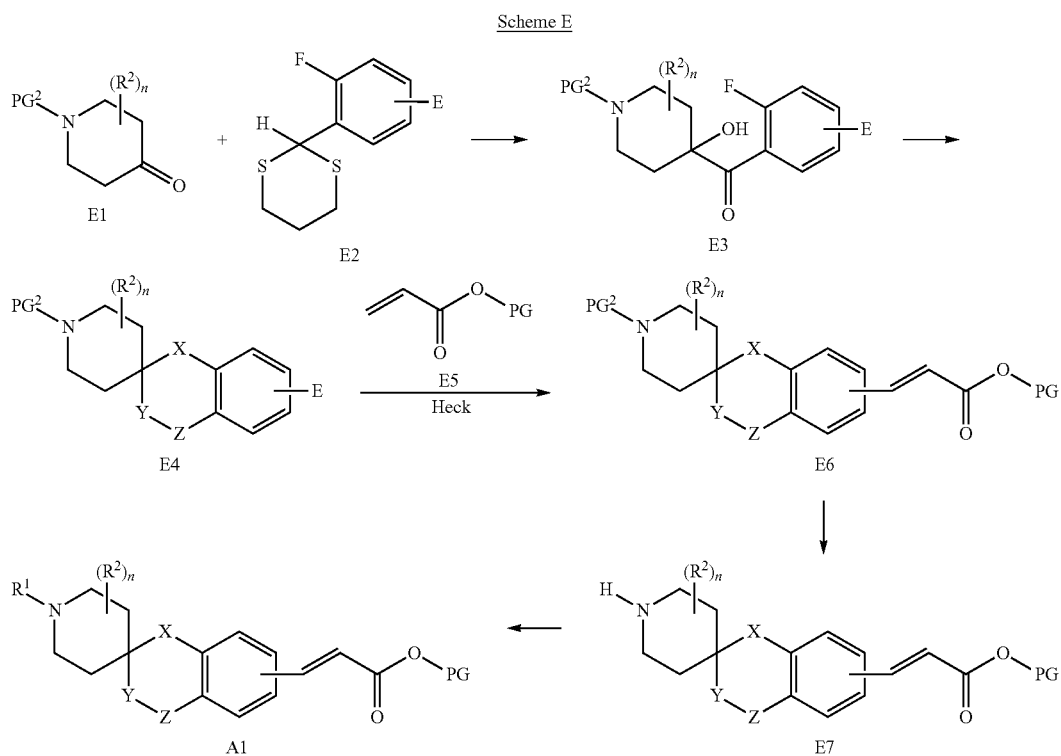

Scheme E wherein n, $R^1$, $R^2$, E, H, PG and $PG^2$ are as defined above and X is oxygen, Y is a bond, Z is C=O, $PG^2$ is a protecting group chosen among those known in the art, for example carboxybenzyl, tert-butyloxycarbonyl, 9-fluorenylmethyloxycarbonyl, etc., F is fluoro and S is sulphur.

Compounds of formula E1 and E2 are known compounds or can be prepared by known methods. Reaction between a compound of formula E1 and a compound of formula E2 can be carried out in a suitable organic solvent, such as tetrahydrofuran, in presence of an appropriate base, for example LDA, at a temperature ranging from about −100° C. to about 0° C. The consequent hydrolysis of the dithial protecting group can be achieved according to known methods, e.g. by treatment of the compound with pyridinium tribromide in an appropriate solvent, such as dichloromethane. The ring closure of a compound of formula E3 to a compound of formula E4 can be achieved in presence of an appropriate base, e.g. potassium tert-butoxide, in an appropriate solvent, e.g. THF, at a temperature ranging from 0° C. to the boiling point of the solvent. The Heck reaction of a compound of formula E4 with a protected acroylester E5 can be carried out at the same conditions like the reaction between a compound of formula in Organic Synthesis", John Wiley & Sons Inc., 1991) or in Kocienski (Kocienski, P. J. "Protecting Groups", George Thieme Verlag, 1994).

Salification of the compounds of formula (I), and the preparation of compounds of formula (I) free of their salts can be carried out by known conventional methods.

The invention also comprises a method for preventing and/or treating diseases linked to the disregulation of histone deacetylase activity characterized by administering to a patient a pharmacologically useful quantity of one or more compounds of formula (I), as previously defined. The invention includes the same compounds for use in the prevention or treatment of the aforesaid diseases. Further provided by the invention is the use of the same compounds for the manufacture of a medicament for the prevention or treatment of the aforesaid diseases.

In view of the above described mechanisms of action, the compounds of the present invention are useful in the prevention or treatment of tumor type diseases, including but not limited to: acute and chronic myeloid leukaemia, acute and chronic lymphoblastic leukaemia, myelodysplastic syndromes, multiple myeloma, Hodgkin's disease, non- Hodgkin's lymphomas, cutaneous and peripheral T-cell lymphoma; mammary tumors; pulmonary tumors and pleural mesotheliomas, adenocarcinoma, non-small lung cancer, small-cell lung cancer; skin tumors including basal cell carcinomas (basaliomas), melanomas, squamous cell carcinoma, Kaposi's sarcoma, keratocanthomas; osteosarcomas, fibrosarcomas, rhabdomyosarcomas, neuroblastomas, glioblastomas, cerebral tumors, testicular and ovarian tumors, endometrial and prostate tumors (for example advanced prostate cancer), thyroid carcinomas (for example tyroid follicular cancer), colon cancers (for example colon adenocarcinoma, colon adenoma), gastric tumors and gastrointestinal adenocarcinomas, hepatic carcinomas, pancreatic carcinomas (for example exocrine pancreatic carcinoma), renal tumors, teratocarcinomas and embryonic carcinomas.

The compounds of the invention are also useful in the prevention or treatment of neurological conditions, including, but not limited to, epilepsy, cerebral ischemia, spinal and bulbar muscular atrophy, Friedreich's ataxia, Huntington's disease, Alzheimer's disease, Parkinson's disease, amyotrophic lateral sclerosis, diseases caused by protein aggregates, Kennedy's disease, and multiple sclerosis.

The compounds of the invention are also useful in the prevention or treatment of mental retardation, including, but not limited to, fragile X syndrome and Rubinstein-Taybi syndrome.

The compounds of the invention are also useful in the prevention or treatment of psychiatric disorders, including, but not limited to, bipolar disorders and schizophrenia.

The compounds of the invention are also useful in the prevention or treatment of inflammatory diseases, including, but not limited to, inflammatory responses of the nervous system, intestinal and colitic diseases and arthritis.

The compounds of the invention are also useful in the prevention or treatment of immune disorders, including, but not limited to, autoimmune diseases, chronic immune reactions against the host, psoriasis, atopic dermatitis and systemic lupus erythematosus.

The compounds of the invention are also useful in the prevention or treatment of infections, including, but not limited to, HIV infections, malaria, leishmaniasis, bilharziosis, African trypanosomiasis, Chagas disease, infections by protozoa, fungi, phytotoxic agents, viruses and parasites.

The compounds of the invention are also useful in the prevention or treatment of cardiovascular disorders, including, but not limited to, hypertrophy and cardiac decompensation, and cardiac ischemia.

The compounds of the invention are also useful in the prevention or treatment of other diseases such as diabetes, fibrotic diseases of the skin, fibrosis, renal diseases, beta thalassemia and respiratory diseases, including, but not limited to, chronic obstructive pulmonary disorders and asthma.

The compounds of formula (I) can also be used in combination with additional agents, in particular anti tumor and differentiating agents, either by separate administrations, or by including the two active principles in the same pharmaceutical formulation. Non-exhaustive examples of suitable additional agents include:

a) other histone deacetylase inhibitors (for example SAHA, PXD101, JNJ-16241199, JNJ-26481585, SB939, ITF-2357, LBH589, PCI-24781, valproic acid, butyric acid, MS-275, MGCD0103 or FK-228);

b) retinoid receptor modulators such as 13-cis-retinoic acid, 9-cis-retinoic acid, bexarotene, alitretinoin, or tretinoin; vitamin D;

c) antiproliferative/antineoplastic drugs and combinations thereof, as used in medical oncology, such as alkylating agents (for example platin derivatives like cis-platin, carboplatin, oxaliplatin, lobaplatin, satraplatin, nedaplatin, heptaplatin; nitrogen mustard such as chlorambucil, chlormethine, cyclophosphamide, ifosfamide, melphalan, uramustine, bendamustine; busulphan, temozolomide or nitrosoureas); antimetabolites (for example antifolates such as aminopterin, methotrexate, pemetrexed, raltitrexed); purines such as cladribine, clofarabine, fludarabine, mercaptopurine, pentostatin, thioguanine; pyrimidines like capecitabine, cytarabine, fluorouracil, floxuridine, gemcitabine; cytosine arabinoside or hydroxyurea; antitumour antibiotics (for example anthracyclines like doxorubicin, daunomycin, epirubicin, idarabicin, mitoxantrone, valrubicin; or antibiotics from streptomyces like actinomycin, bleomycin, mitomycin, or plicamycin); antimitotic agents (for example vinca alkaloids like vincristine, vinblastine, vindesine or vinorelbine; taxoids like docetaxel or paclitaxel; epothilones like ixabepilone) and topoisomerase inhibitors (for example epipodophyllotoxins like etoposide and teniposide; amsacrine, hycaptamine, topotecan, irinotecan, rubitecan and camptothecin);

d) cytostatic agents such as antioestrogens (for example tamoxifen, toremifene, raloxifene, droloxifene and idoxifene), oestrogen receptor down regulators (for example fulvestrant), antiandrogens (for example bicalutamide, flutamide, nilutamide, liarozole or cyproterone acetate), LHRH antagonists or LHRH agonists (for example goserelin, leuprorelin or buserelin), progestogens (for example megestrol acetate), aromatase inhibitors (for example as anastrozole, letrozole, vorazole and exemestane) and inhibitors of 5-alpha-reductase such as finasteride;

e) agents which inhibit cancer cell invasion (for example metalloproteinase inhibitors and inhibitors of urokinase plasminogen activator receptor function);

f) inhibitors of growth factor function, for example growth factor antibodies, growth factor receptor antibodies (for example the anti-erbb2 antibody trastuzumab, the anti-erbb1 antibody cetuximab and panitumumab), farnesyl transferase inhibitors, MEK inhibitors, tyrosine kinase inhibitors and serine/threonine kinase inhibitors, for example dasatinib, erlotinib, gefitinib, imatinib, lapatinib, nilotinib, sorafenib, sunitinib, everolimus, sirolimus or temsirolimus;

g) antiangiogenic agents such as those which inhibit the effects of vascular endothelial growth factor, (for example the anti-vascular endothelial cell growth factor antibody bevacizumab [Avastin™]);

h) cell cycle inhibitors including for example CDK inhibitors (for example flavopiridol, roscovitine) and other inhibitors of cell cycle checkpoints; inhibitors of aurora kinase and other kinases involved in mitosis and cytokinesis regulation;

i) proteasome inhibitors (for example lactacystin, bortezomib, epoxomicin);

j) HSP90 inhibitors (for example 17-AAG, KOS-953, KOS-1022, CNF-1010, CNF-2024, IPI-504 or SNX 5422).

In another aspect, a compound of general formula (I) can be used in combination with radiation therapy. In yet another aspect, a compound of the present invention, or a pharmaceutically acceptable salt may be administered in combination with standard chemotherapy combinations such as, but not restricted to, CMF (cyclophosphamide, methotrexate and 5-fluorouracil), OAF (cyclophosphamide, doxorubicin and 5-fluorouracil), AC (doxorubicin and cyclophosphamide), FEC (5-fluorouracil, epirubicin, and cyclophosphamide), ACT or ATC (doxorubicin, cyclophosphamide, and paclitaxel), or CMFP (cyclophosphamide, methotrexate, 5-fluorouracil and prednisone).

The invention also comprises pharmaceutical compositions characterized by containing one or more active principles of formula (I), in association with pharmaceutically acceptable carrier, excipients and diluents.

The compounds of this invention can be administered via any of the accepted modes of administration or agents for serving similar utilities. Thus, administration can be, for example, oral, nasal, parental (intravenous, subcutaneous, intramuscular), buccal, sublingual, rectal, topical, transdermal, intravesical, or using any other route of administration.

The compounds of formula (I) can be pharmaceutically formulated according to known methods. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable or infusible liquid solutions, suspensions or suppositories.

Tablets and capsules for oral administration are normally presented in unit dose form and contain conventional excipients such as binders, fillers, diluents, tableting agents, lubricants, detergents, disintegrants, coloring agents, flavoring agents and wetting agents. The tablets can be coated using methods well known in the art.

Suitable fillers include cellulose, mannitol, lactose and other similar agents. Suitable disintegrants include polyvinylpyrrolidone and starch derivatives such as sodium glycolate starch. Suitable lubricants include, for example, magnesium stearate. Suitable wetting agents include sodium lauryl sulfate.

These oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents.

Oral formulations also include conventional slow-release formulations such as enterically coated tablets or granules.

For parenteral administration (e.g. bolus injection or continuous infusion), fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. A reference for the formulations is the book by Remington ("Remington: The Science and Practice of Pharmacy", Lippincott Williams & Wilkins, 2000). Creams, as known to formulation experts, are viscous liquids or semisolid emulsions, and contain an oil phase, an emulsifier and an aqueous phase. The oil phase generally contains petrolatum and an alcohol such as cetyl or stearic alcohol. The emulsifier in a cream formulation is chosen from non-ionic, anionic, cationic or amphoteric surface-active agents. The monophasic gels contain the organic molecules uniformly distributed in the liquid, which is generally aqueous, but they also preferably contain an alcohol and optionally an oil. Preferred gelling agents are cross-linked acrylic acid polymers (e.g. carbomer-type polymers, such as carboxypolyalkylenes, which are commercially available under the Carbopol™ trademark). Hydrophilic polymers are also preferred, such as polyoxyethylene, polyoxyethylene-polyoxypropylene copolymers and polyvinyl alcohol; cellulose polymers such as hydroxypropyl cellulose, hydroxyethyl cellulose, hydroxypropyl methylcellulose, hydroxypropyl methylcellulose phthalate and methylcellulose; gums, such as xanthan gum and tragacanth gum; sodium alginate; and gelatin. Dispersing agents such as alcohol or glycerin can be added for gel preparation. The gelling agent can be dispersed by finely chopping and/or mixing.

Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Typical transdermal formulations comprise conventional aqueous and non-aqueous vectors, such as creams, oils, lotions or pastes or can be in the form of membranes or medicated patches. One formulation provides that a compound of the invention is dispersed within a pressure sensitive patch which adheres to the skin. This formulation enables the compound to diffuse from the patch to the patient through the skin. For a constant release of the drug through the skin, natural rubber and silicon can be used as pressure sensitive adhesives.

The above mentioned uses and methods also include the possibility of co-administration of additional therapeutic agents, simultaneously or delayed with respect to the administration of the compound of formula (I).

In the previously mentioned uses and methods, the dosage of the compounds of formula (I), can vary depending upon a variety of factors including the patient type and condition, the degree of disease severity, mode and time of administration, diet and drug combinations. As an indication, they can be administered within a dose range of between 0.001 and 1000 mg/kg/day. The determination of optimum dosages for a particular patient is well known to one skilled in the art.

As is common practice, the compositions are normally accompanied by written or printed instructions for use in the treatment in question.

The following examples serve to provide further appreciation of the invention, but are not meant in any way to restrict the scope of the invention.

EXPERIMENTAL PART

1. Chemical Synthesis

Methods

Unless otherwise indicated, all the starting reagents were found to be commercially available and were used without any further purification. Specifically, the following abbreviations may have been used in the descriptions of the experimental methods.

| | |
|---|---|
| NMR (Nuclear Magnetic Resonance) | $^1$H (proton) |
| MHz (Megahertz) | Hz (Hertz) |
| HPLC (High Performance Liquid Chromatography) | LC-MS (Liquid Chromatography Mass Spectrum) |
| s (seconds) | min (minutes) |
| h (hours) | mg (milligrams) |
| g (grams) | μl (microlitres) |
| ml (millilitres) | mmol (millimoles) |
| M (molarity) | rt (retention time in minutes) |
| RT (room temperature) | AcOH (acetic acid) |
| AcOEt (ethyl acetate) | BOC (tert-butoxycarbonyl) |
| tBuOK (potassium tert-butoxide) | $CH_3CN$ (acetonitrile) |
| $CHCl_3$ (chloroform) | $CDCl_3$ (deuterated chloroform) |
| DCM (dichloromethane) | DMF (dimethylformamide) |
| DMSO (dimethyl sulfoxide) | DMSO-$d_6$ (deuterated dimethyl sulfoxide) |
| EDC (1-3(dimethylaminopropyl)-3-ethylcarbodiimide hydrochloride) | $Et_2O$ (diethyl ether) |
| EtOH (ethanol) | FA (formic acid) |
| $H_2SO_4$ (sulphuric acid) | HCl (hydrochloric acid) |
| HOBT (1-hydroxybenzotriazole) | LDA (lithium diisopropylamide) |
| MeOH (methanol) | $NaBH_4$ (sodium borohydride) |
| $NaHCO_3$ (sodium hydrogen carbonate) | NaOH (sodium hydroxide) |
| $Na_2SO_4$ (sodium sulphate) | $NH_2OTHP$ (O-(tetrahydro-2H-pyran-2-yl)hydroxylamine) |
| $NH_3$, $NH_4OH$ (ammonia) | $NH_4Cl$ (ammonium chloride) |
| $Pd(OAc)_2$ (palladium acetate) | $PPh_3$ (triphenylphosphine) |
| TBAB (tetra-N-butylammonium bromide) | TEA (triethylamine) |
| TFA (trifluoroacetic acid) | THF (tetrahydrofuran) |
| THP (3,4,5,6-tetrahydro-2H-pyranyl) | p-TsOH (p-toluenesulfonic acid) |
| MW (microwave) | HCHO (formaldehyde) |
| $K_2CO_3$ (potassium carbonate) | KI (potassium iodide) |
| $N_2$ (nitrogen) | $Na_2CO_3$ (sodium carbonate) |
| $NaCNBH_3$ (cyanoborohydride) | NaH (sodium hydride) |
| $SnCl_2$ (stannous chloride) | |

Except where indicated otherwise, all temperatures are expressed in ° C. (degrees centigrade).

The $^1$H-NMR spectra were recorded at 300 or 400 MHz on a Bruker spectrometer. The chemical shifts are expressed in parts per million (ppm, δ units). The coupling constants are expressed in Hertz (Hz) and the splitting patterns are described as s (singlet), d (doublet), t (triplet), q (quartet), quint (quintet), m (multiplet), bs (broad signal).

The LC-MS analyses were carried out in accordance with the following methods:

Method A:

Column: Waters Atlantis (50×4.6 mm, 3 μm); Phase A: Milli-Q water containing 0.05% TFA; Phase B: acetonitrile containing 0.05% TFA; flow rate: 1 ml/min, partitioned after UV detector (50% to MS ESI); UV detection at 220 and 254 nm; ESI$^+$ detection in the 50-2000 m/z range with alternating MS/MS. HPLC: Agilent; MS: Bruker ion-trap Esquire 3000+ with ESI.

Gradient: from 10% B to 90% B in 6 min, washing at 100% B for 1 min, equilibration at 10% B in the next 3 min.

Method B:

Column Acquity HPLC-BEH C18 (50×2.1 mm, 1.7 μm); Phase A: Milli-Q water containing 0.07% FA and 5% acetonitrile; Phase B: acetonitrile containing 0.05% FA; flow rate: 0.6 ml/min; UV detection (DIODE array) from 210 to 400 nm; ESI+ detection in the 100-2000 m/z range; HPLC: Waters Acquity HPLC; MS: Micromass SQD Single quadrupole (Waters).

Gradient: from 2% B to 100% B in 3 min, washing at 100% B for 0.5 min, equilibration at 2% B in the next 1 min.

Method C:

Column: Waters Atlantis (100×4.6 mm, 3 μm); Phase A: Milli-Q water containing 0.05% TFA; Phase B: acetonitrile containing 0.05% TFA; flow rate: 1 ml/min, partitioned after UV detector (50% to MS ESI); UV detection at 215 and 254 nm; ESI$^+$ detection in the 50-2000 m/z range with alternating MS/MS, HPLC: Agilent 1100; MS: Bruker ion-trap Esquire 3000+ with ESI.

Gradient: from 0% B to 30% B in 12 min, washing at 50% B for 1 min, equilibration at 0% B in the next 3 min.

Method D:

Column: Supelco Discovery (150×4.6 mm, 5 μm); Phase A: Milli-Q water containing 0.05% TFA; Phase B: acetonitrile containing 0.05% TFA, flow rate: 1 ml/min, partitioned after UV detector (50% to MS ESI); UV detection at 220 and 254 nm; ESI$^+$ detection in the 50-2000 m/z range with alternating MS/MS; HPLC: Agilent; MS: Bruker ion-trap Esquire 3000+ with ESI.

Gradient: from 20% B to 90% B in 15 min, washing at 100% B for 1 min, equilibration at 20% B in the next 4 min.

Method E:

Column: Supelco Discovery (150×4.6 mm, 5 μm), Phase A: Milli-Q water containing 0.05% TFA; Phase B: acetonitrile containing 0.05% TFA; flow rate: 1 ml/min, partitioned after UV detector (50% to MS ESI), UV detection at 220 and 254 nm; ESI$^+$ detection in the 50-2000 m/z range with alternating MS/MS, HPLC: Agilent 1100; MS: Bruker ion-trap Esquire 3000+ with ESI.

Gradient: from 5% B to 50% B in 15 min, washing at 100% B for 1 min, equilibration at 5% B in the next 4 min.

Method F:

Column: Waters Atlantis (50×4.6 mm, 3 μm); Phase A: Milli-Q water containing 0.05% TFA; Phase B: acetonitrile containing 0.05% TFA; flow rate: 1 ml/min, partitioned after UV detector (50% to MS ESI); UV detection at 220 and 254 nm; ESI$^+$ detection in the 50-2000 m/z range with alternating MS/MS. HPLC: Agilent; MS: Bruker ion-trap Esquire 3000+ with ESI.

Gradient: from 10% B to 40% B in 10 min, washing at 100% B for 1 min, equilibration at 10% B in the next 3 min.

Method G:

Column Acquity HPLC-BEH C18 (50×2.1 mm, 1.7 μm); Phase A: water/$CH_3CN$ 95/5+0.1% TFA; Phase B: water/$CH_3CN$ 5/95+0.1% TFA; flow rate: 0.6 ml/min;

UV detection wavelength 254 nm or BPI; ESI+ detection 3.2 KV, 25V, 350° C.; Waters Acquity HPLC, Micromass ZQ 2000 Single quadrupole (Waters).

Gradient: 0-0.25 min (A: 95%, B: 5%), 0.25-3.30 min (A: 0%, B: 100%), 3.30-4.00 min (A: 0%, B: 100%), 4.00-4.10 min (A: 95%, B: 5%); 4.10-5.00 min (A: 95%, B: 5%).

Method H:

Column Acquity HPLC-BEH C18 (50×2.1 mm, 1.7 μm); Phase A: water/$CH_3CN$ 95/5+0.1% TFA; Phase B: water/$CH_3CN$ 5/95+0.1% TFA; flow rate: 0.6 ml/min; UV detection wavelength 254 nm or BPI; ESI+ detection 3.2 KV, 25V, 350° C.; Waters Acquity HPLC, Micromass ZQ 2000 Single quadrupole (Waters).

Gradient: 0-1.00 min (A: 100%, B: 0%), 1.00-1.50 min (A: 95%, B: 5%), 1.50-3.50 min (A: 0%, B: 100%), 3.50-4.00 min (A: 0%, B: 100%); 4.00-4.10 min (A: 100%, B: 0%); 4.10-5.00 min (A: 100%, B: 0%).

Method I:

Column Acquity HPLC-BEH C18 (50×2.1 mm, 1.7 μm); Phase A: water/CH$_3$CN 95/5+0.1% TFA; Phase B: water/CH$_3$CN 5/95+0.1% TFA; flow rate: 0.6 ml/min; UV detection wavelength 254 nm or BPI; ESI+ detection 3.2 KV, 25V, 350° C.; Waters Acquity HPLC, Micromass ZQ Single quadrupole (Waters).

Gradient: 0-0.50 min (A: 95%, B: 5%), 0.50-6.00 min (A: 0%, B: 100%), 6.00-7.00 min (A: 0%, B: 100%), 7.00-7.10 min (A: 95%, B: 5%); 7.10-8.50 min (A: 95%, B: 5%).

Method L:

Column Atlantis dC18 (100×2.1 mm, 3 μm); Phase A: water/CH$_3$CN 95/5+0.1% TFA; Phase B: water/CH$_3$CN 5/95+0.1% TFA; flow rate: 0.30 ml/min; UV detection wavelength 254 nm or BPI; ESI+ detection 3.2 KV, 25V, 350° C.; Waters Acquity HPLC, Micromass ZQ Single quadrupole (Waters).

Gradient: 0-0.20 min (A: 95%, B: 5%), 0.20-5.00 min (A: 0%, B: 100%), 5.00-6.00 min (A: 0%, B: 100%), 6.00-6.10 min (A: 95%, B: 5%); 6.10-7.00 min (A: 95%, B: 5%).

Method M:

Column Synergi (20×2.0 mm 2.5 μm); Phase A: water/CH$_3$CN 95/5+0.1% TFA; Phase B: water/CH$_3$CN 5/95+0.1% TFA; flow rate: 0.7 ml/min; UV detection wavelength 254 nm or BPI; ESI+ detection 3.2 KV, 25V, 350° C.; Waters HPLC, Micromass ZQ 2000 Single quadrupole (Waters).

Gradient: 0-0.25 min (A: 95%, B: 5%), 0.25-3.50 min (A: 0%, B: 100%), 3.50-4.50 min (A: 0%, B: 100%), 4.50-4.60 min (A: 95%, B: 5%); 4.60-6.00 min (A: 95%, B: 5%).

Method N:

Column XBridge C8 (4.6×50 mm 3.5 μm); Phase A: water+0.1% TFA; Phase B: CH$_3$CN+0.1% TFA; flow rate: 2 ml/min; UV detection wavelength 254 nm or BPI; ESI+ detection 3.2 KV, 25V, 350° C.; Waters HPLC, Micromass ZQ 2000 Single quadrupole (Waters).

Gradient: 0 min (A: 95%, B: 5%), 0-8.00 min (A: 0%, B: 100%), 8.00-8.10 min (A: 90%, B 10%).

Most of the reactions were monitored by thin layer chromatography (TLC) with 0.2 mm Merck silica gel plates (60F-254), visualized with UV light (254 nm). The chromatographic columns were packed with Merck silica gel 60 (0.04-0.063 mm).

Intermediate 1: (E)-3-{4-oxo-spiro[chromane-2,4'-piperidine]-6-yl}-acrylic acid methyl ester

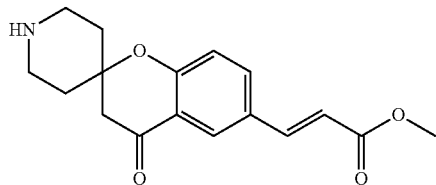 [SMILES: COC(=O)/C=C/c1ccc2c(c1)C(=O)CC1(CCNCC1)O2]

Step A

A mixture of 2-hydroxy-5-bromoacetophenone (10.75 g, 50 mmol), N—BOC-4-piperidone (9.96 g, 50 mmol) and pyrrolidine (2.09 ml, 25 mmol) in MeOH (80 ml) was heated to reflux for 11 h. The solvent was removed under vacuum and the crude mixture was purified by column chromatography (eluent: hexane/AcOEt 90:10 to 80:20) to give 6-bromo-4-oxo-spiro[chromane-2,4'-piperidine]-1'-carboxylic acid tert-butyl ester (18.55 g) as a yellow solid.

Yield=94% (yield will be abbreviated as Y in the rest of the examples)

LC-MS: Method A, rt=6.4 min; (ES+) MNa$^+$: 419.8

$^1$H-NMR (CDCl$_3$) δ (ppm): 7.96 (s, 1H), 7.55 (d, J=8.8 Hz, 1H), 6.82 (d, J=7.6 Hz, 1H), 3.84 (m, 2H), 3.18 (t, J=11.6 Hz, 2H), 2.70 (s, 2H), 2.00 (m, 2H), 1.60 (m, 2H), 1.44 (s, 9H).

Step B

A mixture of 6-bromo-4-oxo-spiro[chromane-2,4'-piperidine]-1'-carboxylic acid tert-butyl ester (1.04 g, 2.62 mmol), Pd(OAc)$_2$ (59 mg, 0.262 mmol), PPh$_3$ (137 mg, 0.52 mmol), TEA (0.73 ml, 5.2 mmol), methyl acrylate (0.47 ml, 5.2 mmol) in dry DMF (10 ml) was heated at 100° C. for 8 h. The mixture was cooled down to RT, filtered on a celite pad and washed with AcOEt (100 ml). The filtrate was washed with NH$_4$Cl and saturated NaHCO$_3$ solution and brine. The organic phase was dried over Na$_2$SO$_4$ and evaporated under vacuum. The crude residue was purified by column chromatography (eluent:hexane/AcOEt 90:10 to 70:30) to give (E)-3-{1'-tert-butoxycarbonyl-4-oxo-spiro[chromane-2,4'-piperidine]-6-yl}-acrylic acid methyl ester (594 mg) as a light yellow solid.

Y=56%

LC-MS: Method A, rt=6.0 min; (ES+) MNa$^+$: 424.0

$^1$H-NMR (CDCl$_3$) δ (ppm): 8.00 (bs, 1H), 7.62 (m, 2H), 7.00 (d, J=8.4 Hz, 1H), 6.31 (d, J=16.0 Hz, 1H), 3.85 (bs, 2H), 3.78 (s, 3H), 3.20 (t, J=12.0 Hz, 2H), 2.73 (s, 2H), 2.00 (d, J=15.2 Hz, 2H), 1.64 (m, 2H), 1.44 (s, 9H).

Step C

A 4 M solution of HCl in dioxane (2 ml, 8 mmol) was added to a solution of (E)-3-{1'-tert-butoxycarbonyl-4-oxo-spiro[chromane-2,4'-piperidine]-6-yl}-acrylic acid methyl ester (590 mg, 1.47 mmol) in DCM (10 ml) and the mixture was stirred at RT for 4 h. The precipitated solid was filtered off and washed with DCM, then dried under vacuum and collected (374 mg) as a white solid (hydrochloride salt).

Y=77%

LC-MS: Method A, rt=3.3 min; (ES+) MH$^+$: 302.3

$^1$H-NMR (DMSO-d$_6$) δ (ppm): 8.95 (bs, 2H), 8.04 (m, 2H), 7.69 (d, J=16.0 Hz, 1H), 7.20 (d, J=7.2 Hz, 1H), 6.60 (d, J=16.0 Hz, 1H), 3.72 (s, 3H), 3.19 (m, 2H), 3.11 (m, 2H), 2.99 (s, 2H), 2.10 (m, 2H), 1.92 (m, 2H).

Intermediate 2: (E)-3-{4-oxo-spiro[chromane-2,4'-piperidine]-7-yl}-acrylic acid methyl ester

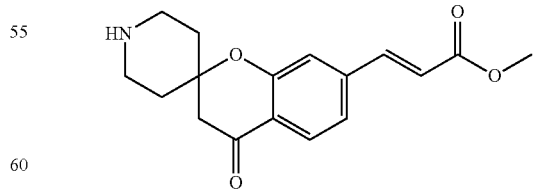

Step A

3-Bromo-phenol (10.0 g, 57.8 mmol) was dissolved in 10 ml of pyridine and 10 ml of acetic anhydride and stirred overnight at RT. The mixture was then poured into water, and 1 M HCl was added until reaching a neutral pH value. Extraction with AcOEt furnished a crude product, which was treated with AlCl$_3$ (13.25 g, 100 mmol) at 140° C. After 2 h, the mixture was poured into water and extracted with diethyl ether. The crude residue was purified by column chromatography (eluent:hexane/AcOEt 70:30) to give 1-(4-bromo-2-hydroxy-phenyl)-ethanone (10.1 g) as a red solid.

Y=81%

LC-MS: Method B, rt=1.95 min; (ES+) MH$^+$: 215

$^1$H-NMR (CDCl$_3$) δ (ppm): 12.34 (s, 1H), 7.58 (d, J=8 Hz, 1H), 7.18 (d, J=2 Hz, 1H), 7.04 (dd, J=8, 2 Hz, 1H), 2.61 (s, 3H).

1-(4-Bromo-2-hydroxy-phenyl)ethanone (10.1 g, 47.0 mmol) was coupled with N—BOC-4-piperidone according to the procedure for preparation of Intermediate 1, Step A, giving 7-bromo-4-oxo-spiro[chromane-2,4'-piperidine]-1'-carboxylic acid tert-butyl ester (18 g) as an orange solid.

Y=98%

LC-MS: Method B, rt=2.57 min; (ES+) MH$^+$: 395

$^1$H-NMR (CDCl$_3$) δ (ppm): 7.70 (d, J=8 Hz, 1H), 7.21 (d, J=1 Hz, 1H), 7.15 (dd, J=1, 8 Hz, 1H), 4.73 (s, 2H), 3.87 (bs, 2H), 3.20 (t, J=12 Hz, 2H), 1.99 (d, J=13 Hz, 2H), 1.61 (dt, J=13, 4 Hz, 2H), 1.46 (s, 9H).

Step B

7-Bromo-4-oxo-spiro[chromane-2,4'-piperidine]-1'-carboxylic acid tert-butyl ester (9.1 g, 23 mmol) was treated with methyl acrylate according to the procedure for preparation of Intermediate 1, Step B, giving (E)-3-{1'-tert-butoxycarbonyl-4-oxo-spiro[chromane-2,4'-piperidine]-7-yl}-acrylic acid methyl ester (7.07 g) as a yellow solid.

Y=77%

LC-MS: Method A, rt=6.0 min; (ES+) MNa$^+$: 424.3

$^1$H-NMR (CDCl$_3$) δ (ppm): 7.86 (d, J=8 Hz, 1H), 7.62 (d, J=16 Hz, 1H), 7.15 (d, J=8 Hz, 1H), 7.12 (s, 1H), 6.50 (d, J=16 Hz, 1H), 3.88 (m, 2H), 3.82 (s, 3H), 3.22 (t, J=11 Hz, 2H), 2.72 (s, 2H), 2.02 (d, J=13 Hz, 2H), 1.63 (dt, J=14, 4 Hz, 2H), 1.95 (s, 9H).

Step C (E)-3-{1'-tert-Butoxycarbonyl-4-oxo-spiro[chromane-2,4'-piperidine]-7-yl}-acrylic acid methyl ester (2.45 g, 6.1 mmol) was deprotected with HCl according to the procedure for preparation of Intermediate 1, Step C, giving (E)-3-{4-oxo-spiro[chromane-2,4'-piperidine]-7-yl}-acrylic acid methyl ester (1.98 g) as a yellow solid (hydrochloride salt).

Y=96%

LC-MS: Method A, rt=3.4 min; (ES+) MH$^+$: 302.2

$^1$H-NMR (DMSO-d$_6$) δ (ppm): 9.04 (bs, 1H), 8.77 (bs, 1H), 7.75 (d, J=8 Hz, 1H), 7.65 (d, J=16 Hz, 1H), 7.52 (d, J=1 Hz, 1H), 7.44 (dd, J=8, 1 Hz, 1H), 6.78 (d, J=16 Hz, 1H), 3.74 (s, 3H), 3.12 (m, 4H), 2.94 (s, 2H), 2.10 (m, 2H), 1.92 (m, 2H).

Intermediate 3: 1'-Benzyl-6-bromo-4-hydroxy-spiro[chromane-2,4'-piperidine]

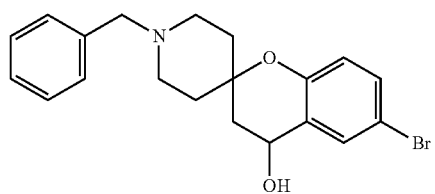 [SMILES: OC1CC2(CCN(Cc3ccccc3)CC2)Oc2ccc(Br)cc21]

Step A

A mixture of 2-hydroxy-5-bromoacetophenone (5.85 g, 27.2 mmol), N-benzyl-4-piperidone (5.14 g, 27.21 mmol) and pyrrolidine (1.11 ml, 13.60 mmol) in MeOH (100 ml) was heated to reflux. After 11 h, the solvent was removed under vacuum and the crude mixture was purified by column chromatography (eluent: hexane/AcOEt 90:10 to 70:30) to give 1'-benzyl-6-bromo-spiro[chromane-2,4'-piperidine]-4-one (7.0 g) as a yellow solid.

Y=66%

LC-MS: Method B, rt=1.35 min; (ES+) MH$^+$: 387

$^1$H-NMR (CDCl$_3$) δ (ppm): 7.79 (d, J=2 Hz, 1H), 7.55 (dd, J=8, 2 Hz, 1H), 7.30 (m, 5H), 6.89 (d, J=8 Hz, 1H), 3.53 (s, 2H), 2.70 (s, 2H), 2.61 (m, 2H), 2.43 (m, 2H), 1.99 (m, 2H), 1.77 (m, 2H).

Step B

A mixture of 1'-benzyl-6-bromo-spiro[chromane-2,4'-piperidine]-4-one (3.0 g, 7.8 mmol) and NaBH$_4$ (1.47 g, 38.75 mmol) in MeOH (20 ml) was stirred at RT. After 3 h, the solution was poured into water and the product was extracted with DCM (50 ml). The organic phase was dried over Na$_2$SO$_4$, filtered and evaporated under vacuum to give 1'-benzyl-6-bromo-4-hydroxy-spiro[chromane-2,4'-piperidine] (3.0 g) as a light yellow solid.

Y=99%

LC-MS: Method B, rt=1.29 min; (ES+) MH$^+$: 389

$^1$H-NMR (CDCl$_3$) δ (ppm): 7.55 (d, J=2 Hz, 1H), 7.29 (m, 6H), 6.73 (d, J=8 Hz, 1H), 4.80 (m, 1H), 3.52 (s, 2H), 2.60 (m, 2H), 2.47 (dt, J=11, 3 Hz, 1H), 2.46 (dt, J=11, 3 Hz, 1H), 2.10 (m, 1H), 1.88 (m, 1H), 1.75 (m, 4H).

Intermediate 4: (E)-3-{3-oxo-spiro[benzofuran-2(3H),4'-piperidin]-5-yl}-acrylic acid methyl ester

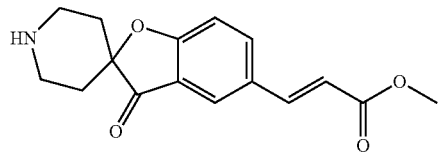 [SMILES: COC(=O)/C=C/c1ccc2c(c1)C(=O)C1(CCNCC1)O2]

Step A

Iodine (944 mg, 3.72 mmol) was added to a solution of 5-bromo-2-fluoro-benzaldehyde (25.0 g, 124 mmol) and 1,3-propanedithiol (13.23 mL, 122.5 mmol) in CHCl$_3$ (400 ml). After stirring at RT for 18 h, the orange solution was poured into a Na$_2$S$_2$O$_3$ solution (0.4 M, 180 ml) and 150 ml of a 40% solution of NaOH was added. The organic phase was separated and the aqueous phase was extracted with a further portion of CHCl$_3$ (300 ml). The combined organic fractions were washed with water (400 ml), brine (400 ml), dried over Na$_2$SO$_4$, then filtered and evaporated to give a yellow solid (32.1 g). Recrystallisation from DCM—hexane afforded 20.0 g of 2-(5-bromo-2-fluoro-phenyl)[1,3]dithiane as a white solid.

Y=55%

LC-MS: Method A, rt=6.4 min; (ES+) MH$^+$: 293

$^1$H-NMR (CDCl$_3$) δ (ppm): 7.74 (dd, J=6, 2 Hz, 1H), 7.39 (ddd, J=8 Hz, 1H), 6.94 (t, J=9 Hz, 1H), 5.47 (s, 1H), 3.10 (ddd, J=14, 12, 2 Hz, 2H), 2.92 (dt, J=14, 4 Hz, 2H), 2.18 (m, 1H), 1.94 (m, 1H).

Step B

A solution of 2-(5-bromo-2-fluoro-phenyl)[1,3]dithiane (19 g, 64.84 mmol) in THF (100 ml) was added to a degassed and stirred 2 M solution of LDA (32.42 ml, 64.84 mmol) in THF dry (150 ml) at −78° C. and the reaction was carried out at −20° C. for 30 min. The reaction was cooled down again to −78° C. and tert-butyl 4-oxo-1-piperidinecarboxylate (13.03 g, 65.5 mmol) in THF (100 ml) was added dropwise. After 30 min, a further portion of tert-butyl 4-oxo-1-piperidinecarboxylate was added (0.5 g, 0.25 mmol). After 1 h, the reaction mixture was poured into a saturated NH$_4$Cl solution (200 ml) and extracted with AcOEt. The combined organic fractions were washed with water (100 ml), brine (100 ml), dried over Na$_2$SO$_4$, then filtered and evaporated to give a yellow oil. The crude product was purified by column chromatography (AcOEt/hexane 30/70) to give 4-[2-(5-bromo-2-fluoro-phenyl)-[1,3]dithian-2-yl]-4-hydroxy-piperidine-1-carboxylic acid tert-butyl ester as a white solid (13 g).

Y=40%

LC-MS: Method B, rt=2.54 min; (ES+) MH$^+$: 493.0

$^1$H-NMR (CDCl$_3$) δ (ppm): 8.21 (dd, J=7, 2 Hz, 1H), 7.44 (ddd, J=8, 3, 2 Hz, 1H), 6.99 (dd, J=12, 8 Hz, 1H), 3.95 (bs, 2H), 2.99 (bs, 2H), 2.86 (dt, J=14, 4 Hz, 2H), 2.64 (ddd, J=14, 9, 5 Hz, 2H), 2.46 (bs, 1H), 1.92-1.85 (m, 2H), 1.84-1.73 (m, 4H), 1.43 (s, 9H).

Step C

Pyridine tribromide (12.7 g, 39.6 mmol) and TBAB (850 mg, 2.64 mmol) were added to a stirred solution of 4-[2-(5-bromo-2-fluoro-phenyl)-[1,3]dithian-2-yl]-4-hydroxy-piperidine-1-carboxylic acid tert-butyl ester (13 g, 26.42 mmol) and pyridine (2.07 ml, 39.63 mmol) in a mixture of DCM/water (5:1, 180 ml). After stirring for 24 h at RT, the solution was poured into water (150 ml) and the product was extracted with DCM. The combined organic layers were washed with water (400 ml), brine (400 ml), dried over Na$_2$SO$_4$, then filtered and evaporated. The crude product was purified by column chromatography (AcOEt/hexane:20/80) to give 9.5 g of 4-(5-bromo-2-fluoro-benzoyl)-4-hydroxy-piperidine-1-carboxylic acid tert-butyl ester as a yellow oil.

Y=89%

LC-MS: Method B, rt=2.14 min; (ES+) MH$^+$: 401

$^1$H-NMR (DMSO-d$_6$) δ (ppm): 7.54 (ddd, J=8, 4, 2 Hz, 1H), 7.49 (dd, J=5, 2 Hz, 1H), 7.01 (t, J=8 Hz, 1H), 3.96 (bs, 2H), 3.47 (bs, 1H), 3.13 (t, J=10 Hz, 2H), 1.96 (td, J=12, 4 Hz, 2H), 1.65 (d, J=13 Hz, 2H), 1.43 (s, 9H).

Step D

A 1 M solution of tBuOK (54.10 ml, 54.10 mmol) in THF was added to a solution of 4-(5-bromo-2-fluoro-benzoyl)-4-hydroxy-piperidine-1-carboxylic acid tert-butyl ester (14.5 g, 36.07 mmol) in THF (200 ml) and the mixture was stirred at 70° C. After 30 min, the solution was poured into ice water (150 ml) and the product was extracted with AcOEt. The combined organic layers were washed with water (50 ml), brine (50 ml), dried over Na$_2$SO$_4$, then filtered and evaporated to give a pale yellow oil. Purification by column chromatography (hexane/AcOEt: 80/20 to AcOEt) gave 1.5 g of 5-bromo-3-oxo-spiro[benzofuran-2(3H),4'-piperidin]-1'-carboxylic acid tert-butyl ester as a yellow crystalline solid.

Y=11%

LC-MS: Method B, rt=2.44 min; (ES+) M-15$^+$: 366

$^1$H-NMR (DMSO-d$_6$) δ (ppm): 7.79 (d, J=2 Hz, 1H), 7.71 (dd, J=8, 2 Hz, 1H), 7.04 (d, J=8 Hz, 1H), 4.15 (bs, 2H), 3.22 (t, J=12 Hz, 2H), 1.94 (ddd, J=13, 12, 5 Hz, 2H), 1.59 (d, J=13 Hz, 2H), 1.49 (s, 9H).

Step E (E)-3-{1'-Tert-butoxycarbonyl-3-oxo-spiro[benzofuran-2(3H),4'-piperidin]-5-yl}-acrylic acid methyl ester was synthesized according to the procedure for preparation of Intermediate 1, Step B starting from 5-bromo-3-oxo-spiro[benzofuran-2(3H),4'-piperidin]-1'-carboxylic acid tert-butyl ester. Purification by column chromatography (eluent hexane/AcOEt:80/20 to 70/30) furnished the desired compound (780 mg).

Y=51%

LC-MS: Method B, rt=2.44 min; (ES+) M-15$^+$: 373

$^1$H-NMR (CDCl$_3$) δ (ppm): 7.81 (m, 2H), 7.68 (d, J=16 Hz, 1H), 7.16 (d, J=9 Hz, 1H), 6.38 (d, J=16 Hz, 1H), 4.13 (bs, 2H), 3.24 (m, 2H), 1.96 (td, J=12, 4 Hz, 2H), 1.60 (d, J=14 Hz, 2H), 1.50 (s, 9H).

Step F (E)-3-{3-Oxo-spiro[benzofuran-2(3H),4'-piperidin]-5-yl}-acrylic acid methyl ester was synthesized according to the procedure for preparation of Intermediate 1, Step C, starting from (E)-3-{1-tert-butoxycarbonyl-3-oxo-spiro[benzofuran-2(3H),4'-piperidin]-5-yl}-acrylic acid methyl ester (750 mg, 1.93 mmol), giving its hydrochloride salt (380 mg).

Y=61%

LC-MS: Method B, rt=1.02 min; (ES+) MH$^+$: 288

$^1$H-NMR (CDCl$_3$) δ (ppm): 9.00 (bs, 1H), 8.84 (bs, 1H), 8.20 (dd, J=8, 2 Hz, 1H), 8.09 (d, J=2 Hz, 1H), 7.74 (d, J=16 Hz, 1H), 7.37 (d, J=8 Hz, 1H), 6.70 (d, J=16 Hz, 1H), 3.72 (s, 3H), 3.45 (bs, 2H), 3.15 (q, J=9 Hz, 2H), 2.37 (t, J=2 Hz, 2H), 2.13 (bs, 2H).

Intermediate 5: (E)-3-{3,4-Dihydro-3-methyl-4-oxo-spiro[2H-(1,3)-benzoxazine-2,4'-piperidin]-6-yl}-acrylic acid methyl ester hydrochloride

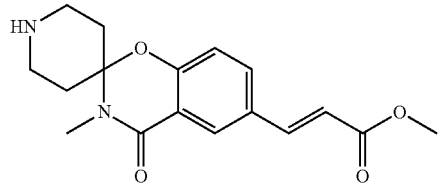 [SMILES: COC(=O)/C=C/c1ccc2c(c1)C(=O)N(C)C1(CCNCC1)O2]

Step A

Three batches of 5-bromo salicylamide (5.00 g each, 23.1 mmol), N-Boc-piperidin-4-one (3.45 g, 17.3 mmol) and pyrrolidine (1.64 g, 23.1 mmol) were heated in different flasks at 72° C. under MW irradiation for 1 h. Further N-Boc-piperidin-4-one (3.45 g, 17.3 mmol) was added and the mixtures were heated for 1 h at 72° C. The resulting precipitates were collected by filtration and washed with MeOH to give 6-bromo-3,4-dihydro-4-oxo-spiro[2H-(1,3)-benzoxazine-2,4'-piperidin]-1'-carboxylic acid tert-butyl ester (17.2 g) as a white solid.

Y=63%

$^1$H NMR (DMSO-d$_6$) δ (ppm): 8.86 (s, 1H), 7.82 (d, J=2.35 Hz, 1H), 7.69 (dd, J=8.66, 2.49 Hz, 1H), 7.06 (d, J=8.80 Hz, 1H), 3.64-3.88 (m, 2H), 3.02-3.21 (m, 2H), 1.91-2.10 (m, 2H), 1.63-1.78 (m, 2H), 1.40 (s, 9H).

Step B

6-Bromo-3,4-dihydro-4-oxo-spiro[2H-(1,3)-benzoxazine-2,4'-piperidin]-1'-carboxylic acid tert-butyl ester (5.00 g, 12.6 mmol) was dissolved in hot DMF (15 ml) and then TEA (5.26 ml, 37.8 mmol), tris(o-tolyl)phosphine (153 mg, 0.504 mmol), Pd(OAc)$_2$ (56 mg, 0.25 mmol) and methyl acrylate (3.25 g, 37.8 mmol) were added at RT. The mixture was heated at 100° C. for 6 h under N$_2$ with a further addition of tris(o-tolyl)phosphine (153 mg, 0.504 mmol) and Pd(OAc)$_2$ (56 mg, 0.25 mmol) after three hours) and then partitioned between brine and AcOEt. The organic phase was rinsed with water and brine, dried over Na$_2$SO$_4$ and evaporated. The residue was triturated in AcOEt and petroleum ether to give (E)-3-{1'-tert-butoxycarbonyl-3,4-dihydro-4- oxo-spiro[2H-(1,3)-benzoxazine-2,4'-piperidin]-6-yl}-acrylic acid methyl ester (5.05 g)

Y=99%

¹H NMR (DMSO-d₆) δ (ppm): 8.82 (s, 1H), 8.03 (d, J=2.05 Hz, 1H), 7.93 (dd, J=8.66, 2.20 Hz, 1H), 7.68 (d, J=16.14 Hz, 1H), 7.12 (d, J=8.51 Hz, 1H), 6.57 (d, J=16.14 Hz, 1H), 3.73-3.83 (m, 2H), 3.72 (s, 3H), 2.98-3.25 (m, 2H), 1.90-2.08 (m, 2H), 1.60-1.83 (m, 2H), 1.41 (s, 9H).

Step C (E)-3-{1'-Tert-butoxycarbonyl-3,4-dihydro-4-oxo-spiro[2H-(1,3)-benzoxazine-2,4'-piperidin]-6-yl}-acrylic acid methyl ester (4.02 g, 10.0 mmol) was dissolved in DMF (35 ml) and added to a stirred suspension of NaH (60% oil dispersion, 480 mg, 12 mmol) in DMF (35 ml) at 4° C. After 10 min CH₃I (2.13 g, 15.0 mmol) was added, the resulting mixture was stirred at RT for 30 min and then partitioned between saturated aqueous solution of NH₄Cl and AcOEt. The organic phase was rinsed with water, dried over Na₂SO₄ and evaporated. The crude mixture was purified by trituration in AcOEt and petroleum ether to give (E)-3-{1'-tert-butoxycarbonyl-3,4-dihydro-3-methyl-4-oxo-spiro[2H-(1,3)-benzoxazine-2,4'-piperidin]-6-yl}-acrylic acid methyl ester (3.66 g).

Y=88%

¹H NMR (DMSO-d₆) δ (ppm): 8.04 (d, J=2.35 Hz, 1H), 7.94 (dd, J=8.51, 2.35 Hz, 1H), 7.69 (d, J=15.85 Hz, 1H), 7.19 (d, J=8.51 Hz, 1H), 6.58 (d, J=15.85 Hz, 1H), 3.96 (d, J=13.20 Hz, 2H), 3.73 (s, 3H), 3.01 (s, 3H), 2.95-3.14 (m, 2H), 1.72-2.19 (m, 4H), 1.41 (s, 9H).

Step D

A mixture of (E)-3-{1'-tert-butoxycarbonyl-3,4-dihydro-3-methyl-4-oxo-spiro[2H-(1,3)-benzoxazine-2,4'-piperidin]-6-yl}-acrylic acid methyl ester (3.00 g, 7.21 mmol) and 4 M HCl in dioxane (5 ml) in DCM (150 ml) was stirred at RT for 4 h. The precipitate was filtered off to give (E)-3-{3,4-dihydro-3-methyl-4-oxo-spiro[2H-(1,3)-benzoxazine-2,4'-piperidin]-6-yl}-acrylic acid methyl ester hydrochloride (2.46 g).

Y=97%

¹H NMR (DMSO-d₆) δ (ppm): 9.21 (bs, 2H), 8.06 (d, J=2.35 Hz, 1H), 7.98 (dd, J=8.66, 2.20 Hz, 1H), 7.70 (d, J=15.85 Hz, 1H), 7.24 (d, J=8.51 Hz, 1H), 6.60 (d, J=16.14 Hz, 1H), 3.73 (s, 3H), 3.21-3.40 (m, 2H), 3.05-3.20 (m, 2H), 3.03 (s, 3H), 2.38-2.48 (m, 2H), 2.12-2.29 (m, 2H).

Intermediate 6: (E)-3-{3,4-Dihydro-3-benzyl-4-oxo-spiro[2H-(1,3)-benzoxazine-2,4'-piperidin]-6-yl}-acrylic acid methyl ester

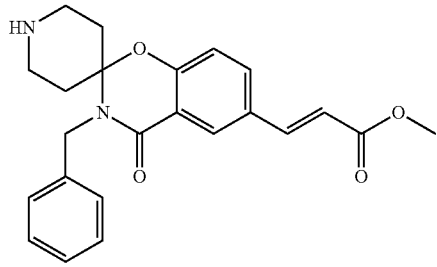 [SMILES: COC(=O)/C=C/c1ccc2c(c1)C(=O)N(Cc1ccccc1)C1(CCNCC1)O2]

Step A (E)-3-{1'-Tert-butoxycarbonyl-3,4-dihydro-4-oxo-spiro[2H-(1,3)-benzoxazine-2,4'-piperidin]-6-yl}-acrylic acid methyl ester (1.8 g, 4.5 mmol, Example 25, Step A) was dissolved in dry DMF (25 ml) under N₂, and NaH (268.6 mg, 6.71 mmol, 60% suspension in mineral oil) was added. After 10 min stirring, benzyl bromide (1.07 ml, 8.95 mmol) was added dropwise and the mixture was heated for 3 h at 80° C. The mixture was poured into water and a saturated NH₄Cl solution was added. The aqueous phase was extracted with DCM, and the combined organic phases were dried and concentrated. The crude residue was purified by column chromatography (eluent:petroleum ether/AcOEt 90:10 to 70:30) to give (E)-3-{1'-tert-butoxycarbonyl-3,4-dihydro-3-benzyl-4-oxo-spiro[2H-(1,3)-benzoxazine-2,4'-piperidin]-6-yl}-acrylic acid methyl ester (1.3 g, 59%) as a white solid.

¹H-NMR (DMSO-d₆) δ (ppm): 8.14 (d, J=2.05 Hz, 1H), 7.99 (dd, J=8.51, 2.35 Hz, 1H), 7.72 (d, J=16.14 Hz, 1H), 7.12-7.46 (m, 6H), 6.61 (d, J=15.85 Hz, 1H), 4.85 (s, 2H), 3.77-3.98 (m, 2H), 3.73 (s, 3H), 2.82-3.14 (m, 2H), 1.75-2.07 (m, 4H), 1.37 (s, 9H).

Step B (E)-3-{1'-Tert-butoxycarbonyl-3,4-dihydro-3-benzyl-4-oxo-spiro[2H-(1,3)-benzoxazine-2,4'-piperidin]-6-yl}-acrylic acid methyl ester (900 mg, 1.83 mmol) was deprotected with HCl according to the procedure for preparation of Intermediate 1, Step C, giving (E)-3-{3,4-dihydro-3-benzyl-4-oxo-spiro[2H-(1,3)-benzoxazine-2,4'-piperidin]-6-yl}-acrylic acid methyl ester (700 mg) as its hydrochloride salt.

Y=89%

¹H-NMR (DMSO-d₆) δ (ppm): 9.09 (bs, 2H), 8.16 (d, J=2.35 Hz, 1H), 8.03 (dd, J=8.66, 2.20 Hz, 1H), 7.73 (d, J=16.14 Hz, 1H), 7.14-7.47 (m, 6H), 6.63 (d, J=16.14 Hz, 1H), 4.81 (s, 2H), 3.74 (s, 3H), 3.18-3.31 (m, 2H), 2.93-3.18 (m, 2H), 2.39 (td, J=13.64, 4.70 Hz, 2H), 1.99-2.20 (m, 2H).

Intermediate 7: (E)-3-{1'-Tert-butoxycarbonyl-3,4-dihydro-3-butyl-4-oxo-spiro[2H-(1,3)-benzoxazine-2,4'-piperidin]-6-yl}-acrylic acid methyl ester

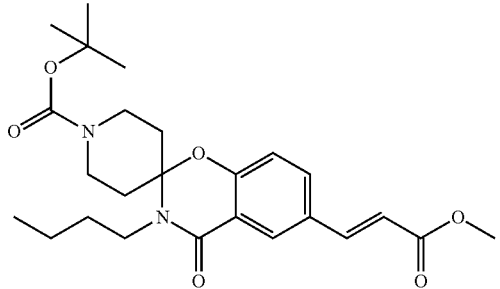 [SMILES: CCCCN1C(=O)c2cc(/C=C/C(=O)OC)ccc2OC12CCN(C(=O)OC(C)(C)C)CC2]

(E)-3-{1'-Tert-butoxycarbonyl-3,4-dihydro-4-oxo-spiro[2H-(1,3)-benzoxazine-2,4'-piperidin]-6-yl}-acrylic acid methyl ester (Intermediate 5 STEP B, 500 mg, 1.24 mmol) was dissolved in dry DMF (4.5 ml) and added dropwise to a stirred suspension of NaH (60% oil dispersion, 59.6 mg, 1.49 mmol) in dry DMF (4.5 ml) cooled at 4° C. The mixture was stirred for 10 min at 0° C. and then 1-bromobutane (0.205 ml, 1.86 mmol) was added dropwise. The resulting yellow solution was stirred overnight at RT and then partitioned between EtOAc and saturated solution of NH₄Cl. The organic layer was rinsed twice with water, dried over Na₂SO₄ and concentrated to dryness. The crude mixture was purified by column chromatography (eluent:petroleum ether:AcOEt 75:25) to give (E)-3-{1'-tert-butoxycarbonyl-3,4-dihydro-3-butyl-4-oxo-spiro[2H-(1,3)-benzoxazine-2,4'-piperidin]-6-yl}-acrylic acid methyl ester as white foam (225 mg).

Y=40%

¹H NMR (DMSO-d₆) δ (ppm): 8.04 (d, J=2.35 Hz, 1H), 7.94 (dd, J=8.66, 2.20 Hz, 1H), 7.69 (d, J=16.14 Hz, 1H), 7.18 (d, J=8.51 Hz, 1H), 6.58 (d, J=16.14 Hz, 1H), 3.88-4.02 (m, 2H), 3.73 (s, 3H), 3.44-3.58 (m, 2H), 2.88-3.15 (m, 2H), 2.04-2.15 (m, 2H), 1.86-2.02 (m, 2H), 1.46-1.58 (m, 2H), 1.41 (s, 9H), 1.23-1.38 (m, 2H), 0.91 (t, J=7.34 Hz, 3H).

Example 1

(E)-3-{4-oxo-spiro[chromane-2,4'-piperidine]-6-yl}-N-hydroxy-acrylamide

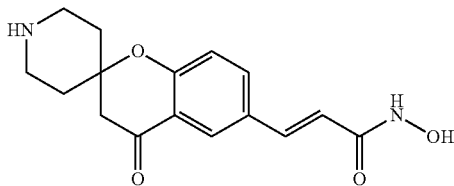 [SMILES: O=C(/C=C/c1ccc2c(c1)C(=O)CC1(CCNCC1)O2)NO]

Step A

NaOH (160 mg, 4 mmol) in H₂O (2 ml) was added to a suspension of (E)-3-{1'-tert-butoxycarbonyl-4-oxo-spiro[chromane-2,4'-piperidine]-6-yl}-acrylic acid methyl ester (462 mg, 1.15 mmol, Intermediate 1, Step B) in MeOH (6 ml). The mixture was stirred at 50° C. After 2 h, MeOH was evaporated and the pH of the aqueous phase was adjusted with 1 M HCl to a pH value of 5. The resulting suspension was extracted with DCM, the organic phase dried over Na₂SO₄ and concentrated to give (E)-3-{1'-tert-butoxycarbonyl-4-oxo-spiro[chromane-2,4'-piperidine]-6-yl}-acrylic acid (410 mg) as a white solid.

Y=92%

LC-MS: Method A, rt=5.2 min; (ES+) MNa⁺: 409.9

¹H-NMR (CDCl₃) δ (ppm): 8.05 (d, J=2.0 Hz, 1H), 7.70 (m, 2H), 7.04 (d, J=8.8 Hz, 1H), 6.39 (d, J=16.0 Hz, 1H), 3.88 (m, 2H), 3.22 (m, 2H), 2.75 (s, 2H), 1.61 (m, 4H), 1.50 (s, 9H).

Step B

A solution of (E)-3-{1'-tert-butoxycarbonyl-4-oxo-spiro[chromane-2,4'-piperidine]-6-yl}-acrylic acid (387 mg, 1 mmol) in DCM (15 ml) was cooled down to 0° C. EDC (383 mg, 2 mmol) and HOBT (135 mg, 1 mmol) were added, and the mixture was stirred at RT for 1 h. NH₂OTHP (146 mg, 1.25 mmol) in DCM (1 ml) was added dropwise and the mixture was stirred at RT. After 4 h, the reaction mixture was washed with a saturated NaHCO₃ solution and brine, dried over Na₂SO₄ and concentrated. The crude residue was purified by column chromatography (eluent:DCM/MeOH 98:2) to give (E)-3-{1'-tert-butoxycarbonyl-4-oxo-spiro[chromane-2,4'-piperidine]-6-yl}-N-(tetrahydro-pyran-2-yloxy)-acrylamide (464 mg) as a light yellow oil.

Y=95%

LC-MS: Method A, rt=5.3 min; (ES+) 2MNa⁺: 995.7

¹H-NMR (DMSO-d₆) δ (ppm): 7.91 (s, 1H), 7.80 (d, J=7.6 Hz, 1H), 7.48 (d, J=16.0 Hz, 1H), 7.14 (d, J=8.4 Hz, 1H), 6.46 (d, J=16.0 Hz, 1H), 4.90 (bs, 1H), 3.85 (m, 1H), 3.75 (m, 2H), 3.54 (m, 1H), 3.13 (m, 2H), 2.88 (s, 2H), 1.86 (m, 4H), 1.65 (m, 6H), 1.40 (s, 9H).

Step C

4 M HCl in dioxane (2 ml, 8 mmol) was added dropwise to a solution of (E)-3-{1'-tert-butoxycarbonyl-4-oxo-spiro[chromane-2,4'-piperidine]-6-yl}-N-(tetrahydro-pyran-2-yloxy)-acrylamide (434 mg, 0.89 mmol) in DCM (10 ml) and the mixture was stirred at RT for 2 h. The precipitate was collected by filtration, washed with DCM, and dried under vacuum to give 260 mg of a white solid (hydrochloride salt).

Y=86%

LC-MS: Method C, rt=7.5 min; (ES+) 2MNa⁺: 627.3

¹H-NMR (DMSO-d₆) δ (ppm): 10.27 (bs, 1H), 8.98 (bs, 1H), 7.90 (d, J=2.0 Hz, 1H), 7.81 (dd, J=8.8, 2.4 Hz, 1H), 7.44 (d, J=16.0 Hz, 1H), 7.19 (d, J=8.4 Hz, 1H), 6.45 (d, J=16.0 Hz, 1H), 3.15 (m, 4H), 2.95 (s, 2H), 2.11 (m, 2H), 1.89 (m, 2H).

Example 2

(E)-3-{1'-Benzyl-4-oxo-spiro[chromane-2,4'-piperidine]-6-yl}-N-hydroxy-acrylamide

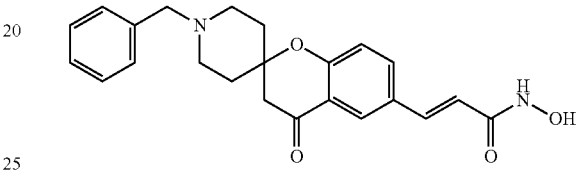

Step A

A suspension of (E)-3-{4-oxo-spiro[chromane-2,4'-piperidine]-6-yl}-acrylic acid methyl ester (451 mg, 1.34 mmol, Intermediate 1) in DCM (12 ml) was treated with TEA (0.42 ml, 3 mmol) and benzyl bromide (0.54 ml, 4.5 mmol), and stirred at RT for 5 h. The mixture was washed with water, the pH value was adjusted to 5 with a 0.5 M HCl, then dried and concentrated. The crude residue was purified by column chromatography (eluent:DCM/MeOH 95:5) to give (E)-3-{1'-benzyl-4-oxo-spiro[chromane-2,4'-piperidine]-6-yl}-acrylic acid methyl ester (440 mg) as a light yellow solid.

Y=84%

LC-MS: Method A, rt=4.1 min; (ES+) 2MNa⁺: 805.5

¹H-NMR (CDCl₃) δ (ppm): 8.02 (d, J=2.0 Hz, 1H), 7.65 (m, 2H), 7.52 (m, 2H), 7.47 (m, 3H), 7.01 (d, J=9.2 Hz, 1H), 6.38 (d, J=16.0 Hz, 1H), 3.80 (s, 3H), 3.55 (m, 2H), 2.76 (m, 2H), 2.62 (m, 2H), 2.46 (m, 2H), 2.04 (m, 2H), 1.77 (m, 2H), 1.57 (m, 2H).

Step B (E)-3-{1'-Benzyl-4-oxo-spiro[chromane-2,4'-piperidine]-6-yl}-acrylic acid methyl ester (414 mg, 1.06 mmol) was hydrolyzed with NaOH following the procedure described in Example 1, Step A, giving (E)-3-{1-benzyl-4-oxo-spiro[chromane-2,4'-piperidine]-6-yl}-acrylic acid (380 mg) as a white solid.

Y=96%

LC-MS: Method A, rt=3.5 min; (ES+) MH⁺: 378.2

¹H-NMR (CDCl₃) δ (ppm): 8.02 (d, J=2.0 Hz, 1H), 7.65 (m, 2H), 7.47 (m, 5H), 7.01 (d, J=9.2 Hz, 1H), 6.38 (d, J=16.0 Hz, 1H), 3.65 (m, 2H), 3.21 (m, 2H), 2.70 (m, 4H), 2.40 (m, 2H), 2.08 (m, 2H).

Step C (E)-3-{1'-Benzyl-4-oxo-spiro[chromane-2,4'-piperidine]-6-yl}-acrylic acid (365 mg, 0.97 mmol) was treated with NH₂OTHP following the procedure described in Example 1, Step B, giving (E)-3-{1-benzyl-4-oxo-spiro[chromane-2,4'-piperidine]-6-yl}-N-(tetrahydro-pyran-2-yloxy)-acrylamide (328 mg) as a light yellow oil.

Y=69%

LC-MS: Method A, rt=3.9 min; (ES+) MH⁺: 477.5

¹H-NMR (CDCl₃) δ (ppm): 8.31 (bs, 1H), 8.05 (d, J=2.0 Hz, 1H), 7.60 (m, 2H), 7.35 (m, 4H), 6.97 (m, 1H), 6.36 (bs, 1H), 4.99 (bs, 1H), 3.96 (m, 1H), 3.60 (m, 1H), 3.53 (m, 1H), 2.76 (s, 2H), 2.64 (m, 2H), 2.46 (m, 2H), 2.09 (m, 2H), 1.82 (m, 4H), 1.55 (m, 6H).

Step D

1 M HCl in Et₂O (1.5 ml, 1.5 mmol) was added dropwise to a solution of (E)-3-{1'-benzyl-4-oxo-spiro[chromane-2,4'-piperidine]-6-yl}-N-(tetrahydro-pyran-2-yloxy)-acrylamide (300 mg, 0.63 mmol) in DCM (10 ml). Precipitation of a solid immediately occurred. The precipitate was filtered off, washed with DCM, dried under vacuum and collected (210 mg) as a light yellow solid as its hydrochloride salt.

Y=78%

LC-MS: Method D, rt=4.1 min; (ES+) MH⁺: 393.0

¹H-NMR (DMSO-d₆) δ (ppm): 10.72 (bs, 1H), 7.90 (m 1H), 7.81 (m 1H), 7.62 (m, 2H), 7.44 (m, 4H), 7.14 (m, 1H), 6.44 (m, 1H), 4.36 (s, 2H), 3.20 (m, 4H), 2.88 (s, 2H), 2.15 (m, 2H), 2.09 (m, 2H).

Example 3

(E)-3-{1'-Acetyl-4-oxo-spiro[chromane-2,4'-piperidine]-6-yl}-N-hydroxy-acrylamide

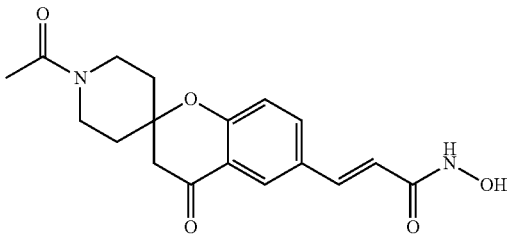 [SMILES: CC(=O)N1CCC2(CC1)CC(=O)c1cc(/C=C/C(=O)NO)ccc1O2]

(E)-3-{1'-Acetyl-4-oxo-spiro[chromane-2,4'-piperidine]-6-yl}-acrylic acid methyl ester was obtained starting from (E)-3-{4-oxo-spiro[chromane-2,4'-piperidine]-6-yl}-acrylic acid methyl ester (301 mg, 1 mmol, Intermediate 1) and acetyl chloride, according to the procedure described in Example 2, Step A, giving a white solid (330 mg, 96%). The methyl ester group was hydrolyzed with NaOH following the procedure described in Example 1, Step A, giving (E)-3-{1-acetyl-4-oxo-spiro[chromane-2,4'-piperidine]-6-yl}-acrylic acid as a white solid (205 mg, 67%). The resulting product was treated with NH₂OTHP according to the procedure described in Example 1, Step B, giving (E)-3-{1-acetyl-4-oxo-spiro[chromane-2,4'-piperidine]-6-yl}-N-(tetrahydro-pyran-2-yloxy)-acrylamide as a yellow solid (164 mg, 62%). Finally, removal of the THP protecting group following the procedure described in Example 2, Step D gave compound (E)-3-{1'-acetyl-4-oxo-spiro[chromane-2,4'-piperidine]-6-yl}-N-hydroxy-acrylamide (59 mg) as a light yellow solid.

Y=15% (over 4 steps)

LC-MS: Method E, rt=8.7 min; (ES+) MH⁺: 344.9

¹H-NMR (DMSO-d₆) δ (ppm): 7.90 (d, J=2.0 Hz, 1H), 7.82 (dd, J=8.8, 2.4 Hz, 1H), 7.44 (d, J=15.6 Hz, 1H), 7.14 (d, J=8.4 Hz, 1H), 6.41 (d, J=15.6 Hz, 1H), 4.19 (m, 1H), 3.64 (m, 1H), 3.35 (m, 1H), 3.01 (m, 1H), 2.88 (s, 2H), 2.01 (s, 3H), 1.95 (m, 2H), 1.76 (m, 1H), 1.60 (m, 1H).

Example 4

(E)-3-{1'-Benzoyl-4-oxo-spiro[chromane-2,4'-piperidine]-6-yl}-N-hydroxy-acrylamide

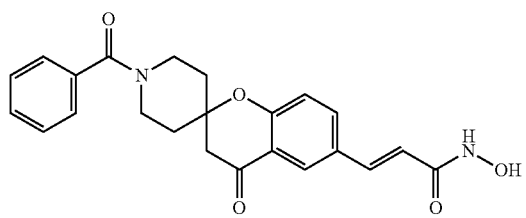 [SMILES: O=C(/C=C/c1ccc2c(c1)C(=O)CC1(CCN(C(=O)c3ccccc3)CC1)O2)NO]

(E)-3-{1'-Benzoyl-4-oxo-spiro[chromane-2,4'-piperidine]-6-yl}-acrylic acid methyl ester was obtained starting from (E)-3-{4-oxo-spiro[chromane-2,4'-piperidine]-6-yl}-acrylic acid methyl ester (301 mg, 1 mmol, Intermediate 1) and benzoyl chloride, according to the procedure described in Example 2, Step A, giving a white solid (357 mg, 88%). The methyl ester was hydrolyzed with NaOH following the procedure described in Example 1, Step A, giving (E)-3-{1'-benzoyl-4-oxo-spiro[chromane-2,4'-piperidine]-6-yl}-acrylic acid as a white solid (287 mg, 83%). The resulting product was treated with NH₂OTHP according to the procedure described in Example 1, Step B, giving (E)-3-{1'-benzoyl-4-oxo-spiro[chromane-2,4'-piperidine]-6-yl}-N-(tetrahydro-pyran-2-yloxy)-acrylamide as a yellow solid (282 mg, 78%). Finally, removal of the THP protecting group following the procedure described in Example 2, Step D gave (E)-3-{1'-benzoyl-4-oxo-spiro[chromane-2,4'-piperidine]-6-yl}-N-hydroxy-acrylamide (176 mg) as a light red solid.

Y=43% (over 4 steps)

LC-MS: Method E, rt=12.6 min; (ES+) MH⁺: 407.0

¹H-NMR (DMSO-d₆) δ (ppm): 7.89 (m, 1H), 7.80 (m, 1H), 7.42 (m, 6H), 7.14 (m, 1H), 6.41 (m, 1H), 3.30 (m, 2H), 2.91 (s, 2H), 1.92 (m, 4H), 1.76 (m, 2H).

Example 5

(E)-3-{1'-Methyl-4-oxo-spiro[chromane-2,4'-piperidine]-6-yl}-N-hydroxy-acrylamide

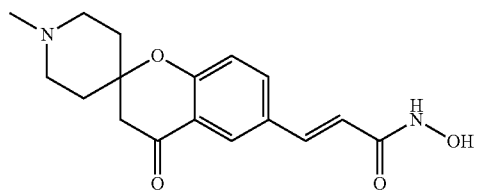 [SMILES: CN1CCC2(CC1)CC(=O)c1cc(/C=C/C(=O)NO)ccc1O2]

Step A

1'-Methyl-6-bromo-spiro[chromane-2,4'-piperidine]-4-one was synthesized according to the procedure for the preparation of Intermediate 1, Step A, using N-methyl-4-piperidone (1.13 g, 10 mmol), and 2-hydroxy-5-bromoacetophenone to give an orange solid (2.29 g).

Y=74%

LC-MS: Method A, rt=3.6 min; (ES+) MH⁺: 311.6

$^1$H-NMR (CDCl$_3$) δ (ppm): 7.95 (d, J=1.6 Hz, 1H), 7.55 (dd, J=8.8, 1.6 Hz, 1H), 6.89 (d, J=8.8 Hz, 1H), 2.70 (s, 2H), 2.61 (m, 2H), 2.43 (m, 2H), 2.33 (s, 3H), 2.03 (m, 2H), 1.76 (m, 2H).

Step B (E)-3-{1'-Methyl-4-oxo-spiro[chromane-2,4'-piperidine]-6-yl}-acrylic acid tert-butyl ester was synthesized starting from 1'-methyl-6-bromo-spiro[chromane-2,4'-piperidine]-4-one (1.62 g, 5.22 mmol) according to the procedure for preparation of Intermediate 1, Step B, using tert-butylacrylate, giving a yellow solid (1.45 g). The resulting product was dissolved in a 20% TFA/DCM mixture (25 ml) and stirred at RT. After 16 h, the solvent was evaporated and the residue was partitioned between DCM and a saturated NaHCO$_3$ solution. Then the aqueous phase was acidified with a 6 M solution of HCl and evaporated. The residue was suspended in a 9:1 DCM/MeOH mixture (70 ml) and the insoluble salts were filtered off. The solvent was dried over Na$_2$SO$_4$ and evaporated, giving (E)-3-{1'-methyl-4-oxo-spiro[chromane-2,4'-piperidine]-6-yl}-acrylic acid (890 mg) as a yellow solid.

Y=57%

LC-MS: Method A, rt=2.8 min; (ES+) MH$^+$: 301.8

$^1$H-NMR (DMSO-d$_6$) δ (ppm): 8.01 (d, J=8.0 Hz, 1H), 7.97 (s, 1H), 7.60 (d, J=16.0 Hz, 1H), 7.17 (d, J=8.8 Hz, 1H), 6.47 (d, J=16.0 Hz, 1H), 3.32 (m, 4H), 2.96 (m, 2H), 2.81 (s, 3H), 2.14 (m, 2H), 1.97 (m, 2H).

Step C (E)-3-{1'-Methyl-4-oxo-spiro[chromane-2,4'-piperidine]-6-yl}-N-(tetrahydro-pyran-2-yloxy)-acrylamide was synthesized starting from (E)-3-{1'-methyl-4-oxo-spiro[chromane-2,4'-piperidine]-6-yl}-acrylic acid (386 mg, 1.28 mmol) according to the procedure described in Example 1, Step B, giving a yellow oil (294 mg).

Y=57%

LC-MS: Method A, rt=3.2 min; (ES+) 2MNa$^+$: 823.6

$^1$H-NMR (DMSO-d$_6$) δ (ppm): 11.14 (bs, 1H), 7.91 (s, 1H), 7.79 (d, J=11.2 Hz, 1H), 7.47 (d, J=15.6 Hz, 1H), 7.10 (d, J=8.8 Hz, 1H), 6.46 (d, J=15.6 Hz, 1H), 4.90 (s, 1H), 3.95 (m, 1H), 3.53 (d, J=11.6 Hz, 1H), 3.30 (m, 2H), 2.84 (s, 2H), 2.55 (m, 2H), 2.33 (m, 2H), 2.22 (s, 3H), 1.90 (m, 2H), 1.75 (m, 4H), 1.54 (m, 2H).

Step D (E)-3-{1'-Methyl-4-oxo-spiro[chromane-2,4'-piperidine]-6-yl}-N-hydroxy-acrylamide was synthesized starting from (E)-3-{1'-methyl-4-oxo-spiro[chromane-2,4'-piperidine]-6-yl}-N-(tetrahydro-pyran-2-yloxy)-acrylamide (234 mg, 0.585 mmol) according to the procedure described in Example 2, Step D, giving a light red solid (55 mg).

Y=30%

LC-MS: Method E, rt=5.8 min; (ES+) MH$^+$: 316.9

$^1$H-NMR (DMSO-d$_6$) δ (ppm): 7.85 (m, 2H), 7.44 (d, J=16.0 Hz, 1H), 7.19 (d, J=8.8 Hz, 1H), 6.44 (d, J=16.0 Hz, 1H), 3.40 (m, 2H), 3.18 (m, 2H), 2.91 (s, 2H), 2.79 (s, 3H), 2.19 (m, 2H), 2.00 (m, 2H).

Example 6

(E)-3-{1'-Ethyloxycarbonyl-4-oxo-spiro[chromane-2,4'-piperidine]-6-yl}-N-hydroxy-acrylamide

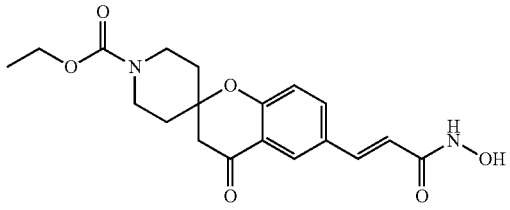 [SMILES: CCOC(=O)N1CCC2(CC1)CC(=O)c1cc(/C=C/C(=O)NO)ccc1O2]

Step A

6-Bromo-4-oxo-spiro[chromane-2,4'-piperidine]-1'-carboxylic acid ethyl ester was synthesized according to the procedure for preparation of Intermediate 1, Step A, using 4-oxo-piperidine-1-carboxylic acid ethyl ester (1.51 ml, 10 mmol) and 2-hydroxy-5-bromo-acetophenone, giving a light yellow solid (3.04 g).

Y=83%

LC-MS: Method A, rt=5.8 min; (ES+) MH$^+$: 369.8

$^1$H-NMR (CDCl$_3$) δ (ppm): 7.95 (d, J=2.4 Hz, 1H), 7.57 (dd, J=8.8, 2.4 Hz, 1H), 6.90 (d, J=8.8 Hz, 1H), 4.14 (q, J=7.2 Hz, 2H), 3.92 (m, 2H), 3.23 (m, 2H), 2.71 (s, 2H), 2.03 (m, 2H), 1.61 (m, 2H), 1.26 (t, J=7.2 Hz, 3H).

Step B (E)-3-{1'-Ethyloxycarbonyl-4-oxo-spiro[chromane-2,4'-piperidine]-6-yl}-acrylic acid was synthesized starting from 6-bromo-4-oxo-spiro[chromane-2,4'-piperidine]-1'-carboxylic acid ethyl ester (2.0 g, 5.43 mmol) according to the procedure described in Example 5, Step B, giving a white solid (621 mg).

Y=32%

LC-MS: Method A, rt=4.6 min; (ES+) MH$^+$: 359.9

$^1$H-NMR (DMSO-d$_6$) δ (ppm): 12.34 (s, 1H), 7.96 (m, 2H), 7.59 (d, J=16.0 Hz, 1H), 7.13 (d, J=8.8 Hz, 1H), 6.45 (d, J=16.0 Hz, 1H), 4.04 (q, J=6.8 Hz, 2H), 3.76 (m, 2H), 3.18 (m, 2H), 2.89 (s, 2H), 1.89 (m, 2H), 1.66 (m, 2H), 1.26 (t, J=7.2 Hz, 3H).

Step C (E)-3-{1'-Ethyloxycarbonyl-4-oxo-spiro[chromane-2,4'-piperidine]-6-yl}-N-(tetrahydro-pyran-2-yloxy)-acrylamide was synthesized starting from (E)-3-{1'-ethyloxycarbonyl-4-oxo-spiro[chromane-2,4'-piperidine]-6-yl}-acrylic acid (610 mg, 1.70 mmol) according to the procedure described in Example 1, Step B, giving a white solid (690 mg).

Y=89%

LC-MS: Method A, rt=4.9 min; (ES+) 2MNa$^+$: 939.2

$^1$H-NMR (CDCl$_3$) δ (ppm): 8.04 (m, 1H), 7.65 (m, 2H), 7.01 (d, J=8.4 Hz, 1H), 6.38 (bs, 1H), 5.01 (bs, 1H), 4.13 (q, J=7.2 Hz, 2H), 3.96 (m, 3H), 3.66 (m, 1H), 3.25 (t, J=11.2 Hz, 2H), 2.92 (m, 1H), 2.74 (s, 2H), 2.04 (m, 2H), 1.85 (m, 2H), 1.63 (m, 6H), 1.26 (t, J=7.2 Hz, 3H).

Step D (E)-3-{1'-Ethyloxycarbonyl-4-oxo-spiro[chromane-2,4'-piperidine]-6-yl}-N-hydroxy-acrylamide was synthesized starting from (E)-3-{1'-ethyloxycarbonyl-4-oxo-spiro[chromane-2,4'-piperidine]-6-yl}-N-(tetrahydro-pyran-2-yloxy)-acrylamide (630 mg, 1.37 mmol) according to the procedure described in Example 2, Step D, giving a white solid (460 mg).

Y=89%

LC-MS: Method D, rt=6.7 min; (ES+) MH$^+$: 374.7

$^1$H-NMR (DMSO-d$_6$) δ (ppm): 7.89 (d, J=2.0 Hz, 1H), 7.78 (dd, J=8.8, 2.0 Hz, 1H), 7.43 (d, J=16.0 Hz, 1H), 7.13 (d, J=8.8 Hz, 1H), 6.42 (d, J=16.0 Hz, 1H), 4.04 (q, J=6.8 Hz, 2H), 3.76 (m, 2H), 3.18 (m, 2H), 2.88 (s, 2H), 1.90 (m, 2H), 1.66 (m, 2H), 1.18 (t, J=7.2 Hz, 3H).

Example 7

(E)-3-{1'-Phenyl-4-oxo-spiro[chromane-2,4'-piperidine]-6-yl}-N-hydroxy-acrylamide

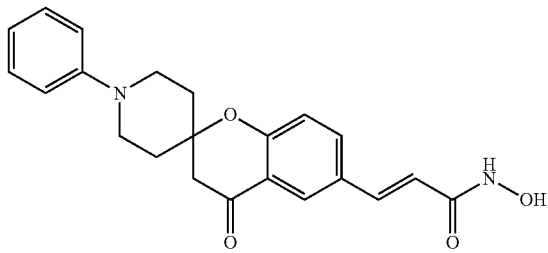 [SMILES: O=C(/C=C/c1ccc2c(c1)C(=O)CC1(CCN(c3ccccc3)CC1)O2)NO]

Step A

1'-Phenyl-6-bromo-spiro[chromane-2,4'-piperidine]-4-one was synthesized according to the procedure for preparation of Intermediate 1, Step A, using 1-phenyl-piperidin-4-one (607 mg, 3.47 mmol) and 2-hydroxy-5-bromoacetophenone (746 mg, 3.47 mmol), giving 650 mg as a white solid.

Y=50%

LC-MS: Method B, rt=2.42 min; (ES+) MH+: 374

$^1$H-NMR (CDCl$_3$) δ (ppm): 7.99 (d, J=2 Hz, 1H), 7.57 (dd, J=8, 2 Hz, 1H), 7.27 (m, 2H), 6.97 (m, 3H), 6.90 (d, J=8 Hz, 1H), 3.45 (d, J=12 Hz, 2H), 3.20 (m, 2H), 2.76 (s, 2H), 2.15 (d, J=12 Hz, 2H), 1.87 (m, 2H).

Step B (E)-3-{1'-Phenyl-4-oxo-spiro[chromane-2,4'-piperidine]-6-yl}-acrylic acid methyl ester was synthesized starting from 1'-phenyl-6-bromo-spiro[chromane-2,4'-piperidine]-4-one (650 mg, 1.75 mmol) and methyl acrylate (541 mg, 6.2 mmol) according to the procedure described for Intermediate 1, Step B, giving 541 mg of the product.

Y=82%

LC-MS: Method B, rt=2.19 min; (ES+) MH+: 378

$^1$H-NMR (DMSO-d$_6$) δ (ppm): 8.05 (s, 1H), 7.68 (m, 1H), 7.65 (d, J=16 Hz, 1H), 7.29 (m, 2H), 7.04 (m, 4H), 6.39 (d, J=16 Hz, 1H), 3.80 (s, 3H), 3.46 (m, 2H), 3.21 (m, 2H), 2.80 (s, 2H), 2.16 (m, 2H), 1.88 (m, 2H).

Step C (E)-3-{1'-Phenyl-4-oxo-spiro[chromane-2,4'-piperidine]-6-yl}-acrylic acid methyl ester (541 mg, 1.43 mmol) was hydrolyzed with NaOH following the procedure described in Example 1, Step A, giving (E)-3-{1-phenyl-4-oxo-spiro[chromane-2,4'-piperidine]-6-yl}-acrylic acid as a white solid (455 mg, 87%). The resulting product was treated with NH$_2$OTHP according to the procedure described in Example 1, Step B, giving (E)-3-{1-phenyl-4-oxo-spiro[chromane-2,4'-piperidine]-6-yl}-N-(tetrahydro-pyran-2-yloxy)-acrylamide as a yellow solid (393 mg, 69%). Finally, the removal of the THP protecting group following the procedure described in Example 2, Step D gave the crude product, which was purified by preparative HPLC giving 50 mg of (E)-3-{1-phenyl-4-oxo-spiro[chromane-2,4'-piperidine]-6-yl}-N-hydroxy-acrylamide as its trifluoro acetic salt.

Y=7% (over 3 steps).

LC-MS: Method E, rt=10.3 min; (ES+) MH+: 379

$^1$H-NMR (DMSO-d$_6$) δ (ppm): 10.69 (bs, 1H), 7.96 (s, 1H), 7.83 (d, J=8 Hz, 1H), 7.40 (m, 5H), 7.26 (d, J=8 Hz, 1H), 7.07 (m, 1H), 6.47 (d, J=16 Hz, 1H), 3.42 (m, 4H), 2.96 (s, 2H), 2.12 (m, 4H).

Example 8

(E)-3-{4-oxo-spiro[chromane-2,4'-piperidine]-7-yl}-N-hydroxy-acrylamide

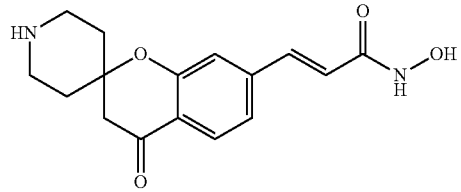 [SMILES: O=C(/C=C/c1ccc2c(c1)OC1(CCNCC1)CC2=O)NO]

(E)-3-{1'-Tert-butoxycarbonyl-4-oxo-spiro[chromane-2,4'-piperidine]-7-yl}-acrylic acid methyl ester (602 mg, 1.5 mmol, Intermediate 2, Step B) was treated with NaOH following the procedure described in Example 1, Step A, giving (E)-3-{1'-tert-butoxycarbonyl-4-oxo-spiro[chromane-2,4'-piperidine]-7-yl}-acrylic acid as a white solid (560 mg, 96%). The resulting product was treated with NH$_2$OTHP according to the procedure described in Example 1, Step B, giving (E)-3-{1'-tert-butoxycarbonyl-4-oxo-spiro[chromane-2,4'-piperidine]-7-yl}-N-(tetrahydro-pyran-2-yloxy)-acrylamide as a yellow solid (572 mg, 81%). Finally, removal of the THP and the BOc protecting groups following the procedure described in Example 1, Step C gave (E)-3-{4-oxo-spiro[chromane-2,4'-piperidine]-7-yl}-N-hydroxy-acrylamide (280 mg, 70%) as a yellow solid (hydrochloride salt).

Y=55% (over 3 steps)

LC-MS: Method E, rt=6.1 min; (ES+) MH+: 303.1

$^1$H-NMR (DMSO-d$_6$) δ (ppm): 9.02 (bs, 1H), 8.76 (bs, 1H), 7.76 (d, J=8.0 Hz, 1H), 7.44 (d, J=16.0 Hz, 1H), 7.29 (m, 2H), 6.60 (d, J=16.0 Hz, 1H), 3.15 (m, 4H), 2.92 (s, 2H), 1.93 (m, 2H), 1.77 (m, 2H).

Example 9

(E)-3-{1'-Benzyl-4-oxo-spiro[chromane-2,4'-piperidine]-7-yl}-N-hydroxy-acrylamide

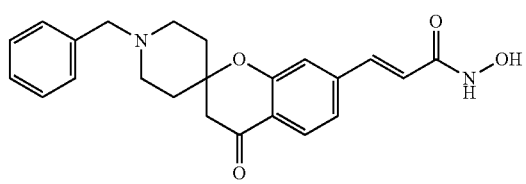 [SMILES: O=C(/C=C/c1ccc2c(c1)OC1(CCN(Cc3ccccc3)CC1)CC2=O)NO]

(E)-3-{1'-Benzyl-4-oxo-spiro[chromane-2,4'-piperidine]-7-yl}-acrylic acid methyl ester was obtained starting from (E)-3-{4-oxo-spiro[chromane-2,4'-piperidine]-7-yl}-acrylic acid methyl ester (1.12 g, 3.32 mmol, Intermediate 2) and benzyl bromide, according to the procedure described in Example 2, Step A, giving a white solid (1.0 g, 77%). The methyl ester was hydrolyzed with NaOH following the procedure described in Example 1, Step A, giving (E)-3-{1-benzyl-4-oxo-spiro[chromane-2,4'-piperidine]-7-yl}-acrylic acid as a white solid (900 mg, 94%). The resulting acid was treated with NH₂OTHP according to the procedure described in Example 1, Step B, giving (E)-3-{1-benzyl-4-oxo-spiro [chromane-2,4'-piperidine]-7-yl}-N-(tetrahydro-pyran-2-yloxy)-acrylamide as a yellow solid (550 mg, 58%). Finally, removal of the THP protecting group following the procedure described in Example 1, Step C gave the crude product, which was purified by preparative LC-MS to give (E)-3-{1'-benzyl-4-oxo-spiro[chromane-2,4'-piperidine]-7-yl}-N-hydroxy-acrylamide (122 mg, 21%) as its trifluoro acetate salt.

Y=7% (over 4 steps)

LC-MS: Method E, rt=8.9 min; (ES+) MH⁺: 393.0

¹H-NMR (DMSO-d₆) δ (ppm): 10.90 (bs, 1H), 9.68 (bs, 1H), 7.80 (d, J=8 Hz, 1H), 7.50 (m, 6H), 7.29 (m, 2H), 6.58 (d, J=16 Hz, 1H), 4.38 (s, 2H), 3.27 (m, 4H), 2.90 (s, 2H), 2.20 (m, 2H), 1.90 (m, 2H).

Example 10

(E)-3-{1'-Acetyl-4-oxo-spiro[chromane-2,4'-piperidine]-7-yl}-N-hydroxy-acrylamide

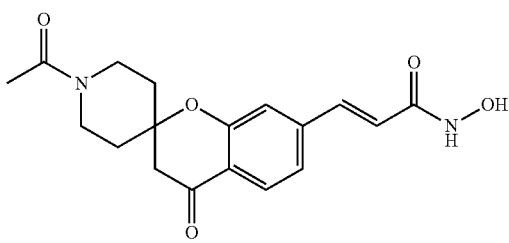 [SMILES: CC(=O)N1CCC2(CC1)CC(=O)c1ccc(/C=C/C(=O)NO)cc1O2]

(E)-3-{1'-Acetyl-4-oxo-spiro[chromane-2,4'-piperidine]-7-yl}-acrylic acid methyl ester was obtained starting from (E)-3-{4-oxo-spiro[chromane-2,4'-piperidine]-7-yl}-acrylic acid methyl ester (1.12 g, 3.32 mmol, Intermediate 2) and acetyl chloride, according to the procedure described in Example 2, Step A, giving a white solid (1.05 g, 92%). The methyl ester was hydrolyzed with NaOH following the procedure described in Example 1, Step A, giving (E)-3-{1-acetyl-4-oxo-spiro[chromane-2,4'-piperidine]-7-yl}-acrylic acid as a white solid (850 mg, 80%). The resulting acid was treated with NH₂OTHP according to the procedure described in Example 1, Step B, giving (E)-3-{1-acetyl-4-oxo-spiro [chromane-2,4'-piperidine]-7-yl}-N-(tetrahydro-pyran-2-yloxy)-acrylamide as a yellow solid (850 mg, 76%). Finally, removal of the THP protecting group following the procedure described in Example 1, Step C, gave (E)-3-{1-acetyl-4-oxo-spiro[chromane-2,4'-piperidine]-7-yl}-N-hydroxy-acrylamide (250 mg, 36%) as a red solid.

Y=22% (over 4 steps)

LC-MS: Method E, rt=8.7 min; (ES+) MH⁺: 345.0

¹H-NMR (DMSO-d₆) δ (ppm): 10.82 (bs, 1H), 7.74 (d, J=8 Hz, 1H), 7.41 (d, J=16 Hz, 1H), 7.23 (m, 2H), 6.58 (d, J=16 Hz, 1H), 4.10 (m, 1H), 3.66 (m, 1H), 3.41 (m, 1H), 3.02 (m, 1H), 2.85 (s, 2H), 2.00 (s, 3H), 1.94 (m, 2H), 1.61 (m, 2H).

Example 11

(E)-3-{1'-Benzoyl-4-oxo-spiro[chromane-2,4'-piperidine]-7-yl}-N-hydroxy-acrylamide

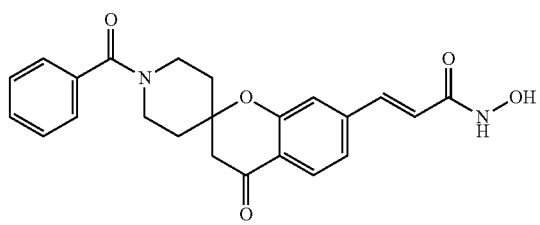 [SMILES: O=C(/C=C/c1ccc2c(c1)OC1(CCN(C(=O)c3ccccc3)CC1)CC2=O)NO]

(E)-3-{1'-Benzoyl-4-oxo-spiro[chromane-2,4'-piperidine]-7-yl}-acrylic acid methyl ester was obtained starting from (E)-3-{4-oxo-spiro[chromane-2,4'-piperidine]-7-yl}-acrylic acid methyl ester (673 mg, 2 mmol) and benzoyl chloride, according to the procedure described in Example 2, Step A, giving a white solid (780 mg, 96%). The methyl ester was hydrolyzed with NaOH following the procedure described in Example 1, Step A, giving (E)-3-{1'-benzoyl-4-oxo-spiro[chromane-2,4'-piperidine]-7-yl}-acrylic acid as a white solid (540 mg, 72%). The resulting product was treated with NH₂OTHP according to the procedure described in Example 1, Step B, giving (E)-3-{1'-benzoyl-4-oxo-spiro [chromane-2,4'-piperidine]-7-yl}-N-(tetrahydro-pyran-2-yloxy)-acrylamide as a yellow solid (427 mg, 63%). Finally, removal of the THP protecting group following the procedure described in Example 1, Step C gave (E)-3-{1'-benzoyl-4-oxo-spiro[chromane-2,4'-piperidine]-7-yl}-N-hydroxy-acrylamide (295 mg, 83%) as a light red solid.

Y=36% (over 4 steps)

LC-MS: Method F, rt=8.1 min; (ES+) MH⁺: 407.0

¹H-NMR (DMSO-d₆) δ (ppm): 7.74 (m, 1H), 7.45 (m, 6H), 7.38 (m, 2H), 6.58 (d, J=16.0 Hz, 1H), 3.20 (m, 4H), 2.88 (s, 2H), 1.80 (m, 4H).

Example 12

(E)-3-{1'-Ethyloxycarbonyl-4-oxo-spiro[chromane-2,4'-piperidine]-7-yl}-N-hydroxy-acrylamide

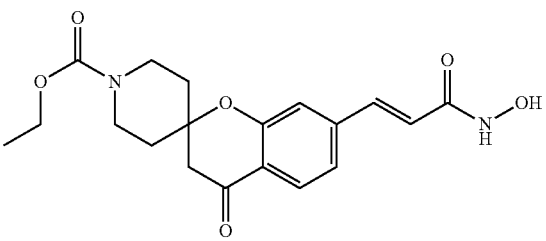 [SMILES: CCOC(=O)N1CCC2(CC1)CC(=O)c1ccc(/C=C/C(=O)NO)cc1O2]

(E)-3-{1'-Ethyloxycarbonyl-4-oxo-spiro[chromane-2,4'-piperidine]-7-yl}-acrylic acid methyl ester was obtained starting from (E)-3-{4-oxo-spiro[chromane-2,4'-piperidine]-7-yl}-acrylic acid methyl ester (1.12 g, 3.32 mmol) and ethyl chloro formate, according to the procedure described in Example 2, Step A, giving a white solid (1.17 g, 94.5%). The methyl ester was hydrolyzed with NaOH following the procedure described in Example 1, Step A, giving (E)-3-{1'-ethyloxycarbonyl-4-oxo-spiro[chromane-2,4'-piperidine]-7-yl}-acrylic acid as a white solid (800 mg, 71%). The resulting acid was treated with NH₂OTHP according to the procedure described in Example 1, Step B, giving (E)-3-{1'-ethyloxycarbonyl-4-oxo-spiro[chromane-2,4'-piperidine]-7-yl}-N-(tetrahydro-pyran-2-yloxy)-acrylamide as a yellow solid (750 mg, 73%). Finally, removal of the THP protecting group following the procedure described in Example 1, Step C gave (E)-3-{1'-ethyloxycarbonyl-4-oxo-spiro[chromane-2,4'-piperidine]-7-yl}-N-hydroxy-acrylamide (300 mg, 49%).

Y=24% (over 4 steps)

LC-MS: Method D, rt=6.6 min; (ES+) MH⁺: 375.0

¹H-NMR (DMSO-d₆) δ (ppm): 7.74 (d, J=8 Hz, 1H), 7.42 (d, J=16 Hz, 1H), 7.25 (m, 2H), 6.59 (d, J=16 Hz, 1H), 4.04 (q, J=7 Hz, 2H), 3.76 (d, 2H), 3.19 (bs, 2H), 2.84 (s, 2H), 1.89 (m, 2H), 1.65 (m, 2H), 1.19 (t, J=7 Hz, 3H).

Example 13

(E)-3-{1'-Benzyl-spiro[chromane-2,4'-piperidine]-6-yl}-N-hydroxy-acrylamide

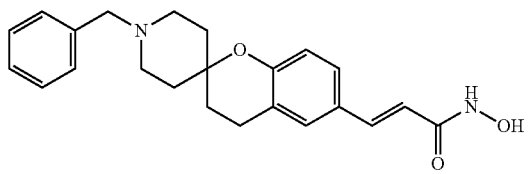 [SMILES: O=C(/C=C/c1ccc2c(c1)CCC1(CCN(Cc3ccccc3)CC1)O2)NO]

Step A

1'-Benzyl-6-bromo-spiro[chromane-2,4'-piperidine]-4-one (2.42 g, 6.27 mmol) was dissolved in EtOH (20 ml) and Zn powder (7.33 g, 113 mmol) was added. After 20 min, 10 ml of concentrated HCl was added dropwise and the mixture was stirred over 2 h. The mixture was filtered and the resulting solution was brought to a pH value of 8 with aqueous NH₃ (30%), extracted with AcOEt, dried over Na₂SO₄ and evaporated under vacuum. The crude product was treated with methyl acrylate following procedure for Intermediate 1, STEP B, to give (E)-3-{1'-benzyl-spiro[chromane-2,4'-piperidine]-6-yl}-acrylic acid methyl ester. The compound (800 mg, 2.12 mmol) was hydrolyzed following the procedure described in Example 1, Step A, giving (E)-3-{1'-benzyl-spiro[chromane-2,4'-piperidine]-6-yl}-acrylic acid as a white solid. The resulting acid was treated with NH₂OTHP and then deprotected according to the procedure described in Example 1, Step B-C, giving (E)-3-{1'-benzyl-spiro[chromane-2,4'-piperidine]-6-yl}-N-hydroxy-acrylamide, which was purified by preparative HPLC to give 43 mg as its trifluoro acetate salt.

Y=2% (over 5 steps)

LC-MS: Method E, rt=10.3 min; (ES+) MH⁺: 379

¹H-NMR (DMSO-d₆) δ (ppm): 10.63 (bs, 1H), 9.76 (bs, 1H), 7.70 (m, 3H), 7.56 (m, 4H), 7.30 (m, 2H), 6.88 (m, 1H), 4.40 (s, 2H), 3.30 (m, 4H), 1.87 (m, 8H).

Example 14

(E)-3-{1'-Benzyl-4-hydroxy-spiro[chromane-2,4'-piperidine]-6-yl}-N-hydroxy-acrylamide

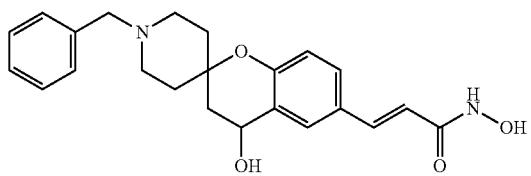 [SMILES: O=C(/C=C/c1ccc2c(c1)C(O)CC1(CCN(Cc3ccccc3)CC1)O2)NO]

Step A

A mixture of (E)-3-{1'-benzyl-4-oxo-spiro[chromane-2,4'-piperidine]-6-yl}-N-hydroxy-acrylamide hydrochloride (60 mg, 0.14 mmol) and NaBH₄ (17.6 mg, 0.459 mmol) in MeOH (5 ml) was stirred at RT. After 3 h, the solution was evaporated under vacuum. The crude residue was purified by preparative HPLC to give (E)-3-{1'-benzyl-4-hydroxy-spiro[chromane-2,4'-piperidine]-6-yl}-N-hydroxy-acrylamide (45 mg) as its trifluoro acetate salt.

Y=58%

LC-MS: Method E, rt=9.2 min; (ES+) MH⁺: 395

¹H-NMR (DMSO-d₆) δ (ppm): 10.64 (bs, 1H), 9.60 (bs, 1H), 7.50 (m, 8H), 6.89 (d, J=8 Hz, 1H), 6.30 (d, J=16 Hz, 1H), 4.71 (bs, 1H), 4.39 (s, 2H), 3.25 (m, 4H), 1.98 (m, 6H).

Example 15

(E)-3-{1'-Benzyl-spiro[chromene-2,4'-piperidine]-6-yl}-N-hydroxy-acrylamide

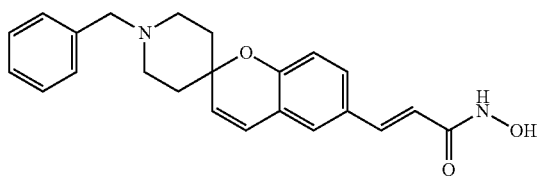 [SMILES: O=C(/C=C/c1ccc2c(c1)C=CC1(CCN(Cc3ccccc3)CC1)O2)NO]

Step A

1'-Benzyl-6-bromo-4-hydroxy-spiro[chromane-2,4'-piperidine] (3.0 g, 7.7 mmol, Intermediate 3) was treated with methyl acrylate according to the procedure for preparation of Intermediate 1, Step B, giving (E)-3-{1-benzyl-4-hydroxy-spiro[chromane-2,4'-piperidine]-6-yl}-acrylic acid methyl ester (3.1 g). The crude intermediate was dissolved in THF (20 ml) under N₂ and p-TsOH (0.15 g, 0.79 mmol) was added. The mixture was heated to reflux. After 16 h, the mixture was poured into water and a 10% NaOH solution was added until reaching a neutral pH value. The solution was extracted with DCM, dried over Na₂SO₄, filtered and evaporated under vacuum. The crude mixture was purified by column chromatography using DCM/MeOH (90/10) and then hexane/AcOEt (70/30) as eluent to give (E)-3-{1'-benzyl-spiro[chromene-2,4'-piperidine]-6-yl}-acrylic acid methyl ester (150 mg).

Y=5%

LC-MS: Method B, rt=1.53 min; (ES+) MH⁺: 376

¹H-NMR (CDCl₃) δ (ppm): 7.59 (d, J=16 Hz, 1H), 7.30 (m, 6H), 7.14 (d, J=2 Hz, 1H), 6.82 (d, J=8 Hz, 1H), 6.34 (d, J=9 Hz, 1H), 6.29 (d, J=16 Hz, 1H), 5.63 (d, J=9 Hz, 1H), 3.78 (s, 3H), 3.55 (s, 2H), 2.61 (m, 2H), 2.54 (m, 2H), 2.02 (m, 2H), 1.77 (m, 2H).

Step B (E)-3-{1'-Benzyl-spiro[chromene-2,4'-piperidine]-6-yl}-acrylic acid methyl ester (150 mg, 0.4 mmol) was hydrolyzed following the procedure described in Example 1, Step A, giving (E)-3-{1'-benzyl-spiro[chromene-2,4'-piperidine]-6-yl}-acrylic acid as a white solid (71 mg, 49%). The product was treated with NH₂OTHP according to the procedure described in Example 1, Step B, giving (E)-3-{1'-benzyl-spiro[chromene-2,4'-piperidine]-6-yl}-N-(tetrahydro-pyran-2-yloxy)-acrylamide as a yellow solid (73 mg, 80%). Finally, removal of the THP protecting group following the procedure described in Example 1, Step C gave (E)-3-{1'-benzyl-spiro[chromene-2,4'-piperidine]-6-yl}-N-hydroxy-acrylamide (57 mg, 96%).

Y=38% (over 3 steps)

LC-MS: Method E, rt=13.8 min; (ES+) MH⁺: 377

¹H-NMR (DMSO-d₆) δ (ppm): 10.76 (bs, 1H), 7.65 (m, 2H), 7.40 (m, 7H), 6.89 (d, J=8 Hz, 1H), 6.59 (d, J=10 Hz, 1H), 6.32 (d, J=16 Hz, 1H), 4.37 (d, J=5 Hz, 2H), 3.24 (m, 4H), 2.09 (m, 4H).

Example 16

(E)-3-{1'-Benzyl-4-acetylamino-spiro[chromane-2,4'-piperidine]-6-yl}-N-hydroxy-acrylamide

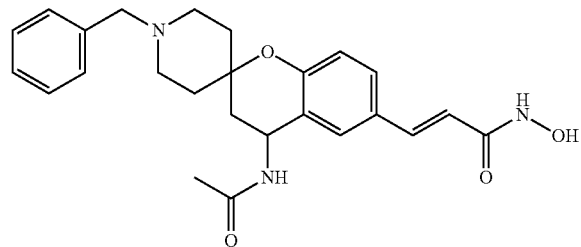 [SMILES: CC(=O)NC1CC2(CCN(Cc3ccccc3)CC2)Oc2ccc(/C=C/C(=O)NO)cc21]

Step A

Concentrated H₂SO₄ (2 ml) was added dropwise to a suspension of 1'-benzyl-6-bromo-4-hydroxy-spiro[chromane-2,4'-piperidine] (1.3 g, 3.3 mmol, Intermediate 3) in CH₃CN (50 ml), keeping the temperature between −10° C. and 0° C. The solution was stirred for 1 h at RT, then poured into cold water, brought to a basic pH value with a saturated NaHCO₃ solution and extracted with AcOEt. The organic layers were collected, dried over Na₂SO₄, filtered and evaporated under vacuum. The crude product was then treated with methyl acrylate according to the procedure for preparation of Intermediate 1, Step B, giving (E)-3-{1'-benzyl-4-acetylamino-spiro[chromane-2,4'-piperidine]-6-yl}-acrylic acid methyl ester (1.4 g, 3.22 mmol) as a white solid.

Y=98%

LC-MS: Method B, rt=1.21 min; (ES+) MH⁺: 435

¹H-NMR (CDCl₃) δ (ppm): 8.22 (d, J=8 Hz, 1H), 7.59 (m, 2H), 7.31 (m, 5H), 6.68 (d, J=8 Hz, 1H), 6.40 (d, J=16 Hz, 1H), 5.07 (m, 1H), 3.70 (s, 3H), 3.49 (s, 2H), 2.50 (m, 2H), 2.25 (m, 1H), 2.09 (m, 1H), 1.93 (s, 3H), 1.68 (m, 6H).

Step B (E)-3-{1'-Benzyl-4-acetylamino-spiro[chromane-2,4'-piperidine]-6-yl}-acrylic acid methyl ester (1.2 g, 2.76 mmol) was hydrolyzed following the procedure described in Example 1, Step A, giving (E)-3-{1'-benzyl-4-acetylamino-spiro[chromane-2,4'-piperidine]-6-yl}-acrylic acid as a white solid (950 mg, 82%). The resulting product was treated with NH₂OTHP according to the procedure described in Example 1, Step B, giving (E)-3-{1'-benzyl-4-acetylamino-spiro[chromane-2,4'-piperidine]-6-yl}-N-(tetrahydro-pyran-2-yloxy)-acrylamide as a yellow solid (624 mg, 53%). Finally, removal of the THP protecting group following the procedure described in Example 1, Step C gave (E)-3-{1'-benzyl-4-acetylamino-spiro[chromane-2,4'-piperidine]-6-yl}-N-hydroxy-acrylamide (40 mg, 7%) as its hydrochloride salt.

Y=3% (over 3 steps)

LC-MS: Method E, rt=9.1 min; (ES+) MH⁺: 436

¹H-NMR (DMSO-d₆) δ (ppm): 10.72 (bs, 1H), 10.31 (bs, 1H), 8.35 (d, J=8 Hz, 1H), 7.63 (m, 3H), 7.46 (m, 4H), 6.91 (d, J=8 Hz, 1H), 6.33 (d, J=16 Hz, 1H), 5.13 (m, 1H), 4.41 (d, J=5 Hz, 2H), 3.22 (m, 4H), 2.08 (m, 9H).

Example 17

(E)-3-{1'-Benzyl-4-benzoyloxyimino-spiro[chromane-2,4'-piperidine]-6-yl}-N-hydroxy-acrylamide

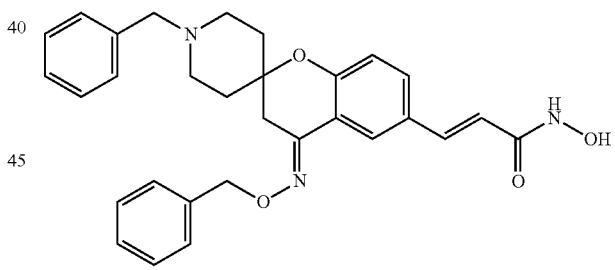

A mixture of (E)-3-{1'-benzyl-4-oxo-spiro[chromane-2,4'-piperidine]-6-yl}-N-hydroxy-acrylamide hydrochloride (150 mg, 0.35 mmol), NH₂OCH₂Ph (94 mg, 0.76 mmol) and pyridine (61 µl, 0.700 mmol) in EtOH (10 ml) was heated to reflux. After 2 h, the solution was cooled down to RT and evaporated under vacuum. The crude residue was triturated with Et₂O/H₂O 90/10 to give (E)-3-{1-benzyl-4-benzyloxyimino-spiro[chromane-2,4'-piperidine]-6-yl}-N-hydroxy-acrylamide (55 mg) as a 70/30 mixture of the two isomers (hydrochloride salts).

Y=30%

LC-MS: Method D, rt=7.5 min; (ES+) MH⁺: 498

¹H-NMR (DMSO-d₆) δ (ppm): 10.73 (bs, 1H), 10.49 (bs, 1H), 7.93 (s, 1H), 7.60 (m, 3H), 7.42 (m, 9H), 7.03 (d, J=4.8

Hz, 1H), 6.36 (d, J=16 Hz, 1H), 5.26 (s, 2H), 4.35 (m, 2H), 3.18 (m, 4H), 2.90 (s, 2H), 2.00 (m, 4H).

Example 18

(E)-3-{1'-Benzyl-4-methyloxyimino-spiro[chromane-2,4'-piperidine]-6-yl}-N-hydroxy-acrylamide

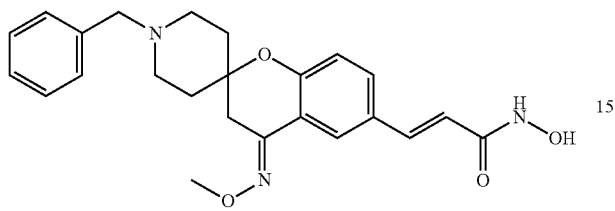

A mixture of (E)-3-{1'-benzyl-4-oxo-spiro[chromane-2,4'-piperidine]-6-yl}-N-hydroxy-acrylamide hydrochloride (150 mg, 0.35 mmol), NH$_2$OCH$_3$.HCl (63.5 mg, 0.76 mmol) and pyridine (61 µl, 0.70 mmol) in EtOH (10 ml) was heated to reflux. After 2 h, the solution was evaporated under vacuum. The crude residue was triturated with Et$_2$O/H$_2$O 90/10 to give (E)-3-{1'-benzyl-4-methyloxyimino-spiro[chromane-2,4'-piperidine]-6-yl}-N-hydroxy-acrylamide (150 mg) as a 90/10 mixture of the two isomers (hydrochloride salts).

Y=94%

LC-MS: Method E, rt=10.8 min; (ES+) MH$^+$: 422

$^1$H-NMR (DMSO-d$_6$) δ (ppm): 10.74 (bs, 1H), 9.03 (bs, 1H), 7.98 (s, 1H), 7.50 (m, 7H), 7.07 (d, J=8 Hz, 1H), 6.42 (d, J=16 Hz, 1H), 4.39 (m, 2H), 3.99 (s, 3H), 3.14 (m, 4H), 2.89 (s, 2H), 2.06 (m, 4H).

Example 19

(E)-3-{1'-Benzyl-4-hydroxyimino-spiro[chromane-2,4'-piperidine]-6-yl}-N-hydroxy-acrylamide

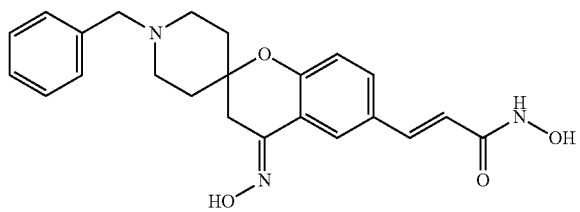 [SMILES: O=C(/C=C/c1ccc2c(c1)/C(=N/O)CC1(CCN(Cc3ccccc3)CC1)O2)NO]

A mixture of (E)-3-{1'-Benzyl-4-oxo-spiro[chromane-2,4'-piperidine]-6-yl}-N-hydroxy-acrylamide hydrochloride (150 mg, 0.35 mmol), NH$_2$OH.HCl (53 mg, 0.76 mmol) and pyridine (61 µl, 0.700 mmol) in EtOH (10 ml) was heated to reflux. After 2 h, the solution was evaporated under vacuum. The crude residue was triturated with Et$_2$O/H$_2$O 90/10 to give (E)-3-{1'-benzyl-4-hydroxyimino-spiro[chromane-2,4'-piperidine]-6-yl}-N-hydroxy-acrylamide (150 mg) as a 98/2 mixture of the two isomers (hydrochloride salts).

Y=97%

LC-MS: Method E, rt=9.7 min; (ES+) MH$^+$: 408

$^1$H-NMR (DMSO-d$_6$) δ (ppm): 11.57 (bs, 1H), 10.71 (bs, 1H), 10.32 (bs, 1H), 7.96 (m, 1H), 7.52 (m, 7H), 7.01 (d, J=8 Hz, 1H), 6.41 (d, J=16 Hz, 1H), 4.36 (m, 2H), 3.40 (m, 4H), 2.85 (s, 2H), 2.11 (m, 4H).

Example 20

(E)-3-{3-oxo-spiro[benzofuran-2(3H),4'-piperidin]-5-yl}-N-hydroxy-acrylamide

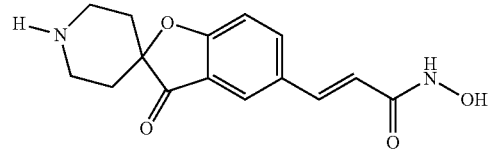 [SMILES: O=C(/C=C/c1ccc2c(c1)C(=O)C1(CCNCC1)O2)NO]

(E)-3-{1'-Tert-butoxycarbonyl-3-oxo-spiro[benzofuran-2(3H),4'-piperidin]-5-yl}-acrylic acid methyl ester (100 mg, 0.258 mmol, Intermediate 4, Step E) was hydrolyzed with NaOH following the procedure described in Example 1, Step A, giving (E)-3-{1'-tert-butoxycarbonyl-3-oxo-spiro[benzofuran-2(3H),4'-piperidin]-5-yl}-acrylic acid as a white solid (95 mg, 98%). The product was treated with NH$_2$OTHP according to the procedure described in Example 1, Step B, giving (E)-3-{1'-tert-butoxycarbonyl-3-oxo-spiro[benzofuran-2(3H),4'-piperidin]-5-yl}-N-(tetrahydro-pyran-2-yloxy)-acrylamide as a yellow solid (89 mg, 74%). Finally, removal of the protecting groups following the procedure described in Example 1, Step C gave (E)-3-{3-oxo-spiro[benzofuran-2(3H),4'-piperidin]-5-yl}-N-hydroxy-acrylamide (14 mg, 23%) as its hydrochloride salt.

Y=17% (over 3 steps)

LC-MS: Method E, rt=4.9 min; (ES+) MH$^+$: 289

$^1$H-NMR (DMSO-d$_6$) δ (ppm): 10.74 (bs, 1H), 8.96 (bs, 1H), 8.80 (bs, 1H), 8.02 (dd, J=8, 1.6 Hz, 1H), 7.87 (d, J=1 Hz, 1H), 7.52 (d, J=16 Hz, 1H), 7.36 (d, J=8 Hz, 1H), 6.46 (d, J=16 Hz, 1H), 3.15 (m, 2H), 2.60 (m, 2H), 2.12 (m, 2H), 1.95 (m, 2H).

Example 21

(E)-3-{1'-Benzyl-3-oxo-spiro[benzofuran-2(3H),4'-piperidin]-5-yl}-N-hydroxy-acrylamide

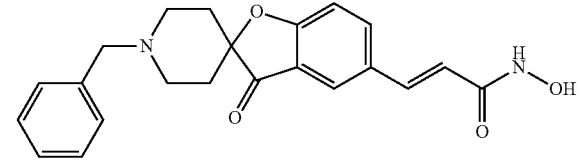 [SMILES: O=C(/C=C/c1ccc2c(c1)C(=O)C1(CCN(Cc3ccccc3)CC1)O2)NO]

(E)-3-{1'-Benzyl-3-oxo-spiro[benzofuran-2(3H),4'-piperidin]-5-yl}-acrylic acid methyl ester was obtained starting from (E)-3-{3-oxo-spiro[benzofuran-2(3H),4'-piperidin]-5-yl}-acrylic acid methyl ester (247 mg, 0.76 mmol, Intermediate 4) and benzyl bromide, according to the procedure described in Example 2, Step A (280 mg, 98%). The methyl ester was hydrolyzed with NaOH following the procedure described in Example 1, Step A, giving (E)-3-{1-benzyl-3-oxo-spiro[benzofuran-2(3H),4'-piperidin]-5-yl}-acrylic acid as a white solid (249 mg, 93%). The resulting acid was treated with NH₂OTHP according to the procedure described in Example 1, Step B, giving (E)-3-{1-benzyl-3-oxo-spiro[benzofuran-2(3H),4'-piperidin]-5-yl}-N-(tetrahydro-pyran-2-yloxy)-acrylamide as a yellow solid (62 mg, 20%). Finally, removal of the THP protecting group following the procedure described in Example 1, Step C gave (E)-3-{1-benzyl-3-oxo-spiro[benzofuran-2(3H),4'-piperidin]-5-yl}-N-hydroxy-acrylamide as its hydrochloride salt (30 mg, 50%).

Y=9% (over 4 steps)

LC-MS: Method D, rt=4.1 min; (ES+) MH⁺: 379

¹H-NMR (DMSO-d₆) δ (ppm): 10.89 (bs, 1H), 8.00 (d, J=8 Hz, 1H), 7.65 (m, 2H), 7.47 (m, 4H), 7.31 (m, 1H), 6.47 (d, J=16 Hz, 1H), 4.42 (d, J=4 Hz, 2H), 3.44 (m, 2H), 3.21 (m, 2H), 2.27 (m, 2H), 1.96 (m, 2H).

Example 22

(E)-3-{1'-Acetyl-3-oxo-spiro[benzofuran-2(3H),4'-piperidin]-5-yl}-N-hydroxy-acrylamide

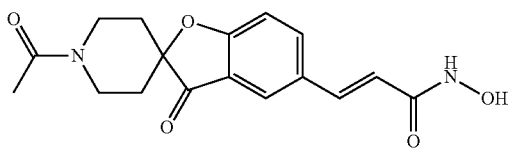 [SMILES: CC(=O)N1CCC2(CC1)Oc1ccc(/C=C/C(=O)NO)cc1C2=O]

(E)-3-{1'-Acetyl-3-oxo-spiro[benzofuran-2(3H),4'-piperidin]-5-yl}-acrylic acid methyl ester was obtained starting from (E)-3-{3-oxo-spiro[benzofuran-2(3H),4'-piperidin]-5-yl}-acrylic acid methyl ester (112 mg, 0.348 mmol, Intermediate 4) and acetyl chloride, according to the procedure described in Example 2, Step A, giving a white solid (100 mg, 87%). The methyl ester group was hydrolyzed with NaOH following the procedure described in Example 1, Step A, giving (E)-3-{1'-acetyl-3-oxo-spiro[benzofuran-2(3H),4'-piperidin]-5-yl}-acrylic acid as a white solid (34 mg, 36%). The product was treated with NH₂OTHP according to the procedure described in Example 1, Step B, giving (E)-3-{1'-acetyl-3-oxo-spiro[benzofuran-2(3H),4'-piperidin]-5-yl}-N-(tetrahydro-pyran-2-yloxy)-acrylamide as a yellow solid (25 mg, 56%). Finally, removal of the THP protecting group following the procedure described in Example 2, Step D and purification by LC-MS gave the requisite (E)-3-{t-acetyl-3-oxo-spiro[benzofuran-2(3H),4'-piperidin]-5-yl}-N-hydroxy-acrylamide (4 mg).

Y=2% (over 4 steps)

LC-MS: Method E, rt=8.3 min; (ES+) MH⁺: 331

¹H-NMR (DMSO-d₆) δ (ppm): 10.75 (bs, 1H), 8.03 (m, 1H), 7.89 (s, 1H), 7.55 (d, J=16 Hz, 1H), 7.41 (d, J=8 Hz, 1H), 6.49 (d, J=16 Hz, 1H), 4.43 (bs, 1H), 3.58 (m, 2H), 3.03 (m, 1H), 2.11 (s, 3H), 1.92 (m, 4H).

Example 23

(E)-3-{1'-Benzoyl-3-oxo-spiro[benzofuran-2(3H),4'-piperidin]-5-yl}-N-hydroxy-acrylamide

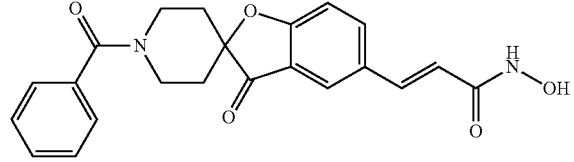 [SMILES: O=C(/C=C/c1ccc2c(c1)C(=O)C1(CCN(C(=O)c3ccccc3)CC1)O2)NO]

(E)-3-{1'-Benzoyl-3-oxo-spiro[benzofuran-2(3H),4'-piperidin]-5-yl}-acrylic acid methyl ester was obtained starting from (E)-3-{3-oxo-spiro[benzofuran-2(3H),4'-piperidin]-5-yl}-acrylic acid methyl ester (100 mg, 0.309 mmol) and benzoyl chloride, according to the procedure described in Example 2, Step A, giving a white solid (110 mg, 91%). The methyl ester was hydrolyzed with NaOH following the procedure described in Example 1, Step A, giving (E)-3-{t-benzoyl-3-oxo-spiro[benzofuran-2(3H),4'-piperidin]-5-yl}-acrylic acid as a white solid (62 mg, 59%). The product was treated with NH₂OTHP according to the procedure described in Example 1, Step B, giving (E)-3-{1'-benzoyl-3-oxo-spiro[benzofuran-2(3H),4'-piperidin]-5-yl}-N-(tetrahydro-pyran-2-yloxy)-acrylamide as a yellow solid (48 mg, 61%). Finally, removal of the THP protecting group following the procedure described in Example 2, Step D gave (E)-3-{1'-benzoyl-3-oxo-spiro[benzofuran-2(3H),4'-piperidin]-5-yl}-N-hydroxy-acrylamide (14 mg, 35%).

Y=11% (over 4 steps)

LC-MS: Method E, rt=12.8 min; (ES+) MH⁺: 393

¹H-NMR (DMSO-d₆) δ (ppm): 10.70 (bs, 1H), 7.99 (d, J=8 Hz, 1H), 7.86 (s, 1H), 7.48 (m, 6H), 7.37 (d, J=8 Hz, 1H), 6.45 (d, J=16 Hz, 1H), 3.50 (m, 4H), 1.83 (m, 4H).

Example 24

(E)-3-{1'-Ethyloxycarbonyl-3-oxo-spiro[benzofuran-2(3H),4'-piperidin]-5-yl}-N-hydroxy-acrylamide

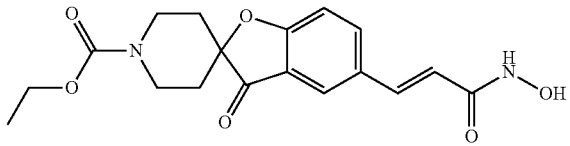 [SMILES: CCOC(=O)N1CCC2(CC1)Oc1ccc(/C=C/C(=O)NO)cc1C2=O]

(E)-3-{1'-Ethyloxycarbonyl-3-oxo-spiro[benzofuran-2(3H),4'-piperidin]-5-yl}-acrylic acid methyl ester was obtained starting from (E)-3-{3-oxo-spiro[benzofuran-2(3H),4'-piperidin]-5-yl}-acrylic acid methyl ester (29 mg, 0.090 mmol, Intermediate 4) and ethyl chloro formate, according to the procedure described in Example 2, Step A, giving a solid (30 mg, 93%). The methyl ester was hydrolyzed with NaOH following the procedure described in Example 1, Step A, giving (E)-3-{1'-ethyloxycarbonyl-3-oxo-spiro[benzofuran-2(3H),4'-piperidin]-5-yl}-acrylic acid as a white solid (28 mg, 97%). The resulting acid was treated with NH₂OTHP according to the procedure described in Example 1, Step B, giving (E)-3-{1'-ethyloxycarbonyl-3-oxo-spiro[benzofuran-2(3H),4'-piperidin]-5-yl}-N-(tetrahydro-pyran-2-yloxy)-acrylamide as a yellow solid (28 mg, 77%). Finally, removal of the THP protecting group following the procedure described in Example 1, Step C gave (E)-3-{1'-ethyloxycarbonyl-3-oxo-spiro[benzofuran-2(3H),4'-piperidin]-5-yl}-N-hydroxy-acrylamide as its hydrochloride salt (10.9 mg, 48%).

Y=34% (over 4 steps)

LC-MS: Method B, rt=1.24 min; (ES+) MH⁺: 361

¹H-NMR (DMSO-d₆) δ (ppm): 10.80 (bs, 1H), 8.03 (d, J=8 Hz, 1H), 7.89 (s, 1H), 7.55 (d, J=16 Hz, 1H), 7.40 (d, J=8 Hz, 1H), 6.49 (d, J=16 Hz, 1H), 4.12 (q, J=7 Hz, 2H), 4.06 (bs, 2H), 3.24 (bs, 2H), 1.76 (m, 4H), 1.26 (t, J=7 Hz, 3H).

Example 25

(E)-3-{1'-Benzyl-3,4-dihydro-4-oxo-spiro[2H-(1,3)-benzoxazine-2,4'-piperidin]-6-yl}-N-hydroxy-acrylamide

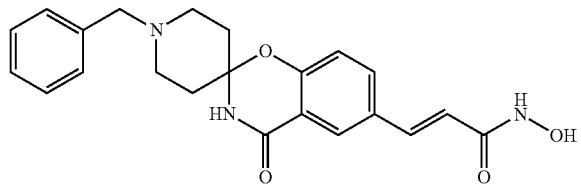 [SMILES: O=C(/C=C/c1ccc2c(c1)C(=O)NC1(CCN(Cc3ccccc3)CC1)O2)NO]

Step A

A mixture of 5-bromo salicylamide (2.5 g, 11.6 mmol), N—BOC-4-piperidone (2.30 g, 11.6 mmol) and pyrrolidine (0.96 ml, 11.6 mmol) in toluene (40 ml) was heated to reflux under $N_2$ atmosphere. After 3 h, the mixture was cooled down to RT, poured into water and extracted with AcOEt. The organic phase was washed with a 2 M solution of NaOH (150 ml) and then with 2 M HCl (150 ml), dried over $Na_2SO_4$, filtered and the solvent was evaporated under vacuum. The crude mixture was purified by column chromatography using DCM/MeOH 90/10 as eluent, to give 1.82 g of 6-bromo-3,4-dihydro-4-oxo-spiro[2H-(1,3)-benzoxazine-2,4'-piperidin]-1'-carboxylic acid tert-butyl ester as a white solid (40%). Reaction with methyl acrylate according to the procedure for preparation of Intermediate 1, Step B, gave (E)-3-{1'-tert-butoxycarbonyl-3,4-dihydro-4-oxo-spiro[2H-(1,3)-benzoxazine-2,4'-piperidin]-6-yl}-acrylic acid methyl ester (1.3 g, 71%) as a yellow solid.

LC-MS: Method B, rt=1.91 min; (ES+) MH$^+$: 403

$^1$H-NMR (DMSO-d$_6$) δ (ppm): 8.81 (s, 1H), 8.03 (d, J=2.35 Hz, 1H), 7.93 (dd, J=8.66, 2.20 Hz, 1H), 7.68 (d, J=16.14 Hz, 1H), 7.12 (d, J=8.51 Hz, 1H), 6.57 (d, J=16.14 Hz, 1H), 3.74-3.82 (m, 2H), 3.73 (s, 3H), 3.00-3.24 (m, 2H), 1.87-2.12 (m, 2H), 1.60-1.84 (m, 2H), 1.41 (s, 9H).

Step B (E)-3-{1'-tert-Butoxycarbonyl-3,4-dihydro-4-oxo-spiro[2H-(1,3)-benzoxazine-2,4'-piperidin]-6-yl}-acrylic acid methyl ester (1.20 g, 3.0 mmol) was deprotected with HCl according to the procedure for preparation of Intermediate 1, Step C, giving (E)-3-{-3,4-dihydro-4-oxo-spiro[2H-(1,3)-benzoxazine-2,4'-piperidin]-6-yl}-acrylic acid methyl ester (694 mg) as its hydrochloride salt.

Y=69%

LC-MS: Method B, rt=0.84 min; (ES+) MH$^+$: 303

$^1$H-NMR (DMSO-d$_6$) δ (ppm): 9.20 (s, 1H), 9.01 (bs, 1H), 8.08 (d, J=2 Hz, 1H), 8.00 (dd, J=8, 2 Hz, 1H), 7.72 (d, J=16 Hz, 1H), 7.21 (d, J=8 Hz, 1H), 6.63 (d, J=16 Hz, 1H), 3.76 (s, 3H), 3.30 (bs, 2H), 3.16 (bs, 2H), 2.26 (bs, 2H), 2.09 (bs, 2H).

Step C (E)-3-{1'-Benzyl-3,4-dihydro-4-oxo-spiro[2H-(1,3)-benzoxazine-2,4'-piperidin]-6-yl}-acrylic acid methyl ester was obtained starting from (E)-3-{-3,4-dihydro-4-oxo-spiro[2H-(1,3)-benzoxazine-2,4'-piperidin]-6-yl}-acrylic acid methyl ester (0.28 g, 0.83 mmol) and benzyl bromide, according to the procedure described in Example 2, Step A, giving a white solid (145 mg, 45%). The methyl ester was hydrolyzed with NaOH following the procedure described in Example 1, Step A, giving (E)-3-{1'-benzyl-3,4-dihydro-4-oxo-spiro[2H-(1,3)-benzoxazine-2,4'-piperidin]-6-yl}-acrylic acid as a white solid (110 mg, 79%). The resulting product was treated with NH$_2$OTHP according to the procedure described in Example 1, Step B, giving (E)-3-{1-benzyl-3,4-dihydro-4-oxo-spiro[2H-(1,3)-benzoxazine-2,4'-piperidin]-6-yl}-N-(tetrahydro-pyran-2-yloxy)-acrylamide as a yellow solid (50 mg, 36%). Finally, removal of the THP protecting group following the procedure described in Example 1, Step C gave (E)-3-{1-benzyl-3,4-dihydro-4-oxo-spiro[2H-(1,3)-benzoxazine-2,4'-piperidin]-6-yl}-N-hydroxy-acrylamide (12 mg, 27%) as its hydrochloride salt.

Y=3% (over 4 steps)

LC-MS: Method E, rt=8.3 min; (ES+) MH$^+$: 394

$^1$H-NMR (DMSO-d$_6$) δ (ppm): 10.78 (bs, 1H), 9.96 (bs, 1H), 9.16 (m, 2H), 8.00 (s, 1H), 7.87 (m, 1H), 7.66 (m, 6H), 7.15 (d, J=2 Hz, 1H), 6.46 (d, J=16 Hz, 1H), 4.42 (bs, 2H), 3.30 (m, 4H), 2.36 (m, 2H), 2.12 (m, 2H).

Example 26

(E)-3-{1-Benzyl-3',4'-dihydro-4'-oxo-spiro[piperidine-4,2'(1'H)-quinazoline]-6'-yl}-N-hydroxy-acrylamide

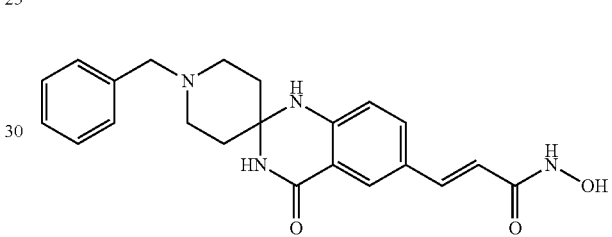

Step A

Isatoic anhydride (5.0 g, 21 mmol) was dissolved in aqueous $NH_3$ (30%) and stirred at RT. After 2 h, the mixture was poured into water and extracted with DCM, dried, filtered and evaporated under vacuum to yield 2-amino-5-bromo-benzamide (4.5 g, 100%), which was used without any further purification.

LC-MS: Method B, rt=1.19 min; (ES+) MH$^+$: 216

$^1$H-NMR (CDCl$_3$) δ (ppm): 7.40 (d, J=2 Hz, 1H), 7.22 (dd, J=8, 2 Hz, 1H), 6.50 (d, J=8 Hz, 1H), 5.62 (bs, 2H).

Step B

N-benzyl 4-piperidone (1.76 g, 9.3 mmol) and concentrated $H_2SO_4$ (2 drops) were added to a solution of 2-amino-5-bromo-benzamide (2 g, 9.3 mmol) dissolved in acetic acid (15 ml). The mixture was stirred at RT for 2 h, then poured into ice water and brought to a pH value of 8-9 with saturated NaHCO$_3$. The white precipitate was filtered off and washed with water, giving 1-benzyl-6'-bromo-3',4'-dihydro-spiro[piperidine-4,2'(1'H)-quinazoline]-4'-one (1.05 g).

LC-MS: Method B, rt=1.16 min; (ES+) MH$^+$: 387

$^1$H-NMR (DMSO-d$_6$) δ (ppm): 8.19 (bs, 1H), 7.66 (d, J=2 Hz, 1H), 7.35 (m, 5H), 7.00 (s, 1H), 6.85 (d, J=8 Hz, 1H), 3.53 (s, 2H), 2.70 (t, J=6 Hz, 1H), 2.59 (m, 1H), 2.45 (m, 1H), 2.38 (t, J=6 Hz, 1H), 1.82 (m, 4H).

Step C (E)-3-{1-Benzyl-3',4'-dihydro-4'-oxo-spiro[piperidine-4,2'(1'H)-quinazoline]-6'-yl}-acrylic acid tert-butyl ester was synthesized starting from 1-benzyl-6'-bromo-3',4'-dihydro-spiro[piperidine-4,2'(1'H)-quinazoline]-4'-one (600 mg, 1.55 mmol) and tert-butyl acrylate according to the procedure described for Intermediate 1, Step B, giving 486 mg of the product.

Y=72%

LC-MS: Method B, rt=1.43 min; (ES+) MH+: 434

¹H-NMR (DMSO-d₆) δ (ppm): 7.80 (m, 1H), 7.65 (dd, J=6, 1 Hz, 1H), 7.49 (s, 1H), 7.38 (m, 5H), 6.90 (d, J=8 Hz, 1H), 6.24 (d, J=16 Hz, 1H), 3.64 (m, 2H), 2.60 (m, 2H), 2.48 (m, 2H), 1.83 (m, 4H), 1.50 (s, 9H).

Step D (E)-3-{1-Benzyl-3',4'-dihydro-4'-oxo-spiro[piperidine-4,2'(1'H)-quinazoline]-6'-yl}-acrylic acid tert-butyl ester (480 mg, 1.08 mmol) was dissolved in a mixture of DCM (5 ml) and TFA (0.82 ml). (E)-3-{1-Benzyl-3',4'-dihydro-4'-oxo-spiro[piperidine-4,2'(1'H)-quinazoline]-6'-yl}-acrylic acid was recovered as a white solid after evaporation under vacuum (520 mg, 98%). The crude product was treated with NH₂OTHP according to the procedure described in Example 1, Step B, giving (E)-3-{1-benzyl-3',4'-dihydro-4'-oxo-spiro[piperidine-4,2'(1'H)-quinazoline]-6'-yl}-N-(tetrahydro-pyran-2-yloxy)-acrylamide as a yellow solid (12 mg, 3%). Finally, removal of the THP protecting group following the procedure described in Example 2, Step D gave (E)-3-{1-benzyl-3',4'-dihydro-4'-oxo-spiro[piperidine-4,2'(1H)quinazoline]-6'-yl}-N-hydroxy-acrylamide (10 mg, 93%) as its hydrochloride salt.

Y=2% (over 3 steps).

LC-MS: Method E, rt=7.5 min; (ES+) MH+: 393

¹H-NMR (DMSO-d₆) δ (ppm): 11.05 (bs, 1H), 10.36 (bs, 1H), 8.50 (m, 2H), 7.64 (m, 5H), 7.09 (m, 1H), 6.81 (m, 1H), 6.30 (m, 1H), 5.80 (bs, 1H), 3.32 (m, 6H), 2.15 (m, 4H).

Example 27

(E)-3-{1'-Pyrimidin-2-yl-4-oxo-spiro[chromane-2,4'-piperidine]-6-yl}-N-hydroxy-acrylamide

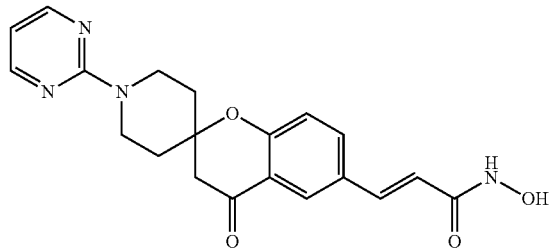 [SMILES: O=C(/C=C/c1ccc2c(c1)C(=O)CC1(CCN(c3ncccn3)CC1)O2)NO]

(E)-3-{1'-Pyrimidin-2-yl-4-oxo-spiro[chromane-2,4'-piperidine]-6-yl}-acrylic acid methyl ester was obtained by reacting (E)-3-{4-oxo-spiro[chromane-2,4'-piperidine]-6-yl}-acrylic acid methyl ester (1.32 g, 3.92 mmol, Intermediate 1) with 2-chloro-pyrimidine (0.536 g, 4.70 mmol) and TEA (1.36 ml, 9.8 mmol) in 20 ml toluene heated to reflux for 8 h. The formed salts were then filtered off, the solvent removed under vacuum and the intermediate was purified by column chromatography (eluent:hexane/AcOEt 7:3 to AcOEt) giving a white solid (530 mg, 36%). The methyl ester was hydrolyzed with NaOH following the procedure described in Example 1, Step A, giving (E)-3-{1'-pyrimidin-2-yl-4-oxo-spiro[chromane-2,4'-piperidine]-6-yl}-acrylic acid as a yellow solid (400 mg, 80%). The resulting acid was treated with NH₂OTHP according to the procedure described in Example 1, Step B, giving (E)-3-{1'-pyrimidin-2-yl-4-oxo-spiro[chromane-2,4'-piperidine]-6-yl}-N-(tetrahydropyran-2-yloxy)-acrylamide as a yellow oil (180 mg, 35%). Finally, removal of the THP protecting group following the procedure described in Example 1, Step C gave (E)-3-{1'-pyrimidin-2-yl-4-oxo-spiro[chromane-2,4'-piperidine]-6-yl}-N-hydroxy-acrylamide (50 mg, 34%).

Y=3% (over 4 steps)

LC-MS: Method E, rt=10.8 min; (ES+) MH+: 381

¹H-NMR (DMSO-d₆) δ (ppm): 10.65 (bs, 1H), 9.07 (bs, 1H), 8.40 (m, 2H), 8.04 (m, 1H), 7.83 (d, J=8 Hz, 1H), 7.46 (d, J=16 Hz, 1H), 7.19 (d, J=8 Hz, 1H), 6.66 (t, J=4, 1H), 6.46 (d, J=16 Hz, 1H), 4.41 (d, J=13 Hz, 2H), 3.40 (m, 2H), 2.94 (s, 2H), 1.99 (d, J=13 Hz, 2H), 1.74 (t, J=10 Hz, 2H).

Example 28

(E)-3-{1'-(2-Methyl-benzyl)-4-oxo-spiro[chromane-2,4'-piperidine]-6-yl}-N-hydroxy-acrylamide

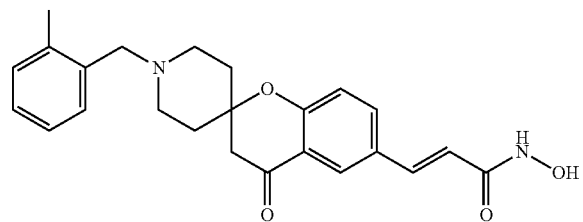 [SMILES: Cc1ccccc1CN1CCC2(CC1)CC(=O)c1cc(/C=C/C(=O)NO)ccc1O2]

The title compound was prepared starting from (E)-3-{4-oxo-spiro[chromane-2,4'-piperidine]-6-yl}-acrylic acid methyl ester hydrochloride (Intermediate 1) and 2-methyl-benzyl bromide according to the procedure described in Example 2. The title compound was obtained as its hydrochloride salt.

LC-MS: Method I rt=1.89; (ES+) MH+: 407

¹H NMR (DMSO-d₆) δ (ppm): 7.77-7.86 (m, 1H), 7.69-7.77 (m, 1H), 6.85-7.33 (m, 6H), 6.37 (d, J=15.85 Hz, 1H), 3.46 (s, 2H), 2.82 (s, 2H), 2.52-2.60 (m, 2H), 2.34-2.46 (m, 2H), 2.32 (s, 3H), 1.80-2.03 (m, 2H), 1.40-1.78 (m, 2H).

Example 29

(E)-3-{1'-(3-Methyl-benzyl)-4-oxo-spiro[chromane-2,4'-piperidine]-6-yl}-N-hydroxy-acrylamide

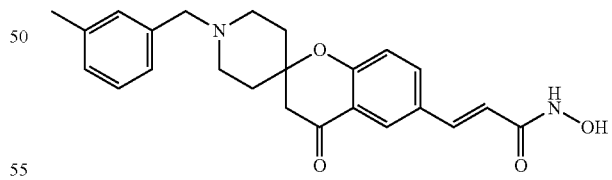

The title compound was prepared starting from (E)-3-{4-oxo-spiro[chromane-2,4'-piperidine]-6-yl}-acrylic acid methyl ester hydrochloride (Intermediate 1) and 3-methyl-benzyl chloride according to the procedure described in Example 2. The title compound was obtained as its hydrochloride salt.

LC-MS: Method G, rt=1.36; (ES+) MH+: 407

¹H NMR (DMSO-d₆ 373K) δ (ppm): 7.90 (d, J=2.35 Hz, 1H), 7.78 (dd, J=8.51, 2.35 Hz, 1H), 7.38-7.50 (m, 3H), 7.34 (t, J=7.34 Hz, 1H), 7.20-7.30 (m, 1H), 7.12 (d, J=8.51 Hz, 1H), 6.52 (d, J=15.85 Hz, 1H), 4.28 (s, 2H), 3.22 (bs, 4H), 2.91 (bs, 2H), 2.36 (s, 3H), 2.13-2.25 (m, 4H).

Example 30

(E)-3-{1'-(4-Methyl-benzyl)-4-oxo-spiro[chromane-2,4'-piperidine]-6-yl}-N-hydroxy-acrylamide

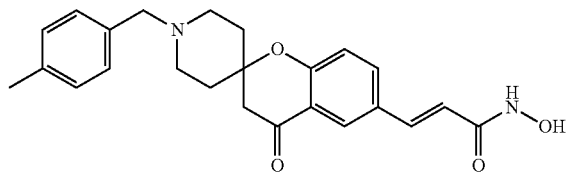 [SMILES: Cc1ccc(CN2CCC3(CC2)CC(=O)c2cc(/C=C/C(=O)NO)ccc2O3)cc1]

The title compound was prepared starting from (E)-3-{4-oxo-spiro[chromane-2,4'-piperidine]-6-yl}-acrylic acid methyl ester hydrochloride (Intermediate 1) and 4-methyl benzyl chloride according to the procedure described in Example 2. The title compound was obtained as its hydrochloride salt.

LC-MS: Method G, rt=1.35; (ES+) MH+: 407

$^1$H NMR (DMSO-d$_6$) δ (ppm): 7.85 (s, 1H), 7.63-7.81 (m, 1H), 7.38 (d, J=15.85 Hz, 1H), 7.18 (m, 2H), 7.11 (m, 2H), 7.08 (d, J=11.15 Hz, 1H), 6.44 (d, J=15.55 Hz, 1H), 3.44 (s, 2H), 2.82 (s, 2H), 2.55 (bs, 2H), 2.28-2.41 (m, 2H), 2.27 (s, 3H), 1.79-2.03 (m, 2H), 1.55-1.80 (m, 2H).

Example 31

(E)-3-{1'-(2-Methoxy-benzyl)-4-oxo-spiro[chromane-2,4'-piperidine]-6-yl}-N-hydroxy-acrylamide

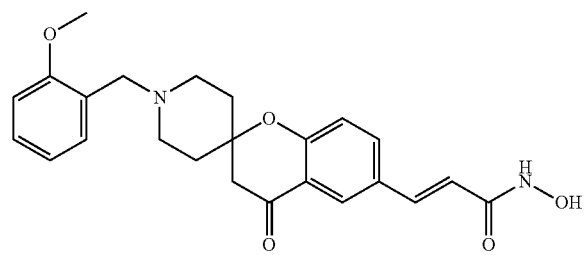 [SMILES: COc1ccccc1CN1CCC2(CC1)CC(=O)c1cc(/C=C/C(=O)NO)ccc1O2]

The title compound was prepared starting from (E)-3-{4-oxo-spiro[chromane-2,4'-piperidine]-6-yl}-acrylic acid methyl ester hydrochloride (Intermediate 1) and 2-methoxybenzyl bromide according to the procedure described in Example 2. The title compound was obtained as its hydrochloride salt.

LC-MS: Method G, rt=1.29; (ES+) MH+: 423

$^1$H NMR (DMSO-d$_6$) δ (ppm): 7.79 (d, J=2.05 Hz, 1H), 7.73 (dd, J=8.51, 2.05 Hz, 1H), 7.14-7.42 (m, 3H), 7.05 (d, J=8.51 Hz, 1H), 6.96 (d, J=7.92 Hz, 1H), 6.91 (td, J=7.41, 1.03 Hz, 1H), 6.36 (d, J=15.55 Hz, 1H), 3.77 (s, 3H), 3.49 (s, 2H), 2.82 (s, 2H), 2.53-2.65 (m, 2H), 2.32-2.46 (m, 2H), 1.81-2.03 (m, 2H), 1.59-1.81 (m, 2H).

Example 32

(E)-3-{1'-(3-Methoxy-benzyl)-4-oxo-spiro[chromane-2,4'-piperidine]-6-yl}-N-hydroxy-acrylamide

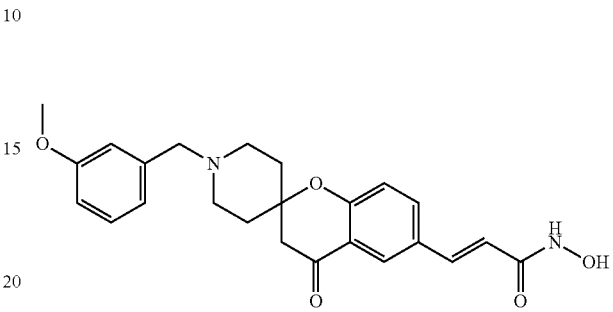

The title compound was prepared starting from (E)-3-{4-oxo-spiro[chromane-2,4'-piperidine]-6-yl}-acrylic acid methyl ester hydrochloride (Intermediate 1) and 3-methoxybenzyl chloride according to the procedure described in Example 2. The title compound was obtained as its hydrochloride salt.

LC-MS: Method G, rt=1.29; (ES+) MH+: 423

$^1$H NMR (DMSO-d$_6$) δ (ppm): 7.77 (d, J=1.76 Hz, 1H), 7.72 (dd, J=8.80, 2.35 Hz, 1H), 7.22 (t, J=8.07 Hz, 1H), 7.17 (d, J=15.85 Hz, 1H), 7.03 (d, J=8.51 Hz, 1H), 6.61-6.96 (m, 3H), 6.35 (d, J=15.85 Hz, 1H), 3.74 (s, 3H), 3.47 (s, 2H), 2.82 (s, 2H), 2.52-2.64 (m, 2H), 2.27-2.45 (m, 2H), 1.82-2.04 (m, 2H), 1.58-1.81 (m, 2H).

Example 33

(E)-3-{1'-(4-Methoxy-benzyl)-4-oxo-spiro[chromane-2,4'-piperidine]-6-yl}-N-hydroxy-acrylamide

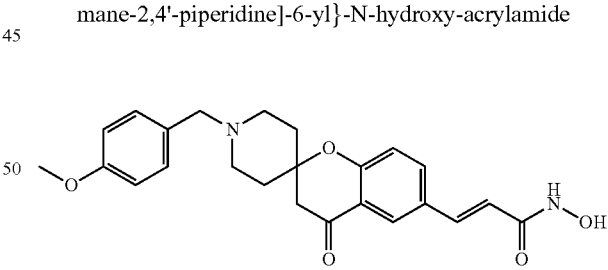

The title compound was prepared starting from (E)-3-{4-oxo-spiro[chromane-2,4'-piperidine]-6-yl}-acrylic acid methyl ester hydrochloride (Intermediate 1) and 4-methoxybenzyl bromide according to the procedure described in Example 2. The title compound was obtained as its hydrochloride salt.

LC-MS: Method G, rt=1.28; (ES+) MH+: 423

$^1$H NMR (DMSO-d$_6$) δ (ppm): 7.79 (d, J=1.76 Hz, 1H), 7.73 (dd, J=8.80, 2.35 Hz, 1H), 7.14-7.29 (m, 3H), 7.04 (d, J=8.51 Hz, 1H), 6.87 (m, 2H), 6.35 (d, J=15.85 Hz, 1H), 3.73

(s, 3H), 3.42 (s, 2H), 2.81 (s, 2H), 2.52-2.60 (m, 2H), 2.29-2.41 (m, 2H), 1.82-1.97 (m, 2H), 1.60-1.79 (m, 2H).

Example 34

(E)-3-{1'-(2-Fluoro-benzyl)-4-oxo-spiro[chromane-2,4'-piperidine]-6-yl}-N-hydroxy-acrylamide

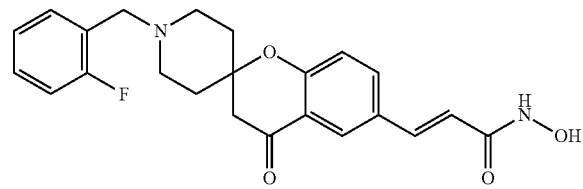 [SMILES: O=C(/C=C/c1ccc2c(c1)C(=O)CC1(CCN(Cc3ccccc3F)CC1)O2)NO]

The title compound was prepared starting from (E)-3-{4-oxo-spiro[chromane-2,4'-piperidine]-6-yl}-acrylic acid methyl ester hydrochloride (Intermediate 1) and 2-fluoro-benzyl bromide according to the procedure described in Example 2. The title compound was obtained as its hydrochloride salt.

LC-MS: Method I, rt=1.72; (ES+) MH+: 411

$^1$H NMR (DMSO-d$_6$) δ (ppm): 7.78 (d, J=1.91 Hz, 1H), 7.73 (dd, J=8.66, 1.91 Hz, 1H), 7.41 (td, J=7.56, 1.91 Hz, 1H), 7.24-7.36 (m, 1H), 7.08-7.25 (m, 3H), 7.03 (d, J=8.51 Hz, 1H), 6.35 (d, J=15.26 Hz, 1H), 3.55 (s, 2H), 2.81 (s, 2H), 2.53-2.67 (m, 2H), 2.31-2.46 (m, 2H), 1.81-2.02 (m, 2H), 1.58-1.81 (m, 2H).

Example 35

(E)-3-{1'-(3-Fluoro-benzyl)-4-oxo-spiro[chromane-2,4'-piperidine]-6-yl}-N-hydroxy-acrylamide

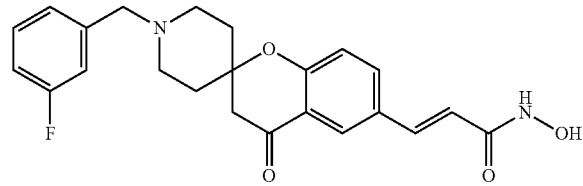 [SMILES: O=C(/C=C/c1ccc2c(c1)C(=O)CC1(CCN(Cc3cccc(F)c3)CC1)O2)NO]

The title compound was prepared starting from (E)-3-{4-oxo-spiro[chromane-2,4'-piperidine]-6-yl}-acrylic acid methyl ester hydrochloride (Intermediate 1) and 3-fluoro-benzyl bromide according to the procedure described in Example 2. The title compound was obtained as its hydrochloride salt.

LC-MS: Method G, rt=1.24; (ES+) MH+: 411

$^1$H NMR (DMSO-d$_6$ 373K) δ (ppm): 7.90 (d, J=2.05 Hz, 1H), 7.78 (dd, J=8.51, 2.35 Hz, 1H), 7.38-7.58 (m, 4H), 7.16-7.31 (m, 1H), 7.12 (d, J=8.80 Hz, 1H), 6.52 (d, J=15.85 Hz, 1H), 4.31 (bs, 2H), 3.20 (bs, 4H), 2.91 (bs, 2H), 2.11-2.26 (m, 4H).

Example 36

(E)-3-{1'-(4-Fluoro-benzyl)-4-oxo-spiro[chromane-2,4'-piperidine]-6-yl}-N-hydroxy-acrylamide

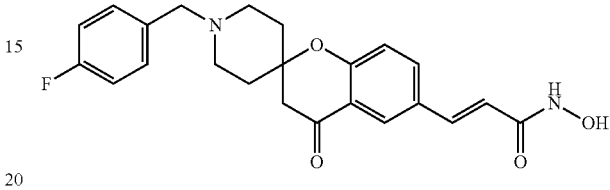

The title compound was prepared starting from (E)-3-{4-oxo-spiro[chromane-2,4'-piperidine]-6-yl}-acrylic acid methyl ester hydrochloride (Intermediate 1) and 4-fluoro-benzyl chloride according to the procedure described in Example 2. The title compound was obtained as its hydrochloride salt.

LC-MS: Method G rt=1.27; (ES+) MH+: 411

$^1$H NMR (DMSO-d$_6$) δ (ppm): 7.79 (d, J=1.47 Hz, 1H), 7.68-7.76 (m, 1H), 7.33 (m, 2H), 7.21 (d, J=16.43 Hz, 1H), 7.13 (m, 2H), 7.04 (d, J=8.51 Hz, 1H), 6.35 (d, J=16.14 Hz, 1H), 3.48 (s, 2H), 2.82 (s, 2H), 2.55-2.60 (m, 2H), 2.29-2.43 (m, 2H), 1.82-1.97 (m, 2H), 1.61-1.79 (m, 2H).

Example 37

(E)-3-{1'-(2-Chloro-benzyl)-4-oxo-spiro[chromane-2,4'-piperidine]-6-yl}-N-hydroxy-acrylamide

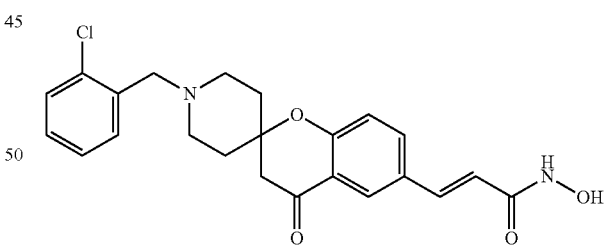

The title compound was prepared starting from (E)-3-{4-oxo-spiro[chromane-2,4'-piperidine]-6-yl}-acrylic acid methyl ester hydrochloride (Intermediate 1) and 2-chloro-benzyl bromide according to the procedure described in Example 2. The title compound was obtained as its hydrochloride salt.

LC-MS: Method G, rt=1.29; (ES+) MH+: 427

$^1$H NMR (DMSO-d$_6$) δ (ppm): 7.79 (d, J=1.76 Hz, 1H), 7.73 (dd, J=8.66, 2.20 Hz, 1H), 7.49 (dd, J=7.48, 1.91 Hz, 1H), 7.38-7.46 (m, 1H), 7.24-7.37 (m, 2H), 7.19 (d, J=15.55 Hz, 1H), 7.06 (d, J=8.51 Hz, 1H), 6.36 (d, J=15.85 Hz, 1H), 3.60 (s, 2H), 2.83 (s, 2H), 2.55-2.67 (m, 2H), 2.37-2.48 (m, 2H), 1.84-2.02 (m, 2H), 1.62-1.83 (m, 2H).

Example 38

(E)-3-{1'-(3-Chloro-benzyl)-4-oxo-spiro[chromane-2,4'-piperidine]-6-yl}-N-hydroxy-acrylamide

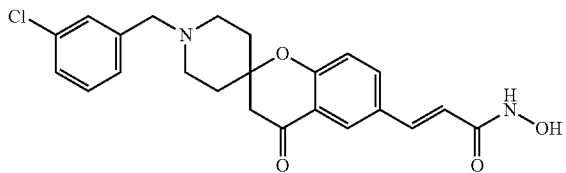 [SMILES: O=C(/C=C/c1ccc2c(c1)C(=O)CC1(CCN(Cc3cccc(Cl)c3)CC1)O2)NO]

The title compound was prepared starting from (E)-3-{4-oxo-spiro[chromane-2,4'-piperidine]-6-yl}-acrylic acid methyl ester hydrochloride (Intermediate 1) and 3-chloro-benzyl bromide according to the procedure described in Example 2. The title compound was obtained as its hydrochloride salt.

LC-MS: Method G, rt=1.37; (ES+) MH+: 427

$^1$H NMR (DMSO-d$_6$ 373K) δ (ppm): 7.91 (d, J=2.35 Hz, 1H), 7.78 (dd, J=8.51, 2.35 Hz, 1H), 7.71 (s, 1H), 7.52-7.62 (m, 1H), 7.38-7.52 (m, 3H), 7.12 (d, J=8.80 Hz, 1H), 6.51 (d, J=15.85 Hz, 1H), 4.28 (bs, 2H), 3.18 (bs, 4H), 2.91 (bs, 2H), 2.04-2.25 (m, 4H).

Example 39

(E)-3-{1'-(4-Chloro-benzyl)-4-oxo-spiro[chromane-2,4'-piperidine]-6-yl}-N-hydroxy-acrylamide

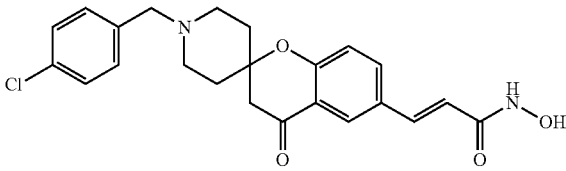 [SMILES: O=C(/C=C/c1ccc2c(c1)C(=O)CC1(CCN(Cc3ccc(Cl)cc3)CC1)O2)NO]

The title compound was prepared starting from (E)-3-{4-oxo-spiro[chromane-2,4'-piperidine]-6-yl}-acrylic acid methyl ester hydrochloride (Intermediate 1) and 4-chloro-benzyl chloride according to the procedure described in Example 2. The title compound was obtained as its hydrochloride salt.

LC-MS: Method G, rt=1.41; (ES+) MH+: 427

$^1$H NMR (DMSO-d$_6$) δ (ppm): 7.65-7.79 (m, 2H), 7.28-7.42 (m, 4H), 7.08 (d, J=16.14 Hz, 1H), 7.01 (d, J=8.22 Hz, 1H), 6.31 (d, J=15.55 Hz, 1H), 3.49 (s, 2H), 2.81 (s, 2H), 2.54-2.59 (m, 2H), 2.31-2.44 (m, 2H), 1.84-1.97 (m, 2H), 1.62-1.78 (m, 2H).

Example 40

(E)-3-{1'-(Pyridin-2-ylmethyl)-4-oxo-spiro[chromane-2,4'-piperidine]-6-yl}-N-hydroxy-acrylamide

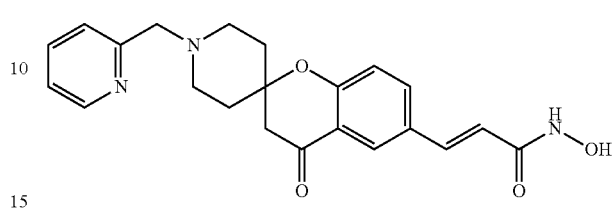

Step A

A suspension of (E)-3-{4-oxo-spiro[chromane-2,4'-piperidine]-6-yl}-acrylic acid methyl ester hydrochloride (150 mg, 0.44 mmol, Intermediate 1) in DCM (7 ml) was treated with TEA (0.49 ml, 3.52 mmol) and 2-(chloromethyl)pyridine hydrochloride (145 mg, 0.89 mmol), and stirred at RT for 48 h. Catalytic amount of KI was added and the reaction was stirred at RT overnight. The mixture was then washed with water and brine, dried and concentrated. The crude residue was purified by column chromatography (eluent: DCM/MeOH/NH$_4$OH 96:4:0.2) to give (E)-3-{1'-(pyridin-2-ylmethyl)-4-oxo-spiro[chromane-2,4'-piperidine]-6-yl}-acrylic acid methyl ester (136 mg).

Y=78%

$^1$H NMR (DMSO-d$_6$) δ (ppm): 8.48 (ddd, J=4.70, 1.76, 0.88 Hz, 1H), 7.99 (dd, J=6.46, 2.05 Hz, 1H), 7.97 (d, J=2.35 Hz, 1H), 7.75 (td, J=7.70, 1.91 Hz, 1H), 7.66 (d, J=15.85 Hz, 1H), 7.44 (d, J=7.63 Hz, 1H), 7.25 (ddd, J=7.41, 4.92, 1.17 Hz, 1H), 7.10 (d, J=9.39 Hz, 1H), 6.55 (d, J=16.14 Hz, 1H), 3.72 (s, 3H), 3.63 (s, 2H), 2.86 (s, 2H), 2.54-2.68 (m, 2H), 2.35-2.47 (m, 2H), 1.85-2.01 (m, 2H), 1.76 (ddd, J=14.38, 10.86, 4.11 Hz, 2H).

Step B

4 M NaOH (0.104 ml, 0.416 mmol) was added to a solution of (E)-3-{1-(pyridin-2-ylmethyl)-4-oxo-spiro[chromane-2,4'-piperidine]-6-yl}-acrylic acid methyl ester (136 mg, 0.347 mmol) in dioxane (2 ml) and water (1 ml) and the resulting mixture was stirred at RT overnight. The pH was brought to 5 with 1 M HCl, the mixture was concentrated under vacuum and the residue was charged on a SCX cartridge. After washing with MeOH, (E)-3-{1'-(pyridin-2-ylmethyl)-4-oxo-spiro[chromane-2,4'-piperidine]-6-yl}-acrylic acid was eluted with 3% NH$_4$OH in MeOH. The crude compound (134 mg) was used in the next step without further purification Y=quantitative Step C (E)-3-{1'-(pyridin-2-ylmethyl)-4-oxo-spiro[chromane-2,4'-piperidine]-6-yl}-acrylic acid (133 mg, crude compound from STEP B) was dissolved in DCM (4 ml) and TEA (0.098 ml, 0.704 mmol). EDC (101 mg, 0.53 mmol) HOBT (71 mg, 0.53 mmol) and NH$_2$OTHP (49 mg, 0.42 mmol) were added, the mixture was stirred at RT overnight and then partitioned between water and DCM. The organic phase was dried over Na$_2$SO$_4$ and evaporated. The crude residue was purified by column chromatography (eluent:DCM/MeOH/NH$_4$OH 96:4: 0.2) and the resulting (E)-3-{1'-(pyridin-2-ylmethyl)-4-oxo-spiro[chromane-2,4'-piperidine]-6-yl}-N-(tetrahydro-pyran- 2-yloxy)-acrylamide was dissolved in DCM and treated with HCl/Et$_2$O for 4 h. The precipitate was filtered and washed with DCM to give (E)-3-{1'-(pyridin-2-ylmethyl)-4-oxo-spiro[chromane-2,4'-piperidine]-6-yl}-N-hydroxy-acrylamide as its di-hydrochloride (66 mg, white powder).

Y=41% (2 steps)

LC-MS: Method G, rt=0.98; (ES+) MH$^+$: 394

$^1$H NMR (DMSO-d$_6$) δ (ppm): 10.94 (bs, 1H), 8.69 (ddd, J=4.77, 1.69, 0.88 Hz, 1H), 7.96 (td, J=7.92, 1.76 Hz, 1H), 7.90 (d, J=2.05 Hz, 1H), 7.83 (dd, J=8.66, 1.91 Hz, 1H), 7.72 (d, J=7.92 Hz, 1H), 7.51 (ddd, J=7.63, 4.99, 1.17 Hz, 1H), 7.44 (d, J=15.85 Hz, 1H), 7.16 (d, J=8.51 Hz, 1H), 6.46 (d, J=15.85 Hz, 1H), 4.56 (s, 2H), 3.23-3.48 (m, 4H), 2.96 (s, 2H), 1.94-2.36 (m, 4H).

Example 41

(E)-3-{1'-(Pyridin-3-ylmethyl)-4-oxo-spiro[chromane-2,4'-piperidine]-6-yl}-N-hydroxy-acrylamide

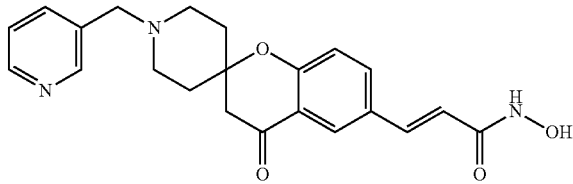 [SMILES: O=C(/C=C/c1ccc2c(c1)C(=O)CC1(CCN(Cc3cccnc3)CC1)O2)NO]

The title compound was prepared starting from (E)-3-{4-oxo-spiro[chromane-2,4'-piperidine]-6-yl}-acrylic acid methyl ester hydrochloride (Intermediate 1) and 3-(chloromethyl)pyridine hydrochloride according to the procedure described in Example 40. The title compound was obtained as its di-hydrochloride salt.

LC-MS: Method G, rt=2.12; (ES+) MH$^+$: 394

$^1$H NMR (DMSO-d$_6$) δ (ppm): 11.93 (bs, 1H), 11.58 (bs, 1H), 9.03 (d, J=1.47 Hz, 1H), 8.84 (dd, J=5.28, 1.17 Hz, 1H), 8.54 (d, J=7.92 Hz, 1H), 7.74-7.99 (m, 3H), 7.45 (d, J=15.85 Hz, 1H), 7.17 (d, J=8.51 Hz, 1H), 6.46 (d, J=15.55 Hz, 1H), 4.54 (bs, 2H), 3.04-3.53 (m, 4H), 2.89 (s, 2H), 2.04-2.32 (m, 4H).

Example 42

(E)-3-{1'-(Pyridin-4-ylmethyl)-4-oxo-spiro[chromane-2,4'-piperidine]-6-yl}-N-hydroxy-acrylamide

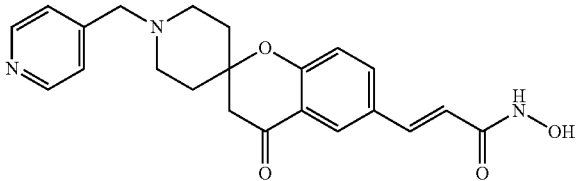 [SMILES: O=C(/C=C/c1ccc2c(c1)C(=O)CC1(CCN(Cc3ccncc3)CC1)O2)NO]

The title compound was prepared starting from (E)-3-{4-oxo-spiro[chromane-2,4'-piperidine]-6-yl}-acrylic acid methyl ester hydrochloride (Intermediate 1) and 4-(chloromethyl)pyridine hydrochloride according to the procedure described in Example 40. The title compound was obtained as its di-hydrochloride salt.

LC-MS: Method G, rt=1.72; (ES+) MH$^+$: 394

$^1$H NMR (DMSO-d$_6$) δ (ppm): 12.26 (bs, 1H), 11.92 (bs, 1H), 8.75-9.05 (m, 2H), 8.08-8.35 (m, 2H), 7.72-8.02 (m, 2H), 7.44 (d, J=15.85 Hz, 1H), 7.17 (d, J=8.51 Hz, 1H), 6.45 (d, J=15.85 Hz, 1H), 4.61 (s, 2H), 3.28 (bs, 4H), 2.89 (bs, 2H), 2.20 (bs, 4H).

Example 43

(E)-3-{1'-Methanesulfonyl-4-oxo-spiro[chromane-2,4'-piperidine]-6-yl}-N-hydroxy-acrylamide

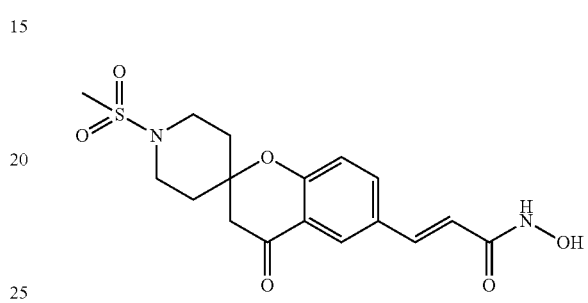

Step A

TEA (0.185 ml, 1.33 mmol) and methanesulfonyl chloride (0.067 ml, 0.88 mmol) were added to a suspension of (E)-3-{4-oxo-spiro[chromane-2,4'-piperidine]-6-yl}-acrylic acid methyl ester hydrochloride (150 mg, 0.44 mmol, Intermediate 1) in DCM (3 ml), and the mixture was stirred at RT overnight. The solvent was removed under vacuum and the residue was purified by column chromatography (eluent: DCM/MeOH 97:3) to give (E)-3-{1'-methanesulfonyl-4-oxo-spiro[chromane-2,4'-piperidine]-6-yl}-acrylic acid methyl ester (162 mg).

Y=97%

$^1$H NMR (CDCl$_3$-d) δ (ppm): 8.05 (d, J=2.35 Hz, 1H), 7.68 (dd, J=8.61, 2.35 Hz, 1H), 7.65 (d, J=15.85 Hz, 1H), 7.04 (d, J=8.80 Hz, 1H), 6.40 (d, J=15.85 Hz, 1H), 3.82 (s, 3H), 3.60-3.72 (m, 2H), 3.14 (td, J=12.03, 2.64 Hz, 2H), 2.85 (s, 3H), 2.78 (s, 2H), 2.09-2.29 (m, 2H), 1.73-1.93 (m, 2H).

Step B (E)-3-{1'-Methanesulfonyl-4-oxo-spiro[chromane-2,4'-piperidine]-6-yl}-acrylic acid methyl ester (162 mg, 0.42 mmol) was hydrolyzed with NaOH following the procedure described in Example 1, Step A, giving (E)-3-{1-methanesulfonyl-4-oxo-spiro[chromane-2,4'-piperidine]-6-yl}-acrylic acid as a white solid (147 mg, 96%). The resulting product was treated with NH$_2$OTHP according to the procedure described in Example 1, Step B, giving (E)-3-{1'-methanesulfonyl-4-oxo-spiro[chromane-2,4'-piperidine]-6-yl}-N-(tetrahydro-pyran-2-yloxy)-acrylamide. Finally, the removal of the THP protecting group following the procedure described in Example 2 Step D, gave the crude product, which was purified by preparative LC-MS giving 35 mg of (E)-3-{1'-methanesulfonyl-4-oxo-spiro[chromane-2,4'-piperidine]-6-yl}-N-hydroxy-acrylamide.

Y=21% (over 3 steps).

LC-MS: Method G, rt=1.24; (ES+) MH$^+$: 381

$^1$H NMR (DMSO-d$_6$) δ (ppm): 10.65 (bs, 1H), 7.90 (d, J=2.05 Hz, 1H), 7.80 (dd, J=8.66, 1.91 Hz, 1H), 7.44 (d, J=15.85 Hz, 1H), 7.14 (d, J=8.51 Hz, 1H), 6.42 (d, J=15.55

Hz, 1H), 3.32-3.48 (m, 2H), 2.98-3.16 (m, 2H), 2.82-2.98 (m, 5H), 1.93-2.14 (m, 2H), 1.67-1.93 (m, 2H).

Example 44

(E)-3-{1'-Phenylsulfonyl-4-oxo-spiro[chromane-2,4'-piperidine]-6-yl}-N-hydroxy-acrylamide

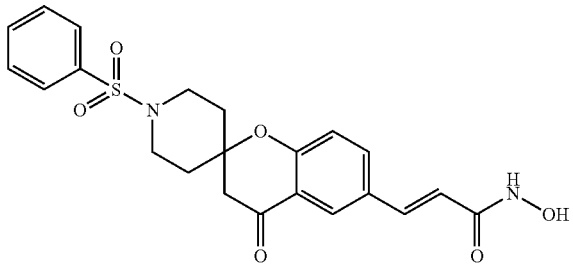 [SMILES: O=C(/C=C/c1ccc2c(c1)C(=O)CC1(CCN(S(=O)(=O)c3ccccc3)CC1)O2)NO]

The title compound was prepared starting from (E)-3-{4-oxo-spiro[chromane-2,4'-piperidine]-6-yl}-acrylic acid methyl ester hydrochloride (Intermediate 1) and phenylsulfonyl chloride according to the procedure described in Example 43. The title compound was triturated with $Et_2O$ and isopropanol and obtained as white solid.

LC-MS: Method G, rt=1.78; (ES+) MH$^+$:443

$^1$H NMR (DMSO-d$_6$) δ (ppm): 10.64 (bs, 1H), 7.86 (d, J=2.05 Hz, 1H), 7.55-7.82 (m, 6H), 7.40 (d, J=15.85 Hz, 1H), 6.84 (d, J=8.80 Hz, 1H), 6.38 (d, J=15.85 Hz, 1H), 3.43-3.58 (m, 2H), 2.84 (s, 2H), 2.61 (td, J=11.81, 1.91 Hz, 2H), 1.91-2.09 (m, 2H), 1.68-1.91 (m, 2H).

Example 45

(E)-3-{1'-(3-Phenyl-propyl)-4-oxo-spiro[chromane-2,4'-piperidine]-6-yl}-N-hydroxy-acrylamide

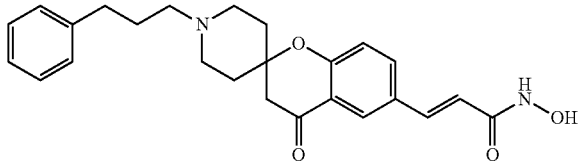 [SMILES: O=C(/C=C/c1ccc2c(c1)C(=O)CC1(CCN(CCCc3ccccc3)CC1)O2)NO]

Step A

TEA (0.185 ml, 1.33 mmol) and (3-bromopropyl)benzene (0.134 ml, 0.88 mmol) were added to a suspension of (E)-3-{4-oxo-spiro[chromane-2,4'-piperidine]-6-yl}-acrylic acid methyl ester hydrochloride (150 mg, 0.44 mmol, Intermediate 1) in DCM (3 ml), and the mixture was stirred at RT for 24 h and then under reflux for 18 h. The solvent was removed and the crude mixture was purified by column chromatography (eluent:DCM/MeOH 97:3) to give (E)-3-{1'-(3-phenyl-propyl)-4-oxo-spiro[chromane-2,4'-piperidine]-6-yl}-acrylic acid methyl ester (173 mg) as a yellow oil.

Y=94%

Step B (E)-3-{1'-(3-Phenyl-propyl)-4-oxo-spiro[chromane-2,4'-piperidine]-6-yl}-acrylic acid methyl ester (173 mg, 0.41 mmol) was hydrolyzed with NaOH following the procedure described in Example 1, Step A, giving (E)-3-{1'-(3-phenyl-propyl)-4-oxo-spiro[chromane-2,4'-piperidine]-6-yl}-acrylic acid as a white solid (165 mg, 98%). The resulting product was treated with $NH_2OTHP$ according to the procedure described in Example 1, Step B, giving (E)-3-{1'-(3-phenyl-propyl)-4-oxo-spiro[chromane-2,4'-piperidine]-6-yl}-N-(tetrahydro-pyran-2-yloxy)-acrylamide. Removal of the THP protecting group following the procedure described in Example 2, Step D gave (E)-3-{1'-(3-phenyl-propyl)1-4-oxo-spiro[chromane-2,4'-piperidine]-6-yl}-N-hydroxy-acrylamide hydrochloride salt as a white solid (48 mg).

Y=26% (over 2 steps).

LC-MS: Method G, rt=1.41; (ES+) MH$^+$:421

$^1$H NMR (DMSO-d$_6$) δ (ppm): 7.81 (d, J=2.05 Hz, 1H), 7.73 (dd, J=8.80, 2.05 Hz, 1H), 7.09-7.38 (m, 6H), 7.05 (d, J=8.80 Hz, 1H), 6.37 (d, J=15.85 Hz, 1H), 2.82 (s, 2H), 2.53-2.65 (m, 4H), 2.13-2.45 (m, 4H), 1.82-1.98 (m, 2H), 1.54-1.81 (m, 4H).

Example 46

(E)-3-{1'-Ethylcarbamoyl-4-oxo-spiro[chromane-2,4'-piperidine]-6-yl}-N-hydroxy-acrylamide

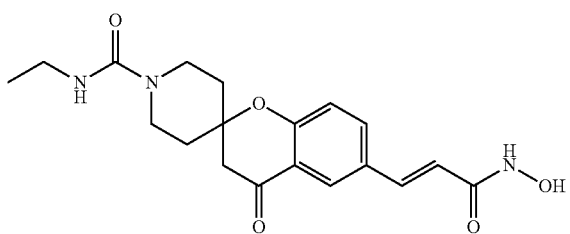 [SMILES: CCNC(=O)N1CCC2(CC1)CC(=O)c1cc(/C=C/C(=O)NO)ccc1O2]

Step A

TEA (0.185 ml, 1.33 mmol) and ethylisocyanate (38 mg, 0.53 mmol) were added to a suspension of (E)-3-{4-oxo-spiro[chromane-2,4'-piperidine]-6-yl}-acrylic acid methyl ester hydrochloride (150 mg, 0.44 mmol, Intermediate 1) in DCM (4 ml), and the mixture was stirred at RT for 1.5 h. The mixture was partitioned between aqueous $NaHCO_3$ (saturated solution) and DCM and the organic phase was dried over $Na_2SO_4$ and evaporated. The crude product was purified by column chromatography (eluent:DCM/MeOH/NH$_4$OH 97:3:0.3) to give (E)-3-{1'-ethylcarbamoyl-4-oxo-spiro[chromane-2,4'-piperidine]-6-yl}-acrylic acid methyl ester (150 mg).

Y=92%

$^1$H NMR (DMSO-d$_6$) δ (ppm): 7.99 (d, J=2.05 Hz, 1H), 8.00 (dd, J=7.34, 2.35 Hz, 1H), 7.67 (d, J=16.14 Hz, 1H), 7.13 (d, J=9.39 Hz, 1H), 6.56 (d, J=16.14 Hz, 1H), 6.47 (t, J=5.28 Hz, 1H), 3.72 (s, 3H), 3.46-3.87 (m, 2H), 2.96-3.20 (m, 4H), 2.88 (s, 2H), 1.74-1.98 (m, 2H), 1.46-1.73 (m, 2H), 1.01 (t, J=7.04 Hz, 3H).

Step B

4 M NaOH (0.148 ml, 0.591 mmol) was added to a solution of (E)-3-{1-ethylcarbamoyl-4-oxo-spiro[chromane-2,4'-piperidine]-6-yl}-acrylic acid methyl ester (220 mg, 0.591 mmol) in dioxane (3 ml) and water (3 ml) and the mixture was stirred at RT for 1 h. Further 4 M NaOH (0.073 ml) was added and the mixture was stirred for additional 2 h. Dioxane was removed under vacuum and the residue was acidified with 2 M HCl. The resulting precipitate was filtered to give (E)-3-{1'-ethylcarbamoyl-4-oxo-spiro[chromane-2,4'-piperidine]-6-yl}-acrylic acid. The crude compound (163 mg) was dissolved in a mixture of DCM (3 ml) and TEA (0.126 ml, 0.91 mmol). EDC (174 mg, 0.91 mmol) and HOBT (61 mg, 0.45 mmol) were added at 0° C. and the resulting solution was stirred at RT for 1 h. NH₂OTHP (66 mg, 0.56 mmol) was added and the mixture was stirred at RT for 4 h and then washed with 5% aqueous solution of NaHCO₃. The organic phase was washed with water, dried over Na₂SO₄ and evaporated. The crude residue was purified by column chromatography (eluent:DCM/MeOH/NH₄OH 97:3:0.3) and the resulting (E)-3-{1'-ethylcarbamoyl-4-oxo-spiro[chromane-2,4'-piperidine]-6-yl}-N-(tetrahydro-pyran-2-yloxy)-acrylamide was dissolved in DCM and treated with 4 M HCl in dioxane for 2 h. The precipitate was filtered and washed with DCM to give the title compound as a pale yellow powder (118 mg).

Y=53% (over 3 steps)
LC-MS: Method G, rt=1.09; (ES+) MH⁺:374
¹H NMR (DMSO-d₆) δ (ppm): 7.89 (d, J=2.05 Hz, 1H), 7.78 (dd, J=8.66, 1.61 Hz, 1H), 7.43 (d, J=15.85 Hz, 1H), 7.12 (d, J=8.80 Hz, 1H), 6.43 (d, J=15.85 Hz, 1H), 3.52-3.80 (m, 2H), 3.06-3.21 (m, 2H), 3.04 (q, J=7.34 Hz, 2H), 2.87 (s, 2H), 1.73-1.97 (m, 2H), 1.41-1.72 (m, 2H), 1.00 (t, J=7.19 Hz, 3H).

Example 47

(E)-3-{1'-Benzylcarbamoyl-4-oxo-spiro[chromane-2, 4'-piperidine]-6-yl}-N-hydroxy-acrylamide

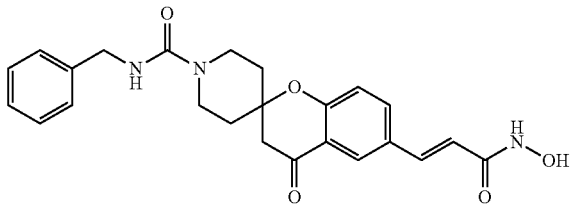 [SMILES: O=C(/C=C/c1ccc2c(c1)C(=O)CC1(CCN(C(=O)NCc3ccccc3)CC1)O2)NO]

The title compound was prepared starting from (E)-3-{4-oxo-spiro[chromane-2,4'-piperidine]-6-yl}-acrylic acid methyl ester hydrochloride (Intermediate 1) and benzylisocyanate, according to the procedure described in Example 46. The title compound was obtained as a pale yellow powder.
LC-MS: Method G, rt=1.64; (ES+) MH⁺:436
¹H NMR (DMSO-d₆) δ (ppm): 10.20-10.33 (m, 1H), 7.89 (d, J=2.05 Hz, 1H), 7.78 (dd, J=8.80, 1.76 Hz, 1H), 7.43 (d, J=15.85 Hz, 1H), 7.16-7.35 (m, 5H), 7.13 (d, J=8.51 Hz, 1H), 6.43 (d, J=15.55 Hz, 1H), 4.24 (s, 2H), 3.64-3.90 (m, 2H), 3.03-3.31 (m, 2H), 2.88 (s, 2H), 1.79-2.00 (m, 2H), 1.52-1.77 (m, 2H).

Example 48

(E)-3-{1'-Phenylcarbamoyl-4-oxo-spiro[chromane-2, 4'-piperidine]-6-yl}-N-hydroxy-acrylamide

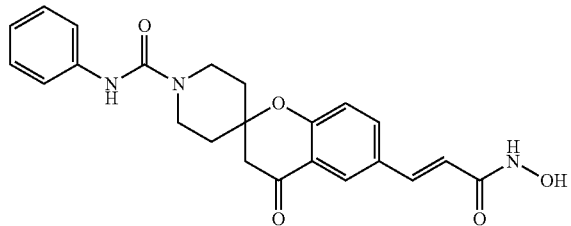 [SMILES: O=C(/C=C/c1ccc2c(c1)C(=O)CC1(CCN(C(=O)Nc3ccccc3)CC1)O2)NO]

The title compound was prepared starting from (E)-3-{4-oxo-spiro[chromane-2,4'-piperidine]-6-yl}-acrylic acid methyl ester hydrochloride (Intermediate 1) and phenylisocyanate, according to the procedure described in Example 46. The title compound was crystallized from CH₃CN and obtained as a white solid.
LC-MS: Method G, rt=1.64; (ES+) MH⁺:422
¹H NMR (DMSO-d₆) δ (ppm): 10.65 (s, 1H), 8.52 (s, 1H), 7.91 (d, J=2.05 Hz, 1H), 7.80 (dd, J=7.92, 1.76 Hz, 1H), 7.35-7.59 (m, 3H), 7.19-7.28 (m, 2H), 7.16 (d, J=8.51 Hz, 1H), 6.78-7.02 (m, 1H), 6.42 (d, J=15.26 Hz, 1H), 3.76-4.02 (m, 2H), 3.14-3.34 (m, 2H), 2.91 (s, 2H), 1.85-2.06 (m, 2H), 1.58-1.84 (m, 2H).

Example 49

(E)-3-{1'-[2-(1H-Indo)-3-yl)ethyl]-4-oxo-spiro[chromane-2,4'-piperidine]-6-yl}-N-hydroxy-acrylamide

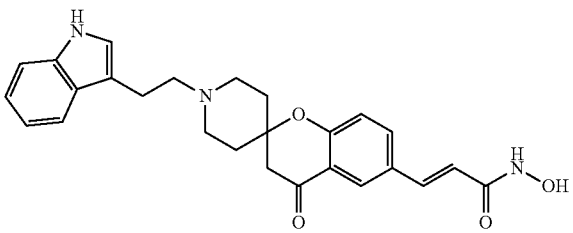 [SMILES: O=C(/C=C/c1ccc2c(c1)C(=O)CC1(CCN(CCc3c[nH]c4ccccc34)CC1)O2)NO]

Step A
TEA (0.46 ml, 3.3 mmol) and 3-(2-bromoethyl)-1H-indole (193 mg, 0.863 mmol) were added to a suspension of (E)-3-{4-oxo-spiro[chromane-2,4'-piperidine]-6-yl}-acrylic acid methyl ester hydrochloride (220 mg, 0.66 mmol, Intermediate 1) in DCM (5 ml), and the mixture was stirred at RT overnight. DCM was evaporated and the residue was dissolved in DMF and heated at 60° C. overnight. The mixture was partitioned between water and AcOEt and the aqueous phase was extracted with DCM. The collected organic phases were dried over Na₂SO₄ and evaporated. The crude mixture was purified by column chromatography (eluent:DCM/MeOH/NH₄OH 94:6:0.2) to give (E)-3-{1'-[2-(1H-indol-3-yl)ethyl]-4-oxo-spiro[chromane-2,4'-piperidine]-6-yl}-acrylic acid methyl ester (130 mg).
Y=45%
¹H NMR (DMSO-d₆) δ (ppm): 10.73 (bs, 1H), 7.92-8.02 (m, 2H), 7.67 (d, J=16.14 Hz, 1H), 7.50 (d, J=7.92 Hz, 1H), 7.32 (d, J=7.92 Hz, 1H), 7.08-7.18 (m, 2H), 7.00-7.09 (m, 1H), 6.89-7.01 (m, 1H), 6.56 (d, J=16.14 Hz, 1H), 3.72 (s, 3H), 2.78-2.99 (m, 4H), 2.59-2.78 (m, 4H), 2.35-2.48 (m, 2H), 1.86-2.06 (m, 2H), 1.63-1.86 (m, 2H).

Step B
(E)-3-{1'-[2-(1H-indol-3-yl)ethyl]-4-oxo-spiro[chromane-2,4'-piperidine]-6-yl}-acrylic acid methyl ester (129 mg, 0.29 mmol) was hydrolyzed with 4 M NaOH following the procedure described in Example 40, Step B, giving (E)-3-{1'-[2-(1H-indol-3-yl)ethyl]-4-oxo-spiro[chromane-2,4'-piperidine]-6-yl}-acrylic acid (109 mg, 87%). The product was treated with NH₂OTHP according to the procedure described in Example 40, Step C, giving (E)-3-{1'-[2-(1H-indol-3-yl)ethyl]-4-oxo-spiro[chromane-2,4'-piperidine]-6-yl}-N-(tetrahydro-pyran-2-yloxy)-acrylamide. Removal of the THP protecting group following the procedure described in Example 40, Step C gave (E)-3-{1'-[2-(1H-indol-3-yl)ethyl]-4-oxo-spiro[chromane-2,4'-piperidine]-6-yl}-N-hydroxy-acrylamide, which was purified by preparative LC-MS and obtained as its trifluoroacetate salt (37 mg, white solid).

Y=26% (over 2 steps).
LC-MS: Method G, rt=1.38; (ES+) MH⁺:446
¹H NMR (DMSO-d₆) δ (ppm): 10.96 (bs, 1H), 10.67 (bs, 1H), 9.39 (bs, 1H), 9.03 (bs, 1H), 7.80-7.98 (m, 2H), 7.62 (d, J=7.92 Hz, 1H), 7.46 (d, J=15.85 Hz, 1H), 7.38 (d, J=7.92 Hz, 1H), 7.26 (d, J=2.35 Hz, 1H), 7.19 (d, J=8.51 Hz, 1H), 7.08-7.16 (m, 1H), 7.03 (t, J=6.90 Hz, 1H), 6.44 (d, J=16.14 Hz, 1H), 3.52-3.69 (m, 2H), 3.19-3.36 (m, 4H), 3.04-3.19 (m, 2H), 2.97 (s, 2H), 2.15-2.35 (m, 2H), 1.79-2.09 (m, 2H).

Example 50

(E)-3-{1'-(1H-Indo)-3-ylmethyl)-4-oxo-spiro[chromane-2,4'-piperidine]-6-yl}-N-hydroxy-acrylamide

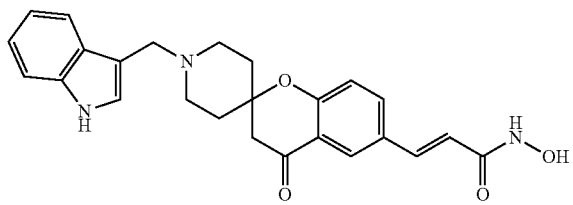 [SMILES: O=C(/C=C/c1ccc2c(c1)C(=O)CC1(CCN(Cc3c[nH]c4ccccc34)CC1)O2)NO]

Step A

A mixture of (E)-3-{4-oxo-spiro[chromane-2,4'-piperidine]-6-yl}-acrylic acid methyl ester (170 mg, 0.564 mmol, Intermediate 1 free base), AcOH (0.039 ml, 0.67 mmol), and HCHO (35% in H₂O, 0.055 ml, 0.67 mmol) in MeOH (8 ml) and dioxane (2 ml) was stirred at RT for 20 min and then treated with indole (94 mg, 0.80 mmol). The resulting solution was stirred at RT overnight and then further HCHO (0.02 ml) was added. After heating at 50° C. for 4 h, the solvent was evaporated and the residue was dissolved with DCM and washed with 5% aqueous NaHCO₃ and brine. The organic phase was dried over Na₂SO₄, evaporated and the crude product was purified by column chromatography (eluent:DCM/MeOH/NH₄OH 96:4:0.4) to give (E)-3-{1'-(1H-indol-3-ylmethyl)-4-oxo-spiro[chromane-2,4'-piperidine]-6-yl}-acrylic acid methyl ester as a white solid (140 mg).
Y=58%

Step B

4 M NaOH (0.081 ml, 0.325 mmol) was added to a solution of (E)-3-{1'-(1H-indol-3-ylmethyl)-4-oxo-spiro[chromane-2,4'-piperidine]-6-yl}-acrylic acid methyl ester (140 mg, 0.325 mmol) in dioxane (2 ml) and water (1 ml) and the mixture was stirred at RT for 10 h. The pH was brought to 4 with 2 M HCl and the solvent was removed under vacuum to give (E)-3-{1'-(1H-indol-3-ylmethyl)-4-oxo-spiro[chromane-2,4'-piperidine]-6-yl}-acrylic acid. The crude compound (135 mg) was dissolved in THF (12 ml). TEA (0.092 ml, 0.66 mmol), EDC (126 mg, 0.66 mmol) HOBT (44 mg, 0.33 mmol) and NH₂OTHP (48 mg, 0.41 mmol) were added and the mixture was stirred at RT overnight. The solvent was removed and the residue was partitioned between DCM and water. The organic phase was dried over Na₂SO₄, evaporated and the crude product was purified by column chromatography (eluent:DCM/MeOH/NH₄OH 96:4:0.4). The resulting (E)-3-{1'-(1H-indol-3-ylmethyl)-4-oxo-spiro[chromane-2,4'-piperidine]-6-yl}-N-(tetrahydro-pyran-2-yloxy)-acrylamide was dissolved in DCM and treated with HCl/Et₂O for 3 h. The precipitate was filtered and washed with DCM to give (E)-3-{1'-(1H-indol-3-ylmethyl)-4-oxo-spiro[chromane-2,4'-piperidine]-6-yl}-N-hydroxy-acrylamide hydrochloride as a white solid (40 mg).
Y=26% (over 3 steps)
LC-MS: Method G, rt=1.35; (ES+) MH⁺:432
¹H NMR (DMSO-d₆) δ (ppm): 10.88 (bs, 1H), 7.67-7.91 (m, 2H), 7.62 (d, J=7.92 Hz, 1H), 7.33 (d, J=7.92 Hz, 1H), 7.21 (s, 1H), 7.16 (d, J=16.14 Hz, 1H), 6.88-7.11 (m, 3H), 6.34 (d, J=15.85 Hz, 1H), 3.65 (s, 2H), 2.80 (s, 2H), 2.56-2.69 (m, 2H), 2.30-2.44 (m, 2H), 1.80-1.98 (m, 2H), 1.57-1.78 (m, 2H).

Example 51

(E)-3-{1'-(2-Methyl-1H-indol-3-ylmethyl)-4-oxo-spiro[chromane-2,4'-piperidine]-6-yl}-N-hydroxy-acrylamide

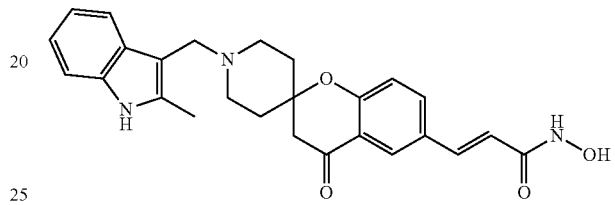

The title compound was prepared starting from (E)-3-{4-oxo-spiro[chromane-2,4'-piperidine]-6-yl}-acrylic acid methyl ester (Intermediate 1, free base) and 2-methyl indole, according to the procedure described in Example 50.
The title compound was obtained as its hydrochloride salt (60 mg, pink solid).
LC-MS: Method G, rt=1.38; (ES+) MH⁺:446
¹H NMR (DMSO-d₆) δ (ppm): 10.76 (s, 1H), 7.60-7.82 (m, 2H), 7.49 (d, J=7.63 Hz, 1H), 7.22 (d, J=7.92 Hz, 1H), 6.87-7.11 (m, 4H), 6.29 (d, J=15.85 Hz, 1H), 3.57 (s, 2H), 2.78 (s, 2H), 2.55-2.68 (m, 2H), 2.34 (s, 3H), 2.32-2.43 (m, 2H), 1.78-1.96 (m, 2H), 1.54-1.77 (m, 2H).

Example 52

(E)-3-{1'-(Biphenyl-4-ylmethyl)-4-oxo-spiro[chromane-2,4'-piperidine]-6-yl}-N-hydroxy-acrylamide

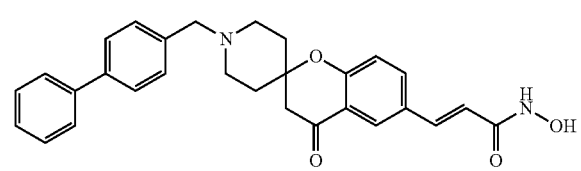 [SMILES: O=C(/C=C/c1ccc2c(c1)C(=O)CC1(CCN(Cc3ccc(-c4ccccc4)cc3)CC1)O2)NO]

(E)-3-{1'-(Biphenyl-4-ylmethyl)-4-oxo-spiro[chromane-2,4'-piperidine]-6-yl}-acrylic acid methyl ester was obtained starting from (E)-3-{4-oxo-spiro[chromane-2,4'-piperidine]-6-yl}-acrylic acid methyl ester (135 mg, 0.45 mmol, Intermediate 1, free base) and 4-phenyl-benzylchloride, according to the procedure described in Example 2, Step A, giving a white solid (200 mg, 95%). The methyl ester was hydrolyzed with 4 M NaOH following the procedure described in Example 40, Step B, giving (E)-3-{1'-(biphenyl-4-ylmethyl)-4-oxo-spiro[chromane-2,4'-piperidine]-6-yl}-acrylic acid as a yellow solid (145 mg, 75%). The resulting product was treated with NH₂OTHP according to the procedure described in Example 40, Step C, giving (E)-3-{1'-(biphenyl-4-ylmethyl)-4-oxo-spiro[chromane-2,4'-piperidine]-6-yl}-N-(tetrahydro-pyran-2-yloxy)-acrylamide. Finally, removal of the THP protecting group following the procedure described in Example 40, Step C gave (E)-3-{1'-(biphenyl-4-ylmethyl)-4-oxo-spiro[chromane-2,4'-piperidine]-6-yl}-N-hydroxy-acrylamide hydrochloride (87 mg) as a white solid.

Y=54% (over 2 steps)

LC-MS: Method G, rt=2.50; (ES+) MH+:469

1H NMR (DMSO-$d_6$) δ (ppm): 10.70 (bs, 1H), 10.59 (bs, 1H), 10.00 (s, 1H), 7.63-7.96 (m, 8H), 7.30-7.59 (m, 4H), 7.17 (d, J=8.51 Hz, 1H), 6.44 (d, J=15.55 Hz, 1H), 4.41 (bs, 2H), 3.11-3.35 (m, 4H), 2.90 (s, 2H), 1.99-2.32 (m, 4H).

Example 53

(E)-3-{1'-(6-Fluoro-1H-indol-3-ylmethyl)-4-oxo-spiro[chromane-2,4'-piperidine]-6-yl}-N-hydroxy-acrylamide

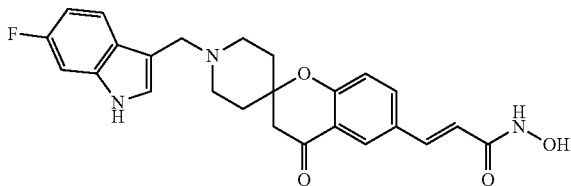 [SMILES: O=C(/C=C/c1ccc2c(c1)C(=O)CC1(CCN(Cc3c[nH]c4cc(F)ccc34)CC1)O2)NO]

Step A

A mixture of (E)-3-{4-oxo-spiro[chromane-2,4'-piperidine]-6-yl}-acrylic acid methyl ester (170 mg, 0.564 mmol, Intermediate 1, free base), AcOH (0.051 ml, 0.90 mmol), and HCHO (35% in $H_2O$, 0.07 ml, 0.847 mmol) in MeOH (12 ml) and dioxane (3 ml) was stirred at RT for 20 min and then treated with 6-fluoro-1H-indole (100 mg, 0.734 mmol). The resulting solution was stirred at 50° C. for 1 h. The solvent was then evaporated, the residue dissolved with DCM and washed with 5% aqueous $NaHCO_3$ and brine. The organic phase was dried over $Na_2SO_4$ and evaporated under vacuum. The crude mixture was purified by column chromatography (eluent:DCM/MeOH/$NH_4OH$ 97:3:0.3) to give (E)-3-{1'-(6-fluoro-1H-indol-3-ylmethyl)-4-oxo-spiro[chromane-2,4'-piperidine]-6-yl}-acrylic acid methyl ester as a brown solid (140 mg).

Y=55%

1H NMR (DMSO-$d_6$) δ (ppm): 10.94 (bs, 1H), 7.85-8.10 (m, 2H), 7.49-7.76 (m, 2H), 7.22 (d, J=1.17 Hz, 1H), 6.96-7.17 (m, 2H), 6.71-6.96 (m, 1H), 6.55 (d, J=16.14 Hz, 1H), 3.71 (s, 3H), 3.64 (bs, 2H), 2.84 (s, 2H), 2.55-2.71 (m, 2H), 2.30-2.46 (m, 2H), 1.80-2.02 (m, 2H), 1.58-1.80 (m, 2H).

Step B (E)-3-{1'-(6-Fluoro-1H-indol-3-ylmethyl)-4-oxo-spiro[chromane-2,4'-piperidine]-6-yl}-acrylic acid methyl ester (130 mg, 0.29 mmol) was hydrolyzed with 4 M NaOH following the procedure described in Example 40, Step B, giving (E)-3-{1'-(6-fluoro-1H-indol-3-ylmethyl)-4-oxo-spiro[chromane-2,4'-piperidine]-6-yl}-acrylic acid as a yellow solid (95 mg, 76%). The product was treated with $NH_2OTHP$ according to the procedure described in Example 40, Step C, giving (E)-3-{1'-(6-fluoro-1H-indol-3-ylmethyl)-4-oxo-spiro[chromane-2,4'-piperidine]-6-yl}-N-(tetrahydro-pyran-2-yloxy)-acrylamide. Removal of the THP protecting group following the procedure described in Example 40, Step C gave (E)-3-{1'-(6-fluoro-1H-indol-3-ylmethyl)-4-oxo-spiro[chromane-2,4'-piperidine]-6-yl}-N-hydroxy-acrylamide that was purified by preparative LC-MS and obtained as its trifluoroacetate salt (15 mg, white solid).

Y=13% (over 2 steps).

LC-MS: Method G, rt=1.32; (ES+) MH+:450

1H NMR (DMSO-$d_6$) δ (ppm): 11.53 (s, 1H), 10.67 (bs, 1H), 9.27 (bs, 1H), 9.00 (bs, 1H), 7.91 (s, 1H), 7.71-7.87 (m, 2H), 7.59 (d, J=2.35 Hz, 1H), 7.45 (d, J=16.43 Hz, 1H), 7.24 (dd, J=9.83, 2.20 Hz, 1H), 7.13 (d, J=8.51 Hz, 1H), 6.94-7.07 (m, 1H), 6.43 (d, J=15.55 Hz, 1H), 4.40-4.66 (m, 2H), 3.13-3.35 (m, 4H), 2.91 (s, 2H), 2.12-2.34 (m, 2H), 1.74-1.98 (m, 2H).

Example 54

(E)-3-{1'-(5-Fluoro-1H-indol-3-ylmethyl)-4-oxo-spiro[chromane-2,4'-piperidine]-6-yl}-N-hydroxy-acrylamide

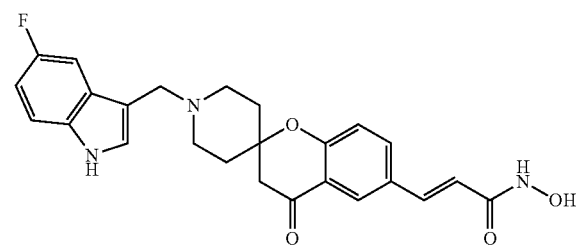 [SMILES: O=C(/C=C/c1ccc2c(c1)C(=O)CC1(CCN(Cc3c[nH]c4ccc(F)cc34)CC1)O2)NO]

(E)-3-{1'-(5-Fluoro-1H-indol-3-ylmethyl)-4-oxo-spiro[chromane-2,4'-piperidine]-6-yl}-acrylic acid methyl ester was obtained starting from (E)-3-{4-oxo-spiro[chromane-2,4'-piperidine]-6-yl}-acrylic acid methyl ester (135 mg, 0.45 mmol, Intermediate 1, free base) and 5-fluoro-1H-indole, according to the procedure described in Example 50, Step A (170 mg, 85%). The methyl ester was hydrolyzed with 4 M NaOH following the procedure described in Example 40, Step B, giving (E)-3-{1'-(5-fluoro-1H-indol-3-ylmethyl)-4-oxo-spiro[chromane-2,4'-piperidine]-6-yl}-acrylic acid (100 mg, 63%). The resulting product was treated with $NH_2OTHP$ according to the procedure described in Example 40, Step C, giving (E)-3-{1'-(5-fluoro-1H-indol-3-ylmethyl)-4-oxo-spiro[chromane-2,4'-piperidine]-6-yl}-N-(tetrahydro-pyran-2-yloxy)-acrylamide. Finally, removal of the THP protecting group following the procedure described in Example 40, Step C gave (E)-3-{1'-(5-fluoro-1H-indol-3-ylmethyl)-4-oxo-spiro[chromane-2,4'-piperidine]-6-yl}-N-hydroxy-acrylamide hydrochloride (76 mg) as a white solid.

Y=35% (over 4 steps)

LC-MS: Method G, rt=1.39; (ES+) MH+:450

1H NMR (DMSO-$d_6$) δ (ppm): 11.44-11.72 (m, 1H), 10.69 (bs, 1H), 9.95 (bs, 1H), 7.75-7.99 (m, 2H), 7.59-7.75 (m, 2H), 7.33-7.55 (m, 2H), 7.13 (m, J=8.51 Hz, 1H), 7.01 (td, J=9.17, 2.49 Hz, 1H), 6.44 (d, J=15.55 Hz, 1H), 4.49 (d, J=4.11 Hz, 2H), 3.23-3.39 (m, 2H), 3.05-3.23 (m, 2H), 2.89 (s, 2H), 2.13-2.35 (m, 2H), 1.89-2.13 (m, 2H).

Example 55

(E)-3-{1'-(2-Phenyl-ethyl)-4-oxo-spiro[chromane-2,4'-piperidine]-6-yl}-N-hydroxy-acrylamide

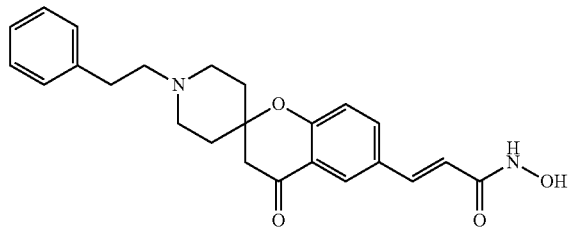 [SMILES: O=C(/C=C/c1ccc2c(c1)C(=O)CC1(CCN(CCc3ccccc3)CC1)O2)NO]

Step A

A suspension of (E)-3-{4-oxo-spiro[chromane-2,4'-piperidine]-6-yl}-acrylic acid methyl ester (2.0 g, 5.9 mmol, Intermediate 1, hydrochloride salt) in 1 M $K_2CO_3$ solution (30 ml) was stirred for 10 minutes, then DCM (3×30 ml) was added to extract the corresponding free base. The organic phase was dried and concentrated to 50 ml, then phenylacetaldehyde (0.79 ml, 7.10 mmol) and sodium triacetoxyborohydride (1.88 g, 8.88 mmol) were subsequently added. The mixture was stirred for 3 h, washed with water, and the pH value was adjusted to 8 with aqueous ammonia. The product was extracted with DCM and the organic solution was dried and concentrated. The crude residue was purified by column chromatography (eluent:DCM/MeOH 99:1 to 97:3) to give (E)-3-{1-(2-phenyl-ethyl)-4-oxo-spiro[chromane-2,4'-piperidine]-6-yl}-acrylic acid methyl ester (1.72 g) as a light yellow solid.

Y=72%

$^1$H NMR (300 MHz, DMSO-$d_6$) δ (ppm): 7.98 (d, J=2.35 Hz, 1H), 7.98 (dd, J=9.39, 2.35 Hz, 1H), 7.67 (d, J=15.85 Hz, 1H), 7.14-7.33 (m, 5H), 7.10 (d, J=9.10 Hz, 1H), 6.56 (d, J=15.85 Hz, 1H), 3.72 (s, 3H), 2.85 (s, 2H), 2.61-2.80 (m, 4H), 2.56 (dd, J=9.54, 6.31 Hz, 2H), 2.33-2.47 (m, 2H), 1.83-2.00 (m, 2H), 1.61-1.82 (m, 2H).

Step B (E)-3-{1'-(2-Phenyl-ethyl)-4-oxo-spiro[chromane-2,4'-piperidine]-6-yl}-acrylic acid methyl ester (1.70 g, 4.19 mmol) was dissolved in acetic acid (20 ml). 6 M HCl (20 ml) was added and the resulting suspension was heated at 85° C. for 4 h, then the solvents were evaporated and the residue was dried under vacuum, giving (E)-3-{1'-(2-phenyl-ethyl)-4-oxo-spiro[chromane-2,4'-piperidine]-6-yl}-acrylic acid (1.73 g) as a light yellow solid (hydrochloride salt).

Y=97%

$^1$H NMR (300 MHz, DMSO-$d_6$) δ (ppm): 12.21 (bs, 1H), 10.40 (bs, 1H), 7.80-8.13 (m, 2H), 7.61 (d, J=16.14 Hz, 1H), 7.23-7.43 (m, 5H), 7.19 (d, J=8.51 Hz, 1H), 6.47 (d, J=16.14 Hz, 1H), 3.43-3.62 (m, 2H), 3.33-3.43 (m, 2H), 3.15-3.25 (m, 2H), 2.98-3.15 (m, 2H), 2.94 (s, 2H), 1.97-2.30 (m, 4H)

Step C (E)-3-{1'-(2-Phenyl-ethyl)-4-oxo-spiro[chromane-2,4'-piperidine]-6-yl}-acrylic acid (1.71 g, 4.00 mmol) obtained in Step B was suspended in DCM (50 ml). TEA (0.84 ml, 6.0 mmol) was added and the clear solution was treated with $NH_2$OTHP following the procedure described in Example 1, Step B, giving (E)-3-{1'-(2-phenyl-ethyl)-4-oxo-spiro[chromane-2,4'-piperidine]-6-yl}-N-(tetrahydro-pyran-2-yloxy)-acrylamide (1.62 g) as a light yellow solid.

Y=83%

$^1$H NMR (300 MHz, DMSO-$d_6$) δ (ppm): 11.10 (bs, 1H), 7.91 (d, J=2.35 Hz, 1H), 7.79 (d, J=8.80 Hz, 1H), 7.47 (d, J=16.14 Hz, 1H), 7.13-7.34 (m, 5H), 7.10 (d, J=8.51 Hz, 1H), 6.47 (d, J=16.43 Hz, 1H), 4.91 (bs, 1H), 3.81-4.14 (m, 1H), 3.44-3.68 (m, 1H), 2.85 (s, 2H), 2.54-2.81 (m, 6H), 2.32-2.46 (m, 2H), 1.83-2.07 (m, 2H), 1.48-1.81 (m, 8H).

Step D

4 M HCl in dioxane (3 ml, 12 mmol) was added dropwise to a solution of (E)-3-{1'-(2-phenyl-ethyl)-4-oxo-spiro[chromane-2,4'-piperidine]-6-yl}-N-(tetrahydro-pyran-2-yloxy)-acrylamide (1.60 g, 3.26 mmol) in DCM (50 ml). After 4 h stirring, the formed precipitate was filtered, washed with DCM, dried under vacuum, then triturated with diethyl ether and finally collected (1.19 g) as a white solid (hydrochloride salt).

Y=82%

LC-MS: Method G, rt=1.32 min; (ES+) MH$^+$: 407

$^1$H NMR (300 MHz, DMSO-$d_6$) δ (ppm): 12.21 (bs, 1H), 10.40 (bs, 1H), 7.80-8.13 (m, 2H), 7.61 (d, J=16.14 Hz, 1H), 7.23-7.43 (m, 5H), 7.19 (d, J=8.51 Hz, 1H), 6.47 (d, J=16.14 Hz, 1H), 3.43-3.62 (m, 2H), 3.33-3.43 (m, 2H), 3.15-3.25 (m, 2H), 2.98-3.15 (m, 2H), 2.94 (s, 2H), 1.97-2.30 (m, 4H).

Example 56

(E)-3-{1'-[2-(4-Fluoro-phenyl)-ethyl]-4-oxo-spiro[chromane-2,4'-piperidine]-6-yl}-N-hydroxy-acrylamide

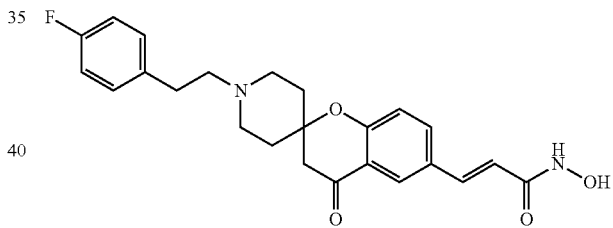

Step A $K_2CO_3$ (414 mg, 3 mmol) and 1-(2-bromo-ethyl)-4-fluorobenzene (0.21 ml, 1.5 mmol) were added to a suspension of (E)-3-{4-oxo-spiro[chromane-2,4'-piperidine]-6-yl}-acrylic acid methyl ester (254 mg, 0.752 mmol, Intermediate 1, hydrochloride salt) in acetone (10 ml). The mixture was stirred at 50° C. for 54 h, then the solvent was evaporated and the residue was partitioned between water and DCM. The organic phase was dried, then evaporated and the crude residue was purified by column chromatography (eluent:DCM/MeOH 99:1 to 98:2) to give (E)-3-{1'-[2-(4-fluoro-phenyl)-ethyl]-4-oxo-spiro[chromane-2,4'-piperidine]-6-yl}-acrylic acid methyl ester (300 mg) as a light yellow solid.

Y=94%

$^1$H NMR (300 MHz, DMSO-$d_6$) δ (ppm): 7.87-8.06 (m, 2H), 7.67 (d, J=15.85 Hz, 1H), 7.18-7.36 (m, 2H), 6.91-7.14 (m, 3H), 6.56 (d, J=16.14 Hz, 1H), 3.72 (s, 3H), 2.85 (s, 2H), 2.60-2.78 (m, 4H), 2.53-2.59 (m, 2H), 2.30-2.47 (m, 2H), 1.82-1.99 (m, 2H), 1.57-1.82 (m, 2H).

Step B (E)-3-{1'-[2-(4-Fluoro-phenyl)-ethyl]-4-oxo-spiro[chromane-2,4'-piperidine]-6-yl}-acrylic acid methyl ester (295 mg, 0.697 mmol) was hydrolyzed as described in Example 55, Step B, giving (E)-3-{1'-[2-(4-fluoro-phenyl)-ethyl]-4-oxo-spiro[chromane-2,4'-piperidine]-6-yl}-acrylic acid (307 mg) as a light orange solid (hydrochloride salt).

Y=99%

$^1$H NMR (300 MHz, DMSO-$d_6$) δ (ppm): 12.16 (bs, 1H), 10.61 (bs, 1H), 8.03 (dd, J=8.51, 2.05 Hz, 1H), 7.98 (d, J=2.35 Hz, 1H), 7.61 (d, J=15.85 Hz, 1H), 7.27-7.40 (m, 2H), 7.03-7.27 (m, 3H), 6.48 (d, J=15.85 Hz, 1H), 3.41-3.57 (m, 2H), 3.00-3.25 (m, 6H), 2.94 (s, 2H), 2.00-2.31 (m, 4H).

Step C (E)-3-{1'-[2-(4-Fluoro-phenyl)-ethyl]-4-oxo-spiro[chromane-2,4'-piperidine]-6-yl}-acrylic acid (300 mg, 0.673 mmol) was suspended in DCM (10 ml). TEA (0.14 ml, 1 mmol) was added and the clear solution was treated with NH$_2$OTHP following the procedure described in Example 1, Step B, giving (E)-3-{1'-[2-(4-fluoro-phenyl)-ethyl]-4-oxo-spiro[chromane-2,4'-piperidine]-6-yl}-N-(tetrahydro-pyran-2-yloxy)-acrylamide (230 mg) as a yellow solid. The protected hydroxamic acid derivative was dissolved in DCM (10 ml) and treated with 4 M HCl in dioxane (1 ml, 4 mmol). After 1 h the solvents were evaporated, the residue was worked up with 1 M NaHCO$_3$, extracted with DCM, which was dried and evaporated. The crude residue was purified by column chromatography (eluent: DCM/MeOH 99:1 to 90:10) to give an orange solid (95 mg) as free base.

Y=34% over 2 steps.

LC-MS: Method G, rt=1.37 min; (ES+) MH$^+$: 425

$^1$H NMR (300 MHz, DMSO-$d_6$) δ (ppm): 10.64 (bs, 1H), 8.99 (bs, 1H), 7.89 (d, J=2.05 Hz, 1H), 7.77 (dd, J=8.66, 1.91 Hz, 1H), 7.43 (d, J=15.85 Hz, 1H), 7.19-7.36 (m, 2H), 6.96-7.17 (m, 3H), 6.41 (d, J=15.55 Hz, 1H), 2.84 (s, 2H), 2.53-2.79 (m, 6H), 2.31-2.46 (m, 2H), 1.80-2.00 (m, 2H), 1.56-1.80 (m, 2H).

Example 57

(E)-3-{1'-[2-(4-Chloro-phenyl)-ethyl]-4-oxo-spiro[chromane-2,4'-piperidine]-6-yl}-N-hydroxy-acrylamide

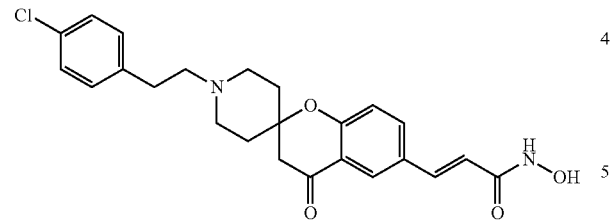

Step A (E)-3-{4-Oxo-spiro[chromane-2,4'-piperidine]-6-yl}-acrylic acid methyl ester (169 mg, 0.500 mmol, Intermediate 1, hydrochloride salt) was alkylated using 1-(2-bromo-ethyl)-4-chloro-benzene (0.15 ml, 1.5 mmol) as described in Example 56, Step A, giving (E)-3-{1'-[2-(4-chloro-phenyl)-ethyl]-4-oxo-spiro[chromane-2,4'-piperidine]-6-yl}-acrylic acid methyl ester (204 mg) as a light yellow solid.

Y=93%

$^1$H NMR (300 MHz, DMSO-$d_6$) δ (ppm): 7.89-8.06 (m, 2H), 7.67 (d, J=16.14 Hz, 1H), 7.29 (m, 4H), 7.10 (d, J=9.39 Hz, 1H), 6.55 (d, J=16.14 Hz, 1H), 3.72 (s, 3H), 2.85 (s, 2H), 2.69-2.78 (m, 2H), 2.59-2.69 (m, 2H), 2.53-2.59 (m, 2H), 2.31-2.47 (m, 2H), 1.82-1.99 (m, 2H), 1.61-1.78 (m, 2H).

Step B (E)-3-{1'-[2-(4-Chloro-phenyl)-ethyl]-4-oxo-spiro[chromane-2,4'-piperidine]-6-yl}-acrylic acid methyl ester (200 mg, 0.455 mmol) was hydrolyzed as described in Example 55, Step B, giving (E)-3-{1'-[2-(4-chloro-phenyl)-ethyl]-4-oxo-spiro[chromane-2,4'-piperidine]-6-yl}-acrylic acid (206 mg) as a light yellow solid (hydrochloride salt).

Y=98%

$^1$H NMR (300 MHz, DMSO-$d_6$) δ (ppm): 12.17 (bs, 1H), 10.40 (bs, 1H), 8.03 (dd, J=8.51, 1.76 Hz, 1H), 7.98 (d, J=2.05 Hz, 1H), 7.61 (d, J=15.85 Hz, 1H), 7.43 (m, J=8.51 Hz, 2H), 7.33 (m, J=8.51 Hz, 2H), 7.18 (d, J=8.51 Hz, 1H), 6.47 (d, J=15.85 Hz, 1H), 3.33-3.58 (m, 4H), 2.99-3.25 (m, 4H), 2.94 (s, 2H), 2.15-2.34 (m, 2H), 1.94-2.15 (m, 2H).

Step C (E)-3-{1'-[2-(4-Chloro-phenyl)-ethyl]-4-oxo-spiro[chromane-2,4'-piperidine]-6-yl}-acrylic acid (200 mg, 0.433 mmol) was suspended in DCM (10 ml). TEA (0.09 ml, 0.6 mmol) was added and the clear solution was treated with NH$_2$OTHP following the procedure described in Example 1, Step B, giving (E)-3-{1'-[2-(4-chloro-phenyl)-ethyl]-4-oxo-spiro[chromane-2,4'-piperidine]-6-yl}-N-(tetrahydro-pyran-2-yloxy)-acrylamide (130 mg) as a yellow solid. The compound was then dissolved in DCM (5 ml) and treated with 4 M HCl in dioxane (0.5 ml, 2 mmol) as described in Example 55, Step D, giving the requisite hydroxamic acid as a light yellow solid (89 mg, hydrochloride salt).

Y=44% over 2 steps.

LC-MS: Method G, rt=1.61 min; (ES+) MH$^+$: 441

$^1$H NMR (300 MHz, DMSO-$d_6$) δ (ppm): 10.84 (bs, 2H), 7.72-8.00 (m, 2H), 7.38-7.57 (m, 3H), 7.28-7.37 (m, 2H), 7.18 (d, J=8.80 Hz, 1H), 6.45 (d, J=15.85 Hz, 1H), 3.02-3.54 (m, 8H), 2.93 (s, 2H), 1.94-2.35 (m, 4H).

Example 58

(E)-3-{1'-[2-(4-Methoxy-phenyl)-ethyl]-4-oxo-spiro[chromane-2,4'-piperidine]-6-yl}-N-hydroxy-acrylamide

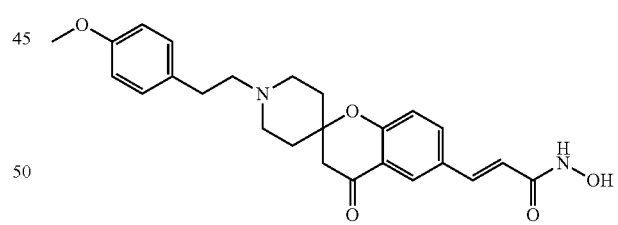

Step A (E)-3-{4-Oxo-spiro[chromane-2,4'-piperidine]-6-yl}-acrylic acid methyl ester (169 mg, 0.500 mmol, Intermediate 1, hydrochloride salt) was alkylated using 1-(2-bromo-ethyl)-4-methoxy-benzene (0.16 ml, 1.5 mmol) as described in Example 56, Step A, giving (E)-3-{1'-[2-(4-methoxy-phenyl)-ethyl]-4-oxo-spiro[chromane-2,4'-piperidine]-6-yl}-acrylic acid methyl ester (181 mg) as a white solid.

Y=83%

$^1$H NMR (300 MHz, DMSO-$d_6$) δ (ppm): 7.87-8.09 (m, 2H), 7.67 (d, J=16.14 Hz, 1H), 6.99-7.22 (m, 3H), 6.73-6.91 (m, 2H), 6.56 (d, J=16.14 Hz, 1H), 3.72 (s, 3H), 3.72 (s, 3H), 2.85 (s, 2H), 2.58-2.71 (m, 4H), 2.54 (bs, 2H), 2.31-2.46 (m, 2H), 1.82-2.00 (m, 2H), 1.59-1.81 (m, 2H).

Step B (E)-3-{1'-[2-(4-Methoxy-phenyl)-ethyl]-4-oxo-spiro[chromane-2,4'-piperidine]-6-yl}-acrylic acid methyl ester (176 mg, 0.404 mmol) was hydrolyzed as described in Example 55, Step B, giving (E)-3-{1'-[2-(4-methoxy-phenyl)-ethyl]-4-oxo-spiro[chromane-2,4'-piperidine]-6-yl}-acrylic acid (171 mg) as a white solid (hydrochloride salt).

Y=92%

$^1$H NMR (300 MHz, DMSO-$d_6$) δ (ppm): 12.28 (bs, 1H), 10.32 (bs, 1H), 7.86-8.15 (m, 2H), 7.61 (d, J=16.14 Hz, 1H), 7.08-7.35 (m, 3H), 6.79-7.07 (m, 2H), 6.47 (d, J=16.14 Hz, 1H), 3.74 (s, 3H), 3.36-3.53 (m, 2H), 3.05-3.20 (m, 4H), 2.77-3.05 (m, 4H), 2.13-2.26 (m, 2H), 1.90-2.13 (m, 2H).

Step C (E)-3-{1'-[2-(4-Methoxy-phenyl)-ethyl]-4-oxo-spiro[chromane-2,4'-piperidine]-6-yl}-acrylic acid (165 mg, 0.360 mmol) was suspended in DCM (5 ml). TEA (0.075 ml, 0.54 mmol) was added and the clear solution was treated with NH$_2$OTHP following the procedure described in Example 1, Step B, giving (E)-3-{1'-[2-(4-methoxy-phenyl)-ethyl]-4-oxo-spiro[chromane-2,4'-piperidine]-6-yl}-N-(tetrahydro-pyran-2-yloxy)-acrylamide (163 mg) as a yellow solid. The compound was then dissolved in DCM (5 ml) and treated with 4 M HCl in dioxane (0.5 ml, 2 mmol) as described in Example 55, Step D, giving the desired hydroxamic acid as a light yellow solid (103 mg, hydrochloride salt).

Y=63% over 2 steps.

LC-MS: Method G, rt=1.43 min; (ES+) MH$^+$: 437

$^1$H NMR (300 MHz, DMSO-$d_6$) δ (ppm): 10.63 (bs, 2H), 7.78-7.99 (m, 2H), 7.45 (d, J=15.55 Hz, 1H), 7.08-7.28 (m, 3H), 6.78-7.04 (m, 2H), 6.45 (d, J=15.85 Hz, 1H), 3.74 (s, 3H), 3.11-3.55 (m, 6H), 2.95-3.09 (m, 2H), 2.93 (s, 2H), 2.01-2.30 (m, 4H).

Example 59

(E)-3-{1'-[2-(2-Fluoro-phenyl)-ethyl]-4-oxo-spiro[chromane-2,4'-piperidine]-6-yl}-N-hydroxy-acrylamide

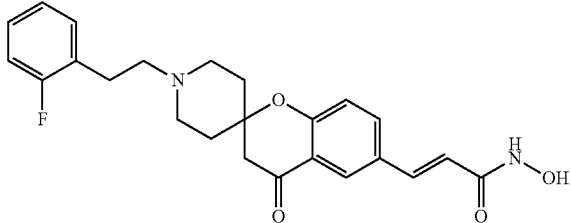 [SMILES: O=C(/C=C/c1ccc2c(c1)C(=O)CC1(CCN(CCc3ccccc3F)CC1)O2)NO]

Step A (E)-3-{4-Oxo-spiro[chromane-2,4'-piperidine]-6-yl}-acrylic acid methyl ester (169 mg, 0.500 mmol, Intermediate 1, hydrochloride salt) was alkylated using 1-(2-bromo-ethyl)-2-fluoro-benzene (0.16 ml, 1.5 mmol) as described in Example 56, Step A, giving (E)-3-{1'-[2-(2-fluoro-phenyl)-ethyl]-4-oxo-spiro[chromane-2,4'-piperidine]-6-yl}-acrylic acid methyl ester (181 mg) as a white solid.

Y=83%

$^1$H NMR (300 MHz, DMSO-$d_6$) δ (ppm): 7.98 (dq, J=4.55, 2.30 Hz, 2H), 7.67 (d, J=15.85 Hz, 1H), 7.20-7.39 (m, 2H), 7.09-7.16 (m, 2H), 7.10 (d, J=8.80 Hz, 1H), 6.56 (d, J=16.14 Hz, 1H), 3.72 (s, 3H), 2.85 (s, 2H), 2.71-2.81 (m, 2H), 2.53-2.71 (m, 4H), 2.41 (td, J=10.93, 2.20 Hz, 2H), 1.82-1.98 (m, 2H), 1.62-1.81 (m, 2H).

Step B (E)-3-{1'-[2-(2-Fluoro-phenyl)-ethyl]-4-oxo-spiro[chromane-2,4'-piperidine]-6-yl}-acrylic acid methyl ester (176 mg, 0.416 mmol) was hydrolyzed as described in Example 55, Step B, giving (E)-3-{1'-[2-(2-fluoro-phenyl)-ethyl]-4-oxo-spiro[chromane-2,4'-piperidine]-6-yl}-acrylic acid (171 mg) as a white solid (hydrochloride salt).

Y=95%

$^1$H NMR (300 MHz, DMSO-$d_6$) δ (ppm): 12.19 (bs, 1H), 10.54 (bs, 1H), 8.03 (dd, J=8.51, 2.05 Hz, 1H), 7.98 (d, J=2.05 Hz, 1H), 7.61 (d, J=16.14 Hz, 1H), 7.30-7.51 (m, 2H), 7.04-7.30 (m, 3H), 6.48 (d, J=15.85 Hz, 1H), 3.44-3.65 (m, 2H), 3.34-3.44 (m, 2H), 3.03-3.25 (m, 4H), 2.94 (s, 2H), 1.98-2.30 (m, 4H).

Step C (E)-3-{1'-[2-(2-Fluoro-phenyl)-ethyl]-4-oxo-spiro[chromane-2,4'-piperidine]-6-yl}-acrylic acid (165 mg, 0.370 mmol) was suspended in DCM (5 ml). TEA (0.075 ml, 0.54 mmol) was added and the clear solution was treated with NH$_2$OTHP following the procedure described in Example 1, Step B, giving (E)-3-{1'-[2-(2-fluoro-phenyl)-ethyl]-4-oxo-spiro[chromane-2,4'-piperidine]-6-yl}-N-(tetrahydro-pyran-2-yloxy)-acrylamide (163 mg) as a yellow solid. The compound was then dissolved in DCM (5 ml) and treated with 4 M HCl in dioxane (0.5 ml, 2 mmol) as described in Example 55, Step D, giving the hydroxamic acid as a light yellow solid (103 mg, hydrochloride salt).

Y=63% over 2 steps.

LC-MS: Method G, rt=1.43 min; (ES+) MH$^+$: 425

$^1$H NMR (300 MHz, DMSO-$d_6$) δ (ppm): 10.33-11.30 (m, 2H), 7.78-8.02 (m, 2H), 7.29-7.54 (m, 3H), 7.08-7.28 (m, 3H), 6.45 (d, J=15.85 Hz, 1H), 3.43-3.56 (m, 2H), 3.21-3.43 (m, 3H), 3.03-3.21 (m, 3H), 2.93 (s, 2H), 2.00-2.30 (m, 4H).

Example 60

(E)-3-{1'-[2-(3-Methoxy-phenyl)-ethyl]-4-oxo-spiro[chromane-2,4'-piperidine]-6-yl}-N-hydroxy-acrylamide

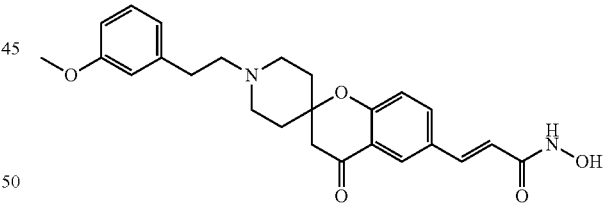

Step A (E)-3-{4-Oxo-spiro[chromane-2,4'-piperidine]-6-yl}-acrylic acid methyl ester (169 mg, 0.500 mmol, Intermediate 1, hydrochloride salt) was alkylated using 1-(2-bromo-ethyl)-3-methoxy-benzene (0.16 ml, 1.5 mmol) as described in Example 56, Step A, giving (E)-3-{1'-[2-(3-methoxy-phenyl)-ethyl]-4-oxo-spiro[chromane-2,4'-piperidine]-6-yl}-acrylic acid methyl ester (181 mg) as a white solid.

Y=83%

$^1$H NMR (300 MHz, DMSO-$d_6$) δ (ppm): 7.90-8.06 (m, 2H), 7.67 (d, J=16.14 Hz, 1H), 7.18 (t, J=8.22 Hz, 1H), 7.10 (d, J=9.10 Hz, 1H), 6.69-6.89 (m, 3H), 6.55 (d, J=16.14 Hz, 1H), 3.72 (s, 3H), 3.73 (s, 3H), 2.85 (s, 2H), 2.53-2.79 (m, 6H), 2.31-2.47 (m, 2H), 1.82-2.00 (m, 2H), 1.60-1.82 (m, 2H).

Step B (E)-3-{1'-[2-(3-Methoxy-phenyl)-ethyl]-4-oxo-spiro[chromane-2,4'-piperidine]-6-yl}-acrylic acid methyl ester (176 mg, 0.404 mmol) was hydrolyzed as described in Example 55, Step B, giving (E)-3-{1'-[2-(3-methoxy-phenyl)-ethyl]-4-oxo-spiro[chromane-2,4'-piperidine]-6-yl}-acrylic acid (171 mg) as a white solid (hydrochloride salt).

Y=92%

$^1$H NMR (300 MHz, DMSO-d$_6$) δ (ppm): 12.18 (bs, 1H), 10.11 (bs, 1H), 7.84-8.13 (m, 2H), 7.61 (d, J=15.85 Hz, 1H), 7.27 (t, J=7.92 Hz, 1H), 7.18 (d, J=8.22 Hz, 1H), 6.75-6.98 (m, 3H), 6.47 (d, J=16.14 Hz, 1H), 3.76 (s, 3H), 3.44-3.61 (m, 2H), 3.32-3.44 (m, 2H), 3.09-3.26 (m, 2H), 2.97-3.07 (m, 2H), 2.95 (s, 2H), 2.18-2.36 (m, 2H), 1.93-2.18 (m, 2H).

Step C (E)-3-{1'-[2-(3-Methoxy-phenyl)-ethyl]-4-oxo-spiro[chromane-2,4'-piperidine]-6-yl}-acrylic acid (165 mg, 0.360 mmol) was suspended in DCM (5 ml). TEA (0.075 ml, 0.54 mmol) was added and the clear solution was treated with NH$_2$OTHP following the procedure described in Example 1, Step B, giving (E)-3-{1'-[2-(3-methoxy-phenyl)-ethyl]-4-oxo-spiro[chromane-2,4'-piperidine]-6-yl}-N-(tetrahydro-pyran-2-yloxy)-acrylamide (163 mg) as a yellow solid. The compound was then dissolved in DCM (5 ml) and treated with 4 M HCl in dioxane (0.5 ml, 2 mmol) as described in Example 55, Step D, giving a light yellow solid (103 mg, hydrochloride salt).

Y=63% over 2 steps.

LC-MS: Method G, rt=1.46 min; (ES+) MH$^+$: 437

$^1$H NMR (300 MHz, DMSO-d$_6$) δ (ppm): 10.33-11.30 (m, 2H), 7.78-8.02 (m, 2H), 7.29-7.54 (m, 3H), 7.08-7.28 (m, 3H), 6.45 (d, J=15.85 Hz, 1H) 3.78 (s, 3H), 3.43-3.56 (m, 2H), 3.21-3.43 (m, 3H), 3.03-3.21 (m, 3H), 2.93 (s, 2H), 2.00-2.30 (m, 4H).

Example 61

(E)-3-{1'-[2-(4-Methyl-phenyl)-ethyl]-4-oxo-spiro[chromane-2,4'-piperidine]-6-yl}-N-hydroxy-acrylamide

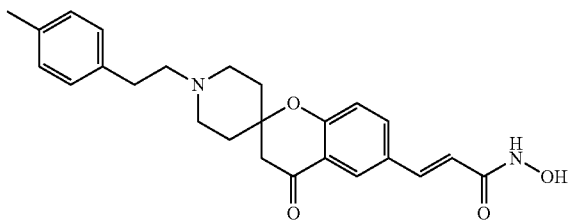 [SMILES: Cc1ccc(CCN2CCC3(CC2)CC(=O)c2cc(/C=C/C(=O)NO)ccc2O3)cc1]

Step A (E)-3-{4-Oxo-spiro[chromane-2,4'-piperidine]-6-yl}-acrylic acid methyl ester (253 mg, 0.749 mmol, Intermediate 1, hydrochloride salt) was alkylated using 1-(2-bromo-ethyl)-4-methyl-benzene (0.23 ml, 1.5 mmol) as described in Example 56, Step A, giving (E)-3-{1'-[2-(4-methyl-phenyl)-ethyl]-4-oxo-spiro[chromane-2,4'-piperidine]-6-yl}-acrylic acid methyl ester (282 mg) as a light brown solid.

Y=90%

$^1$H NMR (300 MHz, DMSO-d$_6$) δ (ppm): 7.98 (d, J=2.35 Hz, 1H), 7.98 (dd, J=9.10, 2.35 Hz, 1H), 7.67 (d, J=16.14 Hz, 1H), 6.96-7.24 (m, 5H), 6.55 (d, J=16.14 Hz, 1H), 3.72 (s, 3H), 2.85 (s, 2H), 2.59-2.79 (m, 4H), 2.53-2.59 (m, 2H), 2.33-2.46 (m, 2H), 2.26 (s, 3H), 1.82-1.99 (m, 2H), 1.60-1.82 (m, 2H).

Step B (E)-3-{1'-[2-(4-Methyl-phenyl)-ethyl]-4-oxo-spiro[chromane-2,4'-piperidine]-6-yl}-acrylic acid methyl ester (270 mg, 0.644 mmol) was hydrolyzed as described in Example 55, Step B, giving (E)-3-{1'-[2-(4-methyl-phenyl)-ethyl]-4-oxo-spiro[chromane-2,4'-piperidine]-6-yl}-acrylic acid (279 mg) as a yellow solid (hydrochloride salt).

Y=98%

$^1$H NMR (300 MHz, DMSO-d$_6$) δ (ppm): 12.23 (bs, 1H), 10.40 (bs, 1H), 8.03 (dd, J=8.66, 2.20 Hz, 1H), 7.98 (d, J=2.05 Hz, 1H), 7.61 (d, J=15.85 Hz, 1H), 7.05-7.35 (m, 5H), 6.47 (d, J=16.14 Hz, 1H), 3.40-3.63 (m, 2H), 3.33-3.40 (m, 2H), 3.22 (d, J=13.50 Hz, 2H), 2.96-3.06 (m, 2H), 2.94 (s, 2H), 2.29 (s, 3H), 2.13-2.27 (m, 2H), 1.95-2.14 (m, 2H).

Step C (E)-3-{1'-[2-(4-Methyl-phenyl)-ethyl]-4-oxo-spiro[chromane-2,4'-piperidine]-6-yl}-acrylic acid (257 mg, 0.581 mmol) was suspended in DCM (5 ml). TEA (0.12 ml, 0.87 mmol) was added and the clear solution was treated with NH$_2$OTHP following the procedure described in Example 1, Step B, giving (E)-3-{1'-[2-(4-methyl-phenyl)-ethyl]-4-oxo-spiro[chromane-2,4'-piperidine]-6-yl}-N-(tetrahydro-pyran-2-yloxy)-acrylamide (265 mg) as a yellow solid. The resulting product was dissolved in DCM (5 ml) and treated with 4 M HCl in dioxane (0.5 ml, 2 mmol) as described in Example 55, Step D, giving the desired hydroxamic acid as a light yellow solid (204 mg, hydrochloride salt).

Y=77% over 2 steps.

LC-MS: Method G, rt=1.26 min; (ES+) MH$^+$: 421

$^1$H NMR (300 MHz, DMSO-d$_6$) δ (ppm): 10.66 (bs, 1H), 7.92 (d, J=2.05 Hz, 1H), 7.84 (dd, J=8.80, 1.76 Hz, 1H), 7.45 (d, J=15.85 Hz, 1H), 7.03-7.29 (m, 5H), 6.45 (d, J=15.85 Hz, 1H), 3.40-3.56 (m, 2H), 3.24-3.40 (m, 2H), 3.10-3.24 (m, 2H), 2.96-3.10 (m, 2H), 2.93 (s, 2H), 2.29 (s, 3H), 2.15-2.26 (m, 2H), 1.99-2.15 (m, 2H).

Example 62

(E)-3-{1'-[2-(4-Amino-phenyl)-ethyl]-4-oxo-spiro[chromane-2,4'-piperidine]-6-yl}-N-hydroxy-acrylamide

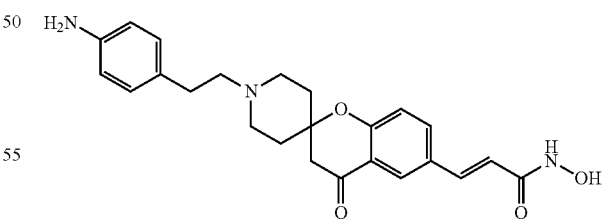

Step A (E)-3-{4-Oxo-spiro[chromane-2,4'-piperidine]-6-yl}-acrylic acid methyl ester (337 mg, 1.00 mmol, Intermediate 1, hydrochloride salt) was alkylated using 1-(2-bromo-ethyl)-4-nitro-benzene (460 mg, 2 mmol) as described in Example 56, Step A, giving (E)-3-{1'-[2-(4-nitro-phenyl)-ethyl]-4-oxo-spiro[chromane-2,4'-piperidine]-6-yl}-acrylic acid methyl ester (420 mg) as a light brown solid.

Y=93%

¹H NMR (300 MHz, DMSO-d₆) δ (ppm): 8.14 (m, 2H), 7.98 (d, J=2.35 Hz, 1H), 7.98 (dd, J=9.39, 2.35 Hz, 1H), 7.67 (d, J=16.14 Hz, 1H), 7.53 (m, 2H), 7.10 (d, J=9.39 Hz, 1H), 6.56 (d, J=16.14 Hz, 1H), 3.72 (s, 3H), 2.86-2.95 (m, 2H), 2.85 (s, 2H), 2.58-2.71 (m, 4H), 2.31-2.48 (m, 2H), 1.82-2.03 (m, 2H), 1.56-1.82 (m, 2H).

Step B (E)-3-{1'-[2-(4-Nitro-phenyl-)ethyl]-4-oxo-spiro[chromane-2,4'-piperidine]-6-yl}-acrylic acid methyl ester (377 mg, 0.833 mmol) was dissolved in AcOEt. SnCl₂.2H₂O (753 mg, 3.35 mmol) was added and the mixture heated under reflux for 12 h. After cooling down to room temperature the solution was treated with an aqueous solution of sodium potassium tartrate and sodium bicarbonate, and the organic phase was separated, dried and evaporated. The crude product was purified by column chromatography (eluent:DCM/MeOH 99:1 to 97:3) to give (E)-3-{1'-[2-(4-amino-phenyl)-ethyl]-4-oxo-spiro[chromane-2,4'-piperidine]-6-yl}-acrylic acid methyl ester (225 mg) as a light brown solid.

Y=65%

¹H NMR (300 MHz, DMSO-d₆) δ (ppm): 7.98 (d, J=2.05 Hz, 1H), 7.98 (dd, J=9.39, 2.05 Hz, 1H), 7.67 (d, J=16.14 Hz, 1H), 7.10 (d, J=9.39 Hz, 1H), 6.85 (m, 2H), 6.55 (d, J=16.14 Hz, 1H), 6.33-6.51 (m, 2H), 4.78 (bs, 2H), 3.72 (s, 3H), 2.85 (s, 2H), 2.54-2.76 (m, 6H), 2.31-2.46 (m, 2H), 1.90 (d, J=13.50 Hz, 2H), 1.53-1.82 (m, 2H).

Step C (E)-3-{1'-[2-(4-Amino-phenyl)-ethyl]-4-oxo-spiro[chromane-2,4'-piperidine]-6-yl}-acrylic acid methyl ester (100 mg, 0.238 mmol) was hydrolyzed as described in Example 55, Step B, giving (E)-3-{1'-[2-(4-amino-phenyl)-ethyl]-4-oxo-spiro[chromane-2,4'-piperidine]-6-yl}-acrylic acid (114 mg) as a yellow solid (di-hydrochloride salt).

Y=100%

¹H NMR (300 MHz, DMSO-d₆) δ (ppm): 10.54 (bs, 1H), 8.03 (dd, J=9.10, 2.35 Hz, 1H), 7.98 (d, J=2.05 Hz, 1H), 7.61 (d, J=16.14 Hz, 1H), 7.27 (m, 2H), 7.19 (d, J=8.51 Hz, 1H), 7.13 (m, 2H), 6.48 (d, J=15.85 Hz, 1H), 3.18-3.49 (m, 5H), 3.15 (bs, 1H), 2.98-3.10 (m, 2H), 2.94 (s, 2H), 1.96-2.27 (m, 4H).

Step D (E)-3-{1'-[2-(4-Amino-phenyl)-ethyl]-4-oxo-spiro[chromane-2,4'-piperidine]-6-yl}-acrylic acid (108 mg, 0.225 mmol) was suspended in DCM (5 ml). TEA (0.09 ml, 0.67 mmol) was added and the clear solution was treated with NH₂OTHP following the procedure described in Example 1, Step B, giving (E)-3-{1'-[2-(4-amino-phenyl)-ethyl]-4-oxo-spiro[chromane-2,4'-piperidine]-6-yl}-N-(tetrahydro-pyran-2-yloxy)-acrylamide (37 mg) as a yellow solid, which was then dissolved in DCM (3 ml) and treated with 4 M HCl in dioxane (0.1 ml, 0.4 mmol) as described in Example 55, Step D, giving a light yellow solid (28 mg, di-hydrochloride salt).

Y=26% over 2 steps.

LC-MS: Method H, rt=2.24 min; (ES+) MH⁺: 422

¹H NMR (300 MHz, DMSO-d₆) δ (ppm): 10.40-11.35 (m, 2H), 7.89-8.05 (m, 1H), 7.69-7.89 (m, 1H), 7.45 (d, J=15.85 Hz, 1H), 7.31-7.40 (m, 2H), 7.23-7.32 (m, 2H), 7.18 (d, J=8.80 Hz, 1H), 6.45 (d, J=15.55 Hz, 1H), 3.42-3.56 (m, 2H), 3.30-3.40 (m, 2H), 3.06-3.28 (m, 4H), 2.93 (s, 2H), 2.03-2.29 (m, 4H).

Example 63

(E)-3-{1'-[2-(4-Methylamino-phenyl)-ethyl]-4-oxo-spiro[chromane-2,4'-piperidine]-6-yl}-N-hydroxy-acrylamide

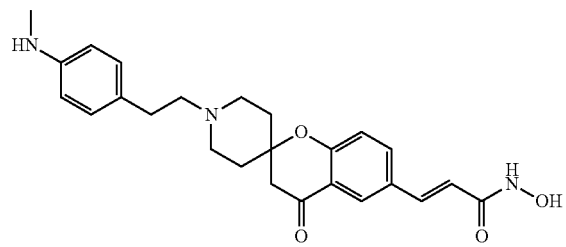 [SMILES: CNc1ccc(CCN2CCC3(CC2)CC(=O)c2cc(/C=C/C(=O)NO)ccc2O3)cc1]

(E)-3-{1'-[2-(4-Amino-phenyl)-ethyl]-4-oxo-spiro[chromane-2,4'-piperidine]-6-yl}-acrylic acid methyl ester (118 mg, 0.281 mmol), obtained as described in Example 62, Step B, was treated with aqueous HCHO (0.024 ml, 0.322 mmol) and sodium triacethoxyborohydride (89 mg, 0.42 mmol) following the procedure described in Example 55, Step A, giving (E)-3-{1-[2-(4-methylamino-phenyl)-ethyl]-4-oxo-spiro[chromane-2,4'-piperidine]-6-yl}-acrylic acid methyl ester (37 mg) as a yellow solid. The ester was hydrolyzed as described in Example 55, Step B, giving (E)-3-{1'-[2-(4-methylamino-phenyl)-ethyl]-4-oxo-spiro[chromane-2,4'-piperidine]-6-yl}-acrylic acid (42 mg) as a yellow solid (di-hydrochloride salt). The acid was suspended in DCM (3 ml), TEA (0.04 ml, 0.28 mmol) was added and the clear solution was treated with NH₂OTHP following the procedure described in Example 1, Step B, giving (E)-3-{1'-[2-(4-methylamino-phenyl)-ethyl]-4-oxo-spiro[chromane-2,4'-piperidine]-6-yl}-N-(tetrahydro-pyran-2-yloxy)-acrylamide (18 mg) as a light yellow solid. The protected hydroxamic acid was dissolved in DCM (3 ml) and treated with 4 M HCl in dioxane (0.1 ml, 0.4 mmol) as described in Example 55, Step D, giving a light yellow solid (9 mg, di-hydrochloride salt).

Y=7% over 4 steps.

LC-MS: Method G, rt=1.37 min; (ES+) MH⁺: 436

¹H NMR (300 MHz, DMSO-d₆) δ (ppm): 10.64 (bs, 2H), 7.72-8.01 (m, 2H), 7.45 (d, J=16.14 Hz, 1H), 7.28 (m, 2H), 6.91-7.23 (m, 3H), 6.45 (d, J=15.55 Hz, 1H), 3.41-3.55 (m, 2H), 3.11-3.41 (m, 4H), 2.98-3.10 (m, 2H), 2.93 (s, 2H), 2.81 (s, 3H), 2.02-2.29 (m, 4H).

Example 64

(E)-3-{1'-(1-Methyl-1H-indol-2-ylmethyl)-4-oxo-spiro[chromane-2,4'-piperidine]-6-yl}-N-hydroxy-acrylamide

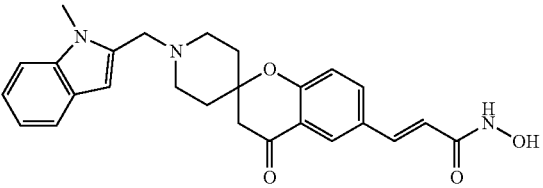 [SMILES: Cn1c(CN2CCC3(CC2)CC(=O)c2cc(/C=C/C(=O)NO)ccc2O3)cc2ccccc21]

A suspension of (E)-3-{4-oxo-spiro[chromane-2,4'-piperidine]-6-yl}-acrylic acid methyl ester (169 mg, 0.500 mmol, Intermediate 1, hydrochloride salt) in 1 M Na₂CO₃, was stirred for 10 minutes, then extracted with DCM and treated with N-methyl-indol-2-carbaldehyde (95 mg, 0.60 mmol) and sodium triacetoxyborohydride (159 mg, 0.750 mmol) following the procedure described in Example 55, Step A, giving (E)-3-{1'-(1-methyl-1H-indol-2-ylmethyl)-4-oxo-spiro[chromane-2,4'-piperidine]-6-yl}-acrylic acid methyl ester (179 mg) as a white solid. The resulting ester was hydrolyzed as described in Example 55, Step B, giving (E)-3-{1'-(1-methyl-1H-indol-2-ylmethyl)-4-oxo-spiro[chromane-2,4'-piperidine]-6-yl}-acrylic acid (187 mg) as an orange solid (hydrochloride salt). The product was suspended in DCM (3 ml), TEA (0.08 ml, 0.58 mmol) was added, and the clear solution was treated with $NH_2OTHP$ following the procedure described in Example 1, Step B, giving (E)-3-{1'-(1-methyl-1H-indol-2-ylmethyl)-4-oxo-spiro[chromane-2,4'-piperidine]-6-yl}-N-(tetrahydro-pyran-2-yloxy)-acrylamide (37 mg) as a light yellow solid. The compound was then dissolved in DCM (3 ml) and treated with 4 M HCl in dioxane (0.1 ml, 0.4 mmol) as described in Example 55, Step D, giving a light yellow solid after aqueous workup and column chromatography (eluent:DCM/MeOH 99:1 to 95:5) (7 mg, free base)

Y=3% over 4 steps.

LC-MS: Method G, rt=1.33 min; (ES+) MH$^+$: 446

$^1$H NMR (300 MHz, DMSO-d$_6$) δ (ppm): 7.83-7.99 (m, 1H), 7.77 (dd, J=8.36, 1.32 Hz, 1H), 7.27-7.57 (m, 3H), 7.04-7.19 (m, 2H), 6.86-7.04 (m, 1H), 6.41 (d, J=15.85 Hz, 1H), 6.34 (s, 1H), 3.76 (s, 3H), 3.68 (s, 2H), 2.85 (s, 2H), 2.54-2.70 (m, 2H), 2.33-2.48 (m, 2H), 1.83-1.99 (m, 2H), 1.58-1.83 (m, 2H).

Example 65

(E)-3-{1'-(Quinolin-2-ylmethyl)-4-oxo-spiro[chromane-2,4'-piperidine]-6-yl}-N-hydroxy-acrylamide

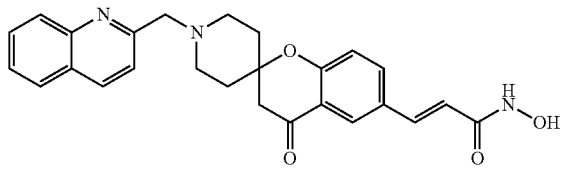 [SMILES: O=C(/C=C/c1ccc2c(c1)C(=O)CC1(CCN(Cc3ccc4ccccc4n3)CC1)O2)NO]

A suspension of (E)-3-{4-oxo-spiro[chromane-2,4'-piperidine]-6-yl}-acrylic acid methyl ester (169 mg, 0.500 mmol, Intermediate 1, hydrochloride salt) in 1 M $Na_2CO_3$, was stirred for 10 minutes, then extracted with DCM and treated with quinoline-2-carbaldehyde (96 mg, 0.61 mmol) and sodium triacethoxyborohydride (159 mg, 0.750 mmol) following the procedure described in Example 55, Step A, giving (E)-3-{1'-(quinolin-2-ylmethyl)-4-oxo-spiro[chromane-2,4'-piperidine]-6-yl}-acrylic acid methyl ester (196 mg) as a yellow solid. The ester was hydrolyzed as described in Example 55, Step B, giving (E)-3-{1'-(quinolin-2-ylmethyl)-4-oxo-spiro[chromane-2,4'-piperidine]-6-yl}-acrylic acid (190 mg) as an orange solid (hydrochloride salt). The acid was suspended in DCM (5 ml), TEA (0.16 ml, 1.16 mmol) was added, and the clear solution was treated with $NH_2OTHP$ following the procedure described in Example 1, Step B, giving (E)-3-{1'-(quinolin-2-ylmethyl)-4-oxo-spiro[chromane-2,4'-piperidine]-6-yl}-N-(tetrahydro-pyran-2-yloxy)-acrylamide (162 mg) as a yellow solid. The compound was then dissolved in DCM (5 ml) and treated with 4 M HCl in dioxane (0.4 ml, 1.6 mmol) as described in Example 55, Step D, giving a yellow solid (145 mg, di-hydrochloride salt)

Y=56% over 4 steps.

LC-MS: Method G, rt=1.35 min; (ES+) MH$^+$: 444

$^1$H NMR (300 MHz, DMSO-d$_6$) δ (ppm): 10.94 (bs, 1H), 8.52 (d, J=8.51 Hz, 1H), 8.01-8.18 (m, 2H), 7.77-8.01 (m, 4H), 7.70 (ddd, J=8.22, 7.04, 1.17 Hz, 1H), 7.44 (d, J=15.85 Hz, 1H), 7.19 (d, J=8.80 Hz, 1H), 6.46 (d, J=15.85 Hz, 1H), 4.77 (s, 2H), 3.37-3.54 (m, 4H), 2.98 (s, 2H), 2.06-2.34 (m, 4H).

Example 66

(E)-3-{1'-(Quinolin-3-ylmethyl)-4-oxo-spiro[chromane-2,4'-piperidine]-6-yl}-N-hydroxy-acrylamide

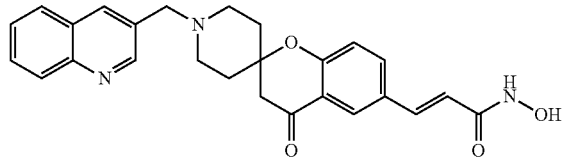 [SMILES: O=C(/C=C/c1ccc2c(c1)C(=O)CC1(CCN(Cc3cnc4ccccc4c3)CC1)O2)NO]

The title compound was prepared according to the procedure described in Example 65, starting from Intermediate 1 (169 mg, 0.500 mmol, hydrochloride salt) and obtaining a white solid (94 mg, di-hydrochloride salt)

Y=36% over 4 steps.

LC-MS: Method G, rt=1.04 min; (ES+) MH$^+$: 444

$^1$H NMR (300 MHz, DMSO-d$_6$) δ (ppm): 11.28 (bs, 1H), 9.25 (d, J=2.05 Hz, 1H), 8.82 (s, 1H), 8.17 (d, J=8.51 Hz, 1H), 8.10 (d, J=7.92 Hz, 1H), 7.82-8.00 (m, 3H), 7.69-7.82 (m, 1H), 7.45 (d, J=15.85 Hz, 1H), 7.19 (d, J=8.51 Hz, 1H), 6.46 (d, J=15.55 Hz, 1H), 4.66 (bs, 2H), 3.15-3.33 (m, 4H), 2.90 (s, 2H), 1.96-2.37 (m, 4H).

Example 67

(E)-3-{1'-(Biphenyl-2-yl-methyl)-4-oxo-spiro[chromane-2,4'-piperidine]-6-yl}-N-hydroxy-acrylamide

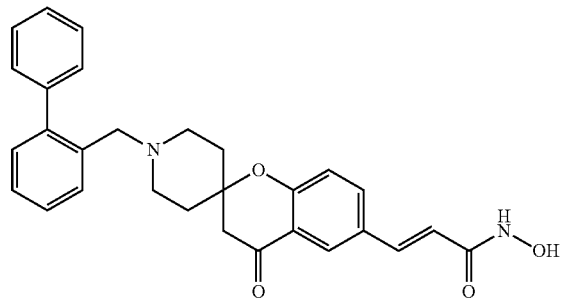 [SMILES: O=C(/C=C/c1ccc2c(c1)C(=O)CC1(CCN(Cc3ccccc3-c3ccccc3)CC1)O2)NO]

(E)-3-{4-Oxo-spiro[chromane-2,4'-piperidine]-6-yl}-acrylic acid methyl ester (169 mg, 0.500 mmol, Intermediate 1, hydrochloride salt) was alkylated using 2-phenylbenzyl bromide (0.18 ml, 1.0 mmol) following the procedure described in Example 2, Step A, giving (E)-3-{1'-(biphenyl-2-yl-methyl)-4-oxo-spiro[chromane-2,4'-piperidine]-6-yl}-acrylic acid methyl ester (163 mg) as a white solid. The intermediate was hydrolyzed as described in Example 55, Step B, giving (E)-3-{1'-(Biphenyl-2-yl-methyl)-4-oxo-spiro[chromane-2,4'-piperidine]-6-yl}-acrylic acid (162 mg) as a white solid (hydrochloride salt). The acid was suspended in DCM (5 ml), TEA (0.07 ml, 0.47 mmol) was added, and the clear solution was treated with NH$_2$OTHP following the procedure described in Example 1, Step B, giving (E)-3-{1'-(biphenyl-2-yl-methyl)-4-oxo-spiro[chromane-2,4'-piperidine]-6-yl}-N-(tetrahydro-pyran-2-yloxy)-acrylamide (163 mg) as a light yellow solid. The compound was dissolved in DCM (5 ml) and treated with 4 M HCl in dioxane (0.4 ml, 1.6 mmol) as described in Example 55, Step D, giving a light yellow solid (114 mg, hydrochloride salt).

Y=45% over 4 steps.

LC-MS: Method G, rt=1.61 min; (ES+) MH$^+$: 469

$^1$H NMR (300 MHz, DMSO-d$_6$) δ (ppm): 7.76-7.84 (m, 1H), 7.71 (dd, J=8.36, 1.32 Hz, 1H), 7.14-7.55 (m, 10H), 7.03 (d, J=8.22 Hz, 1H), 6.37 (d, J=15.55 Hz, 1H), 3.42 (s, 2H), 2.80 (s, 2H), 2.38-2.47 (m, 2H), 2.10-2.37 (m, 2H), 1.78-1.98 (m, 2H), 1.57-1.77 (m, 2H).

Example 68

(E)-3-{1'-Ethyl-4-oxo-spiro[chromane-2,4'-piperidine]-6-yl}-N-hydroxy-acrylamide

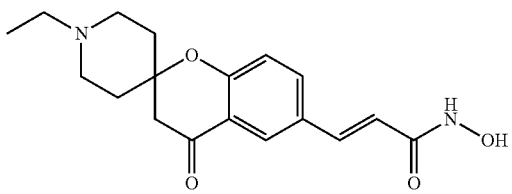 [SMILES: CCN1CCC2(CC1)CC(=O)c1cc(/C=C/C(=O)NO)ccc1O2]

A suspension of (E)-3-{4-oxo-spiro[chromane-2,4'-piperidine]-6-yl}-acrylic acid methyl ester (338 mg, 1.00 mmol, Intermediate 1, hydrochloride salt) in 1 M Na$_2$CO$_3$ was stirred for 10 minutes, then extracted with DCM and treated with acetaldehyde (88 mg, 2.0 mmol) and sodium triacetoxyborohydride (318 mg, 1.5 mmol) following the procedure described in Example 55, Step A, giving (E)-3-{1'-ethyl-4-oxo-spiro[chromane-2,4'-piperidine]-6-yl}-acrylic acid methyl ester (200 mg) as a yellow oil. The ester was hydrolyzed as described in Example 55, Step B, giving (E)-3-{1'-ethyl-4-oxo-spiro[chromane-2,4'-piperidine]-6-yl}-acrylic acid (210 mg) as a white solid (hydrochloride salt). The resulting acid was suspended in DCM (7 ml), TEA (0.13 ml, 0.93 mmol) was added, and the resulting clear solution was treated with NH$_2$OTHP following the procedure described in Example 1, Step B, giving (E)-3-{1'-ethyl-4-oxo-spiro[chromane-2,4'-piperidine]-6-yl}-N-(tetrahydro-pyran-2-yloxy)-acrylamide (180 mg) as a light yellow solid. The compound was dissolved in DCM (6 ml) and treated with 1 M HCl in diethyl ether (6 ml, 6 mmol) as described in Example 2, Step D, giving a light yellow solid (114 mg, hydrochloride salt)

Y=31% over 4 steps.

LC-MS: Method H, rt=2.05 min; (ES+) MH$^+$: 331

$^1$H NMR (300 MHz, DMSO-d$_6$) δ (ppm): 10.70 (bs, 1H), 10.22 (bs, 1H), 7.71-8.01 (m, 2H), 7.45 (d, J=15.85 Hz, 1H), 7.19 (d, J=8.51 Hz, 1H), 6.45 (d, J=15.85 Hz, 0H), 3.27-3.46 (m, 2H), 3.00-3.27 (m, 4H), 2.92 (s, 2H), 1.96-2.29 (m, 4H), 1.26 (t, J=7.34 Hz, 3H).

Example 69

(E)-3-{1'-Isopropyl-4-oxo-spiro[chromane-2,4'-piperidine]-6-yl}-N-hydroxy-acrylamide

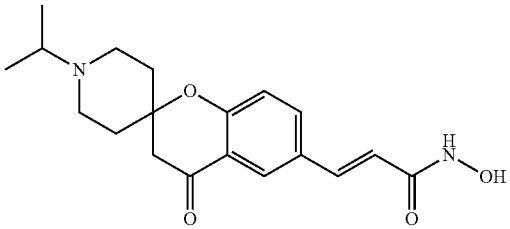 [SMILES: CC(C)N1CCC2(CC1)CC(=O)c1cc(/C=C/C(=O)NO)ccc1O2]

(E)-3-{4-Oxo-spiro[chromane-2,4'-piperidine]-6-yl}-acrylic acid methyl ester (500 mg, 1.48 mmol, Intermediate 1, hydrochloride salt) was suspended in acetonitrile (65 ml). K$_2$CO$_3$ (818 mg, 5.92 mmol) and isopropyl iodide (523 mg, 3.07 mmol) were subsequently added and the mixture was heated at 75° C. for 14 h. The solvent was evaporated and the residue was diluted with water and extracted with ethyl acetate. The combined organic phases were dried, evaporated, and the crude oily residue (575 mg) was hydrolyzed as described in Example 55, Step B, giving (E)-3-{1-isopropyl-4-oxo-spiro[chromane-2,4'-piperidine]-6-yl}-acrylic acid (475 mg) as an orange solid (hydrochloride salt). The resulting acid was suspended in DCM (16 ml), TEA (0.30 ml) was added, and the resulting clear solution was treated with NH$_2$OTHP following the procedure described in Example 1, Step B, giving (E)-3-{1'-isopropyl-4-oxo-spiro[chromane-2,4'-piperidine]-6-yl}-N-(tetrahydro-pyran-2-yloxy)-acrylamide as an orange solid (314 mg). The compound was dissolved in DCM (4 ml) and treated with 1 M HCl in diethyl ether (6 ml, 6 mmol) as described in Example 2, Step D, giving a light pink solid (192 mg, trifluoroacetate salt) after purification by preparative HPLC.

Y=28% in 4 steps.

LC-MS: Method G, rt=0.87 min; (ES+) MH$^+$: 345

$^1$H NMR (300 MHz, DMSO-d$_6$) δ (ppm): 10.67 (bs, 1H), 9.47 (bs, 1H), 7.92 (d, J=2.05 Hz, 1H), 7.84 (dd, J=8.51, 2.05 Hz, 1H), 7.45 (d, J=15.55 Hz, 1H), 7.22 (d, J=8.80 Hz, 1H), 6.44 (d, J=15.85 Hz, 1H), 3.40-3.73 (m, 1H), 3.27-3.40 (m, 2H), 3.02-3.26 (m, 2H), 2.94 (s, 2H), 2.13-2.34 (m, 2H), 1.83-2.13 (m, 2H), 1.30 (d, J=6.46 Hz, 6H).

Example 70

(E)-3-{1'-Cyclopentyl-4-oxo-spiro[chromane-2,4'-piperidine]-6-yl}-N-hydroxy-acrylamide

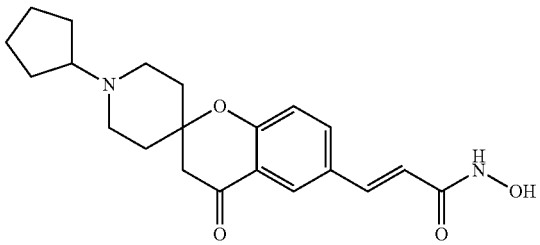 [SMILES: O=C(/C=C/c1ccc2c(c1)C(=O)CC1(CCN(C3CCCC3)CC1)O2)NO]

(E)-3-{4-Oxo-spiro[chromane-2,4'-piperidine]-6-yl}-acrylic acid methyl ester (500 mg, 1.48 mmol, Intermediate 1, hydrochloride salt) was suspended in acetonitrile (65 ml). K$_2$CO$_3$ (818 mg, 5.92 mmol) and cyclopentyl bromide (882 mg, 5.92 mmol) were subsequently added and the mixture was heated at 75° C. for 14 h. The solvent was then evaporated and the residue was diluted with water and extracted with ethyl acetate, which was dried and evaporated. The crude orange solid (540 mg) was hydrolyzed as described in Example 55, Step B, giving (E)-3-{1'-cyclopentyl-4-oxo-spiro[chromane-2,4'-piperidine]-6-yl}-acrylic acid (500 mg) as a light brown solid. The acid was suspended in DCM (16 ml), TEA (0.30 ml) was added and the resulting clear solution was treated with NH$_2$OTHP following the procedure described in Example 1, Step B, giving (E)-3-{1-cyclopentyl-4-oxo-spiro[chromane-2,4'-piperidine]-6-yl}-N-(tetrahydro-pyran-2-yloxy)-acrylamide as an orange solid (360 mg). The protected hydroxamic acid was dissolved in DCM (4 ml) and treated with 1 M HCl in diethyl ether (4 ml, 4 mmol) as described in Example 2, Step D, giving a light pink solid (247 mg, trifluoroacetate salt) after purification by preparative HPLC.

Y=35% in 4 steps.

LC-MS: Method G, rt=1.06 min; (ES+) MH$^+$: 371

$^1$H NMR (300 MHz, DMSO-d$_6$) δ (ppm): 10.67 (bs, 1H), 9.26 (bs, 1H), 7.93 (d, J=8.31 Hz, 1H), 7.85 (m, 1H), 7.46 (d, 1 J=15.85 Hz 1H), 7.19 (d, J=8.31 Hz, 1H), 6.43 (d, J=15.85 Hz, 1H), 3.55-3.71 (m, 1H), 3.40-3.50 (m, 2H), 3.08-3.26 (m, 2H), 2.96 (s, 2H), 2.14-2.27 (m, 2H), 1.82-2.10 (m, 4H), 1.66-1.79 (m, 3H), 1.51-1.66 (m, 3H).

Example 71

(E)-3-{1'-(2-Phenyl-ethyl)-3,4-dihydro-4-oxo-spiro[2H-(1,3)-benzoxazine-2,4'-piperidin]-6-yl}-N-hydroxy-acrylamide

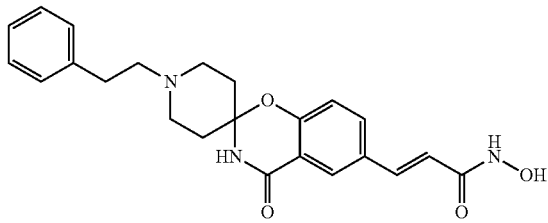 [SMILES: O=C(/C=C/c1ccc2c(c1)C(=O)NC1(CCN(CCc3ccccc3)CC1)O2)NO]

Step A (E)-3-{3,4-Dihydro-4-oxo-spiro[2H-(1,3)-benzoxazine-2,4'-piperidin]-6-yl}-acrylic acid methyl ester hydrochloride (obtained as described in Example 25, Step B, 300 mg, 0.886 mmol) was dissolved in MeOH (30 ml). The pH was adjusted to 5 with AcOH and 1 M NaOH in MeOH, and then phenylacetaldehyde (128 mg, 1.06 mmol) and NaCNBH$_3$ (67 mg, 1.06 mmol) were added. The mixture was stirred overnight at RT, then the solvent was removed and the residue partitioned between 5% aqueous NaHCO$_3$ and DCM. The organic phase was dried over Na$_2$SO$_4$ and evaporated. The crude product was purified by column chromatography (eluent:DCM/MeOH 95:5) to give (E)-3-{1'-(2-phenyl-ethyl)-3,4-dihydro-4-oxo-spiro[2H-(1,3)-benzoxazine-2,4'-piperidin]-6-yl}-acrylic acid methyl ester (322 mg).

Y=92%

$^1$H NMR (DMSO-d$_6$) δ (ppm): 8.77 (s, 1H), 8.02 (d, J=2.05 Hz, 1H), 7.91 (dd, J=8.51, 2.35 Hz, 1H), 7.67 (d, J=16.14 Hz, 1H), 7.12-7.35 (m, 5H), 7.08 (d, J=8.51 Hz, 1H), 6.56 (d, J=15.85 Hz, 1H), 3.72 (s, 3H), 2.67-2.88 (m, 4H), 2.54-2.62 (m, 2H), 2.29-2.45 (m, 2H), 1.93-2.11 (m, 2H), 1.67-1.93 (m, 2H).

Step B (E)-3-{1'-(2-Phenyl-ethyl)-3,4-dihydro-4-oxo-spiro[2H-(1,3)-benzoxazine-2,4'-piperidin]-6-yl}-acrylic acid methyl ester (292 mg, 0.719 mmol) was suspended in dioxane (5 ml) and water (5 ml). 1 M NaOH (0.93 ml) was added and the resulting mixture was stirred overnight at RT. The mixture was neutralized with 1 M HCl and concentrated under vacuum. The pH was brought to 4 with 1 M HCl and the resulting solid was decanted and dried to give (E)-3-{1'-(2-phenyl-ethyl)-3,4-dihydro-4-oxo-spiro[2H-(1,3)-benzoxazine-2,4'-piperidin]-6-yl}-acrylic acid (265 mg).

Y=94%

$^1$H NMR (DMSO-d$_6$) δ (ppm): 12.30 (bs, 1H), 8.81 (bs, 1H), 7.99 (d, J=2.05 Hz, 1H), 7.88 (dd, J=8.66, 2.20 Hz, 1H), 7.60 (d, J=15.85 Hz, 1H), 7.15-7.34 (m, 5H), 7.09 (d, J=8.51 Hz, 1H), 6.45 (d, J=16.14 Hz, 1H), 2.57-3.02 (m, 6H), 1.65-2.45 (m, 6H).

Step C (E)-3-{1'-(2-Phenyl-ethyl)-3,4-dihydro-4-oxo-spiro[2H-(1,3)-benzoxazine-2,4'-piperidin]-6-yl}-acrylic acid (240 mg, 0.612 mmol) was dissolved in DCM (20 ml) and TEA (0.17 ml, 1.23 mmol). EDC (169 mg, 0.88 mmol), HOBT (119 mg, 0.88 mmol) and NH$_2$OTHP (86 mg, 0.74 mmol) were added and the mixture was stirred at RT overnight. The mixture was partitioned between DCM and 5% aqueous NaHCO$_3$ and the organic phase was dried over Na$_2$SO$_4$ and evaporated. The crude mixture was purified by column chromatography (eluent:DCM/MeOH 95:5). The resulting (E)-3-{1'-(2-phenyl-ethyl)-3,4-dihydro-4-oxo-spiro[2H-(1,3)-benzoxazine-2,4'-piperidin]-6-yl}-N-(tetrahydro-pyran-2-yloxy)-acrylamide was dissolved in DCM and treated with 4 M HCl in dioxane for 3 h. The precipitate was filtered off and washed with DCM to give (E)-3-{1-(2-phenyl-ethyl)-3,4-dihydro-4-oxo-spiro[2H-(1,3)-benzoxazine-2,4'-piperidin]-6-yl}-N-hydroxy-acrylamide hydrochloride (175 mg) as a white solid.

Y=64% (over 2 steps)

LC-MS: Method G, rt=1.23; (ES+) MH$^+$:408

$^1$H NMR (DMSO-d$_6$) δ (ppm): 10.81 (bs, 1H), 10.71 (bs, 1H), 9.11 (s, 1H), 7.96 (d, J=2.05 Hz, 1H), 7.77 (dd, J=8.51, 1.76 Hz, 1H), 7.46 (d, J=15.55 Hz, 1H), 7.22-7.40 (m, 5H), 7.15 (d, J=8.22 Hz, 1H), 6.46 (d, J=15.85 Hz, 1H), 3.47-3.66 (m, 2H), 3.15-3.45 (m, 4H), 3.04-3.13 (m, 2H), 2.17-2.39 (m, 4H).

Example 72

(E)-3-{3,4-Dihydro-4-oxo-spiro[2H-(1,3)-benzoxazine-2,4'-piperidin]-6-yl}-N-hydroxy-acrylamide

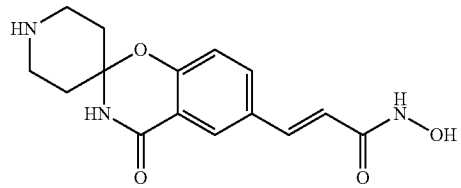 [SMILES: O=C(/C=C/c1ccc2c(c1)C(=O)NC1(CCNCC1)O2)NO]

(E)-3-{1'-Tert-butoxycarbonyl-3,4-dihydro-4-oxo-spiro[2H-(1,3)-benzoxazine-2,4'-piperidin]-6-yl}-acrylic acid methyl ester (obtained as described in Example 25, Step A, 300 mg, 0.745 mmol) was treated with 1 M NaOH following the procedure described in Example 71, Step B, using citric acid instead of hydrochloric acid giving (E)-3-{1'-tert-butoxycarbonyl-3,4-dihydro-4-oxo-spiro[2H-(1,3)-benzoxazine-2,4'-piperidin]-6-yl}-acrylic acid (287 mg, 99%). The resulting product was treated with NH₂OTHP according to the procedure described in Example 71, Step C, giving (E)-3-{1'-tert-butoxycarbonyl-3,4-dihydro-4-oxo-spiro[2H-(1, 3)-benzoxazine-2,4'-piperidin]-6-yl}-N-(tetrahydro-pyran-2-yloxy)-acrylamide. Finally, removal of the THP and BOC protecting groups following the procedure described in Example 71, Step C gave (E)-3-{3,4-dihydro-4-oxo-spiro[2H-(1,3)-benzoxazine-2,4'-piperidin]-6-yl}-N-hydroxy-acrylamide hydrochloride (109 mg) as a white solid.

Y=43% (over 3 steps)

LC-MS: Method L, rt=2.05; (ES+) MH⁺:304

¹H NMR (DMSO-d₆) δ (ppm): 9.29-9.48 (m, 1H), 9.15-9.29 (m, 1H), 9.11 (s, 1H), 7.94 (d, J=2.05 Hz, 1H), 7.74 (dd, J=8.36, 1.91 Hz, 1H), 7.45 (d, J=15.85 Hz, 1H), 7.16 (d, J=8.51 Hz, 1H), 6.46 (d, J=15.85 Hz, 1H), 3.17-3.40 (m, 2H), 2.95-3.17 (m, 2H), 2.02-2.33 (m, 4H).

Example 73

(E)-3-{1'-Methyl-3,4-dihydro-4-oxo-spiro[2H-(1,3)-benzoxazine-2,4'-piperidin]-6-yl}-N-hydroxy-acrylamide

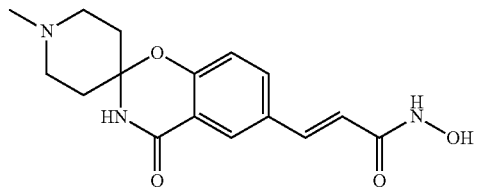

The title compound was obtained starting from (E)-3-{3,4-dihydro-4-oxo-spiro[2H-(1,3)-benzoxazine-2,4'-piperidin]-6-yl}-acrylic acid methyl ester hydrochloride (obtained as described in Example 25, Step B) and formaldehyde, according to synthetic procedure described in Example 71. The title compound was obtained as its hydrochloride salt.

LC-MS: Method L, rt=2.08; (ES+) MH⁺:318

¹H NMR (DMSO-d₆) δ (ppm): 10.93 (bs, 1H), 9.06 (s, 1H), 7.95 (d, J=1.76 Hz, 1H), 7.76 (dd, J=8.36, 1.91 Hz, 1H), 7.45 (d, J=15.85 Hz, 1H), 7.16 (d, J=8.51 Hz, 1H), 6.46 (d, J=15.85 Hz, 1H), 3.28-3.51 (m, 2H), 2.97-3.28 (m, 2H), 2.78 (d, J=4.70 Hz, 3H), 2.07-2.39 (m, 4H).

Example 74

(E)-3-{1'-(4-Fluoro-benzyl)-3,4-dihydro-4-oxo-spiro[2H-(1,3)-benzoxazine-2,4'-piperidin]-6-yl}-N-hydroxy-acrylamide

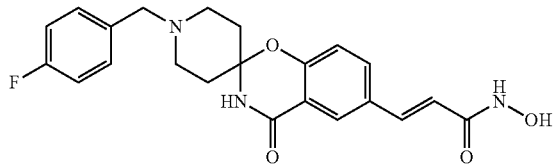 [SMILES: O=C(/C=C/c1ccc2c(c1)C(=O)NC1(CCN(Cc3ccc(F)cc3)CC1)O2)NO]

The title compound was obtained starting from (E)-3-{3,4-dihydro-4-oxo-spiro[2H-(1,3)-benzoxazine-2,4'-piperidin]-6-yl}-acrylic acid methyl ester hydrochloride (obtained as described in Example 25, Step B) and 4-fluoro-benzaldehyde, according to synthetic procedure described in Example 71. The title compound was obtained as its hydrochloride salt (white solid).

LC-MS: Method G, rt=1.16; (ES+) MH⁺:412

¹H NMR (DMSO-d₆) δ (ppm): 11.23 (bs, 1H), 9.12 (s, 1H), 7.94 (d, J=1.76 Hz, 1H), 7.77 (dd, J=8.80, 1.76 Hz, 1H), 7.67-7.75 (m, 2H), 7.45 (d, J=15.85 Hz, 1H), 7.20-7.38 (m, 2H), 7.12 (d, J=8.51 Hz, 1H), 6.46 (d, J=15.85 Hz, 1H), 4.36 (d, J=4.70 Hz, 2H), 3.08-3.41 (m, 4H), 2.15-2.43 (m, 4H).

Example 75

(E)-3-{1'-(4-Fluoro-benzyl)-3,4-dihydro-3-methyl-4-oxo-spiro[2H-(1,3)-benzoxazine-2,4'-piperidin]-6-yl}-N-hydroxy-acrylamide

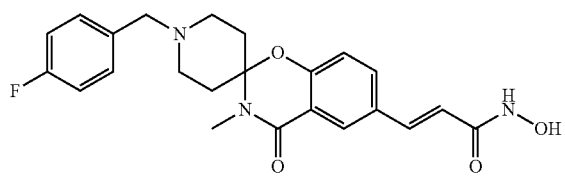 [SMILES: CN1C(=O)c2cc(/C=C/C(=O)NO)ccc2OC12CCN(Cc1ccc(F)cc1)CC2]

Step A (E)-3-{-3,4-Dihydro-3-methyl-4-oxo-spiro[2H-(1,3)-benzoxazine-2,4'-piperidin]-6-yl}-acrylic acid methyl ester hydrochloride (600 mg, 1.70 mmol, Intermediate 5) was treated with 4-fluoro-benzaldehyde according to the procedure described in Example 71, Step A to give (E)-3-{1'-(4-fluoro-benzyl)-3,4-dihydro-3-methyl-4-oxo-spiro[2H-(1,3)-benzoxazine-2,4'-piperidin]-6-yl}-acrylic acid methyl ester (542 mg).

Y=75%

¹H NMR (DMSO-d₆) δ (ppm): 8.03 (d, J=2.05 Hz, 1H), 7.93 (dd, J=8.51, 2.35 Hz, 1H), 7.68 (d, J=16.14 Hz, 1H), 7.28-7.46 (m, 2H), 7.10-7.20 (m, 2H), 7.11 (d, J=8.51 Hz, 1H), 6.56 (d, J=15.85 Hz, 1H), 3.72 (s, 3H), 3.51 (s, 2H), 3.02 (s, 3H), 2.65-2.80 (m, 2H), 2.21-2.41 (m, 2H), 2.02-2.19 (m, 2H), 1.88-2.02 (m, 2H).

Step B (E)-3-{1'-(4-Fluoro-benzyl)-3,4-dihydro-3-methyl-4-oxo-spiro[2H-(1,3)-benzoxazine-2,4'-piperidin]-6-yl}-acrylic acid methyl ester (520 mg, 1.22 mmol) was suspended in dioxane (20 ml) and water (10 ml). 1 M NaOH (1.59 ml) was added and the resulting mixture was stirred at RT for 5 h. The mixture was neutralized with 1 M HCl and the solvent was removed. The resulting acid was dissolved in DCM (10 ml) and TEA (0.338 ml, 2.44 mmol). EDC (350 mg, 1.83 mmol), HOBT (247 mg, 1.83 mmol) and NH₂OTHP (172 mg, 1.46 mmol) were added to the resulting solution. The mixture was stirred for 6 h at RT and then partitioned between 5% aqueous NaHCO₃ and DCM. The organic layer was dried over Na₂SO₄ and evaporated. The crude product was purified by column chromatography (eluent:DCM/MeOH 97:3) and the resulting compound was dissolved in DCM and treated with 4 M HCl in dioxane for 4 h. The precipitate was filtered to give (E)-3-{1'-(4-fluoro-benzyl)-3,4-dihydro-3-methyl-4-oxo-spiro[2H-(1,3)-benzoxazine-2,4'-piperidin]-6-yl}-N-hydroxy-acrylamide hydrochloride (451 mg) as a white solid.

Y=80% (3 steps)

LC-MS: Method G, rt=1.23; (ES+) MH⁺:426

¹H NMR (DMSO-d₆) δ (ppm): 11.32 (bs, 1H), 10.72 (bs, 1H), 7.97 (d, J=1.76 Hz, 1H), 7.79 (dd, J=8.36, 1.91 Hz, 1H), 7.64-7.75 (m, 2H), 7.46 (d, J=15.85 Hz, 1H), 7.23-7.39 (m, 2H), 7.18 (d, J=8.51 Hz, 1H), 6.47 (d, J=15.85 Hz, 1H), 4.38 (d, J=4.40 Hz, 2H), 3.10-3.48 (m, 4H), 3.01 (s, 3H), 2.58-2.85 (m, 2H), 2.11-2.34 (m, 2H).

Example 76

(E)-3-{1'-Benzyl-3,4-dihydro-3-methyl-4-oxo-spiro[2H-(1,3)-benzoxazine-2,4'-piperidin]-6-yl}-N-hydroxy-acrylamide

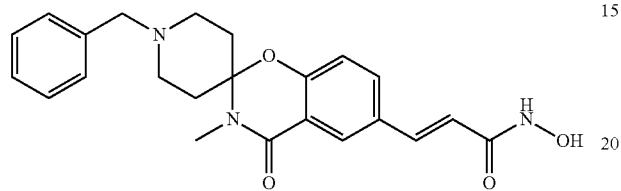

The title compound was obtained starting from (E)-3-{-3,4-dihydro-3-methyl-4-oxo-spiro[2H-(1,3)-benzoxazine-2,4'-piperidin]-6-yl}-acrylic acid methyl ester hydrochloride (Intermediate 5) and benzaldehyde, following the synthetic procedure described in Example 75. The title compound was obtained as its hydrochloride salt (white powder).

LC-MS: Method G, rt=1.17; (ES+) MH$^+$:408

$^1$H NMR (DMSO-d$_6$) δ (ppm): 11.25 (bs, 1H), 7.97 (d, J=2.05 Hz, 1H), 7.73-7.89 (m, 1H), 7.58-7.72 (m, 2H), 7.35-7.57 (m, 4H), 7.18 (d, J=8.51 Hz, 1H), 6.47 (d, J=15.85 Hz, 1H), 4.38 (d, J=4.99 Hz, 2H), 3.10-3.45 (m, 4H), 3.01 (s, 3H), 2.58-2.86 (m, 2H), 2.10-2.34 (m, 2H).

Example 77

(E)-3-{1'-(2-Phenyl-ethyl)-3,4-dihydro-3-methyl-4-oxo-spiro[2H-(1,3)-benzoxazine-2,4'-piperidin]-6-yl}-N-hydroxy-acrylamide

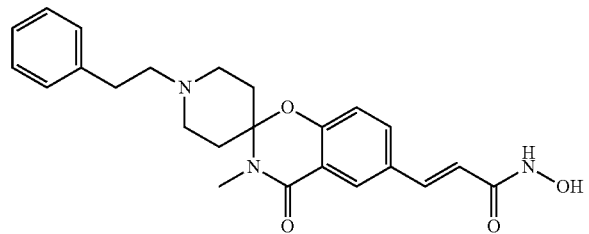 [SMILES: CN1C(=O)c2cc(/C=C/C(=O)NO)ccc2OC12CCN(CCc1ccccc1)CC2]

The title compound was obtained starting from (E)-3-{-3,4-dihydro-3-methyl-4-oxo-spiro[2H-(1,3)-benzoxazine-2,4'-piperidin]-6-yl}-acrylic acid methyl ester hydrochloride (Intermediate 5) and phenyl acetaldehyde, following the synthetic procedure described in Example 75. The title compound was obtained as its hydrochloride salt (white powder)

LC-MS: Method G, rt=1.30; (ES+) MH$^+$:422

$^1$H NMR (DMSO-d$_6$) δ (ppm): 11.31 (bs, 1H), 7.98 (d, J=1.76 Hz, 1H), 7.79 (dd, J=8.51, 1.76 Hz, 1H), 7.46 (d, J=15.85 Hz, 1H), 7.24-7.41 (m, 5H), 7.21 (d, J=8.51 Hz, 1H), 6.48 (d, J=15.85 Hz, 1H), 3.49-3.70 (m, 2H), 3.16-3.49 (m, 4H), 3.07-3.16 (m, 2H), 3.04 (s, 3H), 2.58-2.82 (m, 2H), 2.18-2.37 (m, 2H).

Example 78

(E)-3-{1'-Methyl-3,4-dihydro-3-methyl-4-oxo-spiro[2H-(1,3)-benzoxazine-2,4'-piperidin]-6-yl}-N-hydroxy-acrylamide

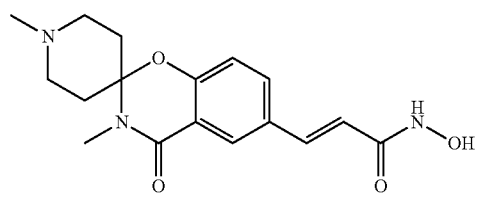 [SMILES: CN1CCC2(CC1)Oc1ccc(/C=C/C(=O)NO)cc1C(=O)N2C]

The title compound was obtained starting from (E)-3-{-3,4-dihydro-3-methyl-4-oxo-spiro[2H-(1,3)-benzoxazine-2,4'-piperidin]-6-yl}-acrylic acid methyl ester hydrochloride (Intermediate 5) and formaldehyde, following the synthetic procedure described in Example 75. The title compound was obtained as its hydrochloride salt (white powder).

LC-MS: Method L, rt=2.20; (ES+) MH$^+$:332

$^1$H NMR (DMSO-d$_6$) δ (ppm): 11.26 (bs, 1H), 10.28 (bs, 1H), 7.97 (d, J=2.05 Hz, 1H), 7.78 (dd, J=8.36, 1.91 Hz, 1H), 7.46 (d, J=15.85 Hz, 1H), 7.22 (d, J=8.51 Hz, 1H), 6.48 (d, J=15.85 Hz, 1H), 3.32-3.49 (m, 2H), 3.15-3.32 (m, 2H), 3.02 (s, 3H), 2.79 (d, J=4.40 Hz, 3H), 2.63 (td, J=13.79, 4.40 Hz, 2H), 2.08-2.34 (m, 2H).

Example 79

(E)-3-{3,4-Dihydro-3-methyl-4-oxo-spiro[2H-(1,3)-benzoxazine-2,4'-piperidin]-6-yl}-N-hydroxy-acrylamide

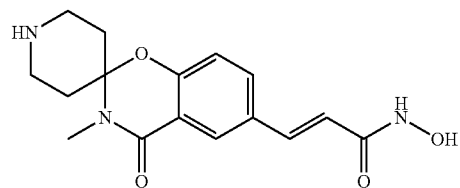 [SMILES: CN1C(=O)c2cc(/C=C/C(=O)NO)ccc2OC12CCNCC2]

The title compound was obtained starting from (E)-3-{1'-tert-butoxycarbonyl-3,4-dihydro-3-methyl-4-oxo-spiro[2H-(1,3)-benzoxazine-2,4'-piperidin]-6-yl}-acrylic acid methyl ester (obtained as described for Intermediate 5, Step C) following the procedure described in Example 72. The title compound was obtained as its hydrochloride salt (white solid)

LC-MS: Method L, rt=2.17; (ES+) MH$^+$:318

$^1$H NMR (DMSO-d$_6$) δ (ppm): 10.30 (s, 1H), 9.06-9.63 (m, 2H), 7.96 (d, J=2.05 Hz, 1H), 7.76 (dd, J=8.51, 2.05 Hz, 1H), 7.46 (d, J=15.85 Hz, 1H), 7.22 (d, J=8.51 Hz, 1H), 6.48 (d, J=15.85 Hz, 1H), 3.18-3.42 (m, 2H), 3.06-3.21 (m, 2H), 3.02 (s, 3H), 2.38-2.58 (m, 2H), 2.10-2.27 (m, 2H).

Example 80

(E)-3-{1'-Benzyl-3,4-dihydro-3-benzyl-4-oxo-spiro [2H-(1,3)-benzoxazine-2,4'-piperidin]-6-yl}-N-hydroxy-acrylamide

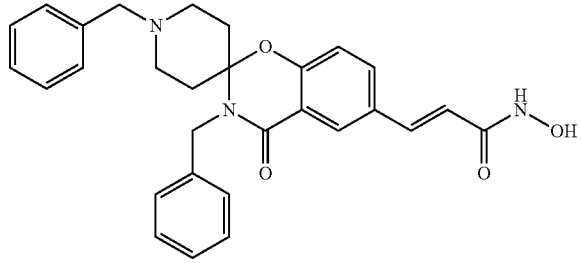 [SMILES: O=C(/C=C/c1ccc2c(c1)C(=O)N(Cc1ccccc1)C1(CCN(Cc3ccccc3)CC1)O2)NO]

(E)-3-{1'-Benzyl-3,4-dihydro-3-benzyl-4-oxo-spiro[2H-(1,3)-benzoxazine-2,4'-piperidin]-6-yl}-acrylic acid methyl ester was obtained by reacting (E)-3-{3,4-dihydro-3-benzyl-4-oxo-spiro[2H-(1,3)-benzoxazine-2,4'-piperidin]-6-yl}-acrylic acid methyl ester (485 mg, 1.13 mmol, Intermediate 6) with benzyl bromide, according to the procedure described in Example 2, Step A, giving a white solid (544 mg, quantitative). The methyl ester (500 mg, 1.03 mmol) was hydrolyzed with HCl 20% and AcOH following the procedure described Example 55, Step B, giving (E)-3-{1'-benzyl-3,4-dihydro-3-benzyl-4-oxo-spiro[2H-(1,3)-benzoxazine-2,4'-piperidin]-6-yl}-acrylic acid as a white solid (500 mg, 95%). The resulting product was treated with NH$_2$OTHP according to the procedure described in Example 1, Step B, giving (E)-3-{1-benzyl-3,4-dihydro-3-benzyl-4-oxo-spiro[2H-(1,3)-benzoxazine-2, 4'-piperidin]-6-yl}-N-(tetrahydro-pyran-2-yloxy)-acrylamide as a yellow solid (228 mg, 40%). Finally, removal of the THP protecting group (177 mg, 0.312 mmol) following the procedure described in Example 1, Step C gave (E)-3-{1'-benzyl-3,4-dihydro-3-benzyl-4-oxo-spiro[2H-(1,3)-benzoxazine-2,4'-piperidin]-6-yl}-N-hydroxy-acrylamide (150 mg, trifluoroacetate salt) after purification by preparative HPLC.

Y=80.5%

LC-MS: Method G, rt=1.55 min; (ES+) MH$^+$: 484

$^1$H-NMR (DMSO-d$_6$) δ (ppm): 10.72 (bs, 1H), 9.51 (bs, 1H), 8.06 (d, J=1.76 Hz, 1H), 7.86 (d, J=8.80 Hz, 1H), 7.42-7.69 (m, 6H), 7.19-7.42 (m, 6H), 6.49 (d, J=15.85 Hz, 1H), 4.76 (s, 2H), 4.36 (bs, 2H), 3.12-3.45 (m, 4H), 2.10-2.34 (m, 4H).

Example 81

(E)-3-{1'-Methyl-3,4-dihydro-3-benzyl-4-oxo-spiro [2H-(1,3)-benzoxazine-2,4'-piperidin]-6-yl}-N-hydroxy-acrylamide

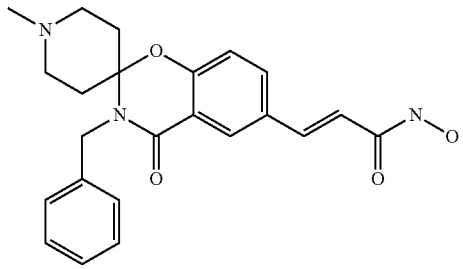 [SMILES: CN1CCC2(CC1)Oc1ccc(/C=C/C(=O)NO)cc1C(=O)N2Cc1ccccc1]

(E)-3-{1'-Methyl-3,4-dihydro-3-benzyl-4-oxo-spiro[2H-(1,3)-benzoxazine-2,4'-piperidin]-6-yl}-acrylic acid methyl ester was obtained by reaction between (E)-3-{3,4-dihydro-3-benzyl-4-oxo-spiro[2H-(1,3)-benzoxazine-2,4'-piperidin]-6-yl}-acrylic acid methyl ester (600 mg, 1.40 mmol, Intermediate 6, hydrochloric salt) and HCHO (125 μl, 1.68 mmol, 37% aqueous solution), according to the procedure described in Example 55, Step A, giving a white solid (495 mg, 87%). The methyl ester (488 mg, 1.20 mmol) was hydrolyzed with HCl 20% and AcOH following the procedure described in Example 55, Step B, giving (E)-3-{1-methyl-3,4-dihydro-3-benzyl-4-oxo-spiro[2H-(1,3)-benzoxazine-2,4'-piperidin]-6-yl}-acrylic acid hydrochloric salt as a white solid (490 mg, 95%). The resulting product (460 mg, 1.07 mmol) was treated with NH$_2$OTHP according to the procedure described in Example 1, Step B, giving (E)-3-{1-methyl-3,4-dihydro-3-benzyl-4-oxo-spiro[2H-(1,3)-benzoxazine-2,4'-piperidin]-6-yl}-N-(tetrahydro-pyran-2-yloxy)-acrylamide as a yellow solid (150 mg, 28%). Finally, removal of the THP protecting group following the procedure described in Example 1, Step C gave after purification by preparative HPLC (E)-3-{1-Methyl-3,4-dihydro-3-benzyl-4-oxo-spiro[2H-(1,3)-benzoxazine-2,4'-piperidin]-6-yl}-N-hydroxy-acrylamide (12 mg) as its trifluoroacetate salt.

Y=7.5%

LC-MS: Method G, rt=1.21 min; (ES+) MH$^+$: 408

$^1$H-NMR (DMSO-d$_6$) δ (ppm): 10.71 (bs, 1H), 9.39 (bs, 1H), 8.07 (d, J=1.76 Hz, 1H), 7.85 (dd, J=8.36, 1.91 Hz, 1H), 7.50 (d, J=15.55 Hz, 1H), 7.12-7.44 (m, 6H), 6.48 (d, J=15.85 Hz, 1H), 4.79 (s, 2H), 3.12-3.46 (m, 4H), 2.81 (bs 3H), 2.04-2.33 (m, 4H).

Example 82

(E)-3-{3,4-Dihydro-3-benzyl-4-oxo-spiro[2H-(1,3)-benzoxazine-2,4'-piperidin]-6-yl}-N-hydroxy-acrylamide

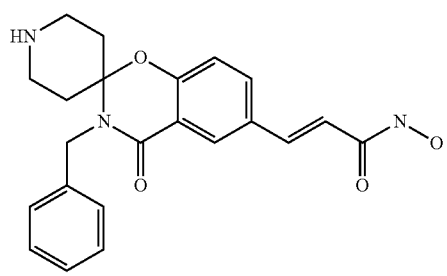 [SMILES: O=C(/C=C/c1ccc2c(c1)C(=O)N(Cc1ccccc1)C1(CCNCC1)O2)NO]

(E)-3-{1'-tert-butoxycarbonyl-3,4-dihydro-3-benzyl-4-oxo-spiro[2H-(1,3)-benzoxazine-2,4'-piperidin]-6-yl}-acrylic acid methyl ester (800 mg, 1.63 mmol, Intermediate 6, Step A) was hydrolyzed with NaOH following the procedure described in Example 1, Step A, to give (E)-3-{1'-tert-butoxycarbonyl-3,4-dihydro-3-benzyl-4-oxo-spiro[2H-(1,3)-benzoxazine-2,4'-piperidin]-6-yl}-acrylic acid as a white solid (750 mg, 96%). The resulting product was treated with NH$_2$OTHP according to the procedure described in Example 1, Step B, obtaining (E)-3-{1'-tert-butoxycarbonyl-3,4-dihydro-3-benzyl-4-oxo-spiro[2H-(1,3)-benzoxazine-2,4'-piperidin]-6-yl}-N-(tetrahydro-pyran-2-yloxy)-acrylamide as a white solid (430 mg, 48%). Finally, removal of the THP and BOC protecting groups (420 mg, 0.73 mmol) following the procedure described in Example 1, Step C gave (E)-3-{3,4- dihydro-3-benzyl-4-oxo-spiro[2H-(1,3)-benzoxazine-2,4'-piperidin]-6-yl}-N-hydroxy-acrylamide (208 mg, trifluoroacetate salt) after purification by preparative HPLC.

Y=56%

LC-MS: Method G, rt=1.22 min; (ES+) MH+: 394

$^1$H-NMR (DMSO-$d_6$) δ (ppm): 10.71 (bs, 1H), 8.59-8.74 (m, 1H), 8.20-8.51 (m, 1H), 8.06 (d, J=2.05 Hz, 1H), 7.82 (dd, J=8.80, 1.76 Hz, 1H), 7.50 (d, J=15.85 Hz, 1H), 7.08-7.41 (m, 6H), 6.48 (d, J=15.85 Hz, 1H), 4.80 (s, 2H), 3.19-3.33 (m, 2H), 2.88-3.16 (m, 2H), 1.99-2.25 (m, 4H).

Example 83

(E)-3-{1'-(4-Fluoro-benzyl)-3,4-dihydro-3-benzyl-4-oxo-spiro[2H-(1,3)-benzoxazine-2,4'-piperidin]-6-yl}-N-hydroxy-acrylamide

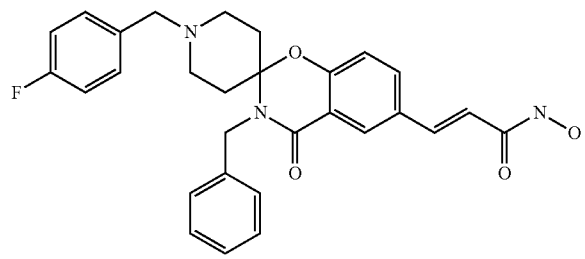 [SMILES: O=C(/C=C/c1ccc2c(c1)C(=O)N(Cc1ccccc1)C1(CCN(Cc3ccc(F)cc3)CC1)O2)NO]

(E)-3-{1'-Methyl-3,4-dihydro-3-benzyl-4-oxo-spiro[2H-(1,3)-benzoxazine-2,4'-piperidin]-6-yl}-acrylic acid methyl ester was obtained by reaction between (E)-3-{3,4-dihydro-3-benzyl-4-oxo-spiro[2H-(1,3)-benzoxazine-2,4'-piperidin]-6-yl}-acrylic acid methyl ester (485 mg, 1.13 mmol, Intermediate 6) and 4-fluoro-benzaldehyde (161 µl, 1.53 mmol), according to the procedure described in Example 55, Step A, giving a white solid (553 mg, 98%). The methyl ester (533 mg, 1.07 mmol) was hydrolyzed with HCl 20% and AcOH following the procedure described in Example 55, Step B, giving (E)-3-{1'-(4-fluorobenzyl)-3,4-dihydro-3-benzyl-4-oxo-spiro[2H-(1,3)-benzoxazine-2,4'-piperidin]-6-yl}-acrylic acid hydrochloric salt as a white solid (510 mg, 92%). The acid (497 mg, 0.95 mmol) was treated with NH$_2$OTHP according to the procedure described in Example 1, Step B, giving (E)-3-{1'-(4-fluorobenzyl)-3,4-dihydro-3-benzyl-4-oxo-spiro[2H-(1,3)-benzoxazine-2,4'-piperidin]-6-yl}-N-(tetrahydro-pyran-2-yloxy)-acrylamide as a white solid (343 mg, 62%). Finally, removal of the THP protecting group following the procedure described in Example 55, Step D gave (E)-3-{1'-(4-fluorobenzyl)-3,4-dihydro-3-benzyl-4-oxo-spiro[2H-(1,3)-benzoxazine-2,4'-piperidin]-6-yl}-N-hydroxy-acrylamide (197 mg, hydrochloride salt) as a white solid.

Y=65%

LC-MS: Method G, rt=1.62 min; (ES+) MH+: 502

$^1$H NMR (300 MHz, DMSO-$d_6$) δ (ppm): 11.09 (bs, 1H), 8.05 (d, J=2.05 Hz, 1H), 7.84 (dd, J=8.36, 1.61 Hz, 1H), 7.66 (m, 2H), 7.49 (d, J=15.85 Hz, 1H), 7.24-7.40 (m, 8H), 6.49 (d, J=15.85 Hz, 1H), 4.79 (s, 2H), 4.34 (d, J=4.40 Hz, 2H), 3.06-3.35 (m, 4H), 2.55-2.77 (m, 2H), 2.00-2.23 (m, 2H).

Example 84

(E)-3-{1'-(2-Phenyl-ethyl)-3,4-dihydro-3-benzyl-4-oxo-spiro[2H-(1,3)-benzoxazine-2,4'-piperidin]-6-yl}-N-hydroxy-acrylamide

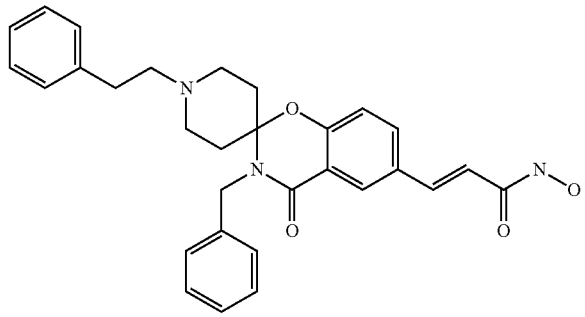 [SMILES: O=C(/C=C/c1ccc2c(c1)C(=O)N(Cc1ccccc1)C1(CCN(CCc3ccccc3)CC1)O2)NO]

(E)-3-{1'-Methyl-3,4-dihydro-3-benzyl-4-oxo-spiro[2H-(1,3)-benzoxazine-2,4'-piperidin]-6-yl}-acrylic acid methyl ester was obtained by reaction between (E)-3-{3,4-dihydro-3-benzyl-4-oxo-spiro[2H-(1,3)-benzoxazine-2,4'-piperidin]-6-yl}-acrylic acid methyl ester (485 mg, 1.13 mmol, Intermediate 6) and phenylacetaldehyde (171 µl, 1.53 mmol), according to the procedure described in Example 55, Step A, giving a white solid (554 mg, 99%). The methyl ester (540 mg, 1.09 mmol) was hydrolyzed with HCl 20% and AcOH following the procedure described in Example 55, Step B, giving (E)-3-{1'-(2-phenyl-ethyl)-3,4-dihydro-3-benzyl-4-oxo-spiro[2H-(1,3)-benzoxazine-2,4'-piperidin]-6-yl}-acrylic acid as a white solid (440 mg, 78%). This acid (423 mg, 0.81 mmol) was treated with NH$_2$OTHP according to the procedure described in Example 1, Step B, giving (E)-3-{1'-(2-phenyl-ethyl)-3,4-dihydro-3-benzyl-4-oxo-spiro[2H-(1,3)-benzoxazine-2,4'-piperidin]-6-yl}-N-(tetrahydro-pyran-2-yloxy)-acrylamide as a white solid (422 mg, 89%). Finally, removal of the THP protecting group starting from 95 mg (0.16 mmol) according to the procedure described in Example 55, Step D gave (E)-3-{1'-(2-phenyl-ethyl)-3,4-dihydro-3-benzyl-4-oxo-spiro[2H-(1,3)-benzoxazine-2,4'-piperidin]-6-yl}-N-hydroxy-acrylamide (37 mg, trifluoroacetate salt) after purification by preparative HPLC.

Y=37%

LC-MS: Method G, rt=1.64 min; (ES+) MH+: 498

$^1$H NMR (300 MHz, DMSO-$d_6$) δ (ppm): 10.71 (bs, 1H), 9.62 (bs, 1H), 8.07 (d, J=1.76 Hz, 1H), 7.85 (dd, J=8.36, 1.91 Hz, 1H), 7.50 (d, J=15.85 Hz, 1H), 7.19-7.44 (m, 11H), 6.49 (d, J=15.85 Hz, 1H), 4.82 (s, 2H), 3.47-3.63 (m, 2H), 3.31-3.47 (m, 2H), 3.10-3.31 (m, 2H), 2.85-3.04 (m, 2H), 2.00-2.44 (m, 4H).

Example 85

(E)-3-{1'-(1-Phenyl-ethyl)-4-oxo-spiro[chromane-2,4'-piperidine]-6-yl}-N-hydroxy-acrylamide

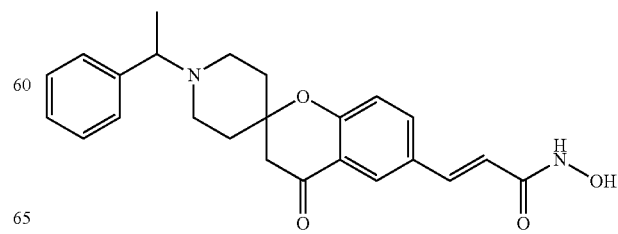

Step A

A mixture of (E)-3-{4-oxo-spiro[chromane-2,4'-piperidine]-6-yl}-acrylic acid methyl ester hydrochloride (500 mg, 1.48 mmol, Intermediate 1), TEA (0.41 ml, 2.96 mmol) and (±)-(1-bromoethyl)benzene (547 mg, 2.96 mmol) in DCM (25 ml) was stirred for 48 h at RT and then washed with brine. The organic phase was dried over $Na_2SO_4$ and evaporated. The crude residue was purified by column chromatography (eluent:from DCM to DCM/MeOH 96:4) to give (±)-(E)-3-{1-(1-phenyl-ethyl)-4-oxo-spiro[chromane-2,4'-piperidine]-6-yl}-acrylic acid methyl ester (546 mg, 90%).

$^1$H NMR (DMSO-$d_6$) δ (ppm) 7.96 (d, J=2.35 Hz, 1H), 7.95 (dd, J=8.51, 2.35 Hz, 1H), 7.65 (d, J=15.85 Hz, 1H), 7.13-7.45 (m, 5H), 7.02 (d, J=9.10 Hz, 1H), 6.54 (d, J=16.14 Hz, 1H), 3.71 (s, 3H), 3.38-3.59 (m, 1H), 2.82 (s, 2H), 2.66 (bs, 1H), 2.19-2.47 (m, 3H), 1.62-1.95 (m, 4H), 1.30 (d, J=6.46 Hz, 3H).

Step B (±)-(E)-3-{1'-(1-Phenyl-ethyl)-4-oxo-spiro[chromane-2,4'-piperidine]-6-yl}-acrylic acid methyl ester (526 mg, 1.30 mmol) was treated with 1 M NaOH following the procedure described in Example 71 Step B, giving (±)-(E)-3-{1-(1-phenyl-ethyl)-4-oxo-spiro[chromane-2,4'-piperidine]-6-yl}-acrylic acid (445 mg, 88%). The resulting product was treated with $NH_2$OTHP according to the procedure described in Example 71 Step C, giving (±)-(E)-3-{1-(1-phenyl-ethyl)-4-oxo-spiro[chromane-2,4'-piperidine]-6-yl}-N-(tetrahydro-pyran-2-yloxy)-acrylamide. Finally, removal of the THP protecting group following the procedure described in Example 71 Step C gave (±)-(E)-3-{1'-(1-phenyl-ethyl)-4-oxo-spiro[chromane-2,4'-piperidine]-6-yl}-N-hydroxy-acrylamide hydrochloride (197 mg).

Y=34% (over 3 steps)

LC-MS: Method G rt=1.4; (ES+) MH$^+$:407

H NMR (DMSO-$d_6$+$Na_2CO_3$) δ (ppm): 7.83 (d, J=1.47 Hz, 1H), 7.73 (dd, J=8.66, 1.91 Hz, 1H), 7.15-7.46 (m, 6H), 7.00 (d, J=8.51 Hz, 1H), 6.41 (d, J=15.55 Hz, 1H), 3.48 (q, J=6.75 Hz, 1H), 2.80 (s, 2H), 2.60-2.76 (m, 1H), 2.14-2.48 (m, 3H), 1.49-2.05 (m, 4H), 1.29 (d, J=6.75 Hz, 3H).

Example 86

(E)-3-{1'-(2-Phenyl-thiazolyl-4-yl-methyl)-4-oxo-spiro[chromane-2,4'-piperidine]-6-yl}-N-hydroxy-acrylamide

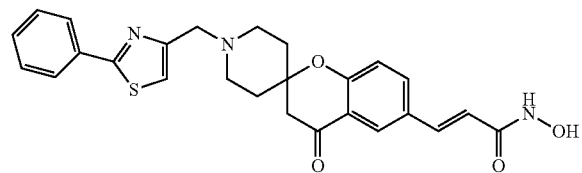 [SMILES: O=C(/C=C/c1ccc2c(c1)C(=O)CC1(CCN(Cc3csc(-c4ccccc4)n3)CC1)O2)NO]

Step A

A suspension of (E)-3-{4-oxo-spiro[chromane-2,4'-piperidine]-6-yl}-acrylic acid methyl ester hydrochloride (600 mg, 1.78 mmol, Intermediate 1) in DCM (30 ml) was treated with TEA (0.25 ml, 1.77 mmol). The pH was adjusted to 5 with AcOH and then 2-phenylthiazole-4-carbaldehyde (404 mg, 2.13 mmol) and NaBH(OAc)$_3$ (554 mg, 2.62 mmol) were added. The mixture was stirred for 2 h at RT and then partitioned between DCM and aqueous NaHCO$_3$ solution. The organic layer was dried over Na$_2$SO$_4$ and evaporated. The crude residue was purified by column chromatography (eluent:DCM/MeOH 99:1) to give (E)-3-{1-(2-phenyl-thiazol-4-yl-methyl)-4-oxo-spiro[chromane-2,4'-piperidine]-6-yl}-acrylic acid methyl ester (602 mg).

Y=71%

$^1$H NMR (DMSO-$d_6$) δ (ppm): 7.98 (d, J=2.05 Hz, 1H), 7.98 (dd, J=8.80, 2.35 Hz, 1H), 7.67 (d, J=16.14 Hz, 1H), 7.37-7.58 (m, 6H), 7.08 (d, J=9.39 Hz, 1H), 6.55 (d, J=16.14 Hz, 1H), 3.72 (s, 3H), 3.70 (s, 2H), 2.86 (s, 2H), 2.60-2.77 (m, 4H), 1.84-1.98 (m, 2H), 1.58-1.84 (m, 2H).

Step B (E)-3-{1'-(2-phenyl-thiazol-4-yl-methyl)-4-oxo-spiro[chromane-2,4'-piperidine]-6-yl}-acrylic acid methyl ester (600 mg, 1.26 mmol) was treated with 1 M NaOH following the procedure described in Example 71 Step B, giving (E)-3-{1'-(2-phenyl-thiazol-4-yl-methyl)-4-oxo-spiro[chromane-2,4'-piperidine]-6-yl}-acrylic acid (548 mg, 95%). The resulting product was treated with NH$_2$OTHP according to the procedure described in Example 71 Step C, giving (E)-3-{1'-(2-phenyl-thiazol-4-yl-methyl)-4-oxo-spiro[chromane-2,4'-piperidine]-6-yl}-N-(tetrahydro-pyran-2-yloxy)-acrylamide. Finally, removal of the THP protecting group following the procedure described in Example 71 Step C gave (E)-3-{1'-(2-phenyl-thiazol-4-yl-methyl)-4-oxo-spiro[chromane-2,4'-piperidine]-6-yl}-N-hydroxy-acrylamide hydrochloride (202 mg).

Y=31% (over 3 steps)

LC-MS: Method M, rt=2.71; (ES+) MH$^+$: 476

$^1$H NMR (DMSO-$d_6$) δ (ppm): 10.54-11.14 (m, 2H), 8.03 (s, 1H), 7.88-8.02 (m, 3H), 7.69-7.87 (m, 1H), 7.50-7.60 (m, 3H), 7.44 (d, J=15.85 Hz, 1H), 7.08 (d, J=8.51 Hz, 1H), 6.45 (d, J=15.85 Hz, 1H), 4.43-4.74 (m, 2H), 3.23-3.56 (m, 4H), 2.90 (s, 2H), 2.17-2.38 (m, 2H), 1.93-2.17 (m, 2H).

Example 87

(E)-3-{1'-Ethyl-3,4-dihydro-3-butyl-4-oxo-spiro[2H-(1,3)-benzoxazine-2,4'-piperidin]-6-yl}-N-hydroxy-acrylamide

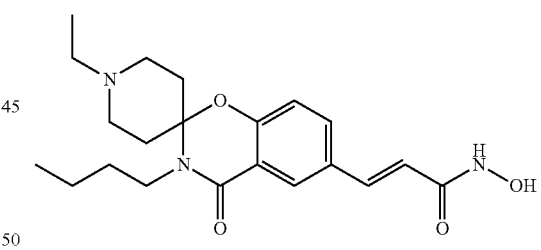

(E)-3-{1'-Tert-butoxycarbonyl-3,4-dihydro-3-butyl-4-oxo-spiro[2H-(1,3)-benzoxazine-2,4'-piperidin]-6-yl}-acrylic acid methyl ester (182 mg, 0.397 mmol, Intermediate 7) was treated with 4 M HCl in dioxane following the procedure described in Example 1 STEP C, to give (E)-3-{3,4-dihydro-3-butyl-4-oxo-spiro[2H-(1,3)-benzoxazine-2,4'-piperidin]-6-yl}-acrylic acid methyl ester hydrochloride (157 mg, 99%). Reaction with acetaldehyde (24 µl, 0.42 mmol) and NaCN(BH$_3$) (26 mg, 0.42 mmol) following the procedure described in Example 71, Step A, gave (E)-3-{1'-ethyl-3,4-dihydro-3-butyl-4-oxo-spiro[2H-(1,3)-benzoxazine-2,4'-piperidin]-6-yl}-acrylic acid methyl ester (123 mg, 80%). The ester was hydrolyzed as described in Example 71, Step B, giving (E)-3-{1'-ethyl-3,4-dihydro-3-butyl-4-oxo-spiro[2H-(1,3)-benzoxazine-2,4'-piperidin]-6-yl}-acrylic acid. The resulting acid was treated with NH$_2$OTHP following the procedure described in Example 71, Step C, giving (E)-3-{1'-ethyl-3,4-dihydro-3-butyl-4-oxo-spiro[2H-(1,3)-benzoxazine-2,4'-piperidin]-6-yl}-N-(tetrahydro-pyran-2-yloxy)-acrylamide. Finally, removal of THP protecting group following the procedure described in Example 71, STEP C gave (E)-3-{1'-ethyl-3,4-dihydro-3-butyl-4-oxo-spiro[2H-(1,3)-benzoxazine-2,4'-piperidin]-6-yl}-N-hydroxy-acrylamide that was purified by preparative LC-MS and obtained as trifluoroacetate salt (18 mg).

Y=11%

LC-MS: Method N, rt=3.19 min; (ES+) MH$^+$: 388

$^1$H NMR (DMSO-d$_6$353K) δ (ppm): 10.75 (bs, 1H), 7.98 (d, J=2.3 Hz, 1H), 7.75 (dd, J=8.5, 2.3 Hz, 1H), 7.46 (d, J=15.8 Hz, 1H), 7.20 (d, J=8.5 Hz, 1H), 6.52 (d, J=15.8 Hz, 1H), 3.51 (m, 5H), 3.15-3.24 (m, 4H), 2.55-2.69 (m, 1H), 2.29-2.42 (m, 2H), 1.53-1.70 (m, 2H), 1.32-1.44 (m, 2H), 1.31 (t, J=7.3 Hz, 3H), 0.97 (t, J=7.3 Hz, 3H).

Analogously, starting from the appropriate intermediates, the following compounds were prepared:

(E)-3-{1'-[2-(4-Fluoro-phenyl)-ethyl)-3,4-dihydro-4-oxo-spiro[2H-(1,3)-benzoxazine-2,4'-piperidin]-6-yl}-N-hydroxy-acrylamide;

(E)-3-{2'-Phenyl-4-oxo-spiro[chromane-2,4'-piperidine]-6-yl}-N-hydroxy-acrylamide;

(E)-3-{1'-Methyl-2'-phenyl-4-oxo-spiro[chromane-2,4'-piperidine]-6-yl}-N-hydroxy-acrylamide;

(E)-3-{1'-Acetyl-2'-phenyl-4-oxo-spiro[chromane-2,4'-piperidine]-6-yl}-N-hydroxy-acrylamide;

(E)-3-{1'-Benzyl-2'-phenyl-4-oxo-spiro[chromane-2,4'-piperidine]-6-yl}-N-hydroxy-acrylamide;

(E)-3-{1'-Benzoyl-2'-phenyl-4-oxo-spiro[chromane-2,4'-piperidine]-6-yl}-N-hydroxy-acrylamide;

(E)-3-{1'-(2-Phenyl-ethyl)-2'-phenyl-4-oxo-spiro[chromane-2,4'-piperidine]-6-yl}-N-hydroxy-acrylamide;

(E)-3-{2'-Phenylcarbamoyl-4-oxo-spiro[chromane-2,4'-piperidine]-6-yl}-N-hydroxy-acrylamide;

(E)-3-{1'-Methyl-2'-phenylcarbamoyl-4-oxo-spiro[chromane-2,4'-piperidine]-6-yl}-N-hydroxy-acrylamide;

(E)-3-{1'-Acetyl-2'-phenylcarbamoyl-4-oxo-spiro[chromane-2,4'-piperidine]-6-yl}-N-hydroxy-acrylamide;

(E)-3-{1'-Benzyl-2'-phenylcarbamoyl-4-oxo-spiro[chromane-2,4'-piperidine]-6-yl}-N-hydroxy-acrylamide;

(E)-3-{1'-Benzoyl-2'-phenylcarbamoyl-4-oxo-spiro[chromane-2,4'-piperidine]-6-yl}-N-hydroxy-acrylamide;

(E)-3-{1'-(2-Phenyl-ethyl)-2'-phenylcarbamoyl-4-oxo-spiro[chromane-2,4'-piperidine]-6-yl}-N-hydroxy-acrylamide.

2. Biological Testing

Methods and Results 2.1 Histone Acetylation Assay

In order to assess the ability of the compounds to modify histone acetylation levels, a dose-response study was carried out using the cell line K562 (derived from human lymphoma). The cells were incubated with the compound for 3 h, then fixed with 1% formaldehyde in PBS and permeabilized with a solution containing 0.1% Triton X-100 in PBS. After washing, the cells were pre-incubated with 10% goat serum in PBS for 30 min at 4° C., exposed for 1 h at RT to a monoclonal antibody against acetylated histones and then incubated for 1 h with a secondary antibody conjugated with FITC. Histone acetylation levels were measured by cytofluorometry (FACS) (Ronzoni, S. et al. *Cytometry A*. 2005, 66, 52-61).

2.2 Assay of Enzyme Inhibition of HDAC

The in-vitro activity of HDAC inhibitors was assayed using a BIOMOL Kit, according to the instructions from the manufacturer (Biomolecular Research Laboratory). 15 μl of 30× diluted nuclear fraction of Hela cells, was diluted to 50 μl with the assay buffer containing the HDAC inhibitor and the substrate (lysine with acetylated amino group on the side chain) at a concentration of 200 μM. The samples were incubated for 15 min at RT and then exposed to a developer (10 min at RT). In this last step a fluorophore was produced, whose fluorescence was measured using an excitation wavelength of 355 nm and an emission at 460 nm. The IC$_{50}$ was calculated using GraphPad Software.

The obtained results are illustrated in the following table 1. IC$_{50}$ results were allocated to one of 3 ranges as follows: Range A: IC$_{50}$≤0.1 μM; Range B: from 0.1 to 1.0 μM; Range C: IC$_{50}$≥1.0 μM.

TABLE 1

Results of the HDAC inhibition assay:

| Example | Biomol IC$_{50}$ [μM] |
|---|---|
| 1 | A |
| 2 | B |
| 3 | B |
| 4 | B |
| 5 | B |
| 6 | B |
| 7 | B |
| 8 | C |
| 9 | C |
| 10 | C |
| 11 | B |
| 12 | B |
| 13 | C |
| 14 | C |
| 15 | C |
| 16 | C |
| 17 | C |
| 18 | B |
| 19 | A |
| 20 | B |
| 21 | B |
| 22 | C |
| 23 | C |
| 24 | C |
| 25 | A |
| 26 | B |
| 27 | B |
| 28 | B |
| 29 | B |
| 30 | B |
| 31 | B |
| 32 | B |
| 33 | B |
| 34 | B |
| 35 | B |
| 36 | B |
| 37 | B |
| 38 | B |
| 39 | B |
| 40 | B |
| 41 | B |
| 42 | B |
| 43 | B |
| 44 | B |
| 45 | B |
| 46 | B |
| 47 | B |
| 48 | B |
| 49 | A |
| 50 | A |
| 51 | A |
| 52 | B |
| 53 | A |
| 54 | A |
| 55 | B |
| 56 | A |
| 57 | B |

TABLE 1-continued

Results of the HDAC inhibition assay:

| Example | Biomol IC$_{50}$ [μM] |
|---|---|
| 58 | A |
| 59 | B |
| 60 | B |
| 61 | A |
| 62 | A |
| 63 | A |
| 64 | B |
| 65 | A |
| 66 | B |
| 67 | B |
| 68 | A |
| 69 | B |
| 70 | B |
| 71 | A |
| 72 | A |
| 73 | A |
| 74 | B |
| 75 | B |
| 76 | B |
| 77 | B |
| 78 | B |
| 79 | B |
| 80 | B |
| 81 | B |
| 82 | A |
| 83 | B |
| 84 | B |

2.3 Cell Growth

CellTiter-Glo® Luminescent Cell Viability Assay (Promega) is a homogeneous method of determining the number of viable cells in culture based on quantitation of the present ATP, which indicates the presence of metabolically active cells. The homogeneous assay procedure involves addition of a single reagent (CellTiter-Glo® Reagent) directly to the cells, which leads to cell lysis and generation of a luminescent signal proportional to the amount of the ATP and the number of cells present in culture. The assay relies on the properties of a proprietary thermostable luciferase (Ultra-Glo® recombinant luciferase), which generates a luminescent signal.

K562, A549 and HCT-116 cells, in exponential growth, were incubated for 72 h with different concentrations of the inhibitors. After 72 h, a volume of CellTiter-Glo® Reagent equal to the volume of cell culture medium was added. The content was mixed for 2 min to induce cell lysis. The luminescence was recorded after further 10 min at RT in order to obtain a stabilized luminescent signal.

The IC$_{50}$ was calculated using GraphPad Software.

The obtained results are illustrated in the following table 2. IC$_{50}$ results were allocated to one of 3 ranges as follows: Range A: IC$_{50}$≤1.0 μM; Range B: from 1.0 to 3.0 μM; Range C: IC$_{50}$≥3.0 μM.

TABLE 2

Results of the antiproliferative assay:

| Example | K562 | A549 | HCT116 |
|---|---|---|---|
| 1 | C | B | B |
| 2 | A | A | A |
| 3 | C | C | C |
| 4 | B | C | B |
| 5 | A | B | A |
| 6 | B | C | B |
| 7 | A | B | B |
| 8 | C | C | C |
| 9 | C | C | C |
| 10 | C | C | C |
| 11 | C | C | C |
| 12 | B | B | C |
| 13 | C | C | C |
| 14 | B | C | B |
| 15 | C | C | C |
| 16 | C | C | C |
| 17 | B | B | B |
| 18 | B | B | A |
| 19 | B | B | A |
| 20 | B | B | A |
| 21 | C | C | C |
| 22 | C | C | C |
| 23 | C | C | C |
| 24 | B | C | C |
| 25 | A | B | A |
| 26 | C | C | C |
| 27 | C | C | B |
| 28 | A | B | B |
| 29 | A | B | A |
| 30 | A | B | A |
| 31 | A | A | A |
| 32 | A | B | A |
| 33 | A | A | A |
| 34 | A | B | A |
| 35 | A | B | B |
| 36 | A | B | A |
| 37 | B | B | B |
| 38 | A | B | B |
| 39 | A | B | A |
| 40 | A | B | A |
| 41 | B | B | A |
| 42 | B | B | A |
| 43 | C | C | C |
| 44 | B | C | B |
| 45 | A | B | A |
| 46 | C | C | C |
| 47 | C | C | C |
| 48 | B | C | B |
| 49 | A | A | A |
| 50 | A | A | A |
| 51 | A | A | A |
| 52 | A | B | A |
| 53 | A | B | A |
| 54 | A | A | A |
| 55 | A | A | A |
| 56 | A | A | A |
| 57 | A | A | A |
| 58 | A | A | A |
| 59 | A | A | A |
| 60 | A | A | A |
| 62 | A | A | A |
| 63 | A | A | A |
| 64 | B | B | B |
| 68 | A | A | A |
| 69 | A | A | A |
| 71 | A | B | A |
| 72 | C | C | C |
| 73 | B | B | A |
| 74 | A | B | A |
| 75 | A | B | A |
| 76 | B | B | A |
| 77 | A | B | B |
| 78 | B | C | B |
| 79 | C | C | C |
| 80 | B | B | B |
| 81 | A | A | A |
| 83 | B | C | B |
| 84 | B | B | B |

What is claimed is:

1. Compounds of formula (I)

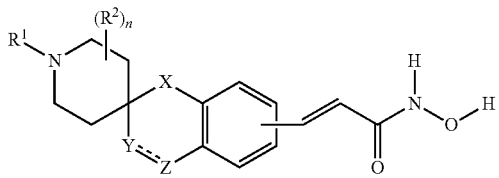

and pharmaceutically acceptable salts thereof, wherein:
the dotted line is an optional additional bond;
n is zero or 1;
$R^1$ is hydrogen; $C_1$-$C_4$ alkyl; $C_1$-$C_4$ alkyl substituted by phenyl or phenyl substituted by halogen, $C_1$-$C_4$ alkyl, $C_1$-$C_4$ alkoxy, amino, $C_1$-$C_4$ alkylamino or phenyl; $C_1$-$C_4$ alkyl substituted by 2-phenyl-thiazolyl, pyridyl, indolyl, quinolyl, or indolyl substituted by halogen or $C_1$-$C_4$ alkyl; (CO)$R^3$; (SO$_2$)$R^4$; cyclopentyl; phenyl; or pyrimidinyl;
$R^2$ is phenyl or (CO)NH-phenyl;
X is oxygen or NH;
Y is a bond; CHR$^7$; NH; N—$C_1$-$C_4$ alkyl; or N—$C_1$-$C_4$ alkyl substituted by phenyl;
Z is CR$^9$R$^{10}$; C=O; C=NOH; C=NO—$C_1$-$C_4$ alkyl; or C=NO—$C_1$-$C_4$ alkyl substituted by phenyl;
$R^3$ is $C_1$-$C_4$ alkyl; phenyl; O—$C_1$-$C_4$ alkyl; NH—$C_1$-$C_4$ alkyl; NH—$C_1$-$C_4$ alkyl substituted by phenyl; or NH-phenyl;
$R^4$ is $C_1$-$C_4$ alkyl or phenyl;
$R^7$ is hydrogen; or is absent, when said additional bond is present;
$R^9$ is hydrogen; or is absent, when said additional bond is present;
$R^{10}$ is hydrogen; hydroxyl; or $C_1$-$C_4$ acylamino;
provided that when said additional bond is present, then Y and Z are CH.

2. Compounds according to claim 1, selected from:
(E)-3-{4-Oxo-spiro[chromane-2,4'-piperidine]-6-yl}-N-hydroxy-acrylamide;
(E)-3-{1'-Benzyl-4-oxo-spiro[chromane-2,4'-piperidine]-6-yl}-N-hydroxy-acrylamide;
(E)-3-{1'-Acetyl-4-oxo-spiro[chromane-2,4'-piperidine]-6-yl}-N-hydroxy-acrylamide;
(E)-3-{1'-Benzoyl-4-oxo-spiro[chromane-2,4'-piperidine]-6-yl}-N-hydroxy-acrylamide;
(E)-3-{1'-Methyl-4-oxo-spiro[chromane-2,4'-piperidine]-6-yl}-N-hydroxy-acrylamide;
(E)-3-{1'-Ethyloxycarbonyl-4-oxo-spiro[chromane-2,4'-piperidine]-6-yl}-N-hydroxy-acrylamide;
(E)-3-{1'-Phenyl-4-oxo-spiro[chromane-2,4'-piperidine]-6-yl}-N-hydroxy-acrylamide;
(E)-3-{4-Oxo-spiro[chromane-2,4'-piperidine]-7-yl}-N-hydroxy-acrylamide;
(E)-3-{1'-Benzyl-4-oxo-spiro[chromane-2,4'-piperidine]-7-yl}-N-hydroxy-acrylamide;
(E)-3-{1'-Acetyl-4-oxo-spiro[chromane-2,4'-piperidine]-7-yl}-N-hydroxy-acrylamide;
(E)-3-{1'-Benzoyl-4-oxo-spiro[chromane-2,4'-piperidine]-7-yl}-N-hydroxy-acrylamide;
(E)-3-{1'-Ethyloxycarbonyl-4-oxo-spiro[chromane-2,4'-piperidine]-7-yl}-N-hydroxy-acrylamide;
(E)-3-{1'-Benzyl-spiro[chromane-2,4'-piperidine]-6-yl}-N-hydroxy-acrylamide;
(E)-3-{1'-Benzyl-4-hydroxy-spiro[chromane-2,4'-piperidine]-6-yl}-N-hydroxy-acrylamide;
(E)-3-{1'-Benzyl-spiro[chromene-2,4'-piperidine]-6-yl}-N-hydroxy-acrylamide;
(E)-3-{1'-Benzyl-4-acetylamino-spiro[chromane-2,4'-piperidine]-6-yl}-N-hydroxy-acrylamide;
(E)-3-{1'-Benzyl-4-benzyloxyimino-spiro[chromane-2,4'-piperidine]-6-yl}-N-hydroxy-acrylamide;
(E)-3-{1'-Benzyl-4-methyloxyimino-spiro[chromane-2,4'-piperidine]-6-yl}-N-hydroxy-acrylamide;
(E)-3-{1'-Benzyl-4-hydroxyimino-spiro[chromane-2,4'-piperidine]-6-yl}-N-hydroxy-acrylamide;
(E)-3-{3-oxo-spiro[benzofuran-2(3H),4'-piperidin]-5-yl}-N-hydroxy-acrylamide;
(E)-3-{1'-Benzyl-3-oxo-spiro[benzofuran-2(3H),4'-piperidin]-5-yl}-N-hydroxy-acrylamide;
(E)-3-{1'-Acetyl-3-oxo-spiro[benzofuran-2(3H),4'-piperidin]-5-yl}-N-hydroxy-acrylamide;
(E)-3-{1'-Benzoyl-3-oxo-spiro[benzofuran-2(3H),4'-piperidin]-5-yl}-N-hydroxy-acrylamide;
(E)-3-{1'-Ethyloxycarbonyl-3-oxo-spiro[benzofuran-2(3H),4'-piperidin]-5-yl}-N-hydroxy-acrylamide;
(E)-3-{1'-Benzyl-3,4-dihydro-4-oxo-spiro[2H-(1,3)-benzoxazine-2,4'-piperidin]-6-yl}-N-hydroxy-acrylamide;
(E)-3-{1-Benzyl-3',4'-dihydro-4'-oxo-spiro[piperidine-4,2'(1'H)-quinazoline]-6'-yl}-N-hydroxy-acrylamide;
(E)-3-{1'-Pyrimidin-2-yl-4-oxo-spiro[chromane-2,4'-piperidine]-6-yl}-N-hydroxy-acrylamide;
(E)-3-{1'-(2-Methyl-benzyl)-4-oxo-spiro[chromane-2,4'-piperidine]-6-yl}-N-hydroxy-acrylamide;
(E)-3-{1'-(3-Methyl-benzyl)-4-oxo-spiro[chromane-2,4'-piperidine]-6-yl}-N-hydroxy-acrylamide;
(E)-3-{1'-(4-Methyl-benzyl)-4-oxo-spiro[chromane-2,4'-piperidine]-6-yl}-N-hydroxy-acrylamide;
(E)-3-{1'-(2-Methoxy-benzyl)-4-oxo-spiro[chromane-2,4'-piperidine]-6-yl}-N-hydroxy-acrylamide;
(E)-3-{1'-(3-Methoxy-benzyl)-4-oxo-spiro[chromane-2,4'-piperidine]-6-yl}-N-hydroxy-acrylamide;
(E)-3-{1'-(4-Methoxy-benzyl)-4-oxo-spiro[chromane-2,4'-piperidine]-6-yl}-N-hydroxy-acrylamide;
(E)-3-{1'-(2-Fluoro-benzyl)-4-oxo-spiro[chromane-2,4'-piperidine]-6-yl}-N-hydroxy-acrylamide;
(E)-3-{1'-(3-Fluoro-benzyl)-4-oxo-spiro[chromane-2,4'-piperidine]-6-yl}-N-hydroxy-acrylamide;
(E)-3-{1'-(4-Fluoro-benzyl)-4-oxo-spiro[chromane-2,4'-piperidine]-6-yl}-N-hydroxy-acrylamide;
(E)-3-{1'-(2-Chloro-benzyl)-4-oxo-spiro[chromane-2,4'-piperidine]-6-yl}-N-hydroxy-acrylamide;
(E)-3-{1'-(3-Chloro-benzyl)-4-oxo-spiro[chromane-2,4'-piperidine]-6-yl}-N-hydroxy-acrylamide;
(E)-3-{1'-(4-Chloro-benzyl)-4-oxo-spiro[chromane-2,4'-piperidine]-6-yl}-N-hydroxy-acrylamide;
(E)-3-{1'-(Pyridin-2-ylmethyl)-4-oxo-spiro[chromane-2,4'-piperidine]-6-yl}-N-hydroxy-acrylamide;
(E)-3-{1'-(Pyridin-3-ylmethyl)-4-oxo-spiro[chromane-2,4'-piperidine]-6-yl}-N-hydroxy-acrylamide;
(E)-3-{1'-(Pyridin-4-ylmethyl)-4-oxo-spiro[chromane-2,4'-piperidine]-6-yl}-N-hydroxy-acrylamide;
(E)-3-{1'-Methanesulfonyl-4-oxo-spiro[chromane-2,4'-piperidine]-6-yl}-N-hydroxy-acrylamide;
(E)-3-{1'-Phenylsulfonyl-4-oxo-spiro[chromane-2,4'-piperidine]-6-yl}-N-hydroxy-acrylamide;
(E)-3-{1'-(3-Phenyl-propyl)-4-oxo-spiro[chromane-2,4'-piperidine]-6-yl}-N-hydroxy-acrylamide;
(E)-3-{1'-Ethylcarbamoyl-4-oxo-spiro[chromane-2,4'-piperidine]-6-yl}-N-hydroxy-acrylamide;

(E)-3-{1'-Benzylcarbamoyl-4-oxo-spiro[chromane-2,4'-piperidine]-6-yl}-N-hydroxy-acrylamide;
(E)-3-{1'-Phenylcarbamoyl-4-oxo-spiro[chromane-2,4'-piperidine]-6-yl}-N-hydroxy-acrylamide;
(E)-3-{1'-[2-(1H-Indol-3-yl)ethyl]-4-oxo-spiro[chromane-2,4'-piperidine]-6-yl}-N-hydroxy-acrylamide;
(E)-3-{1'-(1H-Indol-3-ylmethyl)-4-oxo-spiro[chromane-2,4'-piperidine]-6-yl}-N-hydroxy-acrylamide;
(E)-3-{1'-(2-Methyl-1H-indol-3-ylmethyl)-4-oxo-spiro[chromane-2,4'-piperidine]-6-yl}-N-hydroxy-acrylamide;
(E)-3-{1'-(Biphenyl-4-ylmethyl)-4-oxo-spiro[chromane-2,4'-piperidine]-6-yl}-N-hydroxy-acrylamide;
(E)-3-{1'-(6-Fluoro-1H-indol-3-ylmethyl)-4-oxo-spiro[chromane-2,4'-piperidine]-6-yl}-N-hydroxy-acrylamide;
(E)-3-{1'-(5-Fluoro-1H-indol-3-ylmethyl)-4-oxo-spiro[chromane-2,4'-piperidine]-6-yl}-N-hydroxy-acrylamide;
(E)-3-{1'-(2-Phenyl-ethyl)-4-oxo-spiro[chromane-2,4'-piperidine]-6-yl}-N-hydroxy-acrylamide;
(E)-3-{1'-[2-(4-Fluoro-phenyl)-ethyl]-4-oxo-spiro[chromane-2,4'-piperidine]-6-yl}-N-hydroxy-acrylamide;
(E)-3-{1'-[2-(4-Chloro-phenyl)-ethyl]-4-oxo-spiro[chromane-2,4'-piperidine]-6-yl}-N-hydroxy-acrylamide;
(E)-3-{1'-[2-(4-Methoxy-phenyl)-ethyl]-4-oxo-spiro[chromane-2,4'-piperidine]-6-yl}-N-hydroxy-acrylamide;
(E)-3-{1'-[2-(2-Fluoro-phenyl)-ethyl]-4-oxo-spiro[chromane-2,4'-piperidine]-6-yl}-N-hydroxy-acrylamide;
(E)-3-{1'-[2-(3-Methoxy-phenyl)-ethyl]-4-oxo-spiro[chromane-2,4'-piperidine]-6-yl}-N-hydroxy-acrylamide;
(E)-3-{1'-[2-(4-Methyl-phenyl)-ethyl]-4-oxo-spiro[chromane-2,4'-piperidine]-6-yl}-N-hydroxy-acrylamide;
(E)-3-{1'-[2-(4-Amino-phenyl)-ethyl]-4-oxo-spiro[chromane-2,4'-piperidine]-6-yl}-N-hydroxy-acrylamide;
(E)-3-{1'-[2-(4-Methylamino-phenyl)-ethyl]-4-oxo-spiro[chromane-2,4'-piperidine]-6-yl}-N-hydroxy-acrylamide;
(E)-3-{1'-(1-Methyl-1H-indol-2-ylmethyl)-4-oxo-spiro[chromane-2,4'-piperidine]-6-yl}-N-hydroxy-acrylamide;
(E)-3-{1'-(Quinolin-2-ylmethyl)-4-oxo-spiro[chromane-2,4'-piperidine]-6-yl}-N-hydroxy-acrylamide;
(E)-3-{1'-(Quinolin-3-ylmethyl)-4-oxo-spiro[chromane-2,4'-piperidine]-6-yl}-N-hydroxy-acrylamide;
(E)-3-{1'-(Biphenyl-2-yl-methyl)-4-oxo-spiro[chromane-2,4'-piperidine]-6-yl}-N-hydroxy-acrylamide;
(E)-3-{1'-Ethyl-4-oxo-spiro[chromane-2,4'-piperidine]-6-yl}-N-hydroxy-acrylamide;
(E)-3-{1'-Isopropyl-4-oxo-spiro[chromane-2,4'-piperidine]-6-yl}-N-hydroxy-acrylamide;
(E)-3-{1'-Cyclopentyl-4-oxo-spiro[chromane-2,4'-piperidine]-6-yl}-N-hydroxy-acrylamide;
(E)-3-{1'-(2-Phenyl-ethyl)-3,4-dihydro-4-oxo-spiro[2H-(1,3)-benzoxazine-2,4'-piperidin]-6-yl}-N-hydroxy-acrylamide;
(E)-3-{3,4-Dihydro-4-oxo-spiro[2H-(1,3)-benzoxazine-2,4'-piperidin]-6-yl}-N-hydroxy-acrylamide;
(E)-3-{1'-Methyl-3,4-dihydro-4-oxo-spiro[2H-(1,3)-benzoxazine-2,4'-piperidin]-6-yl}-N-hydroxy-acrylamide;
(E)-3-{1'-(4-Fluoro-benzyl)-3,4-dihydro-4-oxo-spiro[2H-(1,3)-benzoxazine-2,4'-piperidin]-6-yl}-N-hydroxy-acrylamide;
(E)-3-{1'-(4-Fluoro-benzyl)-3,4-dihydro-3-methyl-4-oxo-spiro[2H-(1,3)-benzoxazine-2,4'-piperidin]-6-yl}-N-hydroxy-acrylamide;
(E)-3-{1'-Benzyl-3,4-dihydro-3-methyl-4-oxo-spiro[2H-(1,3)-benzoxazine-2,4'-piperidin]-6-yl}-N-hydroxy-acrylamide;
(E)-3-{1'-(2-Phenyl-ethyl)-3,4-dihydro-3-methyl-4-oxo-spiro[2H-(1,3)-benzoxazine-2,4'-piperidin]-6-yl}-N-hydroxy-acrylamide;
(E)-3-{1'-Methyl-3,4-dihydro-3-methyl-4-oxo-spiro[2H-(1,3)-benzoxazine-2,4'-piperidin]-6-yl}-N-hydroxy-acrylamide;
(E)-3-{3,4-Dihydro-3-methyl-4-oxo-spiro[2H-(1,3)-benzoxazine-2,4'-piperidin]-6-yl}-N-hydroxy-acrylamide;
(E)-3-{1'-Benzyl-3,4-dihydro-3-benzyl-4-oxo-spiro[2H-(1,3)-benzoxazine-2,4'-piperidin]-6-yl}-N-hydroxy-acrylamide;
(E)-3-{1'-Methyl-3,4-dihydro-3-benzyl-4-oxo-spiro[2H-(1,3)-benzoxazine-2,4'-piperidin]-6-yl}-N-hydroxy-acrylamide;
(E)-3-{3,4-Dihydro-3-benzyl-4-oxo-spiro[2H-(1,3)-benzoxazine-2,4'-piperidin]-6-yl}-N-hydroxy-acrylamide;
(E)-3-{1'-(4-Fluoro-benzyl)-3,4-dihydro-3-benzyl-4-oxo-spiro[2H-(1,3)-benzoxazine-2,4'-piperidin]-6-yl}-N-hydroxy-acrylamide;
(E)-3-{1'-(2-Phenyl-ethyl)-3,4-dihydro-3-benzyl-4-oxo-spiro[2H-(1,3)-benzoxazine-2,4'-piperidin]-6-yl}-N-hydroxy-acrylamide;
(E)-3-{1'-(1-Phenyl-ethyl)-4-oxo-spiro[chromane-2,4'-piperidine]-6-yl}-N-hydroxy-acrylamide;
(E)-3-{1'-(2-Phenyl-thiazolyl-4-yl-methyl)-4-oxo-spiro[chromane-2,4'-piperidine]-6-yl}-N-hydroxy-acrylamide;
(E)-3-{1'-Ethyl-3,4-dihydro-3-butyl-4-oxo-spiro[2H-(1,3)-benzoxazine-2,4'-piperidin]-6-yl}-N-hydroxy-acrylamide;
(E)-3-{1'-[2-(4-Fluoro-phenyl)-ethyl]-3,4-dihydro-4-oxo-spiro[2H-(1,3)-benzoxazine-2,4'-piperidin]-6-yl}-N-hydroxy-acrylamide;
(E)-3-{2'-Phenyl-4-oxo-spiro[chromane-2,4'-piperidine]-6-yl}-N-hydroxy-acrylamide;
(E)-3-{1'-Methyl-2'-phenyl-4-oxo-spiro[chromane-2,4'-piperidine]-6-yl}-N-hydroxy-acrylamide;
(E)-3-{1'-Acetyl-2'-phenyl-4-oxo-spiro[chromane-2,4'-piperidine]-6-yl}-N-hydroxy-acrylamide;
(E)-3-{1'-Benzyl-2'-phenyl-4-oxo-spiro[chromane-2,4'-piperidine]-6-yl}-N-hydroxy-acrylamide;
(E)-3-{1'-Benzoyl-2'-phenyl-4-oxo-spiro[chromane-2,4'-piperidine]-6-yl}-N-hydroxy-acrylamide;
(E)-3-{1'-(2-Phenyl-ethyl)-2'-phenyl-4-oxo-spiro[chromane-2,4'-piperidine]-6-yl}-N-hydroxy-acrylamide;
(E)-3-{Z-Phenylcarbamoyl-4-oxo-spiro[chromane-2,4'-piperidine]-6-yl}-N-hydroxy-acrylamide;
(E)-3-{1'-Methyl-2'-phenylcarbamoyl-4-oxo-spiro[chromane-2,4'-piperidine]-6-yl}-N-hydroxy-acrylamide;
(E)-3-{1'-Acetyl-2'-phenylcarbamoyl-4-oxo-spiro[chromane-2,4'-piperidine]-6-yl}-N-hydroxy-acrylamide;
(E)-3-{1'-Benzyl-2'-phenylcarbamoyl-4-oxo-spiro[chromane-2,4'-piperidine]-6-yl}-N-hydroxy-acrylamide;
(E)-3-{1'-Benzoyl-2'-phenylcarbamoyl-4-oxo-spiro[chromane-2,4'-piperidine]-6-yl}-N-hydroxy-acrylamide;
(E)-3-{1'-(2-Phenyl-ethyl)-2'-phenylcarbamoyl-4-oxo-spiro[chromane-2,4'-piperidine]-6-yl}-N-hydroxy-acrylamide.

3. Pharmaceutical composition which comprises a therapeutically effective amount of a compound of claim 1 in combination with a pharmaceutically acceptable carrier.

4. Pharmaceutical composition which comprises a therapeutically effective amount of a compound of claim 2 in combination with a pharmaceutically acceptable carrier.

5. Compounds according to claim 1 wherein n is 0.

6. Compounds according to claim 1 wherein the dotted line is an additional bond, n is 0, and Y is CH; NH; N—$C_1$-$C_4$ alkyl; or N—$C_1$-$C_4$ alkyl substituted by phenyl; Z is $CR^{10}$.

7. Compounds according to claim 1 wherein the dotted line is an additional bond, n is 0, X is NH or O, Y is CH or NH, and Z is $CR^{10}$ or C=O.

8. Pharmaceutical composition which comprises a therapeutically effective amount of a compound of claim 6 in combination with a pharmaceutically acceptable carrier.

9. Pharmaceutical composition which comprises a therapeutically effective amount of a compound of claim 7 in combination with a pharmaceutically acceptable carrier.

\* \* \* \* \*

UNITED STATES PATENT AND TRADEMARK OFFICE
CERTIFICATE OF CORRECTION

PATENT NO. : 8,592,444 B2
APPLICATION NO. : 12/988197
DATED : November 26, 2013
INVENTOR(S) : Varasi et al.

Page 1 of 1

It is certified that error appears in the above-identified patent and that said Letters Patent is hereby corrected as shown below:

In the Claims

Column 101, line 50, claim 2, "-2-yl" should be replaced with --2yl--.

Column 102, line 31, claim 2, "-4-yl" should be replaced with -- -4yl--.

Column 102, line 52, claim 2, "{Z-}" should be replaced with --{2'-}--.

Signed and Sealed this
Sixth Day of May, 2014

Michelle K. Lee
*Deputy Director of the United States Patent and Trademark Office*